United States Patent
Gjermansen et al.

(10) Patent No.: US 11,981,941 B2
(45) Date of Patent: May 14, 2024

(54) POLYPEPTIDES

(71) Applicant: Novozymes A/S, Bagsvaerd (DK)

(72) Inventors: Morten Gjermansen, Greve (DK); Klaus Gori, Copenhagen (DK); Henrik Marcus Geertz-Hansen, Copenhagen (DK); Jesper Salomon, Holte (DK); Thomas Holberg Blicher, Copenhagen (DK); Nikolaj Spodsberg, Holte (DK)

(73) Assignee: NOVOZYMES A/S, Bagsvaerd (DK)

( * ) Notice: Subject to any disclaimer, the term of this patent is extended or adjusted under 35 U.S.C. 154(b) by 0 days.

(21) Appl. No.: 18/168,096

(22) Filed: Feb. 13, 2023

(65) Prior Publication Data

US 2024/0067943 A1    Feb. 29, 2024

Related U.S. Application Data

(62) Division of application No. 17/157,137, filed on Jan. 25, 2021, now Pat. No. 11,613,741, which is a division of application No. 15/766,894, filed as application No. PCT/EP2016/074079 on Oct. 7, 2016, now Pat. No. 10,954,497.

(30) Foreign Application Priority Data

Oct. 7, 2015  (DK) ............ PA 2015 00615
Oct. 7, 2015  (DK) ............ PA 2015 00617
Oct. 7, 2015  (DK) ............ PA 2015 00618

(51) Int. Cl.
| | |
|---|---|
| C12N 9/22 | (2006.01) |
| C11D 3/20 | (2006.01) |
| C11D 3/22 | (2006.01) |
| C11D 3/37 | (2006.01) |
| C11D 3/386 | (2006.01) |

(52) U.S. Cl.
CPC .......... *C12N 9/22* (2013.01); *C11D 3/2065* (2013.01); *C11D 3/22* (2013.01); *C11D 3/3707* (2013.01); *C11D 3/38627* (2013.01); *C11D 3/38636* (2013.01); *C11D 3/38681* (2013.01); *C12Y 301/21* (2013.01); *C12Y 301/21001* (2013.01); *C11D 2111/12* (2024.01)

(58) Field of Classification Search
CPC ................ C12N 9/22; C12Y 301/21
See application file for complete search history.

(56) References Cited

U.S. PATENT DOCUMENTS

| | | | |
|---|---|---|---|
| 6,340,566 B1 | 1/2002 | McCuthen-Maloney | |
| 6,365,355 B1 | 4/2002 | McCutchen-Maloney | |
| 8,377,675 B2 | 2/2013 | Otani et al. | |
| 10,954,497 B2 | 3/2021 | Gjermansen et al. | |
| 2010/0061971 A1 | 3/2010 | Genkin | |
| 2012/0060300 A1 | 3/2012 | Kim et al. | |
| 2013/0189760 A1 | 7/2013 | Mori et al. | |
| 2015/0299623 A1 | 10/2015 | Gori | |
| 2017/0081616 A1 | 3/2017 | Baltsen | |
| 2019/0055528 A1 | 2/2019 | Gori et al. | |
| 2020/0123476 A1 | 4/2020 | Gjermansen et al. | |

FOREIGN PATENT DOCUMENTS

| | | |
|---|---|---|
| CN | 103108950 A | 5/2013 |
| CN | 104837979 A | 8/2015 |
| EP | 2617824 A1 | 7/2013 |
| IN | 201647042277 A | 12/2016 |
| WO | 01/98214 A1 | 12/2001 |
| WO | 2009/107091 A2 | 9/2009 |
| WO | 2009/111258 A2 | 9/2009 |
| WO | 2011/015327 A1 | 2/2011 |
| WO | 2011/098579 A1 | 8/2011 |
| WO | 2012/036241 A1 | 3/2012 |
| WO | 2014/087011 A1 | 6/2014 |
| WO | 2015/181286 A1 | 12/2015 |
| WO | 2017/162836 A1 | 9/2017 |
| WO | 2018/011276 A1 | 1/2018 |

OTHER PUBLICATIONS

Anonymous, NSBI Accession No. WP_004251670 (2013).
Anonymous, UniParc Accession No. UPI0003A82032 (2013).
Anonymous, NCBI Accession No. WP_025722554 (2014).
Anonymous, NCBI Accession No. WP_027924635 (2014).
Anonymous, NCBI Accession No. WP_028551502 (2014).
Anonymous, NCBI Accession No. WP_029440352 (2014).
Anonymous, NCBI Accession No. WP_034664156 (2014).
Anonymous, NCBI Accession No. WP_039304398 (2015).
Anonymous, NCBI Accession No. WP_041089515 (2015).
Anonymous, NCBI Accession No. WP_045521827 (2015).
Anonymous, NCBI Accession No. WP_047969415 (2015).
Anonymous, NCBI Accession No. WP_051450038 (2015).
Anonymous, NCBI Accession No. WP_030603405 (2016).
Anonymous, NCBI Accession No. WP_031424130 (2016).
Anonymous, NCBI Accession No. WP_034817012 (2016).
Anonymous, NCBI Accession No. WP_035510436 (2016).
Anonymous, Merriam-webster Dictionary definition of granule (2020).
Baumgarten, GenBank Accession No. KXJ07836 (2015).
Birren, EBI Accession No. Q5ARC4 (2005).
Birren, EBI Accession No. Q2GRF9 (2006).
Birren, Genbank Accession No. EAT79147.2 (2007).
Birren, Genbank Accession No. EAQ85431.1 (2015).
Chancey, UniProt Accession No. J1GWI8 (2012).

(Continued)

*Primary Examiner* — Tekchand Saidha
(74) *Attorney, Agent, or Firm* — Elias Lambiris

(57) ABSTRACT

The present invention relates to polypeptides, nucleotides encoding the polypeptide, as well as methods of producing the polypeptides. The present invention also relates to detergent composition comprising polypeptides, a laundering method and the use of polypeptides.

16 Claims, 13 Drawing Sheets

Specification includes a Sequence Listing.

(56) References Cited

OTHER PUBLICATIONS

Chen, BMC Genomics, vol. 14, No. 339, pp. 1-18 (2013).
Chen et al., UniProt Accession No. S3D1S1 (2013).
Chen et al., UniProt Accession No. S3DWR8 (2013).
Coleman et al., UniProt Accession No. C7YPZ7 (2009).
Cuomo, EBI Accession No. U7Q814 (2014).
Cuomo, EBI Accession No. A0A0D2ITS4 (2015).
Cuomo, GenBank Accession No. ERT03205.1 (2015).
Cuomo, GenBank Accession No. KIX09484.1 (2015).
Daniel, UniProt Accession No. A0A0E4HDQ4 (2015).
Fedorova, EBI Accession No. A1D7D1 (2007).
Feldgarden, GenBank Accession No. EJR08198 (2012).
Franco, UniProt Accession No. A0A0L1HKH6 (2015).
Gao, Plos Genet , vol. 7, p. E1001264 (2011).
Gibson, EBI Accession No. A0A0A1V6B7 (2015).
Giuliano, Genbank Accession No. EXV05759.1 (2014).
Goh, UniProt Accession No. A0A0C2VMI6 (2015).
Gori, ip.com disclosure No. IPCOM000237363D (2014).
Gostin et al., EBI Accession No. A0A074YFK3—EMBL No. KEQ94839.1 (2014).
Greiner-Stoeffele et al., EBI Accession No. JA286954 (2011).
Greiner-Stoeffele et al., EBI Accession No. JA286959 (2011).
Hane et al., EBI Accession No. QOU4Q1 (2006).
He, Scientific Reports, vol. 5, No. 9747, pp. 1-11 (2015).
Hymes, Journal of Infectious Diseases, vol. 207, No. 10, pp. 1491-1497 (2013).
Klosterman, EBI Accession No. G2WSK6 (2011).
Kwak, UniProt Accession No. A0A086GGG3 (2014).
Lawrence, EBI Accession No. A0A0G2FAG3 (2015).
Lian, GenBank Accession No. AFK65439 (2013).
Liu, GenBank Accession No. ETS77558.1 (2014).
Liu, GenBank Accession No. KMY52255 (2015).
Ma, Genbank Accession No. EGY17920.1 (2011).
Ma, EBI Accession No. H6NAU2 (2012).
Ma, GenBank Accession No. CCF36160.1 (2012).
Marincowitz, GenBank Accession No. EU552123 (2008).
Martin, Trends in Biochemical Sciences, vol. 21, No. 8, pp. 283-285 (1996).
Mccutchen-Maloney, EBI Accession No. AAE89259 (2002).
Mccutchen-Maloney, EBI Accession No. AAM56188 (2002).
Morales-Cruz, GenBank Accession No. KKY31181.1 (2015).
Murphy, UniProt Accession No. A0A0T9L4U8 (2015).
Neafsey, UniProt Accession No. A0A0J8TUN1 (2010).
Ngo et al., The Protein Folding Problem and Tertiary Structure Prediction, vol. 433, pp. 492-495 (1994).
Nierman, Genbank Accession No. EAW21625.1 (2006).
Nijland, PloS One, vol. 5, No. 12, article e15668 (2010).
O'Connell, UniProt Accession No. H1V7F8 (2012).
OHM, EBI Accession No. M2N7N4 (2013).
OHM, EBI Accession No. M2S5C4 (2013).
OHM, GenBank Accession No. EMC94815.1 (2013).
OHM, GenBank Accession No. EMD62363.1 (2013).
OSEI, UniProt Accession No. A0A0P8G0A5 (2015).
PEL, EBI Accession No. A2QFZ2 (2007).
PEL, GenBank Accession No. CAK38102.1 (2011).
Petrusso, Toothpaste obtained from encyclopedia.com (2022).
Sharma, UniProt Accession No. A0A0F5R1U3 (2015).
Shields et al., PLoS One, vol. 8, No. 2, article e55339 (2013).
Singh et al., Current Protein and Peptide Science, vol. 18, pp. 1-11 (2017).
Traeger, EBI Accession No. U4LM18 (2013).
Traeger, GenBank Accession No. CCX32983.1 (2013).
Tran, UniProt Accession No. A0A0K6K3H5 (2015).
Vandeputte, GenBank Accession No. KEZ43987.1 (2014).
Vandeputte, UniProt Accession No. A0A084G9H5 (2014).
Wang, EBI Accession No. W3WUK5 (2014).
Wang, GenBank Accession No. AJK28734 (2015).
Wang, UniProt Accession No. A0A0C5AGR7 (2015).
Wortman, GenBank Accession No. CBF82427.1 (2015).
Yaakop, UniProt Accession No. A0A0B5ASW2 (2015).
Yoon, UniProt Accession No. A0A084H293 (2005).
Yoon, GenBank Accession No. KEZ53705.1 (2014).
Zhang et al., Structure, vol. 26, pp. 1474-1485 (2018).
Zhu et al., UniProt Accession No. A0A0F7TT23—EMBL No. CEJ59844.1 (2015).

GYS –clade alignment

```
                          10        20        30        40
                          |         |         |         |
SEQ_ID_NO_56   1MLKKMLSSLFAIVLVLTTLHFSTPTASALPPNIPSKADALTKLNALTV
SEQ_ID_NO_8    1MLKKSLLFSLSLVLSLLVFQYDLLSASALPPDLPSKSTTQAQLNSLNV
SEQ_ID_NO_62   1MLKKSILVLFTLVLLFSGYQFGLPSALAIPPGTPSKSAAQSQLDSLAV
SEQ_ID_NO_53   1MLKKSFLIVFTLVLLFAGFQLGLPSALAFPPGTPSKSEAQSQLNSLTV
SEQ_ID_NO_71   1MFKKTMLFVVALVLSFSLF···LPSAFATPPVTPSKATSQSQLNGLTV
SEQ_ID_NO_77   1MFKKTMLFVVALVLSFSLF···LPSAFATPPVTPSKETSQSQLNGLTV
SEQ_ID_NO_23   1MLKKMMLFVFALVLSFTLF···LPDAYALPPGTPSKSTAQSQLNALTV
SEQ_ID_NO_21   1MLKKASLSVFALLLSFTLF···LPETMATPPGTPSKSAAQSQLNALTV
SEQ_ID_NO_68   1MLKKASLSVFALLLSFTLF···LPETHATPPGTPSKSTAQTQLNALTV
SEQ_ID_NO_22   1MLKKSMLFVVALLLSFTLF···LPTAFAFPPGTPSKSTAQSQLNSLTV
SEQ_ID_NO_59   1MLKKSLMFVVALLLSFALF···LPSALAFPPGTPSKSTAQSQLNALTV
SEQ_ID_NO_74   1MLKKSMLIVFALVLTFTVLQFETAKAASLPPGIPSLSTAQSQLNSLTV
SEQ_ID_NO_65   1MVKKSRLFVFALVLSLSAGFYGTPTASALPPGTPSKSTAQSQLNSLTV
SEQ_ID_NO_80   1MMKKWIGLVFALVLSVVVFHFDIPTASALPSGIPSKSTAQSQLNSLTV
SEQ_ID_NO_20   1MLKKSMLFVFSLVLSFAVFQYDIPTASAFPPEIPSKSTAQSQLNSLTV
SEQ_ID_NO_19   1MLKKSVLFVFSLALTFAVFLYDIPAASAFPPGTPSKSTAQSQLNSLTV
SEQ_ID_NO_18   1MLKKSVWFVFSLVLTFAVFLYDIPAAAAFPPGTPSKSTAQSQLNSLTV
SEQ_ID_NO_16   1MLRKSLIFIFTLLILFTALQFDIQPASALPPGTPSKSQAQSQLNALTV
SEQ_ID_NO_15   1MLRKSLIFIFLLLILFTALQFDIQPASALPPGTPSKSEAQSQLNALTV
SEQ_ID_NO_17   1MLQKSLSVVFAFVLSFSVFHFDPQTVSALPPGTPSKSEAQSQLTSLTV
SEQ_ID_NO_12   1MFKKSLSIVFAFLLSFSVFHFDPETVSALPPGTPSKSEADSDLNALTV
SEQ_ID_NO_11   1MFKKSLSIVFAFLLSFSVFHFDPETVSALPPGTPSKSEAQSQLNALTV
SEQ_ID_NO_13   1MLKKPLLLVFAFILSFSTLQLDPQTVSALPPGTPSKSEAQSQLNSLTV
SEQ_ID_NO_9    1MLKKSMLVVFAFILSFSALQLDPQTVSALPPGTPTKSEAQNQLNSLTV
SEQ_ID_NO_14   1MLKKSMLVVFAFILSFSAIQLDPQTVSALPPGTPSKSEAQSQLNSLTV
```

FIG. 1A

```
         50        60        70        80        90       100
          |         |         |         |         |         |
QTEGPMTGYSRDLFPHWSSQGNGCNTRHVVLKRDADSVVDTCPVTTGRWYSYYDGLVF106
KNEESMSGYSREKFPHWISQGDGCDTRQVILKRDADNYSGNCPVTSGKWYSYYDGITF106
QSEGSMSGYSRDKFPHWIGQGNGCDTRQLVLQRDADYYSGDCPVTSGKWYSYFDGVQV106
QSEGSMSGYSRDKFPHWIGQGNGCDTRQLVLQRDADYYSGDCPVTSGKWYSYFDGVTV106
KTEGAMTGYSRDKFPHWSSQGGGCDTRQVVLKRDADSYSGNCPVTSGSWYSYYDGVKF103
KTEGAMTGYSRDKFPHWSSQGGGCDTRQVVLKRDADSYSGNCPVTSGSWYSYYDGVKF103
QTEGSMTGYSRDKFPHWISQGNGCDTRQVVLQRDADYYSGTCPVTSGKWYSYYDGVTL103
KTEGSMSGYSRDLFPHWISQGSGCDTRQVVLKRDADSYSGNCPVTSGSWYSYYDGVTF103
KTEGSMTGYSRDLFPHWISQGSGCDTRQVVLKRDADYYSGSCPVTSGKWYSYYDGVTF103
KSEGSMTGYSRDKFPHWIGQGSGCDTRQLVLQRDADYYSGSCPVTSGKWYSYYDGVTF103
KSESSMTGYSRDKFPHWIGQRNGCDTRQLVLQRDADSYSGSCPVTSGSWYSYYDGVTF103
KSEGSLTGYSRDVFPHWISQGSGCDTRQVVLKRDADYYSGNCPVTSGKWYSYYDGVTV106
KSESTMTGYSRDKFPHWTSQGGGCDTRQVVLKRDADYYSGSCPVTSGKWYSYYDGITV106
KSEGSMTGYSRDKFPHWISQGGGCDTRQVVLKRDADYYSGNCPVTSGKWYSYYDGISV106
KSEDAMTGYSRDKFPHWISQGDGCDTRQMVLKRDADYYSGSCPVTSGKWYSYYDGITV106
KSEGSMTGYSRDKFPHWISQGDGCDTRQLVLKRDGDYYSGNCPVTSGKWYSYYDGITV106
KSEGSMTGYSRDKFPHWTSQGDGCDTRQLVLKRDGDYYSGNCPVTSGKWYSYYDGIAV106
KAEDPMTGYSRNLFPHWSSQGNGCNTRQLVLQRDADYYSGNCPVTSGRWYSYFDGVVV106
KAEDPMTGYSRNLFPHWNSQGNGCNTRQLVLQRDADYYSGNCPVTSGRWYSYFDGVVV106
KPEDPMTGYSRDHFPHWISQGNGCNTRQIVLQRDADYYSGNCPVTTGKWYSYFDGVIV106
KPEDPMTGYSRDHFPHWISQGNGCNTRQIVLQRDADYYSGACPVTTGKWYSYFDGVIV106
KPEDPMTGYSRDHFPHWISQGNGCNTRQIVLQRDADYYSGACPVTTGKWYSYFDGVIV106
KSEDPMTGYSRDHFPHWSGQGNGCDTRQIVLQRDADYYSGNCPVTSGKWYSYFDGVIV106
KSEGSMTGYSRDLFPHWSGQGNGCDTRQIVLQRDADYYTGTCPTTSGKWYSYFDGVIV106
KTEDPMTGYSRDLFPHWSGQGSGCDTRQIVLQRDADYFTGTCPTTSGKWYSYFDGVIV106
```

FIG. 1B

```
                        110       120       130       140       150
                         |         |         |         |         |
SEQ_ID_NO_56   107  TSASDIDIDHVVPLAEAWRSGASSWTSTKRQSFANDLNGPQLIAVS
SEQ_ID_NO_8    107  NDPSQLDIDHVVPLAEAWRSGASSWSTAKREDFANDLNGPQLIAVS
SEQ_ID_NO_62   107  YDPSYLDIDHMVPLAEAWRSGASSWSTQKREDFANDLDGPHLIAVT
SEQ_ID_NO_53   107  YDPSDLDIDHMVPMAEAWRSGASSWSTQKREDFANDLSGPHLIAVT
SEQ_ID_NO_71   104  TNPSDLDIDHIVPLAEAWRSGASSWTTAQREAFANDLSGSQLIAVS
SEQ_ID_NO_77   104  THPSDLDIDHIVPLAEAWRSGASSWTTAQREAFANDLSGSQLIAVS
SEQ_ID_NO_23   104  YNPSDLDIDHVVALAEAWRSGASSWTTDKREDFANDLSGTQLIAVS
SEQ_ID_NO_21   104  TNPSDLDIDHIVPLAEAWRSGASSWTTSKRQDFANDLSGPQLIAVS
SEQ_ID_NO_68   104  YDPSDLDIDHIVPLAEAWRSGASSWTTSKRQDFANDLSGPQLIAVS
SEQ_ID_NO_22   104  YDPSDLDIDHVVPLAEAWRSGASSWSTQKRKDFANDLSGPQLIAVS
SEQ_ID_NO_59   104  TDPSDLDIDHVVPLAEAWRSGASSWTTAKREDFANDLSGPQLIAVS
SEQ_ID_NO_74   107  YSPSEIDIDHVVPLAEAWRSGASSWTTEKRQNFANDLNGPQLIAVT
SEQ_ID_NO_65   107  YSPSEIDIDHIVPLAEAWRSGASSWTTEKRQNFANDLGGPQLIAVT
SEQ_ID_NO_80   107  YSPSEIDIDHVVPLAEAWRSGASSWTTTKRQNFANDLNGPQLIAVT
SEQ_ID_NO_20   107  YSPSEIDIDHIVPLAEAWRSGASSWTTEKRRNFANDLNGPQLIAVT
SEQ_ID_NO_19   107  YSPSEIDIDHIVPLAEAWRSGASGWTTEKRQSFANDLNGPQLIAVT
SEQ_ID_NO_18   107  YSPSEIDIDHIVPLAEAWRSGASGWTTEKRQNFANDLNGPQLIAVT
SEQ_ID_NO_16   107  TSPSEIDIDHIVPLAEAWRSGASSWTTEKRREFANDLNGPQLIAVT
SEQ_ID_NO_15   107  TSPSEIDIDHIVPLAEAWRSGASSWTTEKRKEFANDLNGPQLIAVT
SEQ_ID_NO_17   107  YSPSEIDIDHIVPLAEAWRSGASSWTAEQRRNFANDLNGPQLIAVT
SEQ_ID_NO_12   107  YSPSEIDIDHIVPLAEAWRSGASSWTTEQRRSFANDLNGPQLIAVT
SEQ_ID_NO_11   107  YSPSEIDIDHIVPLAEAWRSGASSWTTEKRRSFANDLNGPQLIAVT
SEQ_ID_NO_13   107  YSPSEIDIDHVVPLAEAWRSGASSWTTEQRRSFANDLNGPQLIAVT
SEQ_ID_NO_9    107  YSPSEIDIDHIVPLAEAWRSGASSWTTEQRRAFANDLNGPQLIAVT
SEQ_ID_NO_14   107  YSPSEIDVDHIVPLAEAWRSGASSWTTEQRRAFANDLTGPQLIAVT
```

FIG. 1C

```
                160       170       180       190       200
                 |         |         |         |         |
ATSNRSKGDQDPSTWQPPRAGARCAYAKMWVETKSRWGLTLQSSEKAALQTAINACSY 210
ASSNRSKGDQDPSTWQPPRAGANCAYAKMWINTKYNWGLHLQSSEKTALQGMLNSCSY 210
ASSNRSKGDQDPSTWKPTRYSAHCGYAKWWINTKYVYDLNLQSSEKSALQSMLNTCSY 210
ASSNRSKGDQDPSTWKPTRYGAHCGYAKWWINTKYVYDLTLQSSEKTELQSMLNTCSY 210
ASSNRSKGDQDPSTWQPPRAGAKCGYAKWWISTKSKWNLSLQSSEKTALQGMLNSCVY 207
ASSNRSKGDQDPSTWQPPRAGAKCGYAKWWISTKSKWNLSLQSSEKTALQGMLNSCVY 207
ASTNRSKGDQDPSTWQPPRSGAACGYAKWWISTKYKWNLNLQSSEKTALQSMLNSCSY 207
ASTNRSKGDQDPSTWQPPRSGAACGYSKWWISTKYKWGLSLQSSEKTALQGMLNSCSY 207
ASTNRSKGDQDPSTWQPPRAGAACGYSKWWISTKYKWGLSLQSSEKTALQGMLNSCSY 207
ASSNRSKGDQDPSTWQPTRSGAACGYSKWWISTKHKWGLSLQSSEKNALQGMLNSCVY 207
ASSNRSKGDQDPSTWQPPRSGAACGYSKWWISTKYKWGLSLQSSEKTALQGMLNSCIY 207
ASSNRSKGDQDPSTWQPTRTGARCAYAKMWINTKYRWGLHLQSSEKSALQSMLNTCSY 210
ASSNRAKGDQDPSTWKPTRSGAHCAYAKWWINTKYRWGLHLQSSEKTALQSMLNTCSY 210
ASVNRSKGDQDPSTWQPPRYGARCAYAKMWINTKYRWDLNLQSSEKSSLQSMLDTCSY 210
ASVNRSKGDQDPSTWQPPRSGARCAYAKMWVNTKYRWGLHLQSAEKSGLESMLNTCSY 210
ASVNRSKGDQDPSTWQPPRSGSHCAYAKMWVNTKYRWGLHVQSAEKSALQSMLNACSY 210
ASVNRSKGDQDPSTWQPPRSGSHCAYAKMWVNTKYRWGLHLQSAEKSALQSMLNACSY 210
ASVNRSKGDQDPSTWQPPRVAARCGYAKWWINTKYRWDLSLQSSEKSSLQTMLNTCSY 210
ASVNRSKGDQDPSTWQPPRAAARCGYAKWWINTKYRWDLSLQSSEKSSLQTMLNTCSY 210
ASVNRSKGDQDPSTWQPPRTGARCAYAKWWINTKYRWGLHLQSSEKSSLQSMLNGCAY 210
ASVNRSKGDQDPSTWQPPRAGARCAYAKWWINTKHRWGLHLQSSEKSSLQSMLNGCAY 210
ASVNRSKGDQDPSTWQPPRAGARCAYAKWWINTKHRWGLHLQSSEKSSLQSMLNGCAY 210
ASVNRSKGDQDPSTWQPPRAGARCAYAKWWINTKHRWNLHLQSSEKSALQTMLNGCVY 210
ASVNRSKGDQDPSTWQPPRAGARCAYAKWWINTKHRWNLHLQSSEKSSLQTMLNGCAY 210
ASVNRSKGDQDPSTWQPPRAGARCAYAKWWINTKHRWNLHLQSSEKSSLQTMLNGCAY 210
```

```
                      80         90        100        110        120        130        140
                       -          -          -          -          -          -          -
SEQ_ID_NO_107  QSGSCDTRDVVLKRDGTNVVQSASGCTITSGKWVSPYDGATWTASSDVDIDHLVPLSNAWKSGASGWTTAAA
SEQ_ID_NO_110  QSGSCDTRDVVLERDGTNVVQSSTGCTITGGTWVSPYDGATWTASSDVDIDHLVPLSNAWKSGASAWTTAQR
SEQ_ID_NO_101  ISGACNTRETVLKRDGTNVVVNSA·CAATSGTWVSPYDGATWTAASDVDIDHLVPLSNAWKAGASSWTTAQR
SEQ_ID_NO_80   QSGTCNTREVVLKRDGTNVVTNSA·CASTSGSWLSPYDGKTWDSASDIQIDHLVPLSNAWKSGAAAWTTAQR
SEQ_ID_NO_88   ISGTCNTRETVLKRDGTNVVVDSA·CVATSGSWYSPYDGATWTAASDVDIDHMVPLSNAWKSGASAWTTAQR
SEQ_ID_NO_92   QSGTCNTRETVLKRDGTNVVTDSA·CAATSGTWVSPYDGATWTAASDVDIDHMVPLSNAWKSGAASWTTAQR
SEQ_ID_NO_89   QSGTCNTRETVLKRDGTNVVTNSA·CASTSGSWFSPYDGATWTAASDVDIDHVVPLSNAWKSGAASWTTARR
SEQ_ID_NO_104  QSGTCNTRETVLKRDGTNVVTSSS·CAATSGTWFSPYDGATWTAASDVDIDHMVPLSNAWKSGAASWTTARR
SEQ_ID_NO_95   QSGSCNTREVVLAADGTGVVQDSS·CAATSGTWFSPYDGATWTAASDVDIDHVVPLSNAWKSGAASWTTSRR
SEQ_ID_NO_98   QSGACNTRETVLKRDGTGVVQDSA·CAATSGTWRSPFDGATWTAASDVDIDHMVPLSNAWKSGAASWTTARR
SEQ_ID_NO_113  QSGTCNTRETVLKRDGTGVVTDSA·CASTSGSWYSPYDGATWTAASDVDIDHVVPLSNAWKSGAASWTTARR
SEQ_ID_NO_119  QSGSCNTREVVLQRDGTGVVTDSA·CAATSGSWYSVYDGATWTAASDVDIDHMVPLSNAWKSGAASWTTAAR
SEQ_ID_NO_118  QSGTCNTRETVLKRDGTGVVTDSA·CASTSGSWFSVYDGATWTAASDVDIDHVVPLSNAWKSGAASWTTAAR
```

FIG. 2B

| | 150 | 160 | 170 | 180 | 190 | 200 | 210 |
|---|---|---|---|---|---|---|---|
| SEQ_ID_NO_107 | QAFANDLTNPQLLVVTDNVNESKGDKGPEEWKPPLTSYYCTYAEMWVKVKSVYKLTITSAEKSALTSMLSTC |||||||
| SEQ_ID_NO_110 | QAFANDLTNPQLVAVTDNVNEAKGDKGPEEWKPPLTSYYCTYAHCWVKVKSVYKLTITSAEKSALSSMLNTC |||||||
| SEQ_ID_NO_101 | QAFANDLVNPQLLAVTDSVNQGKSDSGPEAWKPSLKSYWCTYAKMWIKVKYVYDLTITSAEKSALVTMMDTC |||||||
| SEQ_ID_NO_80  | QAFANDLTHPQLVAVTGSVNESKGDDGPEDWKPPLASYYCTYASMWTAVKSNYKLTITSAEKSALTSMLATC |||||||
| SEQ_ID_NO_88  | QTFANDLTNPQLLAVTDNVNQAKGDSGPEDWKPSLTSYWCTYAKMWVKTVYDLTITSAEKTALTTMLNTC |||||||
| SEQ_ID_NO_92  | QAFANDLTNPQLLAVTDNVNQSKGDKGPEDWKPPLTSYYCTYAKMWVKVKSVYSLTITSAEKTALTSMLNTC |||||||
| SEQ_ID_NO_89  | QAFANDLTNPQLLAVTDNVNQAKGDKGPEDWKPPLTSYYCTYSKMWIKVKSVWGLTITSAEKSALTSMLATC |||||||
| SEQ_ID_NO_104 | QAFANDLTNPQLIAVTDSVNQAKGDKGPEDWKPPLSSYYCTYSKMWIKVKSVYGLTVTSAEKSALSSMLATC |||||||
| SEQ_ID_NO_95  | QAFANDLTNPQLIAVTDNVNQSKGDKGPEDWKPPLTSYYCTYAKMWVRVKSVYSLTITSAEKSALTSMLDTC |||||||
| SEQ_ID_NO_98  | QAFANDLTNPQLLAVTDNVNQAKGDKGPEDWKPPLTSYYCTYCIYAAMWKIVKSVYSLTITSAEKSALTSMLGTC |||||||
| SEQ_ID_NO_113 | QSFANDLTNPQLIAVTDNVNQAKGDKGPEDWKPPLTSYYCTYAKMWVKVKSVYKLTITSAEKTALTSMLNTC |||||||
| SEQ_ID_NO_119 | QAFANDLTNPQLLAVTDNVNQAKGDKGPEDWKPPLTSYYCTYAKMWVKVKSVYALTITSAEKTALTSMLNTC |||||||
| SEQ_ID_NO_118 | QSFANDLTNPQLIAVTDNVNQAKMWVKVKSVYAKMWVKVKSVYALTITSAEKTALTSMLNTC |||||||

```
                  80        90        100       110       120       130       140
                  -         -         -         -         -         -         -
SEQ_ID_NO_134   ITG..TCNTREYVLKRDGANVQVGSDCYPTSGTWTSPYDGGKWTSPSDVDIDHMVPLKNAWVSGANKWTTAKR
SEQ_ID_NO_125   VSG..TCNTREYVLKRDGSNVVTNSACQATSGTWYSPYDGATWTAASDIDIDHMVPLKNAWISGANTWSSSKR
SEQ_ID_NO_128   VSG..TCNTREYVLKRDGVNVVTNSACAATSGTWYSPFDGATWTAASDVDIDHMVPLKNAWISGANNWTSTKR
SEQ_ID_NO_140   VEG..NCNAREFVLRRDGDGVSVGNDCYPTAGTWTCPYDGKRHSVPSDVSIDHMVPLHNAWMTGASEWTTAER
SEQ_ID_NO_155   IPGETACSAREYVLRRDGTGVETGSDCYPTSGTWSSPYDGGSWTAPSDVDIDHMVPLKNAWISGASEWTTAER
SEQ_ID_NO_152   VEG..SCDSREYVLKRDGQDVQADSSCKITSGTWVSPYDATTWTNSSKVDIDHLVPLKNAWISGASSWTKAQR
SEQ_ID_NO_137   IEG..TCNAREYVLKRDGQNVVVNSACTAQSGTWKSVYDGETTNSASDLDIDHMIPLKNAWISGAATWTTAQR
SEQ_ID_NO_143   ISG..NCNAREYVLRRDGTNVVVNTACVPQSGTWRSPYDGESTTNASDLDIDHMVPLKNAWISGAASWTTAKR
SEQ_ID_NO_149   ISG..NCNAREFVLERDGTNVVVHNACVAQSGTWRSPYDGETTGNASDLDIDHMVPLKNAWISGASSWSTTRR
SEQ_ID_NO_122   ISG..NCNAREYVLKRDGEGVQVNNACEAQSGSWISPYDNASFTNASSLDIDHMVPLKNAWISGASTWTTAQR
SEQ_ID_NO_131   IQG..TCNAREFVLKRDGTDVKTNNACVAESGNWVSPYDGVKFTAARDLDIDHMVPLKNAWISGASQWTTERR
SEQ_ID_NO_146   IEG..TCNAREFVLKRDGTDVQTNTACVAQSGNWVSPYDGVAFTAASDLDIDHMVPLKNAWISGASQWTTDKR
SEQ_ID_NO_158   IEG..TCNAREFVLKRDGTDVQTNTACVAESGNWVSPYDGVSFTAASDLDIDHMVPLKNAWISGASQWTTDKR
```

FIG. 3B

| | 150 | 160 | 170 | 180 | 190 | 200 | 210 |
|---|---|---|---|---|---|---|---|
| SEQ_ID_NO_134 | EQFANDVDRPQLWAVTDNVNSSKGDKSPDTWKPPLTSFYCTYASAYVAVKSYWGLTITSAEKSALSDMLGTC |
| SEQ_ID_NO_125 | SSFANDINSPQLWAVTDSVNQSKGDKSPDKWKPPLTTFYCTYAKSWITVKYNYNLTITSAEKSALQNMINTC |
| SEQ_ID_NO_128 | TQFANDINLPQLWAVTDDVNQAKGDKSPDKWKPPLTSFYCTYAKSWITVKYNYGLSITSAEKSALTSMINTC |
| SEQ_ID_NO_140 | EAFANDIDGPQLWAVTSTTNSQKGSDAPDEWQPPQTSIHCKYAAAWIQVKSTYDLTVSSAEQAALEEMLGRC |
| SEQ_ID_NO_155 | EAFANDIDGPQLWAVTDEVNQSKSDQSPDEWKPPLSSFYCTYACAWIQVKSTYSLSISSAEQAALEDMLGSC |
| SEQ_ID_NO_152 | QDFANDIKRPQLYAVSENANRSKGDRSPDGWKPPLKSFYCTYAKSWAVKSYYKLTITSAEKSALGDMLDTC |
| SEQ_ID_NO_137 | TSFANDISSPQLWAVTAGVNRSKSDRSPDTWVPPLASFHCTYGKAWVQVKSKWALSITSAEKSALTGLLNKC |
| SEQ_ID_NO_143 | QDFANDVSGPQLWAVTAGVNRSKGDKSPDSWVPPLASFHCTVARSWIQVKSSWALSVTSAEKAALTDLLSTC |
| SEQ_ID_NO_149 | QEFANDVSGPQLWAVTAGVNRSKGDRSPDSWVPPLASFHCTYAKSWVQVKSSWSLSVTSAEKAALSDLLGTC |
| SEQ_ID_NO_122 | EALANDVSRPQLWAVSASSNRSKGDRSPDQWKPPLTSFYCTYAKSWIDVKSYYKLTITSAEKTALSSMLDTC |
| SEQ_ID_NO_131 | KALANDITRPQLWAVSAHANRGKSDDSPDEWKPPLKTFWCTYAKSWVQVKSFYELTITDAEKGALAGMLDSC |
| SEQ_ID_NO_146 | KGLANDITRPQLWAVSAHANRAKGDSSPDEWKPPLKTFWCTVARSWVQVKSYYALTITDAEKGALSGMLDSC |
| SEQ_ID_NO_158 | KDLANDITRPQLWAVSAHANRSKGDSSPDEWKPPLQTFWCTVSKSWIQVKSHYSLTITDAEKGALSGMLDSC |

FIG. 3C

SEQUENCE LISTING

```
Sequence total quantity: 210
SEQ ID NO: 1              moltype = DNA  length = 633
FEATURE                   Location/Qualifiers
source                    1..633
                          mol_type = genomic DNA
                          organism = Bacillus sp.
SEQUENCE: 1
atgttgaaaa agtcgttgct gttctctttg tcgcttgttt tatcattgct tgtttttcag    60
tatgatttat tatccgcttc tgccttgcct ccagatttgc catccaaatc tactacccaa   120
gcacaactta attcgttaaa tgtgaaaaat gaagaatcca tgagtggcta tagtcgagaa   180
aaattccctc actggattag tcaaggggat ggttggtata caaggcaagt gatccttaag   240
cgtgatgccg acaattatag tggtaattgt ccagtgactt caggtaaatg gtatagctat   300
tatgatggca tcactttcaa tgacccctca caattagata ttgaccatgt cgttccactc   360
gcagaagcat ggcgttctgg ggcaagtagt tggtcaactg ctaaaagaga ggacttcgcc   420
aatgacctca atggaccaca actcatcgca gtatcagcca gctcaaatcg atccaaaggt   480
gaccaagatc catccacatg gcaaccacct cgtgcaggtg caaattgtgc ttatgctaaa   540
atgtggatca atacaaaata caattggggt ttgcatttgc agagttctga aaaaacagct   600
cttcaaggaa tgctcaatag ttgctcctat taa                                633

SEQ ID NO: 2              moltype = AA   length = 210
FEATURE                   Location/Qualifiers
```

```
source                   1..210
                         mol_type = protein
                         organism = Bacillus sp.
SEQUENCE: 2
MLKKSLLFSL SLVLSLLVFQ YDLLSASALP PDLPSKSTTQ AQLNSLNVKN EESMSGYSRE    60
KFPHWISQGD GCDTRQVILK RDADNYSGNC PVTSGKWYSY YDGITFNDPS QLDIDHVVPL   120
AEAWRSGASS WSTAKREDFA NDLNGPQLIA VSASSNRSKG DQDPSTWQPP RAGANCAYAK   180
MWINTKYNWG LHLQSSEKTA LQGMLNSCSY                                    210

SEQ ID NO: 3             moltype = DNA   length = 633
FEATURE                  Location/Qualifiers
source                   1..633
                         mol_type = genomic DNA
                         organism = Bacillus horikoshii
SEQUENCE: 3
atgcttaaaa aatccatgtt ggttgttttt gcatttatcc tgtcgttctc agccctgcag    60
cttgacccac aaaccgtctc tgcacttccc cctggcacac cgaccaagtc tgaagcgcaa   120
aaccaattga actccttgac cgtaaaaatcg gagggctcta tgaccgggta ctcgagggac   180
ttattcccac actggagcgg ccaaggcaat ggttgcgata cccgccaaat cgtcttgcaa   240
cgcgatgccg actattacac tggtacctgt cccactactt ccggaaaatg gtatagttat   300
tttgatggtg tcattgtgta ttctccgtct gagattgaca ttgatcacat tgttcctttg   360
gcagagcgtt ggcgttctgg tgccagtagc tggacaaacg aacagcgccg tgcgtttgct   420
aacgacctca acgcccaca gttgattgcc gtgacagcta gcgttaaccg ttccaaagga   480
gaccaagacc catccacatg gcagccacct cgtgccggcg ctcgctgtgc ctatgcaaaa   540
tggtggatca atacgaaaca ccgctggaac ctacaccttc agtcatctga gaaatcttct   600
ttgcaaacga tgcttaacgg ctgcgcttac taa                                633

SEQ ID NO: 4             moltype = AA   length = 210
FEATURE                  Location/Qualifiers
source                   1..210
                         mol_type = protein
                         organism = Bacillus horikoshii
SEQUENCE: 4
MLKKSMLVVF AFILSFSALQ LDPQTVSALP PGTPTKSEAQ NQLNSLTVKS EGSMTGYSRD    60
LFPHWSGQGN GCDTRQIVLQ RDADYYTGTC PTTSGKWYSY FDGVIVYSPS EIDIDHIVPL   120
AEAWRSGASS WTTEQRRAFA NDLNGPQLIA VTASVNRSKG DQDPSTWQPP RAGARCAYAK   180
WWINTKHRWN LHLQSSEKSS LQTMLNGCAY                                    210

SEQ ID NO: 5             moltype = DNA   length = 609
FEATURE                  Location/Qualifiers
source                   1..609
                         mol_type = genomic DNA
                         organism = Paenibacillus sp.
SEQUENCE: 5
ttgaaacgac ggcttattcc tttccttctt gtcctcgtcc tggttgcgac cgggtgcgca    60
ctggcgcaga agcccttgcc cgacgcgccg cggcagacgg agcacgacga ttacgactac   120
gagctgatct ttccaagcga cgactatccc gaaacgctgc tggggcgatc    180
gagcaagggt attccgacgt atgcacgatc gaccgcggcg gggcggaaga gaaccgcaag   240
caatcgctgg ccggaataga gacgcgctcg ggctacgacc gcgacgaatg gccgatggcg   300
atgtgcgagg aaggcggagc gggcgcaagc gtcgcctaca tcgatgccag cgacaaccgg   360
ggagccggca gctgggtcgg gcatcagctg tcggcctatg aagacggcac gaaaattttg   420
tttatcgtag agaaacccaa agttctgttt ccgaaccagc cggcaaccgc ggctccggcc   480
ggcaacaacg aggttcgcta tcccaattgc gccgccgtgc gcgaggcggg caaagcgcct   540
ctgcgcaagg gagatcccgg ctactccgct aaattggacc gggacggcga cggcgtcgct   600
tgcgaatag                                                          609

SEQ ID NO: 6             moltype = AA   length = 202
FEATURE                  Location/Qualifiers
source                   1..202
                         mol_type = protein
                         organism = Paenibacillus sp.
SEQUENCE: 6
MKRRLIPFLL VLVLVATGCA LAQKPLADAP RQTEHDDYDY ELIFPSDDYP ETALHILGAI    60
EQGYSDVCTI DRGGAEENRK QSLAGIETRS GYDRDEWPMA MCEEGGAGAS VAYIDASDNR   120
GAGSWVGHQL SAYEDGTKIL FIVEKPKVLF PNQPATAAPA GNNEVRYPNC AAVREAGKAP   180
LRKGDPGYSA KLDRDGDGVA CE                                            202

SEQ ID NO: 7             moltype = AA   length = 245
FEATURE                  Location/Qualifiers
source                   1..245
                         mol_type = protein
                         organism = Serratia marcescens
SEQUENCE: 7
DTLESIDNCA VGCPTGGSSN VSIVRHAYTL NNNSTTKFAN WVAYHITKDT PASGKTRNWK    60
TDPALNPADT LAPADYTGAN AALKVDRGHQ APLASLAGVS DWESLNYLSN ITPQKSDLNQ   120
GAWARLEDQE RKLIDRADIS SVYTVTGPLY ERDMGKLPGT QKAHTIPSAY WKVIFINNSP   180
AVNHYAAFLF DQNTPKGADF CQFRVTVDEI EKRTGLIIWA GLPDDVQASL KSKPGVLPEL   240
MGCKN                                                               245
```

```
SEQ ID NO: 8            moltype = AA  length = 182
FEATURE                 Location/Qualifiers
source                  1..182
                        mol_type = protein
                        organism = Bacillus sp.
SEQUENCE: 8
LPPDLPSKST TQAQLNSLNV KNEESMSGYS REKFPHWISQ GDGCDTRQVI LKRDADNYSG    60
NCPVTSGKWY SYYDGITFND PSQLDIDHVV PLAEAWRSGA SSWSTAKRED FANDLNGPQL   120
IAVSASSNRS KGDQDPSTWQ PPRAGANCAY AKMWINTKYN WGLHLQSSEK TALQGMLNSC   180
SY                                                                 182

SEQ ID NO: 9            moltype = AA  length = 182
FEATURE                 Location/Qualifiers
source                  1..182
                        mol_type = protein
                        organism = Bacillus horikoshii
SEQUENCE: 9
LPPGTPTKSE AQNQLNSLTV KSEGSMTGYS RDLFPHWSGQ GNGCDTRQIV LQRDADYYTG    60
TCPTTSGKWY SYFDGVIVYS PSEIDIDHIV PLAEAWRSGA SSWTTEQRRA FANDLNGPQL   120
IAVTASVNRS KGDQDPSTWQ PPRAGARCAY AKWWINTKHR WNLHLQSSEK SSLQTMLNGC   180
AY                                                                 182

SEQ ID NO: 10           moltype = AA  length = 180
FEATURE                 Location/Qualifiers
source                  1..180
                        mol_type = protein
                        organism = Paenibacillus sp.
SEQUENCE: 10
QKPLADAPRQ TEHDDYDYEL IFPSDDYPET ALHILGAIEQ GYSDVCTIDR GGAEENRKQS    60
LAGIETRSGY DRDEWPMAMC EEGGAGASVA YIDASDNRGA GSWVGHQLSA YEDGTKILFI   120
VEKPKVLFPN QPATAAPAGN NEVRYPNCAA VREAGKAPLR KGDPGYSAKL DRDGDGVACE   180

SEQ ID NO: 11           moltype = AA  length = 182
FEATURE                 Location/Qualifiers
source                  1..182
                        mol_type = protein
                        organism = Bacillus sp.
SEQUENCE: 11
LPPGTPSKSE AQSQLNALTV KPEDPMTGYS RDHFPHWISQ GNGCNTRQIV LQRDADYYSG    60
ACPVTTGKWY SYFDGVIVYS PSEIDIDHIV PLAEAWRSGA SSWTTEKRRS FANDLNGPQL   120
IAVTASVNRS KGDQDPSTWQ PPRAGARCAY AKWWINTKHR WGLHLQSSEK SSLQSMLNGC   180
AY                                                                 182

SEQ ID NO: 12           moltype = AA  length = 182
FEATURE                 Location/Qualifiers
source                  1..182
                        mol_type = protein
                        organism = Bacillus sp.
SEQUENCE: 12
LPPGTPSKSE AQSQLNALTV KPEDPMTGYS RDHFPHWISQ GNGCNTRQIV LQRDADYYSG    60
ACPVTTGKWY SYFDGVIVYS PSEIDIDHIV PLAEAWRSGA SSWTTEQRRS FANDLNGPQL   120
IAVTASVNRS KGDQDPSTWQ PPRAGARCAY AKWWINTKHR WGLHLQSSEK SSLQSMLNGC   180
AY                                                                 182

SEQ ID NO: 13           moltype = AA  length = 182
FEATURE                 Location/Qualifiers
source                  1..182
                        mol_type = protein
                        organism = Bacillus horikoshii
SEQUENCE: 13
LPPGTPSKSE AQSQLNSLTV KSEDPMTGYS RDHFPHWSGQ GNGCDTRQIV LQRDADYYSG    60
NCPVTSGKWY SYFDGVIVYS PSEIDIDHVV PLAEAWRSGA SSWTTEQRRS FANDLNGPQL   120
IAVTASVNRS KGDQDPSTWQ PPRAGARCAY AKWWINTKHR WNLHLQSSEK SALQTMLNGC   180
VY                                                                 182

SEQ ID NO: 14           moltype = AA  length = 182
FEATURE                 Location/Qualifiers
source                  1..182
                        mol_type = protein
                        organism = Bacillus horikoshii
SEQUENCE: 14
LPPGTPSKSE AQSQLNSLTV KTEDPMTGYS RDLFPHWSGQ GSGCDTRQIV LQRDADYFTG    60
TCPTTSGKWY SYFDGVIVYS PSEIDVDHIV PLAEAWRSGA SSWTTEQRRA FANDLTGPQL   120
IAVTASVNRS KGDQDPSTWQ PPRAGARCAY AKWWINTKHR WNLHLQSSEK SSLQTMLNGC   180
AY                                                                 182

SEQ ID NO: 15           moltype = AA  length = 182
FEATURE                 Location/Qualifiers
source                  1..182
```

```
                         mol_type = protein
                         organism = Bacillus sp.
SEQUENCE: 15
LPPGTPSKSE AQSQLNALTV KAEDPMTGYS RNLFPHWNSQ GNGCNTRQLV LQRDADYYSG    60
NCPVTSGRWY SYFDGVVVTS PSEIDIDHIV PLAEAWRSGA SSWTTEKRKE FANDLNGPQL   120
IAVTASVNRS KGDQDPSTWQ PPRAAARCGY AKWWINTKYR WDLSLQSSEK SSLQTMLNTC   180
SY                                                                 182

SEQ ID NO: 16            moltype = AA  length = 182
FEATURE                  Location/Qualifiers
source                   1..182
                         mol_type = protein
                         organism = Bacillus sp.
SEQUENCE: 16
LPPGTPSKSQ AQSQLNALTV KAEDPMTGYS RNLFPHWSSQ GNGCNTRQLV LQRDADYYSG    60
NCPVTSGRWY SYFDGVVVTS PSEIDIDHIV PLAEAWRSGA SSWTTEKRRE FANDLNGPQL   120
IAVTASVNRS KGDQDPSTWQ PPRVAARCGY AKWWINTKYR WDLSLQSSEK SSLQTMLNTC   180
SY                                                                 182

SEQ ID NO: 17            moltype = AA  length = 182
FEATURE                  Location/Qualifiers
source                   1..182
                         mol_type = protein
                         organism = Bacillus sp.
SEQUENCE: 17
LPPGTPSKSE AQSQLTSLTV KPEDPMTGYS RDHFPHWISQ GNGCNTRQIV LQRDADYYSG    60
NCPVTTGKWY SYFDGVIVYS PSEIDIDHIV PLAEAWRSGA SSWTAEQRRN FANDLNGPQL   120
IAVTASVNRS KGDQDPSTWQ PPRTGARCAY AKWWINTKYR WGLHLQSSEK SSLQSMLNGC   180
AY                                                                 182

SEQ ID NO: 18            moltype = AA  length = 185
FEATURE                  Location/Qualifiers
source                   1..185
                         mol_type = protein
                         organism = Bacillus sp.
SEQUENCE: 18
ASAFPPGTPS KSTAQSQLNS LPVKSEGSMN GYSRDKFPHW ISQGDGCDTR QLVLKRDGDY    60
YSGSCPVTSG KWYSYYDGIT VYSPSEIDID HIVPLAEAWR SGASGWTTEK RQSFANDLNG   120
PQLIAVTASV NRSKGDQDPS TWQPPRSGSH CAYAKMWVNT KYRWGLHLQS AEKSALQSML   180
NACSY                                                              185

SEQ ID NO: 19            moltype = AA  length = 185
FEATURE                  Location/Qualifiers
source                   1..185
                         mol_type = protein
                         organism = Bacillus horneckiae
SEQUENCE: 19
ASAFPPGTPS KSTAQSQLNS LTVKSEGSMT GYSRDKFPHW ISQGDGCDTR QLVLKRDGDY    60
YSGNCPVTSG KWYSYYDGIT VYSPSEIDID HIVPLAEAWR SGASGWTTEK RQSFANDLNG   120
PQLIAVTASV NRSKGDQDPS TWQPPRSGSH CAYAKMWVNT KYRWGLHVQS AEKSALQSML   180
NACSY                                                              185

SEQ ID NO: 20            moltype = AA  length = 182
FEATURE                  Location/Qualifiers
source                   1..182
                         mol_type = protein
                         organism = Bacillus sp.
SEQUENCE: 20
FPPEIPSKST AQSQLNSLTV KSEDAMTGYS RDKFPHWISQ GDGCDTRQMV LKRDADYYSG    60
SCPVTSGKWY SYYDGITVYS PSEIDIDHIV PLAEAWRSGA SSWTTEKRRN FANDLNGPQL   120
IAVTASVNRS KGDQDPSTWQ PPRSGARCAY AKMWVNTKYR WGLHLQSAEK SGLESMLNTC   180
SY                                                                 182

SEQ ID NO: 21            moltype = AA  length = 182
FEATURE                  Location/Qualifiers
source                   1..182
                         mol_type = protein
                         organism = Bacillus cibi
SEQUENCE: 21
TPPGTPSKSA AQSQLNALTV KTEGSMSGYS RDLFPHWISQ GSGCDTRQVV LKRDADSYSG    60
NCPVTSGSWY SYYDGVTFTN PSDLDIDHIV PLAEAWRSGA SSWTTSKRQD FANDLSGPQL   120
IAVSASTNRS KGDQDPSTWQ PPRSGAACGY SKWWISTKYK WGLSLQSSEK TALQGMLNSC   180
SY                                                                 182

SEQ ID NO: 22            moltype = AA  length = 182
FEATURE                  Location/Qualifiers
source                   1..182
                         mol_type = protein
                         organism = Bacillus sp.
```

```
SEQUENCE: 22
FPPGTPSKST AQSQLNSLTV KSEGSMTGYS RDKFPHWIGQ GSGCDTRQLV LQRDADYYSG    60
SCPVTSGKWY SYYDGVTFYD PSDLDIDHVV PLAEAWRSGA SSWSTQKRKD FANDLSGPQL   120
IAVSASSNRS KGDQDPSTWQ PTRSGAACGY SKWWISTKHK WGLSLQSSEK NALQGMLNSC   180
VY                                                                 182

SEQ ID NO: 23          moltype = AA  length = 182
FEATURE                Location/Qualifiers
source                 1..182
                       mol_type = protein
                       organism = Bacillus idriensis
SEQUENCE: 23
LPPGTPSKST AQSQLNALTV QTEGSMTGYS RDKFPHWISQ GNGCDTRQVV LQRDADYYSG    60
TCPVTSGKWY SYYDGVTLYN PSDLDIDHVV ALAEAWRSGA SSWTTDKRED FANDLSGTQL   120
IAVSASTNRS KGDQDPSTWQ PPRSGAACGY AKWWISTKYK WNLNLQSSEK TALQSMLNSC   180
SY                                                                 182

SEQ ID NO: 24          moltype = AA  length = 27
FEATURE                Location/Qualifiers
source                 1..27
                       mol_type = protein
                       organism = Bacillus clausii
SEQUENCE: 24
MKKPLGKIVA STALLISVAF SSSIASA                                       27

SEQ ID NO: 25          moltype = DNA  length = 1633
FEATURE                Location/Qualifiers
sig_peptide            501..584
mat_peptide            585..1130
source                 1..1633
                       mol_type = genomic DNA
                       organism = Bacillus sp.
CDS                    501..1130
SEQUENCE: 25
agaaaatggg gtttgttcaa acgggagccc actcttttta tatgggagat gaagaacaaa    60
ttgacattat catgaccaag acactgtaat tacaggacg gttctttcc ttcttatcta    120
agaagccaaa gaaccgtccc tttacgtcgg aaatctatta gttgcctata gcttttgcct   180
tttaagttt ccattatcat ttgtatagat atctctcctc ataaggcctc cgttcccttta   240
ctagccattt aatcatagtc cccattactt tttgctctcc tagtggttca aaggatgcgg   300
gaggtccgtt ctattttttc atttttacaa aaacttaact tgagtagctt cttaaatgta   360
ctatcattc aagtagatac atattcatt tgcttccccg cagagaactt ctttgccgtg    420
ccgttttgac ttcgaaacta ttaaaatctt attttacatg agattttgat ataaaaaatt   480
aaatagtagg aggcatctct atgtttaaaa aatcattgtc gattgttttt gcatttctcc   540
tttcgttttc tgtttttcat tttgaccctg aaacggtctc ggcacttcct ccgggaacac   600
cgtccaagtc cgaagcccaa tcacaattga acgctctgac tgtgaaacct gaagaccca    660
tgaccggcta ctcgcgggat catttcccgc actggatcag ccaaggaaac ggctgcaaca   720
cccgccagat tgtacttcaa cgggacgccg actactacag cggggcctgc ccgtcacta    780
ccggaaagtg gtacagttac tttgatggc tcattgtgta ctcgccatca gaaattgata   840
ttgatcacat tgttcctttg gccgaagcct ggcgttccgg tgccagcagc tggaccacag   900
aaaagcgccg cagtttcgca aatgacctca acggcccaca gctgattgca gtgacagcaa   960
gcgttaatcg ctccaaaggg gaccaggatc cttccacatg cagccgccg cgtgccggtg   1020
cacgctgcgc ttatgcaaag tggtggatta acacgaagca ccgctgggga ctgcaccttc   1080
agtcatcgga aaaatcgtct ctgcaaagca tgctgaacgg ctgcgcttac taagataaaa  1140
aggagtcatt cttatggaaa agaaatcatc tgtttccaaaa gcaacccatg gagtcatgac   1200
agcggagtt ggtgtcatca gcggagagct cgaactgccg accacctgcg aggaagatgg   1260
tgtcctctcg ctagctatca cctatgtcgg tgccgaggaa tggtacaccc tccccgtga   1320
ggactaccgc ctgcacgatc cgcgtgacca cgaggttgtt caccgcatgc ttgttaaggt   1380
gttagaacgg aattgaggag agtgggtcag agggacatgt tccttgaccc gctctcatta   1440
aattaccaag ttttattaaa ccaccacaca ataaggaata tactcgttat ccccaagct   1500
atagttccca ctaaccacca aataataaat gaaagtgtac tttcatggcg ttccacttt   1560
cttttcataa atgtgagaac aacaaatccg attaagaaaa aaacaactgt aaaccagagt  1620
aatacatcca ctt                                                    1633

SEQ ID NO: 26          moltype = AA  length = 210
FEATURE                Location/Qualifiers
source                 1..210
                       mol_type = protein
                       organism = Bacillus sp.
SEQUENCE: 26
MFKKSLSIVF AFLLSFSVFH FDPETVSALP PGTPSKSEAQ SQLNALTVKP EDPMTGYSRD    60
HPPHWISQGN GCNTRQIVLQ RDADYYSGAC PVTTGKWYSY FDGVIVYSPS EIDIDHIVPL   120
AEAWRSGASS WTTEKRRSFA NDLNGPQLIA VTASVNRSKG DQDPSTWQPP RAGARCAYAK   180
WWINTKHRWG LHLQSSEKSS LQSMLNGCAY                                    210

SEQ ID NO: 27          moltype = DNA  length = 1633
FEATURE                Location/Qualifiers
sig_peptide            501..584
mat_peptide            585..1130
source                 1..1633
```

```
                            mol_type  = genomic DNA
                            organism  = Bacillus sp.
CDS                         501..1130
SEQUENCE: 27
agaaaatggg gtttgttcaa acgggagctc actctttta tatgggagat gaagaacaaa    60
ttgacattat catgaccaag acactgtaat tacagggacg gttctttcc ttcttatcta   120
agaagccaaa gaaccgtccc tttacgtcgg aaatctatta gttgcctata gcttttgcct   180
tttaagtttt ccattatcat ttgtatagat atctctcctc ataaggcctc cgttcctta    240
ctagccattt aatcatagtc cccattactt tttgctctcc tagtggttca aaggatgcgg   300
gaggtccgtt ctatttttc atttttacaa aaacttaact tgagtagctt cttaaatgta    360
ctatcatttc aagtagatac atatttcatt tgcttccccg cagagaactt ctttgccgtg   420
ccgtttgac ttcgaaacta ttaaaatctt attttacatg agattttgat ataaaaaatt    480
aaatagtagg aggcatctct atgtttaaaa aatcattgtc gattgttttt gcatttctcc   540
tttcgtttc tgttttcat tttgaccctg aaacggtctc ggcacttcct ccgggaacac     600
cgtccaagtc cgaagcccaa tcacaattga acgctctgac tgtgaaacct gaagacccca   660
tgaccggcta ctcgcgggat catttcccgc actggatcag ccaaggaaac ggctgcaaca   720
cccgccagat tgtacttcaa cgggacgccg actactacag cggggcctgc cccgtcacta   780
ccggaaagtg gtacagttac tttgatggcg tcattgtgta ctcgccatcc gaaattgata   840
ttgatcacat tgttccttg gccgaagctt ggcgttccgg tgccagcagc tggaccaccg    900
aacagcgccg cagtttcgca aatgacctca acgggccaca gctgattgca gtgacagcaa   960
gcgttaatcg ctccaaaggg gaccaggatc cttccacatg gcagcccct cgtgccggtg   1020
cacgttgcgc ttatgcaaag tggtggatta acacgaagca ccgtcgggga ttaaccttc   1080
agtcatcgga aaaatcgtct ctgcaaagca tgctgaacgg ctgcgcttac taagataaga   1140
aggagtcatt cttatggaaa agaaatcatc tgttttcaaa gcaacccatg gagtcatgac   1200
agcggaggtt ggtgtcatca gcggagagct cgaactgcgc accacctgcg aggaagatgg   1260
tgtcctcttt ctagctatca cctatgtcgg tgccgaggaa tggtacaccc tcccggtga   1320
ggactaccgc ctgcacgatc cgcgtgacca cgaggttgtt caccgcatgc ttgttaaggt   1380
gttagaacgg aattgaggag aatgggtcag agggacatgt tccttgaccc gctctcatta   1440
aattaccaag ttttattaaa ccaccacaca ataaggaata tactcgttat cccccaagct   1500
atagttccca ctaaccacca aataataaat gaaagggtgc tttcatggtg ttcccctttt   1560
ctttcataa gtgtgagaac aacaaagccg attaagaaaa aaacaactgt aaaccagagt   1620
aatacatcca ctt                                                     1633

SEQ ID NO: 28            moltype = AA  length = 210
FEATURE                  Location/Qualifiers
source                   1..210
                         mol_type = protein
                         organism = Bacillus sp.
SEQUENCE: 28
MPKKSLSIVF AFLLSFSVFH FDPETVSALP PGTPSKSEAQ SQLNALTVKP EDPMTGYSRD    60
HFPHWISQGN GCNTRQIVLQ RDADYYSGAC PVTTGKWYSY FDGVIVYSPS EIDIDHIVPL   120
AEAWRSGASS WTTEQRRSFA NDLNGPQLIA VTASVNRSKG DQDPSTWQPP RAGARCAYAK   180
WWINTKHRWG LHLQSSEKSS LQSMLNGCAY                                    210

SEQ ID NO: 29            moltype = DNA   length = 1633
FEATURE                  Location/Qualifiers
sig_peptide              501..584
mat_peptide              585..1130
source                   1..1633
                         mol_type = genomic DNA
                         organism = Bacillus horikoshii
CDS                      501..1130
SEQUENCE: 29
gttaaggaga aattctcatg actcggaaag tgctgaagcc acatgtatcc atcatccacg    60
atgcatacac ttttttcttc atagtgcact gttaatggat ccgtcacttt atgaatgttg   120
agtaaggtaa tatgccctt gaaacccttg gtatccatat atttctgagt gtactgccgt    180
tttaatatcc gtttccattc tgagcggtct ccgtatcttc tttttaacat ggcatcccc    240
ctcttcgata cagacttatt gtactacttt tcagacaaat gatgggtata tcactccttt   300
cttcattcaa aggtagtagg agcactgtac cctttcttaa tatttacaat attttaactt   360
gttaaaaaat tttatgtac tattatttca agtagataca tagctcatat cctgtcctca    420
attgaagcgt gattaagtta ttaaaatctc atccatcaat gagattttga tataaaaatt   480
gtatactagg aggcatacct atgctgaaga aacccctgtt attggtgttt gcatttatcc    540
tgtcgttttc aacactacag cttgaccctc aaacggtctc ggcactcccc cctggaacac    600
cgtccaagtc agaagcacaa tctcaattga actcgttgac tgtgaaatcc gaagacccca   660
tgaccggtta ctcccgggac catttccac attggagcgg ccaagggaat ggctgtgaca    720
cccgccaaat tgtcctgcaa cgcgatgccg actattacag cggcaactgt cccgtcactt    780
ctggaaaatg gtatagttat ttcgatggtg tcatagtgta ttctccgtct gaaattgata   840
ttgatcacgt tgttccttta gccgaggctt ggcgttccgg tgccagcagc tggacgaccg   900
aacagcgtcg tagttttgcc aacgatctca acgggccag actgattgca gtaacagcaa    960
gcgtcaatcg atccaaaggt gaccaggacc cgtcgacatg gcaaccacca cgtgccggca   1020
ctcgttgtgc atatgcaaaa tggtggatca atacgaaca ccgttggaac ttacaccttc   1080
agtcatctga gaatctgct tgcaaacga tgcttaacgg ctgcgtttac taattatttt   1140
atgtgacatg actgcaagta ttgctgcttg cagtcatgct atctaagaga ggagtcttat   1200
ctatgaaaa gctttcatct acttttactg catctcacga agttatgaca gccgaggttg   1260
gagtcatcag cggagaacta gaactacgca ccacctgcga tgaagaaggc gtgctctcgc   1320
ttgccatcac ctatgtcggt gcagaagagt ggtacaccct gcctgagaa gactaccgcc   1380
tgcatgattc gcgggatcat gaggtcgtgc accgtatgct tgtgaagtg ttggagcggg    1440
gttgaggagg taccgtgacc cacctcaaaa agttgcatta aaccaccaaa caacaaggaa   1500
aatggtcact atcccccaaa ctgtagtacc tacaataaac catacgcctg attgtgtagc   1560
```

```
                                              ttctttctta ctctgtaggt tcctcttcag aaaggaaagc accacaaagc caattacgaa   1620
gaaagcaatg gta                                                                                                   1633

SEQ ID NO: 30            moltype = AA  length = 210
FEATURE                  Location/Qualifiers
source                   1..210
                         mol_type = protein
                         organism = Bacillus horikoshii
SEQUENCE: 30
MLKKPLLLVF AFILSFSTLQ LDPQTVSALP PGTPSKSEAQ SQLNSLTVKS EDPMTGYSRD   60
HFPHWSGQGN GCDTRQIVLQ RDADYYSGNC PVTSGKWYSY FDGVIVYSPS EIDIDHVVPL   120
AEAWRSGASS WTTEQRRSFA NDLNGPQLIA VTASVNRSKG DQDPSTWQPP RAGARCAYAK   180
WWINTKHRWN LHLQSSEKSA LQTMLNGCVY                                    210

SEQ ID NO: 31            moltype = DNA  length = 1633
FEATURE                  Location/Qualifiers
sig_peptide              501..584
mat_peptide              585..1130
source                   1..1633
                         mol_type = genomic DNA
                         organism = Bacillus horikoshii
CDS                      501..1130
SEQUENCE: 31
ctccactgtc atcacctaaa ttcttattaa aattcctaag tgtgattttg ccatccccat   60
caacggaaag tcactgttct tcgtgggttg tagggacagg catggcgacg ccaatgacca   120
tttattaggt aaatttagtt tctctcactt acaatatatg gattgtcgtc aatttcaact   180
gatttattga atactttag tggttaagcg tatacttcgt gccatttatt gagtaattgg    240
aagtgtttat tgaataatta agggcttggg tagcgcaccc cgctaaacac tgggtcaacg   300
gacctgtccc ctcgactctt ccccgccctc tctggtccat caggcgcagg aggaccgtac   360
cttttcttaa catttacaat atttaacttt attaaagcac tttatgtat tatattttca    420
agtagataca tagtcgacta ttaaaatctc gtccttccac gaggttttga tataaaaatt   480
ttatagtagg aggcatttct atgctgaaaa agtccatgtt ggtgttttt gcattcatcc    540
tgtcgttctc tgcaattcaa cttgatccac aaaccgtctc ggcacttccc cctggaacac   600
cgtccaagtc agaagctcaa tctcaattga actcgttgac tgtaaaaaca gaagacccca   660
tgaccggta ttcgcgggat ttattcccac attggagcgg ccagggcagt ggctgtgata    720
ctcgccaaat cgtccttcaa cgcgatgcag actatttcac tggcacctgt cccacaacgt   780
ctggaaaatg gtatagttac ttcgatggcg tcattgtcta ttctccgtct gaaattgatg   840
ttgatcacat cgttccattg gctgaagctt ggcgttctgg tgccagcagc tggacaactg   900
aacagcgacg tgcttttgcc aacgacctca caggtccgca actgatcgca gtaacagcaa   960
gcgtcaaccg ttccaaaggg gaccaagatc cgtctacttg caaccacct cgtgccggtg    1020
ctcgctgtgc ctatgcaaaa tggtggatta acacaaaaca ccgttggaac ttacaccttc   1080
agtcatctga gaaatcttct ttacaaacga tgcttaacgg ctgcgcttac taaattagag   1140
attgcgtctg caggcggagt tgaatatgtt tgcagacgcg ttatagatta attgaaacgg   1200
aaggagtttt tacatatgga aaagaaatca tctattttta cagcatcaca cggcgtcatg   1260
acagccgagg ttggtgtcat cagtggcgag ctcgaactgc aaaccacctg tgatgaggac   1320
ggttccctcg cgctcgccat cacctacgtc ggtgctgcag aatggtacac cttgcctggt   1380
gaagactatc gcctgcatga tttacgtgat catgaggtaa ttcaccgcat gcttgttaag   1440
gtgttggagc ggaaatgatg gggtgggtcg tgggggacag gcaccgcgac ccgcttttca   1500
cacacattaa ttctctagct caatatattc cctcaaaagc ttccattggt ttgcttcaag   1560
tctccagata aacatacact gtgcagtaaa aggtttccct ccaataacgt ttgtttccct   1620
acccattaca act                                                     1633

SEQ ID NO: 32            moltype = AA  length = 210
FEATURE                  Location/Qualifiers
source                   1..210
                         mol_type = protein
                         organism = Bacillus horikoshii
SEQUENCE: 32
MLKKSMLVVF AFILSFSAIQ LDPQTVSALP PGTPSKSEAQ SQLNSLTVKT EDPMTGYSRD   60
LFPHWSGQGS GCDTRQIVLQ RDADYFTGTC PTTSGKWYSY FDGVIVYSPS EIDVDHIVPL   120
AEAWRSGASS WTTEQRRAFA NDLTGPQLIA VTASVNRSKG DQDPSTWQPP RAGARCAYAK   180
WWINTKHRWN LHLQSSEKSS LQTMLNGCAY                                    210

SEQ ID NO: 33            moltype = DNA  length = 1633
FEATURE                  Location/Qualifiers
sig_peptide              501..584
mat_peptide              585..1130
source                   1..1633
                         mol_type = genomic DNA
                         organism = Bacillus sp.
CDS                      501..1130
SEQUENCE: 33
gagagttagt ggtgacgcac ctgttattta cacggttcaa tcaggagaca cactttgggc   60
gattgctcag cgttataata cgacagttgc agatgttcgc caagtcaaatg ggcttactag   120
tgatgttatt caaccaggac aaagactaag agtaaggtaa caaaaaccct cacttcggtg   180
ggggccatt taagttttat tttgctcatt catgcccctt aaaaacagaa ccagttaata   240
ccgtttaaaa ccaaaataga agaagttagt ctacatactt atacttattt caagaactgt   300
aacctcgaat aaattatgta tatgtgaatc tattattggg gttgattaaa ttaaagtatt   360
ttatttgtaa acgtgacttt ctattaaaaa acctttacaa atatttacaa actattaact   420
```

```
tgtggcaatt ctcacccctg tactatcatt attaatagag tttatcaaca ttttaaaagt    480
acatataggg aggtaattct atgttaagaa aatccttgat ctttatttt acgttgctta    540
tattgtttac cgcattacaa tttgacatcc aaccagcatc agcattacca cctggaacac   600
cgtccaagtc agaggcacaa tcccagttaa acgctttgac cgtgaaggcc gaagatccaa   660
tgactggtta ctcgcgcaat ttatttccac actggaacag ccagggcaat gggtgtaaca   720
cccgacagtt ggtgctccag cgtgacgctg actactacag tggaaactgt cctgtaactt   780
ccggcagatg gtacagctac ttcgacggcg tcgtagtaac ctcaccgtcc gaaatcgaca   840
ttgatcacat tgtacccttta gctgaagcgt ggcgttctgg agctagtagc tggacgacgg   900
aaaagcgtaa ggaattcgct aatgatctca acggtccgca gctgatcgca gttactgcga   960
gtgtcaaccg ctctaaaggt gatcaagatc cttcaacatg gcagccacct cgtgcagccg  1020
cacgttgcgg atacgctaag tggtggatta acactaagta ccgctgggat ttaagcttgc  1080
agtcttctga gaagtcttca ctgcaaacta tgcttaacac ttgctcatac taagtttaat  1140
agtgtaccct acaaaggctg taaattattt ggaagtcttg cgactaatt cttcaatctc  1200
agaaaggagt cacttatatg gataagaagt cgaccatttt taccgcaacc cacggtgtaa  1260
tgaccaagga ggttggcgtc attagcgggg aacttgaact gcttactacc tgtgatgaca  1320
acggagttct cacactcgcc attacttatg taggagctat ggattggtac acgctgcctg  1380
gtgaagacta ccgcctaaat gacctaaggg atcacgaggt cgtccaccgc atgctcgcca  1440
ctgttcttga gcgcccttga taccatatca aggggctt ttaagaat gtaaaaggc  1500
aatacagtta tgtgattttt aacctaaaac aagcatagac ccgttcttta ttttttgaa  1560
agtctagaag atatttaaaa acgttagaat ttgaattaat ttaatgtcac tcatttaata  1620
agtttaaaag aaa                                                     1633

SEQ ID NO: 34          moltype = AA   length = 210
FEATURE                Location/Qualifiers
source                 1..210
                       mol_type = protein
                       organism = Bacillus sp.
SEQUENCE: 34
MLRKSLIFIF TLLILFTALQ FDIQPASALP PGTPSKSEAQ SQLNALTVKA EDPMTGYSRN    60
LFPHWNSQGN GCNTRQLVLQ RDADYYSGNC PVTSGRWYSY FDGVVVTSPS EIDIDHIVPL   120
AEAWRSGASS WTTEKRKEFA NDLNGPQLIA VTASVNRSKG DQDPSTWQPP RAAARCGYAK   180
WWINTKYRWD LSLQSSEKSS LQTMLNTCSY                                    210

SEQ ID NO: 35          moltype = DNA   length = 1633
FEATURE                Location/Qualifiers
sig_peptide            501..584
mat_peptide            585..1130
source                 1..1633
                       mol_type = genomic DNA
                       organism = Bacillus sp.
CDS                    501..1130
SEQUENCE: 35
accgtcataa atacgataat ccataaagta atcgaggtat atatcaggat aagaccagtc    60
taaatccgtt agtagccaat tatattcttt ttcaagacca ttaaaggaat tcaaaatttc   120
ttttaactct aaaaagtcct ctaaaataga attcatcttg cacctcaatt tatatttccc   180
tttaatctac aactaatgat accaaagaat agtaaataaa tccctttat attcaataac   240
taacaaaaag agccctcact cttgtgggag cttttaaagg tccttatttt gctaataaaa   300
ttcaactaac ttcaaagcat tatctagagt aatcctactg atctcaaatc cccccttctt   360
caaccacttc aaactaactt ttttaataaa acatttacaa atatttacaa actattaact   420
tgtgaaaaaa ttcaccactg tactatcatt gttaatagag tttatcaaca ttttaaaagt   480
acatataggg aggtaattct atgttaagaa aatccttgat ctttatttt acgttgctta   540
tattgtttac cgcattacaa tttgacatcc aaccagcatc agcattacca cctggaacac   600
cgtccaagtc acaggcacaa tcccagttaa acgctttgac cgtgaaggcc gaagatccaa   660
tgactggtta ctcgcgcaac ttgtttccac actggagtag tcagggcaat gggtgtaaca   720
cccgacagtt ggtgctccag cgtgacgctg actactacag tggaaactgt cctgtaactt   780
ccggcagatg gtacagctac ttcgacggcg tcgtagtaac ctctccatcc gaaatcgaca   840
ttgatcacat tgtacccttta gctgaagcat ggcgttccgg agctagcagc tggacgacgg   900
aaaagcgtag agaattcgct aatgatctca acggtccgca gctgatcgct gtaactgcga   960
gtgtcaaccg ctctaaaggt gatcaagatc cttcgacatg gcagccacct cgtagccga  1020
cacgttgcgg atacgctaaa tggtggatta acacaaagta ccgctgggac ctaagcttgc  1080
agtcttctga gaagtcatca ctgcaaacca tgctcaacac ttgctcatac taagtttaat  1140
agtgtaacct actaaggctg tcaattatat ggcagtcttg cgactaatt cttcaatctc  1200
agaaaggagt cactcgtatg gataagaagt ccaccatttt taccgcaacc cacggtgtaa  1260
tgaccaagga ggttggcgtc attagcgggg aacttgaact gctcactacc tgtgatgaca  1320
acggagtact cacactcgcc attacgtatg taggagctat ggattggtac acactgcctg  1380
gtgaaggcta ccgcctgaat gatcgacgcg atcacgaagt cgtccaccgc atgctcgcca  1440
ctgtacttga gcgcccttga taccatatca aggggcttt ttaagaat gtaaaaggc  1500
aataaggtta tgtgattttt aaactaaaac aagcatagcc ccgttcttta ttttttga   1560
aagtctagaa gatatttaaa aacgttataa attaaattaa ttcaatgtca ctcatttaat  1620
aagtttaaaa gaa                                                     1633

SEQ ID NO: 36          moltype = AA   length = 210
FEATURE                Location/Qualifiers
source                 1..210
                       mol_type = protein
                       organism = Bacillus sp.
SEQUENCE: 36
MLRKSLIFIF TLLILFTALQ FDIQPASALP PGTPSKSQAQ SQLNALTVKA EDPMTGYSRN    60
LFPHWSSQGN GCNTRQLVLQ RDADYYSGNC PVTSGRWYSY FDGVVVTSPS EIDIDHIVPL   120
```

```
AEAWRSGASS WTTEKRREFA NDLNGPQLIA VTASVNRSKG DQDPSTWQPP RVAARCGYAK   180
WWINTKYRWD LSLQSSEKSS LQTMLNTCSY                                   210

SEQ ID NO: 37           moltype = DNA  length = 1633
FEATURE                 Location/Qualifiers
sig_peptide             501..584
mat_peptide             585..1130
source                  1..1633
                        mol_type = genomic DNA
                        organism = Bacillus sp.
CDS                     501..1130
SEQUENCE: 37
cgtcgtttcc cattcccgtt gaattttttct ttcaagtaaa tgaccttcaa tttcagctat    60
gaaactctca acataagcaa gacgctcttc ttcaatctcc atcatttgtc tattctccac   120
aaatgcaaaa cggtcagaat gttttgctag gaaatctatt agttgcttat agcttttgcc   180
tttttatgttt tccgttatca tttgcataga gatctctcct aataaggcct tagttccttt   240
actagccatt taatcatagt tttctttact ttatgctccc ctagtggttc aaaggatgca   300
ggaggtccgt tctgtttttt cattttttaca aaaacttaac ttgagtagca acttaaatgt   360
actattattt caagtagata catagttcat ttatttcccc gacgagaacc ttcttgccat   420
gccgttttga ctttgaaact attaaaatct cattcatcat gagatttttga tataaaaaat   480
ttatagtagg aggcacctct atgctgcaga aatcattgtc ggttgttttt gcatttgtcc   540
tgtcgttctc tgtttttcat tttgacccac aaacggttct ggcacttccc ccgggaacac   600
cgtccaagtc cgaagcccaa tcccaattga cctctctgac tgtgaaacct gaagatccca   660
tgaccggcta ctcacgggac catttcccac actggattag ccaaggaaac ggctgcaaca   720
cccgccagat tgtacttcaa cgggacgctg actactacag cgggaactgc cccgtcacta   780
ccggaaagtg gtacagttac tttgatggcg tcattgtata ctcgccatcc gaaattgata   840
ttgatcacat tgttcctttg gccgaagctt ggcgttccgg tgccagcagc tggaccgcca   900
aacagcgtcg caattttgcc aatgatctca acggcccaca gctgattgcc gtgacagcaa   960
gcgtcaatcg ttccaaagga gaccaagatc cttccacatg gcaacctccg cgtaccggtg  1020
cacgctgcgc ttatgcaaag tggtggatta acacgaagta ccgctgggga ttacatcttc  1080
agtcatcgga aaaatcctct ttgcaaagta tgcttaacgg ctgcgcttac taaattcgta  1140
tatgcgtctg caagcacagt actagtacct gtacttaag atgcattatt tatctacaga   1200
aaggagtcat tcgtatggaa aagaaatcat ctgttttcac tgcaacccat ggagtcatga  1260
cagccgaggt tggtgtcatc agcggagagc tcgaactgcg caccacctgc gatgaagatg  1320
gtattctctc gctagctatc acctatgtcg gggccgaaga gtggtacacc ctccctggcg  1380
aagactaccg cctgcacgat tcgcgtgacc acgaggttgt ccaccgcatg cttgttaagg  1440
tgttagaacg aaattgaggg gagtgggtca gagggacagg ttcctcgacc cactctcttt  1500
ttcaatctcc taattttgca gcatagtcaa ttaagaatga aggacgata agtggcaaga   1560
tagagccaat tccaatataa agaatggaga atattattcc aaatatagtt gttcttacta   1620
ctcctgttgt gaa                                                      1633

SEQ ID NO: 38           moltype = AA  length = 210
FEATURE                 Location/Qualifiers
source                  1..210
                        mol_type = protein
                        organism = Bacillus sp.
SEQUENCE: 38
MLQKSLSVVF AFVLSFSVFH FDPQTVSALP PGTPSKSEAQ SQLTSLTVKP EDPMTGYSRD    60
HFPHWISQGN GCNTRQIVLQ RDADYYSGNC PVTTGKWYSY FDGVIVYSPS EIDIDHIVPL   120
AEAWRSGASS WTAEQRRNFA NDLNGPQLIA VTASVNRSKG DQDPSTWQPP RTGARCAYAK   180
WWINTKYRWG LHLQSSEKSS LQSMLNGCAY                                   210

SEQ ID NO: 39           moltype = DNA  length = 1633
FEATURE                 Location/Qualifiers
sig_peptide             501..581
mat_peptide             582..1130
source                  1..1633
                        mol_type = genomic DNA
                        organism = Bacillus sp.
CDS                     501..1130
SEQUENCE: 39
aaggtatgta gtttattaat ttatctatct atgtttgaa aaatagggtg cttaaataaa     60
ggggttagta taacaaaaaa cacagttgat ataactaaac attttctgga atgggtatat   120
acggtgcctt aatgataagc ccattattca ttaacacttc tttaacttgt tctatcaaat   180
ctaagttggc atctatacaa tatctaaaga attcttttac atttgtccta tttacaagaa   240
ttatagctac aaaatagact gattatttac aaattttttaa ctttaaagaa ataatctgt   300
gtaatattat tgcaagtaga agcatttttca atcacagata cctagtttat gttacttttac   360
gcaatagaca ttaaaaataa tgaaagctga tgcgctccat ttcgctttaa ttgcaatcat   420
tttcttacta ttaacatcta tcacaagaaa atgaacatag atgttagtat ataaaaccat   480
tacgtatagg aggaatttga atgctgaaaa aatcggtgtg gtttgttttt tcgttggttt   540
tgacgtttgc tgttttttcta tatgacatac cggcggcagc ggcatttccg cccggtacac   600
cgtccaagtc caccgcccaa tcacagttaa actcgctgac cgttaaatcc gaaggttcta   660
tgaccggcta ctcgcgagac aagttccac attggatcag ccaaggtgat ggctgtgata   720
ctcgccagct ggtgcttaag cgtgatggcg actactacag tgggaactgc cctgtcacgt   780
cgggtaagtg gtacagctac tacgacggca tcgccgtgta ctcaccgtct gaaatcgaca   840
tcgatcacat cgtcccgtta gcagaagcat ggcgttctgg cgctagcggc tggactacgg   900
aaaagcgcca gaatttcgca aacgacctca acggcccaca gctaatcgcg gtaaccgcta   960
gtgtaaatcg atccaaggga gatcaggatc cgtcgacgtg gcagccaccg cgttctggtt  1020
cacactgcgc gtacgcaaag atgtgggtca acaccaagta tcgctggggc ctgcacttgc  1080
```

```
agtcggcgga aaagtccgcg ctgcagagca tgctcaatgc ctgctcctac tagtctgtta  1140
ttctttgcag agaaaccatt ctgcccagaa aggagtcta ctcgtatgga aaagaagtcg    1200
tcaatcttca ccgcaacaca cggtgtaatg acagcggagg tcggcgtaat cagtggggag   1260
ctcgaacttc acagcacctg tgatgacgac ggcaccctca cactagccat cacctatgtc   1320
ggcgccgagg aatggtacac gttgccaggg ggtgattacc tcctgcacga cttgcgtgac   1380
cacgaagtcg tccaccgcct gctcaccgcc gtacttgagc gctcatgagt tggaatgctc   1440
tatcaaaggg tgctttcgtt taattatgca taagatcagc tgcctagtaa ggcagcgatt   1500
tttttataat taaagccgta tagctgaaga agagtttagt ttagtaagaa cacccaattt   1560
ttaaaatgta tagaaaatga tgagataaca tttaatttca tgacttatca actaactttt   1620
aaaataggta att                                                      1633

SEQ ID NO: 40          moltype = AA  length = 210
FEATURE                Location/Qualifiers
source                 1..210
                       mol_type = protein
                       organism = Bacillus sp.
SEQUENCE: 40
MLKKSVWFVF SLVLTFAVFL YDIPAAAAFP PGTPSKSTAQ SQLNSLTVKS EGSMTGYSRD    60
KPPHWISQGD GCDTRQLVLK RDGDYYSGNC PVTSGKWYSY YDGIAVYSPS EIDIDHIVPL   120
AEAWRSGASG WTTEKRQNFA NDLNGPQLIA VTASVNRSKG DQDPSTWQPP RSGSHCAYAK   180
MWVNTKYRWG LHLQSAEKSA LQSMLNACSY                                    210

SEQ ID NO: 41          moltype = DNA  length = 1633
FEATURE                Location/Qualifiers
sig_peptide            501..575
mat_peptide            576..1130
source                 1..1633
                       mol_type = genomic DNA
                       organism = Bacillus horneckiae
CDS                    501..1130
SEQUENCE: 41
actttggtaa atccattaat cagtgcctta cttgttgcct gcgtttccat aatattaaag    60
agctgggcaa tttctaatgc gcgcaatagc cgtacatgtc caaagaatcc gtttgaaaaa   120
tcttgatgaa cgaacgaaac attttctgga attggtatat acggtgcctt aatgatatgc   180
ccattattca ttaacacttc tttaacttgt tctatcaaat ttaagttggc atctatacaa   240
tatctaaaga attcttttac gtctgtccta tttacaagaa ttatagctat aaaaaagact   300
gattatttac aaatttttaa ctttaaagaa aaaaatctgt gtaatattat tgcaagtaga   360
agcattttca atcagacatt aaaaaatg cgcgctccat ttcgctttaa ttgcaatctt    420
tttcttacta ttaacatcta tcacaaaaaa atgaacatag atgttagtat ataaaaccat   480
tacgtatagg aggaatttac atgctgaaga aatcggtgtt gtttgttttt tcgttggctt   540
tgacatttgc tgtttttctt tatgacatac cggcggcatc ggcatttccg cccggtacac   600
cgtccaagtc caccgcccaa tcacagttga attcgctgac cgttaaatcc gaaggttcta   660
tgaccggcta ctcgcgagac aagtttccac attggatcag ccaaggtgat ggctgtgaca   720
ctcgccagct ggtgcttaag cgtgacggcg actactacag tggtaactgt cccgtcacat   780
cgggtaagtg gtacagctac tacgacggca tcaccgtgta ctcaccgtct gaaatcgaca   840
tcgatcacat cgtcccgtta gcagaagcat ggcgttcggg cgctagcggc tggacaacgg   900
aaaagcgcca gagcttcgca aacgacctca acggcccaca gctaatcgcg gtaaccgcta   960
gtgtaaatcg atccaaggga gaccaggatc cgtcgacgtg gcagccaccg cgttctggtt  1020
cacactgcgc gtacgcaaag atgtgggtca acaccaagta tcgctgggc ctgcacgtgc   1080
agtcggcgga aaagtccgcg ctgcagagca tgctcaatgc ctgctcctac tagtctgtta  1140
ttatttgcag agaaaccatt ctgcccagaa aggagtctac tcgtatgaa aagaaatgt    1200
ccatcttcac cgcaacacac ggtgtaatga cagcagaagt cggcgtaatc agtggggagc  1260
tcgaacttcg cagcacctgt gatgacgacg gcacccccac attagccatc acctatgttg  1320
gcgccgagga atggtacacg ttgccagggg atgattacca cctgcacgac ttgcgtgacc  1380
acgaagtcgt ccaccgcctg ctcaccgccg tacttgagcg ctcatgagtt ggtatgctct   1440
atcaaagggt gctttcgttt aattatgcat aagatcagct gcctagttag gcagcgattt   1500
tttttataat taaagcagta tagccgaaga agagtttagc tcagtaagaa cacccaattt   1560
ttaaaatgta taggagataa caattaaatt catgacttat caactaactt ttaaaatagg   1620
taatttaagg tat                                                      1633

SEQ ID NO: 42          moltype = AA  length = 210
FEATURE                Location/Qualifiers
source                 1..210
                       mol_type = protein
                       organism = Bacillus horneckiae
SEQUENCE: 42
MLKKSVLFVF SLALTFAVFL YDIPAASAFP PGTPSKSTAQ SQLNSLTVKS EGSMTGYSRD    60
KPPHWISQGD GCDTRQLVLK RDGDYYSGNC PVTSGKWYSY YDGITVYSPS EIDIDHIVPL   120
AEAWRSGASG WTTEKRQSFA NDLNGPQLIA VTASVNRSKG DQDPSTWQPP RSGSHCAYAK   180
MWVNTKYRWG LHVQSAEKSA LQSMLNACSY                                    210

SEQ ID NO: 43          moltype = DNA  length = 1633
FEATURE                Location/Qualifiers
sig_peptide            501..584
mat_peptide            585..1130
source                 1..1633
                       mol_type = genomic DNA
                       organism = Bacillus sp.
CDS                    501..1130
```

```
SEQUENCE: 43
ggatatagaa aaagtatttc cttttcttcg agaaaacgaa actctcatac gcatttggat   60
tgaacctaaa gaaattcaat acgttttaaa tgaccatgaa ttatcaaccc acgtaataaa  120
tgaagcatta aaaatctctg attcatacat ttagcttagt gtatgttaaa gtttacactt  180
gctgaacaaa cggggcaggt tggttaaaca tggaaaaatt gctgaaggaa gagaaaaaac  240
tatgttttt tctaaaatag acagattatt tacaaatttt taacttttaaa gaaaataatc  300
cgtgtaatat tattcaagt agaggcgttt tcaacttatt accttatttc attaaaaact  360
aaaagaaaca ttaaaagtaa tgaatcgttg acgtgctcta tttcgctttg attgcaattt  420
ttttcttact attaacatct attcattaaa aatgaacata gatgttagta tataaaacaa  480
ttattatagg aggaatttct atgttgaaga aatcgatgtt gtttgttttt tcgttggttt  540
tgtcgtttgc tgttttcaa tatgacatac caacggcatc ggcttttccg cctgaaatac  600
cgtccaagtc taccgcccaa tcccagttga attcgctgac cgttaagtcc gaagacgcta  660
tgaccggcta ctcgcgagac aagtttccgc attggattag ccaaggcgat ggctgtgaca  720
ctcgccagat ggtgctcaag cgtgacgctg actactacag tgggagctgc ccgtcacgt  780
ctggtaagtg gtacagctac tacgacggta tcaccgtgta ctcaccgtct gaaatcgaca  840
tcgatcacat cgtcccgtta gcagaagcgt ggcgttccgg cgctagcagc tggaccacgg  900
aaaagcgccg gaacttcgca aacgacctca acggcccaca gctaattgcg gtgaccgcca  960
gcgttaaccg gtccaagggc gaccaggatc catcgacgtg gcagccaccg cgttccggcg 1020
cccgctgcgc atacgcgaag atgtgggtca acaccaagta ccgctggggc ctgcacctgc 1080
agtcggcgga gaagtccggg ctggagagca tgctcaacac ctgctcctac taagtctgtt 1140
agaacttgca gtgaaaccat ccaacctcag aagggagtct actcgtatgg aaaagaaatc 1200
gtcaatcttc accgcaactc acggtgtaat gaccgctgaa gtcggcgtga tcagtgggga 1260
actcgaactt cgcacaacct gtgatgatga cggcttctc acgctcgcca tcacgtatgt 1320
cggcgccgag gagtggtaca cgctgccggg taaagattac cacctgcacg atccgcgtga 1380
ccatgaagtc gtccaccgca tgctcaccgc cgtactagag cgcccatgag atcgactgct 1440
taactatcaa gaaaaggggta cttttcgttta actatgcagt agatcagctg cctaatcgcg 1500
cagcgatttt cttttttgaac taaagtggga gtttagaata agagttaaatc attcttctat 1560
aatttgatta atactgtata tatagtgtgg gggatgctgt gtgattatta aacagataac 1620
atgtgaagtg aaa                                                   1633

SEQ ID NO: 44              moltype = AA  length = 210
FEATURE                    Location/Qualifiers
source                     1..210
                           mol_type = protein
                           organism = Bacillus sp.
SEQUENCE: 44
MLKKSMLFVF SLVLSFAVFQ YDIPTASAFP PEIPSKSTAQ SQLNSLTVKS EDAMTGYSRD   60
KPPHWISQGD GCDTRQMVLK RDADYYSGSC PVTSGKWYSY YDGITVYSPS EIDIDHIVPL  120
AEAWRSGASS WTTEKRRNFA NDLNGPQLIA VTASVNRSKG DQDPSTWQPP RSGARCAYAK  180
MWVNTKYRWG LHLQSAEKSG LESMLNTCSY                                  210

SEQ ID NO: 45              moltype = DNA  length = 1624
FEATURE                    Location/Qualifiers
sig_peptide                501..575
mat_peptide                576..1121
source                     1..1624
                           mol_type = genomic DNA
                           organism = Bacillus cibi
CDS                        501..1121
SEQUENCE: 45
cctcaacggg agacgcatcc ccggtgagtt tgattttct tgctttatcc tattcccaat   60
agacctctga gaaaagggt ttcctatgaa cttatgggga aaccttttta attttcaaga  120
gcttctgcct gcatctgctc ggaaacacct gtatcattgg actcattttt attccccatt  180
gtaaatttgc agacggaagg gttttgattc cttttttctca ccttaaatga aattgtttca  240
tgacatatgg cctcaaattt ataaatacct ctattcattc ccttcctttg gaacttaaaa  300
tcagcgtaaa ttccatcata catgttaagg agtttacatt tgattaactt gtagaaatct  360
ctctttcat actatgattt ctaatagaga gataaatttc catctttctt atccgccctc  420
attttccttt gtgctgtcta ttaatctcac tgactactgg ttatgggatt agtataaaat  480
tttttacagg aggcatctac atgctgaaaa aagcttcatt atctgttttt gcactgcttc  540
tctcattcac tttgtttctc ccggaaaccc atgctacgcc gccgggcact ccgtcaaagt  600
ccgcagcaca atcccagctt aacgcgctga ccgttaagac agaaggctcc atgagcggct  660
actcacgtga tttattccct cactggatca gtcaggaag cggctgtgac acccgccaag  720
ttgttcttaa acgtgacgca gactcctaca gcggtaattg ccccgtaaca tcaggcagct  780
ggtacagcta ttacgacggt gtaacgttca ccaatcgttc tgatcttgat atcgatcata  840
tcgtccctct tgcagaagca tggagatccg gtgccagcag ctggacaacg tccaagcgcg  900
aggattttgc aaacgattta agcggacctc agctaattgc agtaagtgcc agcaccaacc  960
gttccaaagg tgaccaggat ccttctacat ggcagccacc acgctcaggt gcagcgtgcg 1020
ggtattcaaa atggtggatc agcacaaaat acaaatgggg attaagcctt cagtcttcag 1080
aaaagaccgc gcttcaaggc atgctcaata gctgttctta ttaagggttt aactaaaaaa 1140
acgagcagcc aaaagcggct gctcgttat gctataatct aagcaaatga tggaggtgac 1200
aagcatggag aagaaatcaa cggttttac cgccacccac ggtgtcatga cagcagaagt 1260
cggcgtcatc agcggcgagc ttgaacttgt cacagcctgc agaagacg gcgttcttac 1320
tctttccatt acatacaatg gggctgcaga gtggtactct cttccgggtg aggaataccg 1380
gctgtatgat gtgcgggatc atgaagtggt tcatgagatg ctgttgcagag tgcttgagcg 1440
tccttgattc acctagaacc tagaggatca taaaatgaa agccgcctga caagtccagt 1500
tacggtccta tcaggcggct cttttgtatgc ttcaaacttc cagcagaaat tcatgctccg 1560
caaaagattg ctcaatctaa atcgaatccg acaaacccat tatcctctcc tgaaaaacaa 1620
aacg                                                             1624
```

```
SEQ ID NO: 46              moltype = AA   length = 207
FEATURE                    Location/Qualifiers
source                     1..207
                           mol_type = protein
                           organism = Bacillus cibi
SEQUENCE: 46
MLKKASLSVF ALLLSFTLFL PETHATPPGT PSKSAAQSQL NALTVKTEGS MSGYSRDLFP   60
HWISQGSGCD TRQVVLKRDA DSYSGNCPVT SGSWYSYYDG VTFTNPSDLD IDHIVPLAEA  120
WRSGASSWTT SKRQDFANDL SGPQLIAVSA STNRSKGDQD PSTWQPPRSG AACGYSKWWI  180
STKYKWGLSL QSSEKTALQG MLNSCSY                                     207

SEQ ID NO: 47              moltype = DNA   length = 1624
FEATURE                    Location/Qualifiers
sig_peptide                501..575
mat_peptide                576..1121
source                     1..1624
                           mol_type = genomic DNA
                           organism = Bacillus sp.
CDS                        501..1121
SEQUENCE: 47
cgtattttta aaatgctgca cgtaaatgtg gaaagtggaa tgtattttc  aaaagtggaa    60
cgtaaatgca ggaattggat tgtatttca  atttatatgg aattgacttc tcccgaacgt   120
ttcataagcc aaatttcata gtgggatcga acgtaaagt  gaggatatta gatgacgcca   180
ccatttactt cgggcttttt ctctctcaag taggcacaac gtatcacaag tttagtgctc   240
acagtgaacc cataatcctg agggaccagg aacatagttt caacctttgt aaagcatacc   300
aatttacaaa attttaactt gttagaaggt tattccatcc actatcattc aagtagaagc   360
aaacccgctt ctatccgatc ctcacaaaat tgattcaacc tgaacttaat tcaaagtctg   420
actacatcga ttcactatta acattccatt ctctgagaat gagatgttga tataaaaaaa   480
tacatacagg aggcattatc atgctaaaga aatcgatgct gtttgttgtt gcgctacttc   540
tttcgttcac tttattcctg ccgaccgcct tgcattccc  gcctggtaca ccgtccaaat   600
ctacggcaca atcgcaactg aactcactca ctgttaaatc tgaaggctcc atgaccggtt   660
attcgcggga caagttcccc cattggatcg gtcaagggag cggatgtgac acccgccagc   720
tcgttctcca gcgtgacgcc gactattaca gcggcagttg cccagtaacg tcaggtaaat   780
ggtacagcta ctatgacgga gtcacatttt acgatccgtc cgaccttgat atcgatcacg   840
tcgttccgct tgccgaagcg tggcgttccg gtgcgacgca gttggagcac acagaagcta   900
aagacttcgc caacgatctc agtggcccgc agctgatcgc cgtcagcgca agctccaatc   960
ggtctaaagg cgaccaggat ccatccacat ggcagccaac acgatcaggc gcagcctgcg  1020
gttactcgaa gtggtggatc agcacgaagc acaagtgggg attaagtctt cagtcttcag  1080
agaagaacgc acttcaaggc atgctgaaca gctgcgttta ctgattggaa ccatgaggat  1140
ccccgtacgc tctgcacgta cgggaattgt tcacatccaa ccattagaat ggaggaatat  1200
atgtggaaag gaaatcaact attttttacag caacccatgg cgtcatgacc tcagaggtgg  1260
gtgtaattag cggagacctt gagcttgtca ccacctgtga tgattctggc gttctgacac  1320
tttcaatcac gtatgttgga gctgatgaat ggtatacact acctggtaga gaatatcgat  1380
ttcatgatac gcgagatcat gaggtcgtgc acaaaatgct ttctgcggtg ttggagcgtc  1440
cttgaagttg gggcaatgta cgtatcattt tgagaaatca ttcggggttc cgaatgattt  1500
tttttgaagc gaatagcttg gtcaagcggc ctgttcccg  atccataggg attaaggtcgg  1560
ttggaggtgt ggccccgcgca tttcattgga cgtgaatatc catgacctgt gattttttcga  1620
caag                                                                1624

SEQ ID NO: 48              moltype = AA   length = 207
FEATURE                    Location/Qualifiers
source                     1..207
                           mol_type = protein
                           organism = Bacillus sp.
SEQUENCE: 48
MLKKSMLFVV ALLLSFTLFL PTAFAFPPGT PSKSTAQSQL NSLTVKSEGS MTGYSRDKFP   60
HWIGQGSGCD TRQLVLQRDA DYYSGSCPVT SGKWYSYYDG VTFYDPSDLD IDHVVPLAEA  120
WRSGASSWST QKRKDFANDL SGPQLIAVSA SSNRSKGDQD PSTWQPTRSG AACGYSKWWI  180
STKHKWGLSL QSSEKNALQG MLNSCVY                                     207

SEQ ID NO: 49              moltype = DNA   length = 1624
FEATURE                    Location/Qualifiers
sig_peptide                501..575
mat_peptide                576..1121
source                     1..1624
                           mol_type = genomic DNA
                           organism = Bacillus idriensis
CDS                        501..1121
SEQUENCE: 49
gaatgaagcg acctatccta gagcaaagag aacagcccgc cgaccatttt atgacctcaa    60
tttatttgta tggatctgca aaattcttcc acaagcgaaa atctttgcat caatttcagc   120
tgaaataaat ccaatccaac tcctccttct atgtactcat tttctgatta tattttttaa   180
aatggaacct cttcaatcag agaactttttg atacaacatc ctcattttca gaaaaaaact   240
cattactaat taccctgatt atttaaggag ttatatcgtt actcttcctt atgtacttcc   300
tttctccccc taaatgttaa gggatttaca aatgctaaac ttgttaaaaa ttcaattatt   360
atactatcat ttctcaatgaa gaaacaaatt tccatttacc tgtgaaatac agtccagtgg   420
cttgctgcgc gtttgatgtt aacctctcac ctatcaaaaa tgagagattg atataaaaat   480
tacatacagg aggcatttaa atgctgaaaa aaatgatgtg ttttgttttt gcactagttc   540
tctcgtttac attattcttg ccagacgcct atgcactgcc acccggaact ccgtccaaat   600
```

```
ccactgcaca atcccagctg aacgcgttga ccgtgcagac agaaggctct atgaccggct    660
actctcgtga caaatttccc cattggatca gtcaaggaaa cggctgtgac acccgtcagg    720
tggtgcttca gcgtgatgcc gattactaca gcggcacctg ccctgtgaca tccggcaagt    780
ggtacagtta ctacgacggt gttacgctgt acaatccgtc ggaccttgac atcgatcatg    840
tcgtcgctct tgctgaggcg tggcgttccg gcgcaagcag ctggacaacg gacaaacgtg    900
aggactttgc caacgactta agcggcacgc agctgattgc ggtaagcgcc agcaccaatc    960
gttccaaagg tgaccaagat ccgtctacgt ggcagccgcc tcgttccggt gcagcatgcg   1020
gatatgcaaa gtggtggatc agtacgaagt acaaatggaa tttaaacctg caatcttcag   1080
agaagaccgc gcttcaaagc atgctcaata gttgctctta ttgattatat agctgttcga   1140
acgaacgatt cacagttgat tgttcgttcg tacagtaaat aatggaggtg cttttatgga   1200
aaagaagtca actgctttta cagcaaccca cggtgtcatg acctctgagg ttggtgttat   1260
cagcggtgag cttgagcttg ttacaacgtg cggtgatgac ggtgacctaa ctctcgccat   1320
cacatatgtt ggggctgagg agtggtattc ccttcccggg gagaaataca agttgtatga   1380
cttgcgtgat cacggggtca ttcacgagat gcttgtgagg gtacttgagc gcccttaagg   1440
cattgggtca tttagattat ggtggaatta ttgcgtgagg tatataaaaa caggcaatct   1500
ttcgaaataa ctcaagagac atgaaatgac ttcatgtctc tttttctgtt aaaaaataat   1560
ccccaatcct gcaaaagcaa gatcctcaca atctactttt tgaacataac tttctttttc   1620
aaac                                                                 1624

SEQ ID NO: 50          moltype = AA   length = 207
FEATURE                Location/Qualifiers
source                 1..207
                       mol_type = protein
                       organism = Bacillus idriensis
SEQUENCE: 50
MLKKMMLFVF ALVLSFTLFL PDAYALPPGT PSKSTAQSQL NALTVQTEGS MTGYSRDKFP     60
HWISQGNGCD TRQVVLQRDA DYYSGTCPVT SGKWYSYYDG VTLYNPSDLD IDHVVALAEA    120
WRSGASSWTT DKREDFANDL SGTQLIAVSA STNRSKGDQD PSTWQPPRSG AACGYAKWWI    180
STKYKWNLNL QSSEKTALQS MLNSCSY                                        207

SEQ ID NO: 51          moltype = DNA   length = 1633
FEATURE                Location/Qualifiers
sig_peptide            501..584
mat_peptide            585..1130
source                 1..1633
                       mol_type = genomic DNA
                       organism = Bacillus algicola
CDS                    501..1130
SEQUENCE: 51
aaacgatcag ctagtgaatc acccatccga ttcaacaggt gaacggccag tgtcagatgg     60
gattctcatt tttgaataga aattttggga cgaaaatata gagtctacta tttcgatagt    120
aggcagcaag ccgagggtaa ttcctcggct ttttctaatt catccaaagg tcacactttt    180
tattaagctt gtaaaatttg taggtaatat ctacttaaata ttgaaataac cttcactagc    240
tcatatgaac caactttact tttatggcta tgaactatag aacattgctg gatagatatg    300
ctagatttaa gtcgcgctaa tggaaagatg aaccatctat acataaaaga aacacaaacc    360
tatttcgctt gctaaagagg tcacctcctc ttgttctgtc tcaatttttt gcatgaacta    420
tgaaactatt actatcacct tcacctaaaa gtgaacagtg atgttagtac ataaataaac    480
aaaaaatagg aggctccacc atgcttaaga agtcgttttt gattgttttt acgttggttc    540
tgttgtttgc tgggtttcaa cttggtctgc cgtcagctct tgcgtttccc ccaggtacac    600
cgtctaaatc tgaagctcaa tctcagttga attccctcac tgtacagtca gaaggctcga    660
tgtccggcta ttcgcgcgat aagttcccac actggattgg tcagggtaat gggtgtgata    720
cacgtcagtt agtgcttcag cgtgatgcgg attactacag tggagattgt cctgttacgt    780
ccggtaagtg gtacagctac ttcgatggtg tgacggtgta tgatccgtct gatctagaca    840
tcgatcatat ggtaccgatg gcagaggcgt ggcgttcagg ggcaagcagt tggagtacac    900
agaagcgtga agatttcgcg aacgaccta gtggtcctca cctcattgca gtaacagcaa    960
gcagcaatcg ctccaagggt gaccaggatc cttctacatg gaagccgacg cgttacgggg   1020
cacattgcgg gtatgcgaag tggtggatca atacgaaata tgtgtatgac ctaacccttc   1080
agtcctcgga aaaaactgag cttcaaagca tgcttaatac gtgtagttat taagtcgttt   1140
cgttgctagt gttatagttt gaataaaact tggtcagaagg gagccactca tatggagaag   1200
tcatcgatct tcacggcaac gcatggtgtg atgacggaag aagttggtgt gattagcgag   1260
gaactcgagc tgcgcacatc gtgtgatgaa gaaggtaaca tttcgcttag catcacatac   1320
gtaggtgctg aggagtggta ctcactccct ggtaaagaat atcgcctaca cgatgtgcgt   1380
gatcacgaag tcgttcatca catactcgta tccgtgctgg agcgtcgcta attttcgaca   1440
cgtgcctggc accatagtgc aaaagaagga tagcccactg gctatccttc ttttaaactt   1500
ctcaatctgg tgaatcaaat caacataatc aatttcattt aggtctggat aatcatcgaa   1560
tttcttctaa acaaactcaa gttcaggggg gagttccttt ttcctattca aattatggac   1620
gcaacgaaat cag                                                      1633

SEQ ID NO: 52          moltype = AA   length = 210
FEATURE                Location/Qualifiers
source                 1..210
                       mol_type = protein
                       organism = Bacillus algicola
SEQUENCE: 52
MLKKSFLIVF TLVLLFAGFQ LGLPSALAFP PGTPSKSEAQ SQLNSLTVQS EGSMSGYSRD     60
KFPHWIGQGN GCDTRQLVLQ RDADYYSGDC PVTSGKWYSY FDGVTVYDPS DLDIDHMVPM    120
AEAWRSGASS WSTQKREDFA NDLSGPHLIA VTASSNRSKG DQDPSTWKPT RYGAHCGYAK    180
WWINTKYVYD LTLQSSEKTE LQSMLNTCSY                                    210
```

```
SEQ ID NO: 53              moltype = AA  length = 182
FEATURE                    Location/Qualifiers
source                     1..182
                           mol_type = protein
                           organism = Bacillus algicola
SEQUENCE: 53
FPPGTPSKSE AQSQLNSLTV QSEGSMSGYS RDKFPHWIGQ GNGCDTRQLV LQRDADYYSG    60
DCPVTSGKWY SYFDGVTVYD PSDLDIDHMV PMAEAWRSGA SSWSTQKRED FANDLSGPHL   120
IAVTASSNRS KGDQDPSTWK PTRYGAHCGY AKWWINTKYV YDLTLQSSEK TELQSMLNTC   180
SY                                                                 182

SEQ ID NO: 54              moltype = DNA  length = 1633
FEATURE                    Location/Qualifiers
sig_peptide                501..584
mat_peptide                585..1130
source                     1..1633
                           mol_type = genomic DNA
                           note = xanthan alkaline community J
                           organism = unidentified
CDS                        501..1130
SEQUENCE: 54
caggttccgg gtgttggaac ttcacctcga acagtttctc gtccatcttc ccgccgagca    60
cttttttgaa attggtgagg aacagctctt ggtgttcctg ctctaaaaaa gggaatgagc   120
gcaattcttc atgaaaaatc tcattgctgt cttgtcgaat ataaatatta taaatgtcgg   180
cgattttgac cgcctcggca ttcaatttga atgtttgcg gatggccgcg atgtcttttt    240
gattcatgta tccccactcc ttcgttcttt cctacaaacc gactccatta taccaatagt   300
tcgggtccac gcgaggatgt atagtgctaa agccgggacg tctgatgtca tatattatgt   360
ctctcatctt aacttttata atctttctat tcatttttgt aaatttcaca ctttcttcat   420
cgtagcccat gtatagtcga tgtgcgtcca tcgattggat gcgctcgatt cggttgtcat   480
acatatgagg aggctcaccc atgttgaaga aaatgttctc tattc gccatcgttc        540
tcgttttgac cacgctgcac ttcagtacgc ctaccgcttc ggccttgccg ccgaacatcc   600
catcaaaagc cgacgcgctc acgaaactga acgcgttgac cgttcaaaca gaagggccga   660
tgaccggcta cagccgtgat tgttccccgc attggagcag ccaagggaac ggctgtaaca   720
cccgtcacgt cgtcttgaag cgagatgccg attcggtcgt cgacacttgc ccgtcacga    780
ctggaagatg gtacagttac tatgacggac tcgtcttcac gtccgcttcc gatatccaga   840
tcgaccacgt cgtcccgctc gctgaagcgt ggcgctcagg tgcgagcagc tggacatcga   900
cgaagcgtca aagcttcgcc aacgatttga acggaccgca gttgattgcc gtttcagcca   960
cgtcaaaccg ttcaaaaggg gaccaagacc catcgacatg caaccgccg cgtgccggtg   1020
cgcgctgtgc gtatgcgaag atgtgggtcg agacgaagag ccgttggggg ctcacgtcc   1080
aatcgtcaga aaagcagcg cttcaaacg ccatcaacgc ttgcagctat tgatgtagaa    1140
aggagttcgt tatggatcaa caatcatcta tctttaaagc ctctcacggg gtcatgaccg   1200
aagaagtcgg cgtcatcagt ggagaactcg aactgaagac gacgtgccaa gaggacggca   1260
cgctcgagct cgccatcacc tatgtcggcg ccgccagctg atacatta ccggggaaag    1320
attacaagct tcacgacgtg cgtgaccacg acgtcgtgca tcaactgctc gtaaacgttc   1380
tcgagcgagc gtaaatgtaa aggagtcg acacctcatt tgggtgacga gactcctttt    1440
tgtttggtgc ttacttcacc attttaatga tggcacgaat gacaaggaaa atgacccga   1500
tcatgattcc tgccaacagc aagctggcgc caccgcaat gccgagtgtg aacataacgg   1560
tcctccgtgg tgatgtgatg attacttctc tacgatatca tctgtctcac aatagcataa   1620
gctgagtcta ttt                                                    1633

SEQ ID NO: 55              moltype = AA  length = 210
FEATURE                    Location/Qualifiers
source                     1..210
                           mol_type = protein
                           note = xanthan alkaline community J
                           organism = unidentified
SEQUENCE: 55
MLKKMLSSLF AIVLVLTTLH FSTPTASALP PNIPSKADAL TKLNALTVQT EGPMTGYSRD    60
LPFHWSSQGN GCNTRHVVLK RDADSVVDTC PVTTGRWYSY YDGLVFTSAS DIDIDHVVPL   120
AEAWRSGASS WTSTKRQSFA NDLNGPQLIA VSATSNRSKG DQDPSTWQPP RAGARCAYAK   180
MWVETKSRWG LTLQSSEKAA LQTAINACSY                                   210

SEQ ID NO: 56              moltype = AA  length = 182
FEATURE                    Location/Qualifiers
source                     1..182
                           mol_type = protein
                           note = xanthan alkaline community J
                           organism = unidentified
SEQUENCE: 56
LPPNIPSKAD ALTKLNALTV QTEGPMTGYS RDLFPHWSSQ GNGCNTRHVV LKRDADSVVD    60
TCPVTTGRWY SYYDGLVFTS ASDIDIDHVV PLAEAWRSGA SSWTSTKRQS FANDLNGPQL   120
IAVSATSNRS KGDQDPSTWQ PPRAGARCAY AKMWVETKSR WGLTLQSSEK AALQTAINAC   180
SY                                                                 182

SEQ ID NO: 57              moltype = DNA  length = 1624
FEATURE                    Location/Qualifiers
sig_peptide                501..575
mat_peptide                576..1121
source                     1..1624
```

|  |  |
|---|---|
|  | mol_type = genomic DNA |
|  | organism = Bacillus vietnamensis |
| CDS | 501..1121 |

SEQUENCE: 57

```
gacttcttgg tcggtaacct tttcagcatc ttcaaatgta ctatcgtatt cttgaatggt    60
catgcttttc acgccggaaa aaccgttata taacacggaa tagcttatcc atccaaatac   120
aatgacaaaa aggacagtta ggatgatttt tttcattgtt cccctcccct ttatccaatt   180
atttcaaact ccttctgtca tatccacaca tttctccttg tagtcattac gtcacacaaa   240
tcgctcactc ccgatgaccg tctgattctg aaggaacagg cataaagttt catctttcta   300
aatagcccct gatttacaaa atattaactt gttagaagag cttccatcc cctatcattt    360
taggtagaag cgaacacaac tgatgccaaa tcctcaataa gaatcctttc tcactgcctg   420
actacgttgt ttaactatta acatgctatt ccattaagaa tgacatgttg atataaaaaa   480
tacatacagg aggcatcccc atgctaaaga aatcattgat gtttgtcgtt gccctgcttc   540
tctcgttcgc tttattcctg ccgtctgcac tcgcattccc accggcacc ccgtccaagt    600
ccacggccca atcacagttg aacgcgttga cagtaaagtc ggaaagctcc atgaccggat   660
actcccgtga taagttcccc cactggatcg gccagaggaa cggatgtgac acaagacagc   720
tcgtcctgca gcgtgacgct gacagctaca gtggcagctg cccggtgaca tccggatcat   780
ggtacagtta ttacgacgga gtcacattta cggatccatc cgatcttgac atcgatcacg   840
ttgtcccccct tgcagaagca tggcgctccg gagccagcag ctggacgaca gctaagcgcg   900
aagacttcgc caacgacctg agcggtccac agctgattgc cgtcagcgca agctcaaacc   960
gctccaaagg agatcaggat ccatccactt ggcagccacc gcgttccggc gcagcctgcg  1020
gttactccaa atggtggatc agcacgaaat acaaatggat cttaagcctg caatcttcag  1080
aaaaaaccgc ccttcaaggt atgctaaaca gctgtattta ctgatgtaga ggggagcacg  1140
gggacggttc tcgtgctccc ttttcattca acattgatta tatctacaca tcgaaaggga  1200
ggaatgcata tggaaaagaa atcaacggtt ttcacggcaa cacacggggt catgacgtct  1260
gaagtaggcg tgatcagtgg agaacttgag ctggtgacga catgtgatga agatggttgg  1320
ctaaaactag ctatccaccta tgtagggggcc gaggaatggt attcgctgcc cggtgaggag  1380
taccacttgc atgacgtccg ggatcatgag attgtgcata aaatgcttgc tgctgtgttg  1440
gagcgaccct aagaaggaag cacggggacg gttcccgtgc ttcttttttc gattaagaag  1500
aagcagtaga accgtccccc tgcttctact cctctccat caccgcaaaa taatttttctt   1560
catgatcggc aaagttaaat actctgcccc caggcatatc gacgatttcc cctaccttga  1620
cctt                                                               1624
```

|  |  |
|---|---|
| SEQ ID NO: 58 | moltype = AA  length = 207 |
| FEATURE | Location/Qualifiers |
| source | 1..207 |
|  | mol_type = protein |
|  | organism = Bacillus vietnamensis |

SEQUENCE: 58

```
MLKKSLMFVV ALLLSFALFL PSALAFPPGT PSKSTAQSQL NALTVKSESS MTGYSRDKFP    60
HWIGQRNGCD TRQLVLQRDA DSYSGSCPVT SGSWYSYYDG VTFTDPSDLD IDHVVPLAEA   120
WRSGASSWTT AKREDFANDL SGPQLIAVSA SSNRSKGDQD PSTWQPPRSG AACGYSKWWI   180
STKYKWGLSL QSSEKTALQG MLNSCIY                                       207
```

|  |  |
|---|---|
| SEQ ID NO: 59 | moltype = AA  length = 182 |
| FEATURE | Location/Qualifiers |
| source | 1..182 |
|  | mol_type = protein |
|  | organism = Bacillus vietnamensis |

SEQUENCE: 59

```
FPPGTPSKST AQSQLNALTV KSESSMTGYS RDKFPHWIGQ RNGCDTRQLV LQRDADSYSG    60
SCPVTSGSWY SYYDGVTFTD PSDLDIDHVV PLAEAWRSGA SSWTTAKRED FANDLSGPQL   120
IAVSASSNRS KGDQDPSTWQ PPRSGAACGY SKWWISTKYK WGLSLQSSEK TALQGMLNSC   180
IY                                                                  182
```

|  |  |
|---|---|
| SEQ ID NO: 60 | moltype = DNA  length = 1633 |
| FEATURE | Location/Qualifiers |
| sig_peptide | 501..584 |
| mat_peptide | 585..1130 |
| source | 1..1633 |
|  | mol_type = genomic DNA |
|  | organism = Bacillus hwajinpoensis |
| CDS | 501..1130 |

SEQUENCE: 60

```
aaaaagggta aaaggagcat taattattcc aataattaat gctccttttt ttgatggaat    60
caacagaacc gtcccgacga ttactaaatg acggagcgga aaacaagaag aagccacggt   120
ccctttacct gaaagccatg ggttattccc tcggattttt ttatcaaac caaaggtcac     180
gcttttttatt aagcttgtaa aaattgttgg aacatttac ttataaatga tagaacgctt    240
actagctcat atgaaccaac tttcatttta tgtcttagag ctatagaaca ttgctagaaa   300
ggtgtgctag atttaaggcg cactaatgaa agaatgaaga accagcgata aataaaacaa   360
gcaaattgct tgataaaaga gagcacaagg ctttgttatg tcttactttt cttgtttacc   420
ttaagaacga ttactatctc cttcactcaa agtgaacgga agggtaatac ataaataatc   480
aaaaagtagg aggcattatt tgttaaaga aatcgatttt agttcttttt acgttggttc    540
tgtttttag tggctatcaa tttggtctcc cgtccgctca tgcaatccct cctggaacac    600
cgtcaaagtc tgccgctcaa tctcaattgg attcactagc tgtacagtct gaaggttcca   660
tgtccggata ctcgcgtgat aaattccac actggatcgg cagggggaat ggctgtgaca    720
cccgtcagtt agtgctacag cgggatgctg attattacag cggtgactgt cctgtaacgt   780
ctggtaaatg gtatagctac tttgatgcg tacaggtgta tgaccatct tatctcgata     840
tcgaccacat ggtgccgtta gcagaggcat ggcgttcagg agcaagtagt tggagtacac   900
```

```
aaaagcgtga ggatttcgcg aatgaccttg atggtcctca tctcattgca gtaacggcga  960
gcagcaaccg ttccaagggc gaccaagatc cgtctacatg gaagccaacg cgttacagtg 1020
ctcactgcgg ttatgctaag tggtggatca atacgaagta tgtctatgat ttaaaccttc 1080
agtcttcaga gaaatctgct cttcaaagca tgctgaatac gtgtagttat taagtcgggg 1140
tagttgatag tatgatagtt tcttaatggc tagttgagga ggtgcactca aatggaacag 1200
aagtcatcaa ttttcactgc aactcatggt gttatgaccg aagaagtggg tgtaattagc 1260
ggagagcttg aactgcgtac ttcctgtgat aaggaaggcg atctcacgct acgcattacg 1320
tatgtaggag cagaggagtg gtacacgctg cctggtaaag aatatcgttt acacgacgcg 1380
cgtgaccatg aagtcgttca ccgtttgctc gtatcggtgc ttgacgtcta ttaaaattcg 1440
acaagtgaca ggcaccatgg tcgagcggta ccttatttaa gcatatttcg tattaaagtg 1500
aaaaggagca ttaattattt caataattaa tgctctttttt attttgagat ggaattatca 1560
gaaccgttcc gacgatacccc catcaacact ccttttttagg taattagtcc agggtaaccc 1620
attttgcaat agg                                                   1633

SEQ ID NO: 61          moltype = AA  length = 210
FEATURE                Location/Qualifiers
source                 1..210
                       mol_type = protein
                       organism = Bacillus hwajinpoensis
SEQUENCE: 61
VLKKSILVLF TLVLLFSGYQ FGLPSALAIP PGTPSKSAAQ SQLDSLAVQS EGSMSGYSRD  60
KPFHWIGQGN GCDTRQLVLQ RDADYYSGDC PVTSGKWYSY FDGVQVYDPS YLDIDHMVPL 120
AEAWRSGASS WSTQKREDFA NDLDGPHLIA VTASSNRSKG DQDPSTWKPT RYSAHCGYAK 180
WWINTKYVYD LNLQSSEKSA LQSMLNTCSY                                 210

SEQ ID NO: 62          moltype = AA  length = 182
FEATURE                Location/Qualifiers
source                 1..182
                       mol_type = protein
                       organism = Bacillus hwajinpoensis
SEQUENCE: 62
IPPGTPSKSA AQSQLDSLAV QSEGSMSGYS RDKFPHWIGQ GNGCDTRQLV LQRDADYYSG  60
DCPVTSGKWY SYFDGVQVYD PSYLDIDHMV PLAEAWRSGA SSWSTQKRED FANDLDGPHL 120
IAVTASSNRS KGDQDPSTWK PTRYSAHCGY AKWWINTKYV YDLNLQSSEK SALQSMLNTC 180
SY                                                               182

SEQ ID NO: 63          moltype = DNA  length = 1633
FEATURE                Location/Qualifiers
sig_peptide            501..584
mat_peptide            585..1130
source                 1..1633
                       mol_type = genomic DNA
                       organism = Paenibacillus mucilaginosus
CDS                    501..1130
SEQUENCE: 63
tcccgatgaa atcccggcct gcccggccga gattcgctcc cactgctttt gaccttgatc  60
caaccgaacc aatcccctct ttgagcaatt cttccgacca ataatcccgt atacatccaa 120
tccactgatg tggagatggt cactttatta tggggcataa aaacacaaaa agttaatctt 180
ttcatgcgca ctttagctgt tcaattcatt attgttgtcg gattctgact atgcaaagga 240
cgcatggaca gagataccac atacagaccg agtcattgat acacatgcat cgaaacgcga 300
cagaggatct atgcagtaac ttttgttccgt ccatctccat ctaaaatacc caattgaatg 360
acatattcta ggccctcatt gttcggagta ttgactccat acctgatacc gtttacaaac 420
tattaacttg tacgaaattc tagcgagatg ttacgatctt cacggaatta ttatcatgat 480
ttggggggta tttcctttcc atggtgaaga atcaaggtt gtttgttttt gcgttggttc 540
tgtcgctgtc tgctggtttt tatggcacgc tacggcctc ggcgcttccg ccgggaacac 600
catccaagtc caccgcccaa tcccagctga actcccctgac tgtgaagtcc gaaagcacca 660
tgactggcta ctcgcgcgac aagttccgc actggaccag tcaaggcggt ggctgcgata 720
cccgccaggt ggtgctcaag cgagacgccg actactacag cgggagctgc cccgtcacgt 780
ccggcaagtg gtacagctac tacgacggca ttaccgtgta ctcaccctcc gaaattgaca 840
tcgatcatat tgtgccgctg gccgaggcat ggcgttccgg tgctagcagc tggaccactg 900
aaaagcgtca gaacttcgcc aacgacctgg cgggcccgca gctgatcgcg gtgaccgcca 960
gctccaaccg ggccaagggt gaccaggatc catcgacttg gaagccgacg cgttccggcg 1020
cccactgtgc gtatgcgaag tggtggatca ataccaaata ccgctggggc ttgacctgc 1080
agtcgtcgga gaagaccgct ttgcaaagca tgctcaacac ttgctcctac tgagtcgta 1140
gtgcgtctgc aaggtttgcc aaccgttggc agtacacttg cagcgcagcc atcataaccg 1200
agaagggagt cacctgaatg gaagagaagt cgtcaatctt catcgcaacc cacggtgtga 1260
tgaccgttga ggtcggcgtg atcagcgggg aactcgaact gcgtacgacc tgcgatgacg 1320
agggtgcccct cacgctcgcc atcacgtatg tcggcgccga ggagtgggtat acgctgccag 1380
gtgagcacta tcgcctgcac gatccgcgtg accacgaagt cgtccaccgc atgtccgtca 1440
ccgtactaga gcgcccttga cacagactga cccgccggtc cggtaactta acaagcgttc 1500
tgccgtgcgc ctggcacgtt tgtctgtgct agatacattt actccactta aaagggatg 1560
ctctccgaca cctaatctgg agagcatccc ttttttacgg cagaacgcac gcagttttca 1620
acccagcgtc ccc                                                   1633

SEQ ID NO: 64          moltype = AA  length = 210
FEATURE                Location/Qualifiers
source                 1..210
                       mol_type = protein
                       organism = Paenibacillus mucilaginosus
```

```
SEQUENCE: 64
MVKKSRLFVF ALVLSLSAGF YGTPTASALP PGTPSKSTAQ SQLNSLTVKS ESTMTGYSRD    60
KPPHWTSQGG GCDTRQVVLK RDADYYSGSC PVTSGKWYSY YDGITVYSPS EIDIDHIVPL   120
AEAWRSGASS WTTEKRQNFA NDLGGPQLIA VTASSNRAKG DQDPSTWKPT RSGAHCAYAK   180
WWINTKYRWG LHLQSSEKTA LQSMLNTCSY                                    210

SEQ ID NO: 65           moltype = AA    length = 182
FEATURE                 Location/Qualifiers
source                  1..182
                        mol_type = protein
                        organism = Paenibacillus mucilaginosus
SEQUENCE: 65
LPPGTPSKST AQSQLNSLTV KSESTMTGYS RDKFPHWTSQ GGGCDTRQVV LKRDADYYSG    60
SCPVTSGKWY SYYDGITVYS PSEIDIDHIV PLAEAWRSGA SSWTTEKRQN FANDLGGPQL   120
IAVTASSNRA KGDQDPSTWK PTRSGAHCAY AKWWINTKYR WGLHLQSSEK TALQSMLNTC   180
SY                                                                  182

SEQ ID NO: 66           moltype = DNA   length = 1624
FEATURE                 Location/Qualifiers
sig_peptide             501..575
mat_peptide             576..1121
source                  1..1624
                        mol_type = genomic DNA
                        organism = Bacillus indicus
CDS                     501..1121
SEQUENCE: 66
atatttctga agcactgttt tacatggttg cattctttca gtttgatacc ccatatttct    60
gccgcatcgt tttataggga tgcaaatcac attttaaaac agaggacacc tcctccccat   120
ccaaaatttg caaaaactcc aataaacacc tgcttcgatg gactcatttt tattttccat   180
tgtaaatcat catactaaag agttttgatg cctttttcct acctatata aaaatgtttc   240
atgacatatg gcctcaatct cataaatacc tctattcatc ctcttccttt tggacttaaa   300
atcagcgcaa atccgaacat aaatgttaag aggtttacat ttccttaact tgaagaaatc   360
tctctttca tactatgatt tctaatagag aaacaaattt ccatcacttt ttccctcttc   420
ttccatcgtt ctgtctatta atctcactga ctataagtta tgagattgat atataaaat   480
ttcatacagg aggcatctac atgctgaaaa aagcttcatt atctgttttt gcactgctgc   540
tctcattcac tttatttctg ccggaaacac atgctactcc gccgggcact ccgtcgaagt   600
ccacggcaca aacccagctc aatgctttga cagtcaagac agaaggttcc atgaccggat   660
actcgcgtga tttatttccc cattggatta gccaaggaag cggctgtgac acccgtcagg   720
ttgtgcttaa gcgtgacgct gactactaca gcggcagttg ccctgtgacc tcaggaaaat   780
ggtacagcta ctatgatggt gttacattct atgacccatc tgaccttgac atcgaccata   840
ttgtccctct tgctgaagct tggcgttcag gcgcaagcag ctggacaacg tccaagcgcc   900
aggattttg aaacgactta gcggacctc agctgattgc ggtaagcgcc agcaccaatc   960
gttccaaagg tgaccaggat ccatctacat ggcagcctat ggcagccggt gcagcctatc  1020
gatactcaaa atggtggatc agcacgaaat acaaatgggg cttgagcctt cagtcttcag  1080
aaaaaaccgc gctacagggc atgcttaata gctgttctta ctaatgctta actgaaaacg  1140
agcagccaaa agcggctgct cgtttatgct ataatctaag caaatgacgg aggtgacagc  1200
atggagaaga aatcaacggt ttttaccgca acccacggtg tcatgacag agaagtcggc  1260
gtcatcagcg gcgagcttga acttgtcact gcctcgcgatg aagacggggt cctgaatctc  1320
gctattacat acgccgggc tgcggaatgg tacactcttc ctggtgagga ataccggctg  1380
catgatgtgc gtgatcatga ggttgtgcat gaaatgcttg taagagtgct tgagcgtccg  1440
taattcaata agctgtaaat aaagtgacag ccgcctgtta agtcgatatt cggacttatc  1500
aggcggcttt tttaatgtgc ttaaaatgaa aaatcatttt ttaagataac tcttcaggaa  1560
tatctaaatc aattccaata aacccttat actcgtcttc cgcaaaacaa aacgtaactt  1620
caga                                                               1624

SEQ ID NO: 67           moltype = AA    length = 207
FEATURE                 Location/Qualifiers
source                  1..207
                        mol_type = protein
                        organism = Bacillus indicus
SEQUENCE: 67
MLKKASLSVF ALLLSFTLFL PETHATPPGT PSKSTAQTQL NALTVKTEGS MTGYSRDLFP    60
HWISQGSGCD TRQVVLKRDA DYYSGSCPVT SGKWYSYYDG VTFYDPSDLD IDHIVPLAEA   120
WRSGASSWTT SKRQDFANDL SGPQLIAVSA STNRSKGDQD PSTWQPPRAG AACGYSKWWI   180
STKYKWGLSL QSSEKTALQG MLNSCSY                                      207

SEQ ID NO: 68           moltype = AA    length = 182
FEATURE                 Location/Qualifiers
source                  1..182
                        mol_type = protein
                        organism = Bacillus indicus
SEQUENCE: 68
TPPGTPSKST AQTQLNALTV KTEGSMTGYS RDLFPHWISQ GSGCDTRQVV LKRDADYYSG    60
SCPVTSGKWY SYYDGVTFYD PSDLDIDHIV PLAEAWRSGA SSWTTSKRQD FANDLSGPQL   120
IAVSASTNRS KGDQDPSTWQ PPRAGAACGY SKWWISTKYK WGLSLQSSEK TALQGMLNSC   180
SY                                                                  182

SEQ ID NO: 69           moltype = DNA   length = 1624
FEATURE                 Location/Qualifiers
```

-continued

| | |
|---|---|
| sig_peptide | 501..575 |
| mat_peptide | 576..1121 |
| source | 1..1624 |
| | mol_type = genomic DNA |
| | organism = Bacillus marisflavi |
| CDS | 501..1121 |

SEQUENCE: 69

```
ttacaaagaa tcagataaat tcggtggatt tccagtccct caattggcga aaaaaacagt    60
gagtcgggat gactttgaat cgtacacatg ggctggtact tctgaagcga aggaggatgg   120
acttcccttc ctttaccgtt cacatatcaa agcgggtgga tggaaaaaaa cgtttcaaga   180
aggaacgctg acgacgtatg aaaaaggtga acataaaatt gacgtaatcg cacaaacaag   240
ttatctttcc ataaacgtta gtagagagta gccgtgtatt ctgcatgaac caatccctta   300
atgataaggc ggttggttct ttttcatttc aagacattcg tttatcatca attttaaaaa   360
tccgaaagaa gtctgaatct ttacaaaaaa cctcttgtaa acctctctct ccctcccccta  420
tcatggcagt agaggcacct tatcccagta tgcgcatcca ccagatgttc atataaaaaa   480
ctacatacag gaggctctcc atgttcaaga aaaccatgtt gtttgtcgtt gcccttgtcc   540
tttccttctc gctgttcctg ccgtccgcgt tgccactcc gcctgtcacg ccgtcgaaag    600
cgacgtccca atcccagttg aacggactca cggtgaagac cgaggggggcg atgaccggct   660
actcccggga caagttcccc cactggagca gtcagggcgg cggctgtgat acccgccagg   720
tcgtcctgaa gcgcgatgcc gattcgtaca gcggcaactg cccggtgacg tcgggaagct   780
ggtacagcta ctatgacggc gttaagttta ccaatccttc cgacctcgat atcgatcaca   840
tcgtgcctct tgccgaagca tggcgctcgg gtgccgagtc gggaccacc gccagcgcg    900
aggcattcgc caatgatctg agcggctccc agctcatcgc cgtctccgcg agcagcaacc   960
gctccaaggg cgaccaggac ccatcccacct ggcagccacc ccgtgccggt gcaaaatgtg  1020
gctatgcgaa aatggtggatc agcaccaagt ctaaatggaa cctgagcctg caatcgtccg  1080
agaagaccgc ccttcaaggg atgctgaaca gctgcgtata ctgataagaat aaaagaaaaa  1140
cggacgatcc tcaccgggat cgtccgtttc aaacaggagg ccaaaccatg gaaaccaaat  1200
caaccacgtt caacgcaagc cacggcgtca tgaccgaaga gtcggcgtc gtcagcgggg   1260
agcttgagct tgtcaccacc tgcgatgaag agggcatcct ctcctcaag atcacctatg   1320
tgggtgccga agaatggtac accctgcccg tgagggta tcggctgttt gatgcgaggg   1380
atcatgaggt gattcatggg atgctggtga aggtattgga agaagttga ttctctacta   1440
taaaaagagt aaagacgctt ggactccaag cgtctttgtc aattctatct tctactgaaa   1500
tagggttcga gccaatcggt ctcatgcgtg aggacgaaca tccaacgtg tatacaacat    1560
agatggccca ccccacttca caacattctt cttagtgagc tcactagtta aggaacttca   1620
atct                                                               1624
```

| | |
|---|---|
| SEQ ID NO: 70 | moltype = AA length = 207 |
| FEATURE | Location/Qualifiers |
| source | 1..207 |
| | mol_type = protein |
| | organism = Bacillus marisflavi |

SEQUENCE: 70

```
MFKKTMLFVV ALVLSFSLFL PSAFATPPVT PSKATSQSQL NGLTVKTEGA MTGYSRDKFP    60
HWSSQGGGCD TRQVVLKRDA DSYSGNCPVT SGSWYSYYDG VKFTNPSDLD IDHIVPLAEA   120
WRSGASSWTT AQREAFANDL SGSQLIAVSA SSNRSKGDQD PSTWQPPRAG AKCGYAKWWI   180
STKSKWNLSL QSSEKTALQG MLNSCVY                                      207
```

| | |
|---|---|
| SEQ ID NO: 71 | moltype = AA length = 182 |
| FEATURE | Location/Qualifiers |
| source | 1..182 |
| | mol_type = protein |
| | organism = Bacillus marisflavi |

SEQUENCE: 71

```
TPPVTPSKAT SQSQLNGLTV KTEGAMTGYS RDKFPHWSSQ GGGCDTRQVV LKRDADSYSG    60
NCPVTSGSWY SYYDGVKFTN PSDLDIDHIV PLAEAWRSGA SSWTTAQREA FANDLSGSQL   120
IAVSASSNRS KGDQDPSTWQ PPRAGAKCGY AKWWISTKSK WNLSLQSSEK TALQGMLNSC   180
VY                                                                 182
```

| | |
|---|---|
| SEQ ID NO: 72 | moltype = DNA length = 1633 |
| FEATURE | Location/Qualifiers |
| sig_peptide | 501..578 |
| mat_peptide | 579..1130 |
| source | 1..1633 |
| | mol_type = genomic DNA |
| | organism = Bacillus luciferensis |
| CDS | 501..1130 |

SEQUENCE: 72

```
tggattaatt tttttatcta ttgttatttt tgtattagtg ttaataacac caataaatga    60
tttaattaca atagcgttgt aatctcttat ttttgttgta tcaatgttta tgttatttag   120
aaaagaaata gaacttattg aactaactgg cgcgatagtt acaaactaac tctcagcttt   180
aatagaaaat taagagttgt caatggcaac tcttttttt gctaaccggc aggtgaacaa   240
ggattccatt aaatcatgtt gaatattatc taataaaata aatattatca ggacagaaaa   300
atgaaaagaa tttcatatat atagttataa acaaatattt tctttattta ttttaatact   360
tctatccatg gttgaatca catgaataat acatttgaac ccatattgc aatttaatc    420
ttattattaa catctcttc attaaaattg taagtagatg ttagtatata aaaaaattaa    480
tacatatagg aggaatttct atgctgaaaa atcgatgtt gattgttttt gcgttggttc   540
tgacgtttac tgttttacag tttgaaactg cgaaggccgc atcgttaccg cccggaatac   600
catcctatc cacagcccaa tcccagctga attcattgac cgttaagtca gaaggttccc   660
tgactggcta ctctcgcgac gttttccctc actggatcag ccaaggaagt ggctgcgata   720
```

```
cacgtcaggt ggtgctcaag cgtgatgccg actactatag cgggaactgc cctgtaacgt    780
ccggtaaatg gtacagctac tacgacgggg tcacagtgta ctcgccgtcc gaaatcgaca    840
ttgatcatgt cgtcccattg gcagaggcgt ggcgttctgg tgccagcagt tggaccacag    900
aaaagcgtca gaacttcgcc aacgacctta atggtccgca gttgatagca gtgactgcta    960
gctctaaccg ctcaaagggt gaccaagatc ctttctacatg gcagccaact cgtaccggtg   1020
cacgctgcgc gtatgcgaag atgtggataa acaccaagta ccgctgggga ttgcacctac   1080
aatcatctga gaagtccgca ctgcagagca tgctcaatac ctgctcttat tgatttcatt   1140
attcgtctac aaataatatc accgaccgtt ggtagtactt gcatcgcaac cattcaaacc   1200
cagatgggag gaggcactcg tatggaaaag aagtctacaa tcttcaccgc aactcacggt   1260
gtaatgacca cagaggtcgg tgtaatcagt ggggagctcg aactacgcac cacctgcgat   1320
gacggaggag cactcacact tgccatcacg tatgttggtg ctgaggagtg gtacactctg   1380
cctgggaaag attccaccct gttcgattcg cgtgatcatc aagtcgtcca ccgcatgctc   1440
gccacggtgc tagctcgtcc ttgagacaga ctgacaactc tgcataagtc taatggctcg   1500
tactactggg cattgtggtt gaaaaaacaa aaattgaaat taagtgcagg atctataagg   1560
attctgtgct tttttattga agcattagta aaatgaacag gagtaatcta attccttatt   1620
caactaactg gcg                                                       1633

SEQ ID NO: 73           moltype = AA  length = 210
FEATURE                 Location/Qualifiers
source                  1..210
                        mol_type = protein
                        organism = Bacillus luciferensis
SEQUENCE: 73
MLKKSMLIVF ALVLTFTVLQ FETAKAASLP PGIPSLSTAQ SQLNSLTVKS EGSLTGYSRD     60
VFPPHWISQGS GCDTRQVVLK RDADYYSGNC PVTSGKWYSY YDGVTVYSPS EIDIDHVVPL   120
AEAWRSGASS WTTEKRQNFA NDLNGPQLIA VTASSNRSKG DQDPSTWQPT RTGARCAYAK   180
MWINTKYRWG LHLQSSEKSA LQSMLNTCSY                                    210

SEQ ID NO: 74           moltype = AA  length = 184
FEATURE                 Location/Qualifiers
source                  1..184
                        mol_type = protein
                        organism = Bacillus luciferensis
SEQUENCE: 74
ASLPPGIPSL STAQSQLNSL TVKSEGSLTG YSRDVFPHWI SQGSGCDTRQ VVLKRDADYY     60
SGNCPVTSGK WYSYYDGVTV YSPSEIDIDH VVPLAEAWRS GASSWTTEKR QNFANDLNGP   120
QLIAVTASSN RSKGDQDPST WQPTRTGARC AYAKMWINTK YRWGLHLQSS EKSALQSMLN   180
TCSY                                                                184

SEQ ID NO: 75           moltype = DNA  length = 1624
FEATURE                 Location/Qualifiers
sig_peptide             501..575
mat_peptide             576..1121
source                  1..1624
                        mol_type = genomic DNA
                        organism = Bacillus marisflavi
CDS                     501..1121
SEQUENCE: 75
tcattttaac aatgcaatgc cccagcaaaa tcacgcgtta tttcacaccc caaaaaaata     60
ctcatacttc ttaaaatcca tcctatgctt cagaaaggaa tggaacaagt ccttatgtgg    120
ccttcccttc ctttaccgtt cgcatatcaa agcggggcgt tggaaaaaaa cgtttcaaga    180
aggaacgctg acgacgtatg aaaaaggtga acataaaatt gatgtgatct cacaaacagg    240
ctatctttcc ataaacgtta gtagagagta gtcgggtatt ctgcatgaac caatccctta    300
ataataaggt ggttggttct ttttcatttc aagatattct ttcatcacca attttaaaaa    360
tccaaaagaa gtctgaatct ttacaaaaaa actcttgtaa acctctcact ccctcccctta   420
tcatggcagt agaggcacct tatcacagta tgcgcatcgt gctgatgttc atataaaaaa   480
ctacatacag gaggctctcc atgttcaaga aaaccatgtt gtttgtcgtt gcccttgtcc    540
tttccttctc cctgttccta ccgtccgcct tgccactcc gctgttacg ccgtcgaaag     600
agacgtccca gtcccagctg aatgggctca cggtgaagac cgaggggcg atgaccgct     660
actcccggga caagttcccc cactgagca gtcagggcgg cggatgtgat acccgccagg    720
tcgtcctgaa gcgcgatgcc gattcgtaca gcggcaactg cccggtgacg tctgaagct    780
ggtacagcta ctatgacggc gttaagttta cccatccgtc tgacctcgat atcgaccaca    840
tcgtcccact agctgaagca tggcgctccg ggccagcag ctggaccacc gcccagcgcg    900
aagcattcgc caatgacctg agcggttccc agctcatcgc ctccgca agcagcaacc      960
gctccaaggg tgaccaggat ccatccacct ggcagccgcc ccgtgccggt gcaaaatgtg   1020
gctacgccaa atggtggatc agcaccaagt ccaaatggaa cctgagcctg cagtcatccg   1080
agaaaaccgc ccttcagggg atgctgaaca gctgcgtata ctgatagaat aaaagaaaaa   1140
cggacgatcc tcaccgggat cgtccgtttc aaacaggagg ccaaaccatg gaaaccaaat   1200
caaccacgtt caacgcaagc cacggccgtca tgaccgagga agtcggccgtc atcagcggat   1260
agcttgagct cgtcaccacc tgcgatgaaa atgcatcct ctccctcaag atcacctatg    1320
tgggtcagaa agaatggtac accctgcccg gtgaggagta tcgactgttt gatgcaaggg   1380
atcatgaggt ggttcatggg attcttgtga aggtattgga agaagttgaa gtttctacta   1440
gagtacgatc aatgacaaag acgcttgaaa tctcaagctt ctttgtcttc tctatctcct   1500
actgaaataa ggtccgagct acggttttc atgcgtgagc acgaacgtcc aacgaactg    1560
tttatctacg acatagatgt cccgcccac ctcacttgat aggtcgatca catcaaaccc   1620
cgat                                                                1624

SEQ ID NO: 76           moltype = AA  length = 207
FEATURE                 Location/Qualifiers
```

```
source                    1..207
                          mol_type = protein
                          organism = Bacillus marisflavi
SEQUENCE: 76
MFKKTMLFVV ALVLSFSLFL PSAFATPPVT PSKETSQSQL NGLTVKTEGA MTGYSRDKFP    60
HWSSQGGGCD TRQVVLKRDA DSYSGNCPVT SGSWYSYYDG VKFTHPSDLD IDHIVPLAEA   120
WRSGASSWTT AQREAFANDL SGSQLIAVSA SSNRSKGDQD PSTWQPPRAG AKCGYAKWWI   180
STKSKWNLSL QSSEKTALQG MLNSCVY                                      207

SEQ ID NO: 77             moltype = AA  length = 182
FEATURE                   Location/Qualifiers
source                    1..182
                          mol_type = protein
                          organism = Bacillus marisflavi
SEQUENCE: 77
TPPVTPSKET SQSQLNGLTV KTEGAMTGYS RDKFPHWSSQ GGGCDTRQVV LKRDADSYSG    60
NCPVTSGSWY SYYDGVKFTH PSDLDIDHIV PLAEAWRSGA SSWTTAQREA FANDLSGSQL   120
IAVSASSNRS KGDQDPSTWQ PPRAGAKCGY AKWWISTKSK WNLSLQSSEK TALQGMLNSC   180
VY                                                                 182

SEQ ID NO: 78             moltype = DNA  length = 1633
FEATURE                   Location/Qualifiers
sig_peptide               501..584
mat_peptide               585..1130
source                    1..1633
                          mol_type = genomic DNA
                          organism = Bacillus sp.
CDS                       501..1130
SEQUENCE: 78
agcgttgact tttgtttcat ccctgtcgat gcaaacgact tcgtgaccca tttccgcaag    60
gcaaactcca tttaccagtc ctacataccc agttccagca acagtgattt tcattcaatc   120
cctcccgaaa gtaatgcttg cttattttca ttttattaga agaacatgca tactttcttg   180
aggcagcgta aagggattgt aaaattgttg taacattttc aaattttctg tgttttccca   240
ggtgggtttc atgaaagaat actttcggcc tatcactatc attcctttg atgcctctct    300
aaaatatcaa gattttttaag atttggtata caggttggag gaagcaaact gagaatttat   360
aaatgagaaa gagtttttga accaactgct gactttacaa tttacggaat atttacaaat   420
atttaacttt taatcaggta atttatcaac tatcatttct agtggaggaa tagtaaaaat   480
acatactggg aggaaatttt atgatgaaga aatggatagg gttggttttt gcgctcgttt   540
tgtcggtggt tgttttcat tttgatattc ctactgcatc cgctttaccg tcaggaattc   600
cgtccaagtc caccgcccaa tctcagttga actcgctgac cgtcaagtcc gaaggttcca   660
tgaccggtta ctcgcgggac aagttccgc actggatcag ccaggggcgg ggctgtgata   720
cccgtcaggt ggtgctcaag cgtgatgcgg actactacag cgggaattgc cccgtcacat   780
ccggcaaatg gtacagctac tatgatggca ttccgtgta ctcaccttcc gaaatcgaca   840
tcgaccacgt cgtcccgctt gcagaagcat ggcgttccgg cgccagcagc tggactacga   900
caaagcgcca gaattttgca aacgacctca acggcccgca gctcattgcg gtgaccgcga   960
gcgttaaccg gtccaagggt gaccaggatc cgtcaacctg gcagccaccg cgttatggag  1020
cacgctgtgc atacgccaag atgtggatca acaccaagta ccgtcgggac ctgaacctgc  1080
aatcatcgga gaagtcttcc ctgcaaagca tgcttgacac ctgctcctat taagactgtt  1140
ataatattt aaagtattac caagctaaaa ctgttatagc ccaatcatta gcatagaagg  1200
gagacaacca tatggaaacg aagtcgtcaa ttttccacgc aacccatggg gtaatgacca  1260
aggaggtcgg cgtgatcagt ggggacctcg aacttcgcac cacatgcagc gacaatggtg  1320
tccttacact cgccattacc tatgttggcg ctgaagaatg gtatacgctg ccgggtgaaa  1380
attatcatct gcacgatccg cgtgaccatg aagtcgtcca ccgcatgctc actgctgtcc  1440
ttgagcgctc ttgagatgga aatatatacg gtgcatgttc agggtgtcat aaatttcggg  1500
ttgtgacagg cactttttta atacgagtac tcggcttata tgcgatactg gtgcacagtc  1560
acaaccaggg agtgtctaat aaaatagagga gcctatcct ttggtggata aggctctttt  1620
gtagcgtatt gct                                                    1633

SEQ ID NO: 79             moltype = AA  length = 210
FEATURE                   Location/Qualifiers
source                    1..210
                          mol_type = protein
                          organism = Bacillus sp.
SEQUENCE: 79
MMKKWIGLVF ALVLSVVVFH FDIPTASALP SGIPSKSTAQ SQLNSLTVKS EGSMTGYSRD    60
KFPHWISQGG GCDTRQVVLK RDADYYSGNC PVTSGKWYSY YDGISVYSPS EIDIDHVVPL   120
AEAWRSGASS WTTTKRQNFA NDLNGPQLIA VTASVNRSKG DQDPSTWQPP RYGARCAYAK   180
MWINTKYRWD LNLQSSEKSS LQSMLDTCSY                                   210

SEQ ID NO: 80             moltype = AA  length = 182
FEATURE                   Location/Qualifiers
source                    1..182
                          mol_type = protein
                          organism = Bacillus sp.
SEQUENCE: 80
LPSGIPSKST AQSQLNSLTV KSEGSMTGYS RDKFPHWISQ GGGCDTRQVV LKRDADYYSG    60
NCPVTSGKWY SYYDGISVYS PSEIDIDHVV PLAEAWRSGA SSWTTTKRQN FANDLNGPQL   120
IAVTASVNRS KGDQDPSTWQ PPRYGARCAY AKMWINTKYR WDLNLQSSEK SSLQSMLDTC   180
SY                                                                 182
```

```
SEQ ID NO: 81           moltype = DNA  length = 912
FEATURE                 Location/Qualifiers
sig_peptide             1..45
mat_peptide             46..909
source                  1..912
                        mol_type = genomic DNA
                        organism = Pyrenochaetosis sp.
CDS                     1..369
CDS                     559..690
CDS                     793..909
SEQUENCE: 81
atgaagtccc tcgtcctcct cagcctcgcc tccctcatcg ccgccctcc ctccccctc    60
ctcatcgccc gctccccacc caacatcccc agcgccacca ccgccaaaac ccaactcgcc   120
ggcctcaccg tcgcaccca aggacccag acaggctact cgcgcgacct attcccgcac    180
tggatcacg agtcgggaac atgcaacacg cgcgaggtcg tcttgaagcg cgatggtacc    240
aacgtggtta cgaactctgc gtgcgcgagt acgagcggga gctggttgag tccgtatgat   300
ggcaagacgt gggactcggc gagtgatatt cagattgatc atcttgtgcc gttgagtaat   360
gcgtggaagg tatgttcata gtctccttt actgttttgt ctaggtgctt tacgctctgt    420
tcggactttg tgatatgtga tcacgtgcgt caccgaagag acgagaatac gaatcagat    480
ggaaagcaat atgaacacaa ctctaggaag gatctagagc gactgaatgt tgaggaattc    540
aactaaccaa ctcccccagtc cggagcagca gcctgacccc agtcaagcctc             600
gccaacgacc taacccaccc acaactcgtc gccgtaacag gcagcgtcaa tgaatccaag   660
ggagacgatg gccggaaga ctggaagcct gtgagttcct gctctccacc aatttacttc     720
aattccacgc cacatgacca aaatgagaca tatcgagtat aagggacgat ggctaacgat   780
ctataccaac agccgctagc aagctactac tgcacctacg catcgatgtg gacggcggtg   840
aaatctaact ataagctgac gattacgagt gcagagaaga gcgcgttgac gagtatgttg   900
gcaacttgct ag                                                       912

SEQ ID NO: 82           moltype = AA  length = 206
FEATURE                 Location/Qualifiers
source                  1..206
                        mol_type = protein
                        organism = Pyrenochaetosis sp.
SEQUENCE: 82
MKSLVLLSLA SLIAALPSPL LIARSPPNIP SATTAKTQLA GLTVAPQGPQ TGYSRDLFPH    60
WITQSGTCNT REVVLKRDGT NVVTNSACAS TSGSWLSPYD GKTWDSASDI QIDHLVPLSN   120
AWKSGAAAWT TAQRQAFAND LTHPQLVAVT GSVNESKGDD GPEDWKPPLA SYYCTYASMW   180
TAVKSNYKLT ITSAEKSALT SMLATC                                       206

SEQ ID NO: 83           moltype = AA  length = 191
FEATURE                 Location/Qualifiers
source                  1..191
                        mol_type = protein
                        organism = Pyrenochaetopsis sp.
SEQUENCE: 83
LPSPLLIARS PPNIPSATTA KTQLAGLTVA PQGPQTGYSR DLFPHWITQS GTCNTREVVL    60
KRDGTNVVTN SACASTSGSW LSPYDGKTWD SASDIQIDHL VPLSNAWKSG AAAWTTAQRQ   120
AFANDLTHPQ LVAVTGSVNE SKGDDGPEDW KPPLASYYCT YASMWTAVKS NYKLTITSAE   180
KSALTSMLAT C                                                       191

SEQ ID NO: 84           moltype = DNA  length = 831
FEATURE                 Location/Qualifiers
sig_peptide             1..57
mat_peptide             58..828
source                  1..831
                        mol_type = genomic DNA
                        organism = Vibrissea flavovires
CDS                     1..379
CDS                     507..644
CDS                     719..828
SEQUENCE: 84
atgtatacct ccctcctcgt ctctgtcctc ctctcctccc tccctctcgt cctcaccacc    60
cccctcccca tcatcgcgcg gacaccgccc aatatcccca caaccgctac cgcgaagtcc   120
cagctcgcgg ccttgactgt tgcggccgcg gtccgcaga ccgggtactc gcgtgacctg    180
tttccgacct ggatcacgat ctctgggacg tgtaatacga gggagacggt gctgaagagg   240
gatgggacga atgtggtagt tgattcgcg tgtgtggcta cgagtgggag ttggtatagt    300
ccgtatgatg ggcgacttg gacggcggct agtgatgata atattgatca tatgttccg    360
ttgagtaatg cttggaagag tgagtgcttt ccacaattat ctgaagtccg agatcttgtc   420
aagttgtcca tgtccagttc gagtgctggg tttgagtctg ggatttggaa gctcaatgta   480
ctggatggtt attgactttg tgataggtgg tgcgagtgcc tggacaacag cacagagaca   540
gacttttgcc aatgatctga ctaatcctca actattggcc gttacggaca atgtcaatca   600
agctaagggt gatagtggac cggaggactg gaagccatcg ttgagtatgt cttgtgatct   660
agatctctcc tgggagataa ataatttgcg atggcgaaaca atagctaatg atatatgcc   720
tcatactggt gcacatatgc caaaatgtgg gttaaggtca agactgttta tgatcttacg   780
atcacgtcgg ctgagaagac tgctttgact actatgctga acacttgttg a            831

SEQ ID NO: 85           moltype = AA  length = 209
FEATURE                 Location/Qualifiers
```

```
source                  1..209
                        mol_type = protein
                        organism = Vibrissea flavovires
SEQUENCE: 85
MYTSLLVSVL LSSLPLVLTT PLPIIARTPP NIPTTATAKS QLAALTVAAA GPQTGYSRDL  60
FPTWITISGT CNTRETVLKR DGTNVVVDSA CVATSGSWYS PYDGATWTAA SDVDIDHMVP  120
LSNAWKSGAS AWTTAQRQTF ANDLTNPQLL AVTDNVNQAK GDSGPEDWKP SLTSYWCTYA  180
KMWVKVKTVY DLTITSAEKT ALTTMLNTC                                   209

SEQ ID NO: 86           moltype = AA  length = 190
FEATURE                 Location/Qualifiers
source                  1..190
                        mol_type = protein
                        organism = Vibrissea flavovirens
SEQUENCE: 86
TPLPIIARTP PNIPTTATAK SQLAALTVAA AGPQTGYSRD LFPTWITISG TCNTRETVLK  60
RDGTNVVVDS ACVATSGSWY SPYDGATWTA ASDVDIDHMV PLSNAWKSGA SAWTTAQRQT  120
FANDLTNPQL LAVTDNVNQA KGDSGPEDWK PSLTSYWCTY AKMWVKVKTV YDLTITSAEK  180
TALTTMLNTC                                                        190

SEQ ID NO: 87           moltype = DNA  length = 727
FEATURE                 Location/Qualifiers
sig_peptide             1..51
mat_peptide             52..724
source                  1..727
                        mol_type = genomic DNA
                        organism = Setosphaeria rostrate
CDS                     1..378
CDS                     476..724
SEQUENCE: 87
atgaaggcct ctcttatcat tgccgccgct tccctagccc tcacctccgc ggctcccacc  60
tcatcacccc tcgtcgctcg tgctcctccc aatgtcccca gcaaagccga ggcaacctcc  120
caactcgcag gcctgaccgt cgcacctcaa ggtccgcaaa ccggttactc gcgcgacctg  180
tttccccact ggatcactca gtccggcacg tgcaacaccc gagagactgt cctgaagcgc  240
gacggcacaa acgtcgttac caacagcgcg tgcgcatcca cctctggctc ctggttcagc  300
ccatacgacg gagcgacatg gacagccgcc agtgacgtag acattgacca catggtccca  360
ttgagcaacg cctggaaggt gagttttctt tttccttttc cttcgttatt ccccgcattc  420
taagtatcac acatacctcc atgtaaccat gtatgctaac acatctctcc accagtctgg  480
tgccgcatcc tggaccactg cccgccgcca ggcctttgcc aacgacctta ccaaccccca  540
gctgctcgct gtcaccgaca acgtgaacca agccaagggc gacaagggcc ccgaggactg  600
gaagcccccg ctaaccagct actactgcac ttacagcaag atgtggatca aggttaagag  660
cgtgtggggc ttgacgatta cgagtgccga gaagagtgcg ttgacgagca tgttggcgac  720
gtgctag                                                           727

SEQ ID NO: 88           moltype = AA  length = 209
FEATURE                 Location/Qualifiers
source                  1..209
                        mol_type = protein
                        organism = Setosphaeria rostrate
SEQUENCE: 88
MKASLIIAAA SLALTSAAPT SSPLVARAPP NVPSKAEATS QLAGLTVAPQ GPQTGYSRDL  60
FPHWITQSGT CNTRETVLKR DGTNVVTNSA CASTSGSWFS PYDGATWTAA SDVDIDHMVP  120
LSNAWKSGAA SWTTARRQAF ANDLTNPQLL AVTDNVNQAK GDKGPEDWKP PLTSYYCTYS  180
KMWIKVKSVW GLTITSAEKS ALTSMLATC                                   209

SEQ ID NO: 89           moltype = AA  length = 192
FEATURE                 Location/Qualifiers
source                  1..192
                        mol_type = protein
                        organism = Setosphaeria rostrata
SEQUENCE: 89
APTSSPLVAR APPNVPSKAE ATSQLAGLTV APQGPQTGYS RDLFPHWITQ SGTCNTRETV  60
LKRDGTNVVT NSACASTSGS WFSPYDGATW TAASDVDIDH MVPLSNAWKS GAASWTTARR  120
QAFANDLTNP QLLAVTDNVN QAKGDKGPED WKPPLTSYYC TYSKMWIKVK SVWGLTITSA  180
EKSALTSMLA TC                                                     192

SEQ ID NO: 90           moltype = DNA  length = 838
FEATURE                 Location/Qualifiers
sig_peptide             1..48
mat_peptide             49..835
source                  1..838
                        mol_type = genomic DNA
                        organism = Endophragmiella valdina
CDS                     1..203
CDS                     263..434
CDS                     521..659
CDS                     726..835
SEQUENCE: 90
atgaagtacc tcgccctcac catggccttt gcggccgtat caatggccgc ccccgtgcca  60
```

-continued

```
ggccatctga tgcctcgcgc accgccaaac gtccccacca ccgctgccgc gaagaccgcc  120
ctcgccggcc tcaccgtcca ggcccagggc tcccagaccg gctactcgcg tgatctgttc  180
ccccattgga tcacccagag cgggtaaggc tatgctctcc ctttttatgc cattatcgga  240
cgtaaactca ccgttttaat agaacctgca cacccgtga ggtcgtgctc aagcgtgatg   300
gtaccaacgt agtcaccgac tctgcctgcg ctgccacatc cggaacctgg gtgtcgccct  360
acgacggcgc tacctggacc gccgccagcg acgtcgacat tgaccacatg gtccctctgt  420
ccaacgcctg gaaggtgcgt atttttcttt tcttccttt ctgttcttga tccagccatt   480
ccctctgcga aaaattacat gctaacagaa cccctgatag tctggcgccg cctcctggac  540
taccgcccag aggcaggcat cgcaaacga cttgacgaac ccccagctgc tggctgtgac   600
ggacaacgtc aaccagtcca agggcgacaa gggccctgag gactggaagc ccccacttag  660
taagtgtttc cccaggggag atgtgagcca tggcatgttt cggccggcta acggcttgtt  720
tctagcttcg tactactgca cctatgccaa gatgtgggtc aaggtcaaga gcgtgtattc  780
gctcaccatc accagcgctg agaagacggc gcttacgagc atgttgaaca cttgctag    838
```

```
SEQ ID NO: 91           moltype = AA  length = 208
FEATURE                 Location/Qualifiers
source                  1..208
                        mol_type = protein
                        organism = Endophragmiella valdina
SEQUENCE: 91
MKYLALTMAF AAVSMAAPVP GHLMPRAPPN VPTTAAAKTA LAGLTVQAQG SQTGYSRDLF   60
PHWITQSGTC NTREVVLKRD GTNVVTDSAC AATSGTWVSP YDGATWTAAS DVDIDHMVPL  120
SNAWKSGAAS WTTAQRQAFA NDLTNPQLLA VTDNVNQSKG DKGPEDWKPP LTSYYCTYAK  180
MWVKVKSVYS LTITSAEKTA LTSMLNTC                                    208

SEQ ID NO: 92           moltype = AA  length = 192
FEATURE                 Location/Qualifiers
source                  1..192
                        mol_type = protein
                        organism = Endophragmiella valdina
SEQUENCE: 92
APVPGHLMPR APPNVPTTAA AKTALAGLTV QAQGSQTGYS RDLFPHWITQ SGTCNTREVV   60
LKRDGTNVVT DSACAATSGT WVSPYDGATW TAASDVDIDH MVPLSNAWKS GAASWTTAQR  120
QAFANDLTNP QLLAVTDNVN QSKGDKGPED WKPPLTSYYC TYAKMWVKVK SVYSLTITSA  180
EKTALTSMLN TC                                                     192

SEQ ID NO: 93           moltype = DNA  length = 735
FEATURE                 Location/Qualifiers
sig_peptide             1..48
mat_peptide             49..732
source                  1..735
                        mol_type = genomic DNA
                        organism = Corynespora cassiicola
CDS                     1..369
CDS                     431..569
CDS                     623..732
SEQUENCE: 93
atgaagtgcc tcctccttgc tctggcctcc accgcctgg tgtccgccct ccccgctccg    60
cttgtgcctc gcgccctcc cggcatcccc accacctcgg ccgccaggtc ccagcttgct  120
ggcctcaccg tcgctgccca gggccctcag accggctact cccgtgatct gttccccac   180
tggatcaccc agagcggaag ctgcaacacg cgcgaggtcg tcctcgcccg cgacggcacc  240
ggcgttgtcc aggactcttc ctgtgccgcc acctcgggaa cctggcgctc gcccttcgac  300
ggcgccactt ggaccgctgc tagcgacgtc gacattgacc acatggttcc tctctccaat  360
gcttggaagt atgggcagc cgtgtaccta ctacatctgt gcacaaagac actgtgctaa  420
ccgcctgcag tctggagccg catcctggac cacgtccgc cgcaggcat ttgccaacga   480
cttgaccaac cctcagctga ttgctgtgac ggacaacgtt aaccagtcca agggtgacaa   540
gggcccggaa gactggaagc cgccgctcag tacgccatgc cccgcctcat cctacgaaga  600
cgccacactg actagcctac agcctcgtac tactgcacct atgccaagat gtgggtgagg  660
gtcaagagcg tgtactcttt gaccattacc agcgctgaga gagtgcgct cacgagcatg   720
ttggacactt gctag                                                  735

SEQ ID NO: 94           moltype = AA  length = 206
FEATURE                 Location/Qualifiers
source                  1..206
                        mol_type = protein
                        organism = Corynespora cassiicola
SEQUENCE: 94
MKCLLLALAS TALVSALPAP LVPRAPPGIP TTSAARSQLA GLTVAAQGPQ TGYSRDLFPH   60
WITQSGSCNT REVVLARDGT GVVQDSSCAA TSGTWRSPFD GATWTAASDV DIDHMVPLSN  120
AWKSGAASWT TSRRQAFAND LTNPQLIAVT DNVNQSKGDK GPEDWKPPLT SYYCTYAKMW  180
VRVKSVYSLT ITSAEKSALT SMLDTC                                      206

SEQ ID NO: 95           moltype = AA  length = 190
FEATURE                 Location/Qualifiers
source                  1..190
                        mol_type = protein
                        organism = Corynespora cassiicola
SEQUENCE: 95
LPAPLVPRAP PGIPTTSAAR SQLAGLTVAA QGPQTGYSRD LFPHWITQSG SCNTREVVLA   60
```

```
RDGTGVVQDS SCAATSGTWR SPFDGATWTA ASDVDIDHMV PLSNAWKSGA ASWTTSRRQA    120
FANDLTNPQL IAVTDNVNQS KGDKGPEDWK PPLTSYYCTY AKMWVRVKSV YSLTITSAEK    180
SALTSMLDTC                                                          190

SEQ ID NO: 96           moltype = DNA  length = 703
FEATURE                 Location/Qualifiers
sig_peptide             1..51
mat_peptide             52..700
source                  1..703
                        mol_type = genomic DNA
                        organism = Paraphoma sp.
CDS                     1..378
CDS                     452..700
SEQUENCE: 96
atgaagtcca ccatccttct cgcgctggct tcagcggcct tcgtctccgc ggcaccagca    60
ccagttcacc tcgttgctcg cgcgccaccc aatgtcccaa ccgccgccca agcacaaact    120
caacttgccg gcctcactgt tgctgctcaa ggtccccaga ctggctacag ccgcgatctc    180
ttcccccatt ggatcaccca gtccggtgcc tgcaacacgc gtgagactgt cctcaagcgt    240
gatggcaccg gcgtcgtgca agactccgca tgtgctgcca ccagcggaac ctggaagagt    300
ccatacgacg cgcaaacatg gaccgctgcc agcgacgtcg acattgacca catggtcccc    360
ttgagcaacg cctggaaggt ccgtctcatc ccacccaat tcccacattg cttccatttc    420
caacgaacaa aatcgctaac ttatcatcta gtccggcgca gcatcctgga ccacggcccg    480
ccgccaggcc ttcgccaatg acttgaccaa ccccaactc ctagccgtca ccgacaacgt    540
caaccaggcc aagggcgaca agggccccga agactggaag cccccgctaa cgagctacta    600
ctgcatctac gcccgcatgt ggatcaaggt caagagcgtg tacagcctta ctatcacaag    660
tgctgagaag tcggcgttga cgagcatgtt gggcacctgc tga                     703

SEQ ID NO: 97           moltype = AA  length = 209
FEATURE                 Location/Qualifiers
source                  1..209
                        mol_type = protein
                        organism = Paraphoma sp.
SEQUENCE: 97
MKSTILLALA SAAFVSAAPA PVHLVARAPP NVPTAAQAQT QLAGLTVAAQ GPQTGYSRDL    60
FPHWITQSGA CNTRETVLKR DGTGVVQDSA CAATSGTWKS PYDGATWTAA SDVDIDHMVP    120
LSNAWKSGAA SWTTARRQAF ANDLTNPQLL AVTDNVNQAK GDKGPEDWKP PLTSYYCIYA    180
RMWIKVKSVY SLTITSAEKS ALTSMLGTC                                     209

SEQ ID NO: 98           moltype = AA  length = 192
FEATURE                 Location/Qualifiers
source                  1..192
                        mol_type = protein
                        organism = Paraphoma sp.
SEQUENCE: 98
APAPVHLVAR APPNVPTAAQ AQTQLAGLTV AAQGPQTGYS RDLFPHWITQ SGACNTRETV    60
LKRDGTGVVQ DSACAATSGT WKSPYDGATW TAASDVDIDH MVPLSNAWKS GAASWTTARR    120
QAFANDLTNP QLLAVTDNVN QAKGDKGPED WKPPLTSYYC IYARMWIKVK SVYSLTITSA    180
EKSALTSMLG TC                                                       192

SEQ ID NO: 99           moltype = DNA  length = 795
FEATURE                 Location/Qualifiers
sig_peptide             1..54
mat_peptide             55..792
source                  1..795
                        mol_type = genomic DNA
                        organism = Monilinia fructicola
CDS                     1..174
CDS                     280..607
CDS                     683..792
SEQUENCE: 99
atggttccga ctcttctcct cagtatccta gcaacaggac tcctcgttca cgcaactccg    60
gtcccagcac caactggtat tccatctact tctgttgcca atactcaact tgctgctttg    120
acagtggctg ccgctggaag tcaagacggt tattcaagag atttgtttcc tcacgtccgt    180
tcacctgaac actttctct ccattccatc cccaacgcgg cccccccccc ccacacacat    240
ctccacaaac taaactaacc ctccctaccc ctgatttagt ggataaccat ctccggcgcc    300
tgcaacacgc gcgaaaccgt cctcaagcgc gacggcacca cgtcgtcgt taattctgcc    360
tgtgcagcca catctggcac atgggtctct ccctacgacg cgctacctg gaccgccgca    420
tccgacgttg atatcgatca tcttgtccct taagcaatga catggaaagc tggggcttct    480
tcatggacca cggcccaacg tcaagcattc gctaacgatc ttgtgaaccc caactgctg    540
gccgtgacgg acagcgttaa tcagggaaaa tcggatagcg gacctgaagc gtggaaacca    600
agtttgagta tgtttctctt tggactgtgg atattggatg gggggaagtg ggatccaaga    660
caattgctaa tgagaaaatt agaatcttac tggtgcacat atgctaagat gtggattaaa    720
gttaaatatg tgtatgatct cacaattacg agtgcggaga aatcggcctt ggttactatg    780
atggatactt gttag                                                    795

SEQ ID NO: 100          moltype = AA  length = 204
FEATURE                 Location/Qualifiers
source                  1..204
                        mol_type = protein
```

```
                               organism = Monilinia fructicola
SEQUENCE: 100
MVPTLLLSIL ATGLLVHATP VPAPTGIPST SVANTQLAAL TVAAAGSQDG YSRDLFPHWI    60
TISGACNTRE TVLKRDGTNV VVNSACAATS GTWVSPYDGA TWTAASDVDI DHLVPLSNAW   120
KAGASSWTTA QRQAFANDLV NPQLLAVTDS VNQGKSDSGP EAWKPSLKSY WCTYAKMWIK   180
VKYVYDLTIT SAEKSALVTM MDTC                                         204

SEQ ID NO: 101             moltype = AA   length = 186
FEATURE                    Location/Qualifiers
source                     1..186
                           mol_type = protein
                           organism = Monilinia fructicola
SEQUENCE: 101
TPVPAPTGIP STSVANTQLA ALTVAAAGSQ DGYSRDLFPH WITISGACNT RETVLKRDGT    60
NVVVNSACAA TSGTWVSPYD GATWTAASDV DIDHLVPLSN AWKAGASSWT TAQRQAFAND   120
LVNPQLLAVT DSVNQGKSDS GPEAWKPSLK SYWCTYAKMW IKVKYVYDLT ITSAEKSALV   180
TMMDTC                                                             186

SEQ ID NO: 102             moltype = DNA   length = 692
FEATURE                    Location/Qualifiers
sig_peptide                1..51
mat_peptide                52..689
source                     1..692
                           mol_type = genomic DNA
                           organism = Curvularia lunata
CDS                        1..372
CDS                        441..689
SEQUENCE: 102
atgaaggccg ctctcctcct tgctgccgtc tccgcagccc tcacctcggc ggcacccgcc    60
cccctctctg ctcgcgcacc ccccaatatt cccagcaaag ctgatgccac ctctcaactc   120
gccggcctga ccgtcgccgc ccaaggccct cagactggct actctcgcga tctcttcccc   180
cactggatca ctcagtctgg aacctgcaat acgcgcgaaa ccgtgctcaa gcgtgacggc   240
acaaacgtcg tcacgagcag ctcctgcgcc gcgacatctg gaacatggtt tagtccctat   300
gacggcgcga cgtggacggc ggccagtgat gtcgatatcg accatgtggt gccgttgagt   360
aacgcgtgga aggtacattg tctccctctc tcttcctatt tccctatctc gaagtaaacg   420
gtgactaacg aaacaaatag tccggtgccg catcctggac tacggcccgc cgccaggcct   480
ttgccaatga cttgacgaac ccgcagttga ttgccgtgac cgacagcgtc aaccaggcca   540
agggcgacaa gggccctgag gattggaagc ctccgctatc gagctactac tgcacataca   600
gtaagatgtg gattaaggtt aagagcgtgt acggggtgac ggtgacaagc gcggagaaga   660
gtgcgctgtc gagtatgctt gcgacttgct ag                                 692

SEQ ID NO: 103             moltype = AA   length = 207
FEATURE                    Location/Qualifiers
source                     1..207
                           mol_type = protein
                           organism = Curvularia lunata
SEQUENCE: 103
MKAALLLAAV SAALTSAAPA PLSARAPPNI PSKADATSQL AGLTVAAQGP QTGYSRDLFP    60
HWITQSGTCN TRETVLKRDG TNVVTSSSCA ATSGTWFSPY DGATWTAASD VDIDHVVPLS   120
NAWKSGAASW TTARRQAFAN DLTNPQLIAV TDSVNQAKGD KGPEDWKPPL SSYYCTYSKM   180
WIKVKSVYGL TVTSAEKSAL SSMLATC                                      207

SEQ ID NO: 104             moltype = AA   length = 190
FEATURE                    Location/Qualifiers
source                     1..190
                           mol_type = protein
                           organism = Curvularia lunata
SEQUENCE: 104
APAPLSARAP PNIPSKADAT SQLAGLTVAA QGPQTGYSRD LFPHWITQSG TCNTRETVLK    60
RDGTNVVTSS SCAATSGTWF SPYDGATWTA ASDVDIDHVV PLSNAWKSGA ASWTTARRQA   120
FANDLTNPQL IAVTDSVNQA KGDKGPEDWK PPLSSYYCTY SKMWIKVKSV YGLTVTSAEK   180
SALSSMLATC                                                         190

SEQ ID NO: 105             moltype = DNA   length = 807
FEATURE                    Location/Qualifiers
sig_peptide                1..69
mat_peptide                70..804
source                     1..807
                           mol_type = genomic DNA
                           organism = Penicillium reticulisporum
CDS                        1..218
CDS                        272..446
CDS                        503..641
CDS                        695..804
SEQUENCE: 105
atgagatttt ctcaactcac acagaccttg ataggtcttt ggcttttca gcctgctctg     60
atcgcaggac tccggcccc ggaagctctc cagccccctc ctggcgtccc tagtgcttca   120
actgcccaga gcgaactggc tgcactgaca gtcgccgctc aaggatcgca agatggttat   180
tctcgaagca agttccctca ctggatcaca caatctgggt aagagaattt aatttcacag   240
```

```
ttcgtgtatg gcgcgctcat tatccatgca ggagctgcga cacccgggat gtagtgctga  300
agcgtgacgg gacaaatgtg gtacaaagcg cgagtggatg taccattacc agcggtaaat  360
gggtttcacc atatgacggt gcaacctgga ctgcctcgag cgatgtcgac attgaccacc  420
ttgtcccgct gtccaatgcc tggaaggtaa gaatatcccc caagtagtga aaccgggtca  480
agacgactga tgtgtttgat agtcgggtgc ttctggatga ccaccgcag cgcgacaggc  540
ctttgcgaat gacctgacca atccacaact cctggtcgtg actgacaatg tcaacgagtc  600
caagggcgat aaaggtcccg aggaatggaa acctccactt agtatgtgtg cttttttata  660
acggccattg aagatatagc taacctggga atagcctcgt actattgcac ctacgctgag  720
atgtgggtga aggtcaagtc ggtctacaaa ctcactatca cgtccgctga gaaatccgcc  780
ctgacgagca tgctcagtac ttgctag                                      807

SEQ ID NO: 106          moltype = AA  length = 214
FEATURE                 Location/Qualifiers
source                  1..214
                        mol_type = protein
                        organism = Penicillium reticulisporum
SEQUENCE: 106
MRFSQLTQTL IGLLAFQPAL IAGLPAPEAL PAPPGVPSAS TAQSELAALT VAAQGSQDGY   60
SRSKFPHWIT QSGSCDTRDV VLKRDGTNVV QSASGCTITS GKWVSPYDGA TWTASSDVDI  120
DHLVPLSNAW KSGASGWTTA ARQAFANDLT NPQLLVVTDN VNESKGDKGP EEWKPPLTSY  180
YCTYAEMWVK VKSVYKLTIT SAEKSALTSM LSTC                              214

SEQ ID NO: 107          moltype = AA  length = 191
FEATURE                 Location/Qualifiers
source                  1..191
                        mol_type = protein
                        organism = Penicillium reticulisporum
SEQUENCE: 107
LPAPEALPAP PGVPSASTAQ SELAALTVAA QGSQDGYSRS KFPHWITQSG SCDTRDVVLK   60
RDGTNVVQSA SGCTITSGKW VSPYDGATWT ASSDVDIDHL VPLSNAWKSG ASGWTTAARQ  120
AFANDLTNPQ LLVVTDNVNE SKGDKGPEEW KPPLTSYYCT YAEMWVKVKS VYKLTITSAE  180
KSALTSMLST C                                                       191

SEQ ID NO: 108          moltype = DNA  length = 814
FEATURE                 Location/Qualifiers
sig_peptide             1..69
mat_peptide             70..811
source                  1..814
                        mol_type = genomic DNA
                        organism = Penicillium quercetorum
CDS                     1..218
CDS                     271..445
CDS                     504..642
CDS                     702..811
SEQUENCE: 108
atgggctttg cacaagtatc tcaagtcttg atcggtcttt tggctctcca gccaggtctg   60
attgcaggcc ttcccgctcc tgaacctgct ccgtctcccc ggggatccc gtctgcttca  120
accgcgcgaa gcgagctggc tagtttgacg gtggctcccc aaggatctca agatggttat  180
tctcgagcca agtttcctca ctggatcaag cagagcgggt gagacattca cgtccacatc  240
tcttcctggt cgtactgatc gattttgcag gagttgtgac acccgagacg ttgtcctcga  300
gcgtgatggg acaaacgtag tccagagttc gactggctga accattaccg gtggcacatg  360
ggtctcacca tatgatggtg caacctggac tgcctcgagc gatgtcgaca ttgatcatct  420
tgttccgctg tcgaatggct ggaaggtacg catattctct agccagcgaa gcttttgtca  480
gaggactgac atgttttcga tagtcgggtg cctctgcatg gaccacagcc caacgacaag  540
cctttgccaa tgacttgacc aatccacaac tcgtcgcagt gacagacaat gtcaatgagg  600
caaagggtga taaaggcccc gaggaatgga agcctcctct tagtatgtta catgtatacc  660
tcttgtgact tgttcatcca cacattactg actggaacaa gcatcgtact attgcacgta  720
cgcggaaatg tgggtgaagg tcaagtccgt ctacaagctc accatcacat ccgccgagaa  780
gtccgccctc tcgagcatgc ttaatacttg ctag                             814

SEQ ID NO: 109          moltype = AA  length = 214
FEATURE                 Location/Qualifiers
source                  1..214
                        mol_type = protein
                        organism = Penicillium quercetorum
SEQUENCE: 109
MGFAQVSQVL IGLLALQPGL IAGLPAPEPA PSPPGIPSAS TARSELASLT VAPQGSQDGY   60
SRAKFPHWIK QSGSCDTRDV VLERDGTNVV QSSTGCTITG GTWVSPYDGA TWTASSDVDI  120
DHLVPLSNAW KSGASAWTTA QRQAFANDLT NPQLVAVTDN VNEAKGDKGP EEWKPPLTSY  180
YCTYAEMWVK VKSVYKLTIT SAEKSALSSM LNTC                              214

SEQ ID NO: 110          moltype = AA  length = 191
FEATURE                 Location/Qualifiers
source                  1..191
                        mol_type = protein
                        organism = Penicillium quercetorum
SEQUENCE: 110
LPAPEPAPSP PGIPSASTAR SELASLTVAP QGSQDGYSRA KFPHWIKQSG SCDTRDVVLE   60
RDGTNVVQSS TGCTITGGTW VSPYDGATWT ASSDVDIDHL VPLSNAWKSG ASAWTTAQRQ  120
```

| | | |
|---|---|---|
| AFANDLTNPQ LVAVTDNVNE AKGDKGPEEW KPPLTSYYCT YAEMWVKVKS VYKLTITSAE | 180 | |
| KSALSSMLNT C | 191 | |

```
SEQ ID NO: 111          moltype = DNA   length = 808
FEATURE                 Location/Qualifiers
sig_peptide             1..51
mat_peptide             52..805
source                  1..808
                        mol_type = genomic DNA
                        organism = Setophaeosphaeria sp.
CDS                     1..378
CDS                     438..569
CDS                     622..655
CDS                     723..805
SEQUENCE: 111
atgaggtcct ccatcctcgt tgctctttct tcactggctc ttgtctctgc tttgccagca   60
ccagtgacac ttgaagcccg tgctccacct aacattccct ccacggcatc agccaacacc  120
ttgcttgcag gcctcactgt cgctgctcaa ggctctcaga ccggctactc tcgtgatctg  180
ttccctcatt ggatcaccca atctggaacc tgcaataccc gcgagactgt cctgaagcgt  240
gatggtaccg gggttgtcac tgattctgcg tgtgcttcaa cctctggcag ttggtactct  300
gtctatgatg agcaacttg gactgcggca agcgatgtcg acattgacca cgtcgtgcca  360
ttgagcaatg cctggaaggt tcgtagctca gccttctgga gggagtttag aatacaaggt  420
cactaacgaa aaaacagtct ggtgccgcaa gctggacgac cgcacgccgc caaagctttg  480
caaatgactt gaccaatccc cagctcattg ctgtgacaga taatgtcaac caggctaagg  540
gagacaaggg tcccgaggac tggaagcccg taagttatga aactagtcaa agcatatttc  600
aaaatgactg acgtatagca gccgctaacc agctactact gcacctatgc gaagagtaag  660
tgccttgcat tttctagcag tgccgcttcc actaagaaga cgtatgctga ctacataaat  720
agtgtgggtc aaagtcaaga gtgtgtacag cctgaccatc acaagtgcgg agaagactgc  780
tctgacaagc atgttgaaca cttgctaa                                     808

SEQ ID NO: 112          moltype = AA   length = 209
FEATURE                 Location/Qualifiers
source                  1..209
                        mol_type = protein
                        organism = Setophaeosphaeria sp.
SEQUENCE: 112
MRSSILVALS SLALVSALPA PVTLEARAPP NIPSTASANT LLAGLTVAAQ GSQTGYSRDL   60
FPHWITQSGT CNTRETVLKR DGTGVVTDSA CASTSGSWYS VYDGATWTAA SDVDIDHVVP  120
LSNAWKSGAA SWTTARRQSF ANDLTNPQLI AVTDNVNQAK GDKGPEDWKP PLTSYYCTYA  180
KMWVKVKSVY SLTITSAEKT ALTSMLNTC                                    209

SEQ ID NO: 113          moltype = AA   length = 192
FEATURE                 Location/Qualifiers
source                  1..192
                        mol_type = protein
                        organism = Setophaeosphaeria sp.
SEQUENCE: 113
LPAPVTLEAR APPNIPSTAS ANTLLAGLTV AAQGSQTGYS RDLFPHWITQ SGTCNTRETV   60
LKRDGTGVVT DSACASTSGS WYSVYDGATW TAASDVDIDH VVPLSNAWKS GAASWTTARR  120
QSFANDLTNP QLIAVTDNVN QAKGDKGPED WKPPLTSYYC TYAKMWVKVK SVYSLTITSA  180
EKTALTSMLN TC                                                      192

SEQ ID NO: 114          moltype = DNA   length = 819
FEATURE                 Location/Qualifiers
sig_peptide             1..51
mat_peptide             52..816
source                  1..819
                        mol_type = genomic DNA
                        organism = Alternaria sp.
CDS                     1..378
CDS                     448..579
CDS                     635..668
CDS                     734..816
SEQUENCE: 114
atgaagtcct ccatcctcgt tgccctctct tcaattgctc tcgtctctgc tctgccagca   60
ccagtgaccc tcgaagcccg agctccccc aacatcccca cgaccgcagc agccaaaacc  120
cagcttgccg gcctcactgt tgccgctcaa ggccctcaga ccggctactc cgtgacctc  180
ttccctcact ggatcactca atctggcacc tgcaacacgc gcgagactgt cctcaagcgc  240
gacggcaccg gcgttgtcac tgattccgcg tgcgcctcaa cctctggcag ctggttctcg  300
gtctacgatg gtgctacgtg gactgcggcg tcagatgtcg atatcgacca cgtcgtgcca  360
ttgagcaatg cctggaaggt tcgtgtgaag ccccaagtga acgtgaaacc atatttagta  420
cagagacact aacatatgcc aaaacagtct ggagcagcaa gctggaccac cgcacgcgc   480
cagtcttttg ccaatgacct caccaacccg cagctcatcg ctgtcaccga caacgtcaac  540
caggcgacaa gggcccgagg actggaagcc cgtaagtttt tctatgccgg                600
agatgagacc ttcagagaga ctgacgtatc gtagccgcta accagctatt actgcactta  660
tgcgaagagt aagtctttcc tttcccaag atcaccgtac tcgtcacggg aattcaagct  720
aattattgga cagtgtgggt caaggtcaag agcgtgtacg cccttaccat caccagcgcc  780
gagaagacgg ccctgacgag catgttgaac acgtgctaa                         819
```

```
SEQ ID NO: 115              moltype = AA  length = 209
FEATURE                     Location/Qualifiers
source                      1..209
                            mol_type = protein
                            organism = Alternaria sp.
SEQUENCE: 115
MKSSILVALS SIALVSALPA PVTLEARAPP NIPTTAAAKT QLAGLTVAAQ GPQTGYSRDL    60
FPHWITQSGT CNTRETVLKR DGTGVVTDSA CASTSGSWFS VYDGATWTAA SDVDIDHVVP   120
LSNAWKSGAA SWTTARRQSF ANDLTNPQLI AVTDVNQAK GDKGPEDWKP PLTSYYCTYA    180
KMWVKVKSVY ALTITSAEKT ALTSMLNTC                                     209

SEQ ID NO: 116              moltype = AA  length = 192
FEATURE                     Location/Qualifiers
source                      1..192
                            mol_type = protein
                            organism = Alternaria sp.
SEQUENCE: 116
LPAPVTLEAR APPNIPTTAA AKTQLAGLTV AAQGPQTGYS RDLFPHWITQ SGTCNTRETV    60
LKRDGTGVVT DSACASTSGS WFSVYDGATW TAASDVDIDH VVPLSNAWKS GAASWTTARR   120
QSFANDLTNP QLIAVTDVN QAKGDKGPED WKPPLTSYYC TYAKMWVKVK SVYALTITSA    180
EKTALTSMLN TC                                                       192

SEQ ID NO: 117              moltype = DNA  length = 810
FEATURE                     Location/Qualifiers
sig_peptide                 1..51
mat_peptide                 52..807
source                      1..810
                            mol_type = genomic DNA
                            organism = Alternaria sp.
CDS                         1..378
CDS                         446..577
CDS                         637..670
CDS                         725..807
SEQUENCE: 117
atgaagtcct ccatcctcgt tgccctctct tcaatcgctc tcgtctctgc tctgccagca    60
ccagtgaccc tcgaagcccg agctcctccc aacatcccca cgaccgcagc agccaaaacc   120
cagctcgccg gctcactgt cgctgctcaa ggccctcaga ccggctattc cgtgacctc    180
ttccctcact ggatcaccca gtccggctcc tgcaacacgc gcgaggtcgt cctccagcgc   240
gatggtactg gcgttgtcac tgattccgcg tgcgccgcga cctctggcag ctggtactg    300
gtctacgatg gtgctacctg gactgcggcg tcagatgtcg acatcgacca tgtggtgcca   360
ttgagcaatg cctggaaggt tcgtgtgctg cccaagtga atgtcaagct acaattagta    420
caaagacact gacatgataa aatagtctgg agcagcgagc tggaccaccg cacgccgcca   480
ggcgttcgcc aacgacctca ccaaccgca gctcctcgcc gtgaccgaca acgtcaacca   540
ggccaagggc gacaagggcc ccgaggactg gaagcccgta agttctttgc tgccaacgag   600
atgagcctac agaaaccagt aactgatgct tcatagccgc tgaccagcta ttactgcact   660
tatgcgaaga gtaagtcttt cctttcctca agattgcggg aatacatgct gattgattga    720
acagtgtggg tcaaggtcaa gagcgtgtac gcccttacca ttaccagcgc cgagaagacg   780
gccctgacga gcatgttgaa cacgtgctaa                                    810

SEQ ID NO: 118              moltype = AA  length = 209
FEATURE                     Location/Qualifiers
source                      1..209
                            mol_type = protein
                            organism = Alternaria sp.
SEQUENCE: 118
MKSSILVALS SIALVSALPA PVTLEARAPP NIPTTAAAKT QLAGLTVAAQ GPQTGYSRDL    60
FPHWITQSGS CNTREVVLQR DGTGVVTDSA CAATSGSWYS VYDGATWTAA SDVDIDHMVP   120
LSNAWKSGAA SWTTARRQAF ANDLTNPQLL AVTDVNQAK GDKGPEDWKP PLTSYYCTYA    180
KMWVKVKSVY ALTITSAEKT ALTSMLNTC                                     209

SEQ ID NO: 119              moltype = AA  length = 192
FEATURE                     Location/Qualifiers
source                      1..192
                            mol_type = protein
                            organism = Alternaria sp.
SEQUENCE: 119
LPAPVTLEAR APPNIPTTAA AKTQLAGLTV AAQGPQTGYS RDLFPHWITQ SGSCNTREVV    60
LQRDGTGVVT DSACAATSGS WYSVYDGATW TAASDVDIDH MVPLSNAWKS GAASWTTARR   120
QAFANDLTNP QLLAVTDVN QAKGDKGPED WKPPLTSYYC TYAKMWVKVK SVYALTITSA    180
EKTALTSMLN TC                                                       192

SEQ ID NO: 120              moltype = DNA  length = 1004
FEATURE                     Location/Qualifiers
sig_peptide                 1..57
mat_peptide                 58..1001
source                      1..1004
                            mol_type = genomic DNA
                            organism = Trichoderma reesei
CDS                         1..75
```

```
CDS                       157..290
CDS                       360..516
CDS                       753..1001
SEQUENCE: 120
atgaagctgt ctttctctat tgccctcgcc tcggccatcg cggctctcgc tgctccggct    60
cctctacctg caccggtgcg taacttctcc tccgaccagt ctcagcacca taaatctaca   120
tacacatcag atatactgac gacccaactg taatagcccg ggatcccatc cgaagacacg   180
gcgagaaccc agctcgccgg cctcacagtc gccgttgttg gttctggcac gggctactcc   240
cgcgacttgt ttcctacctg ggatgccatc tccggcaact gcaatgctcg gtacgtcaag   300
cttccttgga ttcctactga taaaatacga agaggctgac tggcatattg ccataacagc   360
gagtacgtgt tgaagcgaga tggcgagggc gtccaggtca acaatgcctg cgaggcccag   420
tctgggagct ggatcagccc ctatgacaat gccagtttca caaacgcgtc cagcctggac   480
attgaccaca tggtgcctct gaagaatgcc tggattgtga gtctgccatc ttgcttctcc   540
gtggtctcag tctccatgtc cctctctgtc catcgttgcc ctctgatata ccccctggaac   600
tgttttcacc tctgcctcac acccacataa cctcagcatc tttgtcacac tcatcacttc   660
actacagttc ttctacttac tttattctcc ccttcgacct tcttccac cccctctcat    720
ctcatctcat acaccaact gactcgaccc agtccggcgc ctcaacctgg accaccgccc    780
agcgcgaggc cctcgccaac gacgtctccc gcccgcagtc ctgggccgtc tccgcgagct   840
ccaaccgctc caagggcgac cgcagccccg accagtggaa gccccgctg accagcttct   900
actgcacgta cgccaagtcg tggattgacg tcaagagcta ttacaagttg actattcga   960
gcgcggagaa gacggcgctg agcagcatgt tggatacctg ctag                  1004

SEQ ID NO: 121            moltype = AA   length = 205
FEATURE                   Location/Qualifiers
source                    1..205
                          mol_type = protein
                          organism = Trichoderma reesei
SEQUENCE: 121
MKLSFSIALA SAIAALAAPA PLPAPPGIPS EDTARTQLAG LTVAVVGSGT GYSRDLFPTW    60
DAISGNCNAR EYVLKRDGEG VQVNNACEAQ SGSWISPYDN ASFTNASSLD IDHMVPLKNA   120
WISGASTWTT AQREALANDV SRPQLWAVSA SSNRSKGDRS PDQWKPPLTS FYCTYAKSWI   180
DVKSYYKLTI TSAEKTALSS MLDTC                                        205

SEQ ID NO: 122            moltype = AA   length = 186
FEATURE                   Location/Qualifiers
source                    1..186
                          mol_type = protein
                          organism = Trichoderma reesei
SEQUENCE: 122
APLPAPPGIP SEDTARTQLA GLTVAVVGSG TGYSRDLFPT WDAISGNCNA REYVLKRDGE    60
GVQVNNACEA QSGSWISPYD NASFTNASSL DIDHMVPLKN AWISGASTWT TAQREALAND   120
VSRPQLWAVS ASSNRSKGDR SPDQWKPPLT SFYCTYAKSW IDVKSYYKLT ITSAEKTALS   180
SMLDTC                                                             186

SEQ ID NO: 123            moltype = DNA   length = 1049
FEATURE                   Location/Qualifiers
sig_peptide               1..48
mat_peptide               49..1046
source                    1..1049
                          mol_type = genomic DNA
                          organism = Chaetomium thermophilum
CDS                       1..72
CDS                       170..303
CDS                       563..719
CDS                       798..1046
SEQUENCE: 123
atgaagtttg tcacgatttt ctctttactt gccgctgttg tttcagccgc ccctgcgccg    60
cagccgactc tgtacgtaa agctcaagcc aacttccagt cttttgttct tcgattcgac   120
tcttgtcctc cgtttggaaa tacttgttcg gtcgactaac agcacgcagc cgggcatcc   180
gagtaggtcg actgctcaga gctatctcaa ttctctgaca gttgctgcct cgtacgacga   240
tgggaattac aaccgcgact tgttccccca ctggaacact gttagcggga cctgtaaatac   300
tcggtaagtc acccagctgt gaaagttgtc gggtgatgat gctggcacgc tgtgcaatga   360
gagtggtgga agatgcgagc gcaggtgtg ctccacttct gcctcgtgca actttggacg    420
tcctgctttc catctccagc gtctttgcga aagtgatgat cgccactcat ggtcgcttt    480
gcgacacatc gcctgtcttg ttatttgcac gattaaaagc tctatgcttc catccgacct   540
tcataactaa cgattgaccc agcgagtatg tcctcaagcg catggctcc aatgtcgtga    600
cgaactcggc ctgccaggct acttctggca catggtacag cccgtatgac ggcgctacgt   660
ggacagcagc atcagatatc gatatcgatc atatggtccc cttgaagatt gcttggattg   720
taggtctcca gcaacttagc aagattggcg tcgtgctgta cgtgctgtag acgttggtgg    780
ctaacgcata gagacagtct ggcgccaaca cctggtcgtc ctcgaagcgg tcctcctttg    840
ccaacgacat taatagccca cagctctggg ctgtcactga cagtgtcaac cagtctaagg    900
gcgacaagag ccctgacaag tggaagcctc ctctcaccac gttttactgc acctatgcca    960
agagttggat cacggtgaag tacaactata atttgaccat cacatctgca gagaagtctg   1020
ctctacagaa catgattaat acgtgctaa                                   1049

SEQ ID NO: 124            moltype = AA   length = 204
FEATURE                   Location/Qualifiers
source                    1..204
                          mol_type = protein
```

-continued

```
                        organism = Chaetomium thermophilum
SEQUENCE: 124
MKFVTIFSLL AAVVSAAPAP QPTPPGIPSR STAQSYLNSL TVAASYDDGN YNRDLFPHWN    60
TVSGTCNTRE YVLKRDGSNV VTNSACQATS GTWYSPYDGA TWTAASDIDI DHMVPLKNAW   120
ISGANTWSSS KRSSFANDIN SPQLWAVTDS VNQSKGDKSP DKWKPPLTTF YCTYAKSWIT   180
VKYNYNLTIT SAEKSALQNM INTC                                         204

SEQ ID NO: 125          moltype = AA  length = 188
FEATURE                 Location/Qualifiers
source                  1..188
                        mol_type = protein
                        organism = Chaetomium thermophilum
SEQUENCE: 125
APAPQPTPPG IPSRSTAQSY LNSLTVAASY DDGNYNRDLF PHWNTVSGTC NTREYVLKRD    60
GSNVVTNSAC QATSGTWYSP YDGATWTAAS DIDIDHMVPL KNAWISGANT WSSSKRSSFA   120
NDINSPQLWA VTDSVNQSKG DKSPDKWKPP LTTFYCTYAK SWITVKYNYN LTITSAEKSA   180
LQNMINTC                                                           188

SEQ ID NO: 126          moltype = DNA  length = 873
FEATURE                 Location/Qualifiers
sig_peptide             1..48
mat_peptide             49..870
source                  1..873
                        mol_type = genomic DNA
                        organism = Scytalidium thermophilum
CDS                     1..78
CDS                     179..312
CDS                     373..529
CDS                     622..870
SEQUENCE: 126
atgaagtcct ttattgtcta ttctttcctc gccgcggtgg ctacggcctt gccggccccg    60
gcgccgatgc ctactcccgt aagccctatt actgctcgag tcaatctgag gcgttctcga   120
aaggattatt atgcatgagg ataacctcca atgctaacat ggacgtctta atcccagcc   180
gggcattccc tcaaaatcaa cggcccagtc ccagctgaac gccctgacgg tcaaggcgg   240
ctatgacgat ggcaagtata agccgcgacc gttcctccac tggaacaccg tcagcggac   300
ttgcaacacc cggtaggttg atctttatgt ggttgagatt ctcagcagaa cgcagtctga   360
ctgtcgcaac agcgaaatatg tcctgaagcg cgacggggtc aacgtcgtca ccaactcggc   420
ctgcgctgcc acctcgggca catggtactc gcctttcgac ggcgccacct ggactgcggc   480
atctgatgtc gatattgacc acatggtgcc cctgaagaat gcctggattg taagcttctg   540
ctcaccgtcc aactgtttaa atgacagttt cgtgtcata agaatgattg agacctatac   600
tcacgctcgt tgacaatgca gtccggcgca acaactggaa cctcaaccaa gcggacgcag   660
ttcgccaacg acatcaacct gccccagctg tgggcggtca cggacgacgt gaaccaggcc   720
aagggcgaca agtctcccga caagtggaag cctcctccta cctccttcta ctgcacctac   780
gccaagagct ggatcacggt caagtacaac tacggcctca gcatcacgtc ggccgagaag   840
tcggcgttga ctagcatgat caacacttgc tga                               873

SEQ ID NO: 127          moltype = AA  length = 206
FEATURE                 Location/Qualifiers
source                  1..206
                        mol_type = protein
                        organism = Scytalidium thermophilum
SEQUENCE: 127
MKSFIVYSFL AAVATALPAP APMPTPPGIP SKSTAQSQLN ALTVKASYDD GKYKRDLFPH    60
WNTVSGTCNT REYVLKRDGV NVVTNSACAA TSGTWYSPFD GATWTAASDV DIDHMVPLKN   120
AWISGANNWT STKRTQFAND INLPQLWAVT DDVNQAKGDK SPDKWKPPLT SFYCTYAKSW   180
ITVKYNYGLS ITSAEKSALT SMINTC                                       206

SEQ ID NO: 128          moltype = AA  length = 190
FEATURE                 Location/Qualifiers
source                  1..190
                        mol_type = protein
                        organism = Scytalidium thermophilum
SEQUENCE: 128
LPAPAPMPTP PGIPSKSTAQ SQLNALTVKA SYDDGKYKRD LFPHWNTVSG TCNTREYVLK    60
RDGVNVVTNS ACAATSGTWY SPFDGATWTA ASDVDIDHMV PLKNAWISGA NNWTSTKRTQ   120
FANDINLPQL WAVTDDVNQA KGDKSPDKWK PPLTSFYCTY AKSWITVKYN YGLSITSAEK   180
SALTSMINTC                                                         190

SEQ ID NO: 129          moltype = DNA  length = 802
FEATURE                 Location/Qualifiers
sig_peptide             1..54
mat_peptide             55..799
source                  1..802
                        mol_type = genomic DNA
                        organism = Metapochonia suchlasporia
CDS                     1..72
CDS                     143..276
CDS                     329..485
CDS                     551..799
```

```
SEQUENCE: 129
atgaagttct cttcggcatc tctcgtcgtg tccgccgccg cgcttgtcct cggtgtgcct    60
gtgcctgcgc ccgtaagcaa tcccactcct gacacgctgt cattgtgtaa caaagcctga   120
taatgttttc ttgctcttct agccgggtat cccaagcact cgacagcca agactcttct   180
tgctggcctc aaggttgctg ttccattgag tggcgatggg tacagtcgtg agaagttccc   240
tcttttgggag accattcagg gaacttgcaa tgctcggtgg gtttatcaca tcttctctta   300
ttcctttcat gttgctaatg ccatgtagcc agtttgtcct taagcgagac ggaacagacg   360
tcaagaccaa caacgcatgt gtcgcagagt ctggcaactg gtctctccg tatgacgggg    420
tcaagttcac cgcagcacgc gatctcgaca ttgaccacat ggttccactg aagaacgctg   480
ggattgtaag actactgccc aactcttcct ctcctcaact tcacctactc tgtctaactt   540
tccttgccag tccggtgcct cacaatggac caccgagcgg cgcaaagctc tggccaacga   600
catcacccgc cccagcttt gggctgtatc agcccatgcc aaccgcggca agagtgacga    660
tagccccgat gagtggaagc ctcctctgaa gacgttttgg tgcacatacg ccaagagttg   720
ggtccaagtg aagagctttt atgagctgac tattacggat gccgagaagg gtgctctggc   780
tggcatgctg gattcatgct aa                                             802

SEQ ID NO: 130          moltype = AA   length = 204
FEATURE                 Location/Qualifiers
source                  1..204
                        mol_type = protein
                        organism = Metapochonia suchlasporia
SEQUENCE: 130
MKFSSASLVV SAAALVLGVP VPAPPGIPST STAKTLLAGL KVAVPLSGDG YSREKFPLWE    60
TIQGTCNARE FVLKRDGTDV KTNNACVAES GNWVSPYDGV KFTAARDLDI DHMVPLKNAW   120
ISGASQWTTE RRKALANDIT RPQLWAVSAH ANRGKSDDSP DEWKPPLKTF WCTYAKSWVQ   180
VKSFYELTIT DAEKGALAGM LDSC                                           204

SEQ ID NO: 131          moltype = AA   length = 186
FEATURE                 Location/Qualifiers
source                  1..186
                        mol_type = protein
                        organism = Metapochonia suchlasporia
SEQUENCE: 131
VPVPAPPGIP STSTAKTLLA GLKVAVPLSG DGYSREKFPL WETIQGTCNA REFVLKRDGT    60
DVKTNNACVA ESGNWVSPYD GVKFTAARDL DIDHMVPLKN AWISGASQWT TERRKALAND   120
ITRPQLWAVS AHANRGKSDD SPDEWKPPLK TFWCTYAKSW VQVKSFYELT ITDAEKGALA   180
GMLDSC                                                               186

SEQ ID NO: 132          moltype = DNA   length = 771
FEATURE                 Location/Qualifiers
sig_peptide             1..54
mat_peptide             55..768
source                  1..771
                        mol_type = genomic DNA
                        organism = Daldinia fissa
CDS                     1..108
CDS                     177..467
CDS                     520..768
SEQUENCE: 132
atgaggttct cattcaccct tggcagtctc tatccgcga gcgccgtgct cgccgcgccg     60
gcgccaattc cggttgccga gcccgccccc atgcccatgc ctactcccgt tcgtaatcac   120
cttgccctat ccataaacgc aacaacagct cttcaaaac tgacagatgt aattagcctg    180
gcatcccatc tgcctcgtca gctaaatctc aactcgcaag cttgaccgtc aaggcggcgg   240
tcgacgacgg aggataccag cgggacttgt tcccgacgtg ggacaccatc acgggaacct   300
gtaacacgcg cgagtacgtc ctcaagcgcg acggcgccaa cgtccaggtc ggctctgact   360
gttatccgac gagcggcaca tggaccagtc cctacgatgg tgggaagtgg acatccaccgt   420
ctgatgtgga tatcgaccac atggtacctt gaagaatgc ctgggttgta tgtatttcat    480
gctttacctg tttatcaccg tttaactaat tatatgtagt ccggggcgaa caaatggaca   540
actgccaagc gcgagcaatt cgccaacgat gttgatcgac cacagctctg ggccgtaacg   600
gataacgtta attcatctaa gggcgacaaa tctcccgata cctgaagcc gcctctaaca    660
agcttctatt gcacttatgc gagcgcttac gtcgccgtca agagctattg ggcttaact   720
atcacgtcgg ctgagaaatc ggctctaagt gacatgttag gaacttgtta g             771

SEQ ID NO: 133          moltype = AA   length = 216
FEATURE                 Location/Qualifiers
source                  1..216
                        mol_type = protein
                        organism = Daldinia fissa
SEQUENCE: 133
MRFSFTLGSL LSASAVLAAP APIPVAEPAP MPMPTPPGIP SASSAKSQLA SLTVKAAVDD    60
GGYQRDLFPT WDTITGTCNT REYVLKRDGA NVQVGSDCYP TSGTWTSPYD GGKWTSPSDV   120
DIDHMVPLKN AWVSGANKWT TAKREQFAND VDRPQLWAVT DNVNSSKGDK SPDTWKPPLT   180
SFYCTYASAY VAVKSYWGLT ITSAEKSALS DMLGTC                              216

SEQ ID NO: 134          moltype = AA   length = 198
FEATURE                 Location/Qualifiers
source                  1..198
                        mol_type = protein
                        organism = Daldinia fissa
```

```
SEQUENCE: 134
APAPIPVAEP APMPMPTPPG IPSASSAKSQ LASLTVKAAV DDGGYQRDLF PTWDTITGTC    60
NTREYVLKRD GANVQVGSDC YPTSGTWTSP YDGGKWTSPS DVDIDHMVPL KNAWVSGANK   120
WTTAKREQFA NDVDRPQLWA VTDNVNSSKG DKSPDTWKPP LTSFYCTYAS AYVAVKSYWG   180
LTITSAEKSA LSDMLGTC                                                198

SEQ ID NO: 135          moltype = DNA  length = 805
FEATURE                 Location/Qualifiers
sig_peptide             1..51
mat_peptide             52..802
source                  1..805
                        mol_type = genomic DNA
                        organism = Acremonium sp.
CDS                     1..75
CDS                     152..442
CDS                     554..802
SEQUENCE: 135
atgaagttct ccatcgcaac cctcctcacg gccgtgtcca ccatcaccgc cctcccgctc    60
caatctcgtg accccgtacg tatttttatc ccttctccaa ctcataatcc catatcgtca   120
agacctctca gactaaacat cgtcaaaaca gcccggcatt ccctccaccg caaccgccaa   180
atctctcctc aacggcctca ccgtaaaggc atggtccaac gaaggaacct atgatcgtga   240
cctctttcct cactggcaga ccatcgaggg gacgtgcaac gcgagggaat acgttctgaa   300
gagggatggc cagaatgttg tggtaaacag tgcttgcacg gcacagtctg ggacgtggaa   360
gagtgtttat gatggggaga ctaccaactc tgcatcggat cttgacattg atcacatgat   420
ccccttgaag aatgcttgga tcgtgagttc ccccctccc cttcgcagca ttctcaaaaa   480
aaaaaacaat gtctacccac atccctcgca tcttcaactg ttgcccaact aacaaacaac   540
cccccaacc cagtccggcg ccgcaccctg gaccaccgca cagcgcacct cctttgcaaa   600
cgacatttcc tcccccagc tctgggccgt caccgcgggc gtcaaccgct cgaaatctga   660
ccgctcgccg gatacctggg tgccccccct ggccagcttc cactgcacgt atggcaaagc   720
gtgggtgcag gtcaagagca gtgggcgtt gagcatcacg agcgcggaga agagtgcgct   780
tacggggttg ttgaacaagt gctaa                                        805

SEQ ID NO: 136          moltype = AA  length = 205
FEATURE                 Location/Qualifiers
source                  1..205
                        mol_type = protein
                        organism = Acremonium sp.
SEQUENCE: 136
MKFSIATLLT AVSTITALPL QSRDPPGIPS TATAKSLLNG LTVKAWSNEG TYDRDLFPHW    60
QTIEGTCNAR EYVLKRDGQN VVVNSACTAQ SGTWKSVYDG ETTNSASDLD IDHMIPLKNA   120
WISGAATWTT AQRTSFANDI SSPQLWAVTA GVNRSKSDRS PDTWVPPLAS FHCTYGKAWV   180
QVKSKWALSI TSAEKSALTG LLNKC                                        205

SEQ ID NO: 137          moltype = AA  length = 188
FEATURE                 Location/Qualifiers
source                  1..188
                        mol_type = protein
                        organism = Acremonium sp.
SEQUENCE: 137
LPLQSRDPPG IPSTATAKSL LNGLTVKAWS NEGTYDRDLF PHWQTIEGTC NAREYVLKRD    60
GQNVVVNSAC TAQSGTWKSV YDGETTNSAS DLDIDHMIPL KNAWISGAAT WTTAQRTSFA   120
NDISSPQLWA VTAGVNRSKS DRSPDTWVPP LASFHCTYGK AWVQVKSKWA LSITSAEKSA   180
LTGLLNKC                                                           188

SEQ ID NO: 138          moltype = DNA  length = 663
FEATURE                 Location/Qualifiers
sig_peptide             1..51
mat_peptide             52..660
source                  1..663
                        mol_type = genomic DNA
                        organism = Acremonium dichromosporum
CDS                     1..348
CDS                     412..660
SEQUENCE: 138
atgagggctg tactcgctgc cgtgctctac tccgctgtcg cggttgttgc cattcctcct    60
ggtattccca gtgaggcgac tgcgcgctcg cttctcagca gcctgactgt ggcgcccacc   120
gttgacgatg gcacctacga tcgcgacctg ttccctcact ggtcttcagt cgagggcaac   180
tgcaacgcgc gagagttcgt tctccgtcgt gatggtgacg gtgtctcggt tggaaatgac   240
tgctatccca ccgctggcac ctggacgtgc ccatatgatg gaaagagaca cagcgtgccc   300
agcgatgtct caatcgacca catggtgcct ctgcacaacg cgtggatggt acgttgcctc   360
atcgtagaaa acatgcacga ttcgcccctg ctgacatgat tctccaaaaa gactggtgct   420
tctgagtgga ccacgcgga acgcgaggcg tttgccaatg acattgacgg ccccagctg   480
tgggctgtca ctagcacgac caactcgcaa aaggggtcgg acgcgccaga tgagtggcag   540
cctccccaga cgagcattca ctgcaagtac gctgctgcgt ggatccaggt caagagcacc   600
tacgacctga ctgtgagctc ggcagagcag gccgctctgg aggaaatgct gggcaggtgc   660
tga                                                                663

SEQ ID NO: 139          moltype = AA  length = 199
FEATURE                 Location/Qualifiers
```

```
source                   1..199
                         mol_type = protein
                         organism = Acremonium dichromosporum
SEQUENCE: 139
MRAVLAAVLY SAVAVVAIPP GIPSEATARS LLSSLTVAPT VDDGTYDRDL FPHWSSVEGN    60
CNAREFVLRR DGDGVSVGND CYPTAGTWTC PYDGKRHSVP SDVSIDHMVP LHNAWMTGAS   120
EWTTAEREAF ANDIDGPQLW AVTSTTNSQK GSDAPDEWQP PQTSIHCKYA AAWIQVKSTY   180
DLTVSSAEQA ALEEMLGRC                                                199

SEQ ID NO: 140           moltype = AA  length = 182
FEATURE                  Location/Qualifiers
source                   1..182
                         mol_type = protein
                         organism = Acremonium dichromosporum
SEQUENCE: 140
IPPGIPSEAT ARSLLSSLTV APTVDDGTYD RDLFPHWSSV EGNCAREFV LRRDGDGVSV    60
GNDCYPTAGT WTCPYDGKRH SVPSDVSIDH MVPLHNAWMT GASEWTTAER EAFANDIDGP   120
QLWAVTSTTN SQKGSDAPDE WQPPQTSIHC KYAAAWIQVK STYDLTVSSA EQAALEEMLG   180
RC                                                                 182

SEQ ID NO: 141           moltype = DNA  length = 802
FEATURE                  Location/Qualifiers
sig_peptide              1..51
mat_peptide              52..799
source                   1..802
                         mol_type = genomic DNA
                         organism = Sarocladium sp.
CDS                      1..75
CDS                      141..274
CDS                      331..487
CDS                      551..799
SEQUENCE: 141
atgaagttct tcattcctac cttgttgtcg gcggtggtga ccgttctggc ggtgccgatt    60
cctctccctg atccggtaag catcttctcg tcttggcttt gtcttcacat gtgtcgagca   120
ggagcttatc tcgagtatag ccgggcattc ctagctcttc gactgcgaat acgttgctgg   180
ccggcctgac agttcgtgcc tctagcaatg aggacactta caaccgtgat ctgttcccgc   240
actgggtcgc catttcgggc aactgcaacg ctcggtgagt tttccaatgc tggatcgact   300
tcacatggca ttgacggact cgcctctag tgaatatgtt cttcggcgtg atggcaccaa   360
tgtggtagtc aatactgcct gcgtcccgca gtccggcaca tggcgcagtc cttacgatgg   420
cgagtcgacc accaacgcaa gtgacctcga cattgaccac atggtccctc tcaagaacgc   480
atggatcgta agtcttcccc gtcctcaa tcacactaca taatctcttg ctaacaccac   540
ctgtgcaaag tccggcgctg cttcctggac caccgccaag cgccaggact cgccaacga   600
cgtgtccggc ccccagctgt gggctgtcac tgccggtgtg aaccggtcca agggtgacaa   660
gagccctgat tcatgggtgc cgccgttggc gagtttccat tgcacatatg caaggtcttg   720
gatccaggtg aagagctcat gggccctgag cgtgacgagc gcggagaagg ctgctttgac   780
cgacttgctg agcacttgct ga                                           802

SEQ ID NO: 142           moltype = AA  length = 205
FEATURE                  Location/Qualifiers
source                   1..205
                         mol_type = protein
                         organism = Sarocladium sp.
SEQUENCE: 142
MKFFIPTLLS AVVTVLAVPI PLPDPPGIPS SSTANTLLAG LTVRASSNED TYNRDLFPHW    60
VAISGNCNAR EYVLRRDGTN VVVNTACVPQ SGTWRSPYDG ESTTNASDLD IDHMVPLKNA   120
WISGAASWTT AKRQDFANDV SGPQLWAVTA GVNRSKGDKS PDSWVPPLAS FHCTYARSWI   180
QVKSSWALSV TSAEKAALTD LLSTC                                         205

SEQ ID NO: 143           moltype = AA  length = 188
FEATURE                  Location/Qualifiers
source                   1..188
                         mol_type = protein
                         organism = Sarocladium sp.
SEQUENCE: 143
VPIPLPDPPG IPSSSTANTL LAGLTVRASS NEDTYNRDLF PHWVAISGNC NAREYVLRRD    60
GTNVVVNTAC VPQSGTWRSP YDGESTTNAS DLDIDHMVPL KNAWISGAAS WTTAKRQDFA   120
NDVSGPQLWA VTGVNRSKG DKSPDSWVPP LASFHCTYAR SWIQVKSSWA LSVTSAEKAA   180
LTDLLSTC                                                           188

SEQ ID NO: 144           moltype = DNA  length = 815
FEATURE                  Location/Qualifiers
sig_peptide              1..57
mat_peptide              58..812
source                   1..815
                         mol_type = genomic DNA
                         organism = Metarhizium sp.
CDS                      1..75
CDS                      160..293
CDS                      348..504
```

```
CDS                     564..812
SEQUENCE: 144
atgaggttct cctcggcatc atttcttgtc gtgtctgccg ctgcggttgt cctcggtgtg   60
cctgtgcctg cgcccgtaag ccctctcccg cctgtcctat gccatgccat gccatccatc  120
ttgtgtaaca agaagaaaca aaacgctgac gcttttcagc cgggtatccc aactgcttcc  180
accgccagga ctcttcttgc tggcctcaag gttgctacgc cgttgagcgg tgatggctac  240
tctcgcaccc tgttccctac gtgggagacc atcgagggaa cctgcaacgc tcggtaggct  300
ttttcttctc ttctctgtca gagacaaggt actaaacatg tatgtagcga gtttgtactc  360
aagcgagatg gaacagacgt ccagaccaac accgcatgtc tcgcccagtc tggcaactgg  420
gtttctccgt atgacggcgt cgcattcact gccgcctcgg atctcgacat tgaccacatg  480
gttccactga agaatgcctg gattgtaaga ccaaagacag cattgataac aaggagtcac  540
cctgtctaac tctcatctca cagtccggcg cctcgcaatg gaccacggac aagcgcaaag  600
gtctcgccaa cgacatcacc cgtcctcagc tctgggccgt ctctgcccat gccaaccgcg  660
ccaagggcga cagcagcccc gacgagtgga gcctcctcca gaagacgttc tggtgtactt  720
acgcgaggag ttgggtccag gtcaagagct attatgcgct gaccattact gatgctgaga  780
gggcgcgct gtcaggcatg ctggattctt gctaa                              815

SEQ ID NO: 145          moltype = AA   length = 205
FEATURE                 Location/Qualifiers
source                  1..205
                        mol_type = protein
                        organism = Metarhizium sp.
SEQUENCE: 145
MRFSSASFLV VSAAAVVLGV PVPAPPGIPT ASTARTLLAG LKVATPLSGD GYSRTLFPTW   60
ETIEGTCNAR EFVLKRDGTD VQTNTACVAQ SGNWVSPYDG VAFTAASDLD IDHMVPLKNA  120
WISGASQWTT DKRKGLANDI TRPQLWAVSA HANRAKGDSS PDEWKPPLKT FWCTYARSWV  180
QVKSYYALTI TDAEKGALSG MLDSC                                        205

SEQ ID NO: 146          moltype = AA   length = 186
FEATURE                 Location/Qualifiers
source                  1..186
                        mol_type = protein
                        organism = Metarhizium sp.
SEQUENCE: 146
VPVPAPPGIP TASTARTLLA GLKVATPLSG DGYSRTLFPT WETIEGTCNA REFVLKRDGT   60
DVQTNTACVA QSGNWVSPYD GVAFTAASDL DIDHMVPLKN AWISGASQWT TDKRKGLAND  120
ITRPQLWAVS AHANRAKGDS SPDEWKPPLK TFWCTYARSW VQVKSYYALT ITDAEKGALS  180
GMLDSC                                                             186

SEQ ID NO: 147          moltype = DNA   length = 794
FEATURE                 Location/Qualifiers
sig_peptide             1..51
mat_peptide             52..791
source                  1..794
                        mol_type = genomic DNA
                        organism = Acremonium sp.
CDS                     1..75
CDS                     136..269
CDS                     326..482
CDS                     543..791
SEQUENCE: 147
atgaggttca tcattccgac ttttcttggc cactgcggcc actgtgctgg agcgccgatc   60
gctgtccggg acccagttag ctctcactcc ccgtctcagg catgtaacga gagtaaggag  120
ctaacttata tacagcctgg tatcccaagt gcatcgacgg ccaacacgtt gctggcgggt  180
ctgacggtta gggcttcaag caacgaagac agttatgatc gcaacctctt ccccactgg  240
tctgccatat ccggaaattg caacgctcgg taggacaacg cccccaagca ctgcgatgga  300
acgaacgccg cttaccaaat attagtgagt tcgtcctcga gcgcgacggc accaacgtcg  360
tggtcaacaa cgcctgcgtc gcccagtcgg ggacttggcg cagcccttat gacggcgaga  420
cgacgggtaa tgccagtgac ctggacatcg accacatggt gcctctcaag aacgcctgga  480
tcgtaggtgt cccgtactcg atcacccgag ttagtaggcc ggagctgacc atgtctctgc  540
agtctggcgc ctcttcatgg agcaccacga gactgcagga gtttgccaac gatgtctccg  600
ggcctcagct gtgggccgtc accgcgggtg tgaaccgctc aagggtgac aggagccccg  660
actcgtgggt gccgcctctg gctagcttcc actgcactgta cgcgaagtct tgggtgcagg  720
tgaagagctc atggtccttg agtgtgacga gcgcggaaaa ggcggcgcta tcggacctcc  780
tgggtacttg ctga                                                    794

SEQ ID NO: 148          moltype = AA   length = 205
FEATURE                 Location/Qualifiers
source                  1..205
                        mol_type = protein
                        organism = Acremonium sp.
SEQUENCE: 148
MRFIIPTFLA TAATVLAAPI AVRDPPGIPS ASTANTLLAG LTVRASSNED SYDRNLFPHW   60
SAISGNCNAR EFVLERDGTN VVVNNACVAQ SGTWRSPYDG ETTGNASDLD IDHMVPLKNA  120
WISGASSWST TRRQEFANDV SGPQLWAVTA GVNRSKGDRS PDSWVPPLAS FHCTYAKSWV  180
QVKSSWSLSV TSAEKAALSD LLGTC                                        205

SEQ ID NO: 149          moltype = AA   length = 188
FEATURE                 Location/Qualifiers
```

```
source                  1..188
                        mol_type = protein
                        organism = Acremonium sp.
SEQUENCE: 149
APIAVRDPPG IPSASTANTL LAGLTVRASS NEDSYDRNLF PHWSAISGNC NAREFVLERD    60
GTNVVVNNAC VAQSGTWRSP YDGETTGNAS DLDIDHMVPL KNAWISGASS WSTTRRQEFA   120
NDVSGPQLWA VTAGVNRSKG DRSPDSWVPP LASFHCTYAK SWVQVKSSWS LSVTSAEKAA   180
LSDLLGTC                                                            188

SEQ ID NO: 150           moltype = DNA   length = 964
FEATURE                  Location/Qualifiers
sig_peptide              1..45
mat_peptide              46..961
source                   1..964
                         mol_type = genomic DNA
                         organism = Isaria tenuipes
CDS                      1..63
CDS                      126..259
CDS                      393..549
CDS                      713..961
SEQUENCE: 150
atgcgcatct ctggcctcct cgccgctgcc acaatcgccc tcgcggctcc cgtgccggag    60
cctgtaagag ccctccctct ccgttggcca ccttctcgcg tataagccac taacagacga   120
cgcagcccgg gatccccagc accagccacg cccaaagcga cctcaacagc ctccaggtcg   180
ctgcctctgc tccggtgat  ggctactcgc gcgccgagtt ccctcactgg gtctcggttg   240
agggcagctg tgactctcgg tatgaaccag cctcccccc aagttccacc gcatgggtca    300
tgtttcccac gttttgtttc tggccgacgc aacgttgtgc tccctgacca caaacgctaa   360
cggccctttt cttcttctgt ccattcatgt agtgaatacg tcctgaagcg tgacggccag   420
gacgtccagg ccgactcgtc ctgcaagatt acttccggca cctgggtcag tccctacgac   480
gcgaccacct ggaccaacag ctccaaggtc gacattgacc acctggtgcc tctcaagaat   540
gcctggattg tacgtctctg ccctttcccc tttgctctcc tcatctctca gcgctgtgtc   600
tttcccccaa aagctcacaa cgcccaacat ccctcatcga gtggcccggg gggggggcac   660
aacatctctg ctgtgcgagt aaacaacgtt tcgccaacta ccctctccc agtctggtgc    720
ctcgagctgg accaaggcac agcgtcaaga ctttgccaac gacatcaagc gcccccagct   780
ctacgccgtc agcgagaacg ccaaccgctc caagggcgac gcagcccgga acggctggaa   840
gccccgctg aagagcttct actgcaccta tgccaagtcc tgggtcgccg tcaagagcta   900
ctacaagctg accattacct cggccgagaa gtcggccctg gcgacatgc tcgacacttg   960
ctga                                                                964

SEQ ID NO: 151           moltype = AA   length = 201
FEATURE                  Location/Qualifiers
source                   1..201
                         mol_type = protein
                         organism = Isaria tenuipes
SEQUENCE: 151
MRISGLLAAA TIALAAPVPE PPGIPSTSTA QSDLNSLQVA ASGSGDGYSR AEFPHWVSVE    60
GSCDSREYVL KRDGDVQAD SSCKITSGTW VSPYDATTWT NSSKVDIDHL VPLKNAWISG    120
ASSWTKAQRQ DFANDIKRPQ LYAVSENANR SKGDRSPDGW KPPLKSFYCT YAKSWVAVKS   180
YYKLTITSAE KSALGDMLDT C                                             201

SEQ ID NO: 152           moltype = AA   length = 186
FEATURE                  Location/Qualifiers
source                   1..186
                         mol_type = protein
                         organism = Isaria tenuipes
SEQUENCE: 152
APVPEPPGIP STSTAQSDLN SLQVAASGSG DGYSRAEFPH WVSVEGSCDS REYVLKRDGQ    60
DVQADSSCKI TSGTWVSPYD ATTWTNSSKV DIDHLVPLKN AWISGASSWT KAQRQDFAND   120
IKRPQLYAVS ENANRSKGDR SPDGWKPPLK SFYCTYAKSW VAVKSYYKLT ITSAEKSALG   180
DMLDTC                                                              186

SEQ ID NO: 153           moltype = DNA   length = 779
FEATURE                  Location/Qualifiers
sig_peptide              1..51
mat_peptide              52..776
source                   1..779
                         mol_type = genomic DNA
                         organism = Scytalidium circinatum
CDS                      1..57
CDS                      112..251
CDS                      316..472
CDS                      528..776
SEQUENCE: 153
atgaagtcg agctcgctgc cctcgtctcc gccgcctctc tggctgttgc cgctcccgta     60
tgctcgtctc gatccaacat cctcttaata gatgctgacc aagctgtcta gcccggcatt   120
cccagcgcct ccactgccag ctcccttcctt ggtgaactgg ccgtcgctga ccagtggac   180
gacggcagct atgaccgtga cctgttcccc cactgggagc ccatccctgg cgagactgcc   240
tgcagtgctc ggtaggttac gccattatgt tctaagccgt actgcctcga ccgcccactg   300
acagattctc aacagcgagt atgttctgcg ccgtgatggc accggcgttg agaccggcag   360
```

```
cgactgctat ccgacttcgg gcacatggtc cagcccctac gatggcggca gctggaccgc    420
tcccagcgac gtggacattg accacatggt tcctctgaag aacgcctgga tcgtatgtct    480
tgcattcgaa cccacatgaa aggcaggccc atgctaactt tacccagtct ggtgcctccg    540
agtggactac cgctgagcgc gaggcctttg ccaacgacat cgatggaccc agctatgggc    600
ccgtcaccga cgaggtcaac cagagcaaga gtgaccagag ccccgactgg tggaagcccc    660
ctctgtccag cttctactgc acctatgcct gcgcctggat ccaggtcaag agcacctaca    720
gcctgtccat cagctctgcc gagcaggctg ccttggaaga tatgctcggt agctgctag    779
```

SEQ ID NO: 154          moltype = AA  length = 201
FEATURE                 Location/Qualifiers
source                  1..201
                         mol_type = protein
                         organism = Scytalidium circinatum
SEQUENCE: 154
```
MKFELAALVS AASLAVAAPP GIPSASTASS LLGELAVAEP VDDGSYDRDL FPHWEPIPGE    60
TACSAREYVL RRDGTGVETG SDCYPTSGTW SSPYDGGSWT APSDVDIDHM VPLKNAWISG   120
ASEWTTAERE AFANDIDGPQ LWAVTDEVNQ SKSDQSPDEW KPPLSSFYCT YACAWIQVKS   180
TYSLSISSAE QAALEDMLGS C                                            201
```

SEQ ID NO: 155          moltype = AA  length = 184
FEATURE                 Location/Qualifiers
source                  1..184
                         mol_type = protein
                         organism = Scytalidium circinatum
SEQUENCE: 155
```
APPGIPSAST ASSLLGELAV AEPVDDGSYD RDLFPHWEPI PGETACSARE YVLRRDGTGV    60
ETGSDCYPTS GTWSSPYDGG SWTAPSDVDI DHMVPLKNAW ISGASEWTTA EREAFANDID   120
GPQLWAVTDE VNQSKSDQSP DEWKPPLSSF YCTYACAWIQ VKSTYSLSIS SAEQAALEDM   180
LGSC                                                               184
```

SEQ ID NO: 156          moltype = DNA  length = 805
FEATURE                 Location/Qualifiers
sig_peptide            1..57
mat_peptide            58..802
source                  1..805
                         mol_type = genomic DNA
                         organism = Metarhizium lepidiotae
CDS                     1..75
CDS                     133..266
CDS                     338..494
CDS                     554..802
SEQUENCE: 156
```
atgaagttct cctcggcatc atttctcgtc gtgtctgccg ctgcggttgt ccttggtgtg     60
cctgtgcctg cgcccgtaag ccctcccatc ttgtgtaaca aggggaaaca aaaaaatgct    120
gactcttttcc agccgggtat tccaactgct tcgaccgcca ggactcttct tgctggcctc    180
aaggttgcta cgccgttgag cggtgatggc tactctcgca ccctgttccc tacgtgggag    240
accatcgagg gaacttgcaa cgctcggtgg gcatttcttt ttcttctttt tcttcttctc    300
ttctctgtca gagacaaggt gctaaacatg aatctagcga gttttgtactc aagcgagatg    360
gaacagacgt ccagaccaac acggcatgtg tcgccgagtc tggcaactgg gtttctccgt    420
atgacgcgct ctcattcacc gccgcctcgg atctcgacat tgaccacatg gttccactca    480
agaatgcctg gattgtaaga cccaagaccg cattgatacc aaggagcctc cctgtctaac    540
tctcgtctcc cagtccggcg cctcgcaatg gaccacggac aagcgcaaag atctcgccaa    600
cgacatcacc cgtcctcagc tctgggccgt ctctgcccat gccaaccgtt ccaagggcga    660
cagcagcccc gacgagtgga agcctccct gcagaccttc tggtgcacct actccaagag    720
ctggatccag gtcaagagcc attactcact gaccattacc gatgctgaga gggcgcgct    780
gtcaggcatg ctagactctt gctaa                                         805
```

SEQ ID NO: 157          moltype = AA  length = 205
FEATURE                 Location/Qualifiers
source                  1..205
                         mol_type = protein
                         organism = Metarhizium lepidiotae
SEQUENCE: 157
```
MKFSSASFLV VSAAAVVLGV PVPAPPGIPT ASTARTLLAG LKVATPLSGD GYSRTLFPTW    60
ETIEGTCNAR EFVLKRDGTD VQTNTACVAE SGNWVSPYDG VSFTAASDLD IDHMVPLKNA   120
WISGASQWTT DKRKDLANDI TRPQLWAVSA HANRSKGDSS PDEWKPPLQT FWCTYSKSWI   180
QVKSHYSLTI TDAEKGALSG MLDSC                                        205
```

SEQ ID NO: 158          moltype = AA  length = 186
FEATURE                 Location/Qualifiers
source                  1..186
                         mol_type = protein
                         organism = Metarhizium lepidiotae
SEQUENCE: 158
```
VPVPAPPGIP TASTARTLLA GLKVATPLSG DGYSRTLFPT WETIEGTCNA REFVLKRDGT    60
DVQTNTACVA ESGNWVSPYD GVSFTAASDL DIDHMVPLKN AWISGASQWT TDKRKDLAND   120
ITRPQLWAVS AHANRSKGDS SPDEWKPPLQ TFWCTYSKSW IQVKSHYSLT ITDAEKGALS   180
GMLDSC                                                             186
```

| SEQ ID NO: 159 | moltype = DNA length = 1759 |
|---|---|
| FEATURE | Location/Qualifiers |
| sig_peptide | 501..578 |
| mat_peptide | 579..1256 |
| source | 1..1759 |
| | mol_type = genomic DNA |
| | organism = Thermobispora bispora |
| CDS | 501..1256 |

SEQUENCE: 159

| | | | | | | |
|---|---|---|---|---|---|---|
| ccgccgtacg | ccctgggctg | tgacaaggat | ccggagcggg | tggcctgcga | ctacccgccg | 60 |
| tacctgctgg | acaagatcgt | cagcgcgcgg | ttcgcggaga | acggcggcaa | ggcctacgag | 120 |
| ctcatcaaga | acttcacctg | gaccaacgag | gaccagagcg | cggtcgcgta | cgacatggcg | 180 |
| gtgaacaaca | tgtccgccga | cgacgcgcg | cggaagtgga | tcgaggcgaa | caaggtcgtc | 240 |
| tggcagtcct | ggctcccgtc | ctgagcggtg | ggcccgtgga | accggcccgg | ccggagccgc | 300 |
| gccggaggcc | atgagcgcgt | tgcgctgccc | gctgtgcccg | cgtacccgct | gtgcccgccc | 360 |
| acccggcgtc | ccgggcttcc | ggccggtga | tctcgacgcg | cccggcggg | gccacaccct | 420 |
| gacgaccggg | gtgatttctc | ccgcttattt | gcctttgcta | tagataccta | ggtcaagatc | 480 |
| accaagacct | aggggggcca | ttgggcggga | gacgatccct | gatcgcgagc | gcggccctg | 540 |
| cgctggccgt | gctgaccgga | tgcggaacgg | cggacggcct | cgacatcgcc | gacggccgcc | 600 |
| cggcgggcgg | gaaggccgcc | gaggcggcga | ccggcaccag | cccgctggcg | aatccggacg | 660 |
| gcacgcgtcc | cgggctggcc | gcgatcacct | cggccgatga | gcgggccgag | gcacgggctc | 720 |
| tgatcgagcg | gctccggacc | aaggggcgag | gaccgaaggc | gctacgaggt | cgggagaagt | 780 |
| tcgggtacgc | ctgggccgac | tccgtgacgg | gcatcccgtt | cggcgcaac | ggatgcgaca | 840 |
| cccgcaacga | cgtgctgaag | cggacggcc | agcggctgca | gttccggagc | gggtcggact | 900 |
| gcgtggtgat | ctcgatgacc | ctgttcgacc | cgtacaccgg | caagaccatc | gagtggacca | 960 |
| agcagaacgc | ggccgaggtg | cagatcgacc | acgtggtgcc | gctctcctac | tcctggcaga | 1020 |
| tgggcgcgtc | ccggtggagt | gacgagaagc | gccggcagct | cgccaacgac | ccgctcaacc | 1080 |
| tcatgccggt | cgacgcgcc | acgaactcgc | ggaagggcga | ctccggcccg | gcgtcctggc | 1140 |
| tgccgccgcg | ccgggagatc | cgctgcgcgt | acgtggtccg | gttcgcccag | gtggcgctca | 1200 |
| agtacgacct | gcccgtcacc | accgacaaga | aggagaccat | gctgcagcaa | tgctcctgag | 1260 |
| cgcggccgcc | gcgcggccgg | acaggggcgc | cgccggggca | cggggcgtc | gccgggacgg | 1320 |
| gaggcagggc | cgctcggccg | tgggccggtg | acgtgcgcgc | gccgggccg | cgtcggcgg | 1380 |
| gtgccgtcgc | cgcgccgcgc | cccgcgcggg | ccgcagcgcc | ccgcgccggc | cgcacggtgg | 1440 |
| ccggggccgcg | cccccggtcgg | ccagtggccg | gaactgcgct | cccccggtcag | ccggtggccg | 1500 |
| aggggctccg | ctccggtca | gccggtggcg | cggccggagc | tccggtcag | ctgccgcgg | 1560 |
| agcgacgcgt | cgagcacctc | ggcggtgtgc | gcgaccctga | gcggcccctt | gccggccgc | 1620 |
| cggaccgcgg | cggcgatctg | cagggtgcac | ccgggttcg | cggagacgag | caggtcggca | 1680 |
| ccggtggcga | gcacgtgccc | ggccttccgg | gcgccgagct | cccgggccgc | ctccggctgg | 1740 |
| aacaggttgt | aggtgccgg | | | | | 1759 |

| SEQ ID NO: 160 | moltype = AA length = 252 |
|---|---|
| FEATURE | Location/Qualifiers |
| source | 1..252 |
| | mol_type = protein |
| | organism = Thermobispora bispora |

SEQUENCE: 160

| | | | | | | |
|---|---|---|---|---|---|---|
| LGGRRSLIAS | AALALAVLTG | CGTADGLDIA | DGRPAGGKAA | EAATGTSPLA | NPDGTRPGLA | 60 |
| AITSADERAE | ARALIERLRT | KGRGPKTGYE | REKFGYAWAD | SVDGIPFGRN | GCDTRNDVLK | 120 |
| RDGQRLQFRS | GSDCVVISMT | LFDPYTGKTI | EWTKQNAAEV | QIDHVVPLSY | SWQMGASRWS | 180 |
| DEKRRQLAND | PLNLMPVDGA | TNSRKGDSGP | ASWLPPRREI | RCAYVVRFAQ | VALKYDLPVT | 240 |
| TADKETMLQQ | CS | | | | | 252 |

| SEQ ID NO: 161 | moltype = AA length = 226 |
|---|---|
| FEATURE | Location/Qualifiers |
| source | 1..226 |
| | mol_type = protein |
| | organism = Thermobispora bispora |

SEQUENCE: 161

| | | | | | | |
|---|---|---|---|---|---|---|
| LDIADGRPAG | GKAAEAATGT | SPLANPDGTR | PGLAAITSAD | ERAEARALIE | RLRTKGRGPK | 60 |
| TGYEREKFGY | AWADSVDGIP | FGRNGCDTRN | DVLKRDGQRL | QFRSGSDCVV | ISMTLFDPYT | 120 |
| GKTIEWTKQN | AAEVQIDHVV | PLSYSWQMGA | SRWSDEKRRQ | LANDPLNLMP | VDGATNSRKG | 180 |
| DSGPASWLPP | RREIRCAYVV | RFAQVALKYD | LPVTTADKET | MLQQCS | | 226 |

| SEQ ID NO: 162 | moltype = DNA length = 925 |
|---|---|
| FEATURE | Location/Qualifiers |
| sig_peptide | 1..48 |
| mat_peptide | 49..922 |
| source | 1..925 |
| | mol_type = genomic DNA |
| | organism = Sporormia fimetaria |
| CDS | 1..200 |
| CDS | 353..524 |
| CDS | 616..754 |
| CDS | 813..922 |

SEQUENCE: 162

| | | | | | | |
|---|---|---|---|---|---|---|
| atgaaatacc | tcctcgtcac | cctcgcctcc | acgtcctcg | ccactgccct | ccagcaccc | 60 |
| gttctggaga | aaaggactcc | gccaaatatt | ccctcaacgt | ccactgcaca | gagtcttctt | 120 |
| tctgattaa | ccgttgcccc | acaaggatcg | cagaccgggt | attcgcgtga | tttgtttcca | 180 |
| cactggatca | cagtgagcgg | gtatgtacga | aacgctgatc | atatgtgtac | atcttgcaca | 240 |

```
ttaccttaaa acattctgtg tcaattttcc tatttgaaag atccatccat tgtcccttc    300
tgtctttttt tggcgatcat tgctcgatgt gccaactgac tccattccgc agaacatgca    360
acactcgcga aaccgtcctc aagcgcgacg gctcaaacgt agtcacagac tctgcttgcg    420
catcagtatc cggctcgtgg tactcaacgt acgacggtgc gacgtggacg gcggctagcg    480
acgtcgatat tgatcatgtt gtgccccttt ccaatgtcgt gaaggtgtgt aaatcctcta    540
cttccccgtt tccattgaaa tgaacccact acttggtaga agggaaagag atttgtaact    600
gacactgttt acaagtccgg cgcagcatcc tggaccactg cccgccgcca ggccttcgcc    660
aacgacctga ctaacccgca actcattgcc gtgaccgaca atgttaatca agcgaagggt    720
gaccaggggc cagagtcgtg gaaaccgcca ctaagtgagt cttttcacca atggtatgaa    780
actgaaaatg catgtggcta atatgtgttt agcttcgtac tactgcactt acgccaagat    840
gtgggtcaag gtcaagagtg tgtactcttt gactgtcact tcggcagaga gagcgcgct    900
gtcgagtatg ttggggactt gctaa                                         925

SEQ ID NO: 163           moltype = AA  length = 207
FEATURE                  Location/Qualifiers
source                   1..207
                         mol_type = protein
                         organism = Sporormia fimetaria
SEQUENCE: 163
MKYLLVTLAS TLLATALPAP VLEKRTPPNI PSTSTAQSLL SGLTVAPQGS QTGYSRDLFP    60
HWITVSGTCN TRETVLKRDG SNVVTDSACA SVSGSWYSTY DGATWTAASD VDIDHVVPLS   120
NAWKSGAASW TTARRQAFAN DLTNPQLIAV TDNVNQAKGD QGPESWKPPL TSYYCTYAKM   180
WVKVKSVYSL TVTSAEKSAL SSMLGTC                                      207

SEQ ID NO: 164           moltype = AA  length = 191
FEATURE                  Location/Qualifiers
source                   1..191
                         mol_type = protein
                         organism = Sporormia fimetaria
SEQUENCE: 164
LPAPVLEKRT PPNIPSTSTA QSLLSGLTVA PQGSQTGYSR DLFPHWITVS GTCNTRETVL    60
KRDGSNVVTD SACASVSGSW YSTYDGATWT AASDVDIDHV VPLSNAWKSG AASWTTARRQ   120
AFANDLTNPQ LIAVTDNVNQ AKGDQGPESW KPPLTSYYCT YAKMWVKVKS VYSLTVTSAE   180
KSALSSMLGT C                                                       191

SEQ ID NO: 165           moltype = DNA  length = 814
FEATURE                  Location/Qualifiers
sig_peptide              1..48
mat_peptide              49..811
source                   1..814
                         mol_type = genomic DNA
                         organism = Pycnidiophora dispera
CDS                      1..206
CDS                      264..435
CDS                      507..645
CDS                      702..811
SEQUENCE: 165
atgaagtccc tcctcctcac cctcgccgcc gctaccctgg ccttgccct cccggctcct     60
gcaccgtcc tggtggctcg cgagccccca aacattcctt ccacctcgtc ggcccagagc    120
atgctctctg gtctcaccgt caaggcccag ggacctcagg atgggtactc gagggatctg    180
ttcccgcact ggatcaccat cagcgggtag ccactccaga atctatccaa aggaacact    240
gagctgatca tcctccaatc caggacctgc aacaccgtg agaccgtcct gaagcgtgat    300
ggcacaaaacg tcgtcaccaa ctcggcctgc gcctccacct cgggctcctg gtactcgccc    360
tatgacggtg caacctggac tgccgccagc gatgtcgaca tcgatcacat cgtcccgctg    420
tccaatgctt ggaaggtgcg cattcgcacc cgaagctccc cagtgagta tcaaagtgct    480
catcatgctg attccttct ttctagtccg gcgctgcgag ctggaccaca tctcgccgcc    540
agcagttcgc caacgacctg accaaccccc agctcattgc tgtgaccgac agcgttaacc    600
aggccaaggg tgacaagggc cctgaggact ggaagccgtc ccgaagtagg tttcggatgc    660
aacgtttccc ccttcgaact agagaagctg acagtgtcca gctcgtacc actgcactta    720
tgccaagatg tggatcaagg tcaagagcgt gtattccctg acggtgactt cggctgagaa    780
gagcgctttg acgaccatgc tcaatacgtg ctga                               814

SEQ ID NO: 166           moltype = AA  length = 209
FEATURE                  Location/Qualifiers
source                   1..209
                         mol_type = protein
                         organism = Pycnidiophora dispera
SEQUENCE: 166
MKSLLLTLAA ATLGLALPAP APVLVAREPP NIPSTSSAQS MLSGLTVKAQ GPQDGYSRDL    60
FPHWITISGT CNTRETVLKR DGTNVVTNSA CASTSGSWYS PYDGATWTAA SDVDIDHIVP   120
LSNAWKSGAA SWTTSRRQQF ANDLTNPQLI AVTDSVNQAK GDKGPEDWKP SRTSYHCTYA   180
KMWIKVKSVY SLTVTSAEKS ALTTMLNTC                                    209

SEQ ID NO: 167           moltype = AA  length = 193
FEATURE                  Location/Qualifiers
source                   1..193
                         mol_type = protein
                         organism = Pycnidiophora dispera
SEQUENCE: 167
```

```
LPAPAPVLVA REPPNIPSTS SAQSMLSGLT VKAQGPQDGY SRDLFPHWIT ISGTCNTRET  60
VLKRDGTNVV TNSACASTSG SWYSPYDGAT WTAASDVDID HIVPLSNAWK SGAASWTTSR 120
RQQFANDLTN PQLIAVTDSV NQAKGDKGPE DWKPSRTSYH CTYAKMWIKV KSVYSLTVTS 180
AEKSALTTML NTC                                                   193

SEQ ID NO: 168          moltype = DNA   length = 1714
FEATURE                 Location/Qualifiers
sig_peptide             501..614
mat_peptide             615..1211
source                  1..1714
                        mol_type = genomic DNA
                        organism = Xanthan alkaline
CDS                     501..1211
SEQUENCE: 168
aggccgtggc gcccagggcg agcggcttgt ccaccacgac ggggacgcct gcgcgcacga   60
gcgccgtcgc gtggtccgcg tggagcgcgg acgggctggc cacgaccacg acgtcgtagg  120
ccgcgcggtc ggcgaggagc gcctcgacgt cgtcgtgcag gtgcacgccg gccagtcct   180
cggccggcgg ggcgcgtcgc tccggcgagc gcacgacgag ggccgtgacg gtgtgcccg   240
cctcgcgcac gagacgtgcg tggatgccgc ggccggcccc tccgtacccg acgatcccg   300
ccctgagcgt gcgtgcggcg gtgtccatgc cgaccaatct agccgcgtcg cggccggggcg  360
ccggggcgcg acggggcacg tcgggcgcgg gccgagcac tccgggcgac ctggcagaat   420
gtgcgcgttg gtccgatatg gagcgctgcg taccgtctcg ggggtcgcg agagaatc    480
ggtttcggga aggtcgaccc ttgagcacca cgagccgcca ggtccctcgt cggagcgtcc   540
tgcgctacgt cctcatcgcc ctggcgatcg cgatcgtcgt cgcgaacgtc atcaaccagc   600
ggtccgtcgc ggcggacacc gacccggagc cggtcgccgg gagcgcgctc gaggccctcg   660
ccggcctcga ggtcaagggc cccggcccgg acaccggcta cgagcgcgcg ttgttcggtc   720
cgccgtgggc cgacgtcgac ggcaacgggt gcgacactcg caacgacatc ctcgcgcgcg   780
acctcacgga cctgaccttc tcgacgcgcg gcgacgtctg cgaggtccgc accgggacct   840
tcgacgaccc ctacacgggc gagacgatcg acttccgccg cggcaacgcg acgagcgcgg   900
cggttccagat cgaccacgtc gtgccgctgc tcgacgcgtg gcgcaagggc gctcgacgc    960
gggacgacga gacgcgtcgg cagttcgcga acgaccccct caacctgctc cgctcgacg   1020
gcccggcgaa ccagtcgaag ggcgcgcgcg acgcgtcggc gtggctgccc cgaaccacg   1080
cgttccggtg cccgtacgtc gccggacaga tcgccgtgaa ggcggcctac gagctctcgg   1140
tcacgccgtc ggagtcggag gcgatggcgc gcgtgctggc ggactgcccc gccgagccgc   1200
tcccggcggg ctgagccggc tcccccggtc cgccggtccag acgcccgagg gcgctcggcg   1260
accaggcgcg acggccgacg tcgtgcacga gggcgggcac gaggagcgac cgcaccacga   1320
gggtgtcgac gaggacgccg aacgcgacga tgaacgcgag ctgggcgagg aagagcagcg   1380
ggatgatccc gagcgcggcg aacgtggccg cgagcacgac gcccgcggac gtgatgaccg   1440
accccgtgac cgcgagcccg cgcagcacgc cgcgccgcgt cccgacgcgc aggctctccg   1500
cgcgcacccg cgtcatgagg aagatcgagt agtccacgcc cagcgcgacg aggaagcaga   1560
acgcgtagag cgggacggcc gggtccgcgc cggggaagtc gagcacgtgg ttgaagacga   1620
tcgcggcgac gccgagcgcg gccccgaacg acagcacgtt cgcgagcatg agcagacgg   1680
gcgcgagcac ggaccgcagc agcaggacga ggat                             1714

SEQ ID NO: 169          moltype = AA   length = 237
FEATURE                 Location/Qualifiers
source                  1..237
                        mol_type = protein
                        organism = Xanthan alkaline
SEQUENCE: 169
LSTTSRQVPR RSVLRYVLIA LAIAIVVANV INQRSVAADT DPEPVAGSAL EALAGLEVKG  60
PGPDTGYERA LFGPPWADVD GNGCDTRNDI LARDLTDLTF STRGDVCEVR TGTFDDPYTG 120
ETIDFRRGNA TSAAVQIDHV VPLLDAWRKG ARAWDDETRR QFANDPLNLL ASDGPANQSK 180
GARDASAWLP PNHAFRCPYV ARQIAVKAAY ELSVTPSESE AMARVLADCP AEPLPAG    237

SEQ ID NO: 170          moltype = AA   length = 199
FEATURE                 Location/Qualifiers
source                  1..199
                        mol_type = protein
                        organism = Xanthan alkaline
SEQUENCE: 170
DTDPEPVAGS ALEALAGLEV KGPGPDTGYE RALFGPPWAD VDGNGCDTRN DILARDLTDL  60
TFSTRGDVCE VRTGTFDDPY TGETIDFRRG NATSAAVQID HVVPLLDAWR KGARAWDDET 120
RRQFANDPLN LLASDGPANQ SKGARDASAW LPPNHAFRCP YVARQIAVKA AYELSVTPSE 180
SEAMARVLAD CPAEPLPAG                                              199

SEQ ID NO: 171          moltype = DNA   length = 1714
FEATURE                 Location/Qualifiers
sig_peptide             501..614
mat_peptide             615..1211
source                  1..1714
                        mol_type = genomic DNA
                        organism = Xanthan alkaline
CDS                     501..1211
SEQUENCE: 171
ggcgcgggac gccgtggcgc cgagcgcgag cggcttgtcg acgacgaccg gcacgccggc   60
ccgggcgagc gcgtggcgt ggtcggcgtg caggcggac gggctcgcga ccacgacgac  120
gtcgtaggcc gtccggtcgg cgaggagcgc gtcgaggtcg tcgtgcaggt gcacgtccgg  180
ccagtcctcg accgcggcgg cgcggcgctc ggcgaccgg accacgaccg ccgtgacgac  240
```

```
gtgcccggcc tcgcggacga ggcgtgcgtg gatgccgcgg cccgctcctc cgtacccgac  300
gatcccgacc ctgagcgtgc gtgcggcggt gtccatggcg accaatctag ccgcgccgtc  360
gaccggtacc cgcggggtcc tgtcggagtg gtctgagcac tctccgcaac ctggcagaat  420
gtgcgcgttg gtccggtatg gagcgctgcg taccgtctcg cgcgggtcgg gccgagaatc  480
ggtttcggga aggtcgtccc ttgagcacca cgagccgccg cgtccctcgt cggagcgtcc  540
tgcgctacgt cctgatcgcg ttggcggtcg ccatcgtggt cgcgaacgtc atcaaccagc  600
agtcggtcgc cgccgacgac gagccggaac ccgcccgggg cagcgcgctc gaggcgctgg  660
cgcgcctcga ggtcgtgggg cccggcccgg acacgggcta cgagcgggag ctcttcggtc  720
ccgcgtgggc cgacgtcgac ggcaacgggt gcgacacccg caacgacatc ctcgcgcgcg  780
acctcaccga cctcaccttc tcgacgcggg gcgaggtctg cgaggtacgg acgggcgcgt  840
tccaggaccc gtacaccggc gagaccatcg acttccgccg cggcaacgcg accagcatgg  900
cggtccagat cgaccacgtg gtcccgctga tggacgcgtg gcgcaagggc gcgcgcgcct  960
gggacgacga gacgcgtcgg cagttcgcca acgacccgct caacctgctc cgcgtccgacg 1020
gccccgcgaa ccagtccaag ggccgcgcg acgcgtccgc gtggctcccc ccgaaccacg 1080
cgttccgctg cccgtacgtc gcgcggcaga tcgcggtgaa gaccgcctac gagctctcgg 1140
tgacgccgtc cgagtcggag gcgatggcgc gcgtgctcga ggactgcccg gccgagcccg 1200
tccccgcggg ctgacccttc tccccgggcc ccggtcggc gcgcccgagg gcgctcggcc  1260
accaggcccg acgaccgacg tcgtgcacga gcgcggggac cagcagccgc cgcacgacga 1320
gcgtgtcgac gaggacgccg aacgcgacga tgaacgcgag ctgggcgagg aacagcagcg 1380
ggatgatccc gagcgcggcg aacgtcgtcg cgaggaccac gcctgcggac gtgatgaccg 1440
acccggtgac cgcgagaccg cgcagcacgc cgcgccgcgt cccgacccgc aggctctcct 1500
cccgcacgcg cgtcatgaag aagatcgagt agtcgaccgg acgcgcgacg aggaagcaga 1560
acgcgtagag cgggacggcc gggtcggcgc ccgggaagtc gagcacgtgg ttgaagacga 1620
tcgcggcgac gccgagcgct gcgccgaacg acacacgtt ggcgagcatg agcaggaccg 1680
gcgcgacgat cgaccgcagc agcaggatga ggat                             1714
```

```
SEQ ID NO: 172        moltype = AA   length = 237
FEATURE               Location/Qualifiers
source                1..237
                      mol_type = protein
                      organism = Xanthan alkaline
SEQUENCE: 172
LSTTSRRVPR RSVLRYVLIA LAVAIVVANV INQQSVAADD EPEPARGSAL EALARLEVVG  60
PGPDTGYERE LFGPAWADVD GNGCDTRNDI LARDLTDLTF STRGEVCEVR TGTFQDPYTG 120
ETIDFRRGNA TSMAVQIDHV VPLMDAWRKG ARAWDDETRR QFANDPLNLL ASDGPANQSK 180
GARDASAWLP PNHAFRCPYV ARQIAVKTAY ELSVTPSESE AMARVLEDCP AEPVPAG    237

SEQ ID NO: 173        moltype = AA   length = 199
FEATURE               Location/Qualifiers
source                1..199
                      mol_type = protein
                      organism = Xanthan alkaline
SEQUENCE: 173
DDEPEPARGS ALEALARLEV VGPGPDTGYE RELFGPAWAD VDGNGCDTRN DILARDLTDL  60
TFSTRGEVCE VRTGTFQDPY TGETIDFRRG NATSMAVQID HVVPLMDAWR KGARAWDDET 120
RRQFANDPLN LLASDGPANQ SKGARDASAW LPPNHAFRCP YVARQIAVKT AYELSVTPSE 180
SEAMARVLED CPAEPVPAG                                              199

SEQ ID NO: 174        moltype = DNA   length = 800
FEATURE               Location/Qualifiers
sig_peptide           1..54
mat_peptide           55..797
source                1..800
                      mol_type = genomic DNA
                      organism = Clavicipitaceae sp.
CDS                   1..72
CDS                   142..275
CDS                   329..485
CDS                   549..797
SEQUENCE: 174
atgaagttct cttcggcatc tctcgtcgtg tccgctgctg cgcttgtcct cggtgtgcct  60
gtgcctgcgc ccgtaagcaa tcctactcct gacacgctgt catcgtgtaa caaagcctaa 120
ctcttttttt tgttcttcta gccggcatc ccaagcacgt cgacagccaa gactcttctt 180
gctggcacca aggttgctac ccgttgagt ggtgatgggt actctcgtga taagttccct 240
acttgggaga ccattcaggg aacttgcaat gctcggtgag tttgcccatc tccttttgtt 300
cttgtcaggt tgctaatgcc catggtagcc agtttgtcat taagcgagac ggaacagacg 360
tcaagaccaa cagcgcatgc gtcgcagagt ccggcaactg gtctctccg tatgacgggg 420
tcaagttcac cgcagcacgc gatctcgaca ttgaccaacat ggttccactg aagaatgcct 480
ggattgtaag acgactacct aaccatcttg tcctcaattc cacgtaccttt gtctaacttg 540
cttgtcagtc cggtgcctca caatggacca ccgagcagca caaagctctc gccaacgaca 600
ttacccgtcc ccagctctgg gccgtatcag cccatgccaa ccgcggcaag agtgacgata 660
gccccgacga gtgaagcct cctctgaaga ctttctggtg cacatacgcc aagagttggg 720
tgcaggtgaa gagcttctat aagttgacta ttacggatac cgagaaaggt gctttggctg 780
gcatgctgga tacttgctaa                                             800

SEQ ID NO: 175        moltype = AA   length = 204
FEATURE               Location/Qualifiers
source                1..204
                      mol_type = protein
```

```
                        organism = Clavicipitaceae sp.
SEQUENCE: 175
MKFSSASLVV  SAAALVLGVP  VPAPPGIPST  STAKTLLAGL  KVATPLSGDG  YSRDKFPTWE    60
TIQGTCNARE  FVIKRDGTDV  KTNSACVAES  GNWVSPYDGV  KFTAARDLDI  DHMVPLKNAW   120
ISGASQWTTE  QRKALANDIT  RPQLWAVSAH  ANRGKSDDSP  DEWKPPLKTF  WCTYAKSWVQ   180
VKSFYKLTIT  DTEKGALAGM  LDTC                                            204

SEQ ID NO: 176          moltype = AA  length = 186
FEATURE                 Location/Qualifiers
source                  1..186
                        mol_type = protein
                        organism = Clavicipitaceae sp.
SEQUENCE: 176
VPVPAPPGIP  STSTAKTLLA  GLKVATPLSG  DGYSRDKFPT  WETIQGTCNA  REFVIKRDGT    60
DVKTNSACVA  ESGNWVSPYD  GVKFTAARDL  DIDHMVPLKN  AWISGASQWT  TEQRKALAND   120
ITRPQLWAVS  AHANRGKSDD  SPDEWKPPLK  TFWCTYAKSW  VQVKSFYKLT  ITDTEKGALA   180
GMLDTC                                                                  186

SEQ ID NO: 177          moltype = DNA  length = 897
FEATURE                 Location/Qualifiers
sig_peptide             1..48
mat_peptide             49..894
source                  1..897
                        mol_type = genomic DNA
                        organism = Westerdykella sp.
CDS                     1..206
CDS                     290..461
CDS                     535..673
CDS                     727..773
CDS                     850..894
SEQUENCE: 177
atgaagtccc tcctcgtcac cctcgctgct gcaacactgg gtgctgcctt cccagcaccc         60
gcgtccgtcc tggaggctcg cgctccgccg aacatcccct cggcgtcgac cgctcagagc        120
ctgctggttg ggttgacggt ccagcctcag ggtccacaag atgggtactc gagggatctc        180
ttcccacatt ggatcaccat aagtgggtag gtgagaccat tccctattg ttccgtgctc         240
tttgagacac cattgcagag aaaacacggg ctaatcatgc cccacccagg acctgcaaca        300
cccgcgagac ggtcctgaag cgcgacggca gcaacgtcgt caccaactcg gcctgcgcgg        360
ccacctccgg gacctggtac tcgccctatg acggcgcaac atggacttct gccagcgacg        420
tcgacatcga tcacctggtg ccgctttcca atgcttggaa ggtatgtagc ccgtctctcc        480
gctttcgcat gtagcagtag aaggtgaacg tactgaccgt gagaacttcc ccagtccggt        540
gctgccagct ggaccacggc caaacgccag caattcgcca atgaccgac aaatccacag         600
ctccttgctg tgactgacag ggtcaaccaa gccaagggcg acaagggccc cgaggcctgg        660
aagccgtcgt taggtagacc actccgtcac tctcgcgtgc aacaagtgat ggctaatgcc        720
ttctagcttc gtaccactgc acctatgcca agatgtgggt caaggttaag agcgtatggg        780
ctttgaccgt aacgtcggct gagaagagcg ctctaacaac aatgtggct acgtgctgaa         840
cacgcgcaga aggacgttcg gctgaccggg aattggacga aggacgacgg ctggtga           897

SEQ ID NO: 178          moltype = AA  length = 203
FEATURE                 Location/Qualifiers
source                  1..203
                        mol_type = protein
                        organism = Westerdykella sp.
SEQUENCE: 178
MKSLLVTLAA  ATLGAAFPAP  ASVLEARAPP  NIPSASTAQS  LLVGLTVQPQ  GPQDGYSRDL    60
FPHWITISGT  CNTRETVLKR  DGSNVVTNSA  CAATSGTWYS  PYDGATWTSA  SDVDIDHLVP   120
LSNAWKSGAA  SWTTAKRQQF  ANDLTNPQLL  AVTDRVNQAK  GDKGPEAWKP  SLASYHCTYA   180
KMWVKVKSKD  VRLTGNWTKD  DGW                                             203

SEQ ID NO: 179          moltype = AA  length = 187
FEATURE                 Location/Qualifiers
source                  1..187
                        mol_type = protein
                        organism = Westerdykella sp.
SEQUENCE: 179
FPAPASVLEA  RAPPNIPSAS  TAQSLLVGLT  VQPQGPQDGY  SRDLFPHWIT  ISGTCNTRET    60
VLKRDGSNVV  TNSACAATSG  TWYSPYDGAT  WTSASDVDID  HLVPLSNAWK  SGAASWTTAK   120
RQQFANDLTN  PQLLAVTDRV  NQAKGDKGPE  AWKPSLASYH  CTYAKMWVKV  KSKDVRLTGN   180
WTKDDGW                                                                 187

SEQ ID NO: 180          moltype = DNA  length = 781
FEATURE                 Location/Qualifiers
sig_peptide             1..57
mat_peptide             58..778
source                  1..781
                        mol_type = genomic DNA
                        organism = Humicolopsis cephalosporioides
CDS                     1..390
CDS                     450..588
CDS                     669..778
```

```
SEQUENCE: 180
atgaagacca cttggatcct caccagcctt ttggcacaag ctttcctctc cttggctgct   60
cctacgcctg cccagtgga gctagagcgt cgcactcctc caaatatccc aaccactgct  120
tcggcgaagt ctcttctcgc tggcctgact gttgctgctc aaggtccaca aactggctac  180
agtcgtgacc ttttccctca ctggatcaca atctctgctt cttgcaacac tcgcgaaacg  240
gtcctcaagc gcgacggcac cggtgtcgtg acagattccg cttgcgcttc gacagctggc  300
agttggtaca gcccttatga tggagctact tggactgctg caagtgatgt ggatatcgac  360
catatggttc ctttgtccaa tgcttggaag gtgaatatcg caacaaatca attatgggat  420
atatcgaata atttgctgac ttgacatagt ccggtgctgc caatggacc accgctgca   480
ggcaggattt cgccaatgat ctgaccaatc cccagctctt cgcggtgact gataatgtca  540
accaggagaa gggcgacaag ggaccagaag actggaagcc ttctttgagt aagtatagat  600
ttacttgcag cctcaagct ccgccgtgga agcttagtat ctagtgctcg tcctaacatg   660
ctatctagct tcctattact gcacttacgc caaagcttgg gttaaagtca agagtgtatg  720
ggcttttaact attacatcgg ccgaaaagtc tgcgttgact actatgctca ataccgctg   780
a                                                                  781

SEQ ID NO: 181         moltype = AA  length = 213
FEATURE                Location/Qualifiers
source                 1..213
                       mol_type = protein
                       organism = Humicolopsis cephalosporioides
SEQUENCE: 181
MKTTWILTSL LAQAFLSLAA PTPAPVELER RTPPNIPTTA SAKSLLAGLT VAAQGPQTGY   60
SRDLFPHWIT ISGSCNTRET VLKRDGTGVV TDSACASTAG SWYSPYDGAT WTAASDVDID  120
HMVPLSNAWK SGAAQWTTAR RQDFANDLTN PQLFAVTDNV NQEKGDKGPE DWKPSLTSYY  180
CTYAKAWVKV KSVWALTITS AEKSALTTML NTC                               213

SEQ ID NO: 182         moltype = AA  length = 194
FEATURE                Location/Qualifiers
source                 1..194
                       mol_type = protein
                       organism = Humicolopsis cephalosporioides
SEQUENCE: 182
APTPAPVELE RRTPPNIPTT ASAKSLLAGL TVAAQGPQTG YSRDLFPHWI TISGSCNTRE   60
TVLKRDGTGV VTDSACASTA GSWYSPYDGA TWTAASDVDI DHMVPLSNAW KSGAAQWTTA  120
RRQDFANDLT NPQLFAVTDN VNQEKGDKGP EDWKPSLTSY YCTYAKAWVK VKSVWALTIT  180
SAEKSALTTM LNTC                                                    194

SEQ ID NO: 183         moltype = DNA  length = 769
FEATURE                Location/Qualifiers
sig_peptide            1..51
mat_peptide            52..766
source                 1..769
                       mol_type = genomic DNA
                       organism = Neosartorya massa
CDS                    1..200
CDS                    245..416
CDS                    465..603
CDS                    657..766
SEQUENCE: 183
atgactgcc ttctcctcgc agcccttctg ggcacctctc ttgtcacagc catcccggca   60
ccagttgctc tcccaactcc cccaggaatc ccctctgccg ctaccgcaga gtccgagctg  120
gctgctctga ctgtcgcggc gcaaggctcc agctctggat actctcgcga cctcttcccc  180
cactggatca gtcaaggcgg gtacgtacag cccttcttcc tagcaagcta agctaacagc  240
ccagctcctg caacacccgc gaggtcgtcc tcgcccgcga cggcagcggc gtcgtcaagg  300
attccaactg ctatcccacc agcggatcat ggtactgcc ctacgacgga gccacctgga   360
cgcaggccag cgatgtagac attgaccatg tcgttcctct cgccaacgcc tggagagtaa  420
gaccatcccc tattcctatc gccgatccag ctaacttgcg atagtccggc gcatctaaat  480
ggactacctc gcagcggcag gcgttttgcca acgacctgac caacccgcag ctgatggcgg  540
tgacggataa cgtcaaccag gccaagggcg acgatgacc ggaggcgtgg aagcctcctc  600
ttagtaagtt ccctttcctg tcttctctgg ggtggatggt gatgctaacg ggctagcttc  660
gtattattgc acgtatgcga agatgtgggt tagggtcaag tatgtgtatg atttgaccat  720
tacctcggcg gagaagagtg ctctggtgag catgttggat acttgctag                769

SEQ ID NO: 184         moltype = AA  length = 207
FEATURE                Location/Qualifiers
source                 1..207
                       mol_type = protein
                       organism = Neosartorya massa
SEQUENCE: 184
MTRLLLAALL GTSLVTAIPA PVALPTPPGI PSAATAESEL AALTVAAQGS SSGYSRDLFP   60
HWISQGGSCN TREVVLARDG SGVVKDSNCY PTSGSWYSPY DGATWTQASD VDIDHVVPLA  120
NAWRSGASKW TTSQRQAFAN DLTNPQLMAV TDNVNQAKGD DGPEAWKPPL TSYYCTYAKM  180
WVRVKYVYDL TITSAEKSAL VSMLDTC                                      207

SEQ ID NO: 185         moltype = AA  length = 190
FEATURE                Location/Qualifiers
source                 1..190
                       mol_type = protein
```

```
                              organism = Neosartorya massa
SEQUENCE: 185
IPAPVALPTP PGIPSAATAE SELAALTVAA QGSSSGYSRD LFPHWISQGG SCNTREVVLA     60
RDGSVVKDS NCYPTSGSWY SPYDGATWTQ ASDVDIDHVV PLANAWRSGA SKWTTSQRQA    120
FANDLTNPQL MAVTDNVNQA KGDDGPEAWK PPLTSYYCTY AKMWVRVKYV YDLTITSAEK   180
SALVSMLDTC                                                          190

SEQ ID NO: 186          moltype = DNA  length = 828
FEATURE                 Location/Qualifiers
sig_peptide             1..48
mat_peptide             49..825
source                  1..828
                        mol_type = genomic DNA
                        organism = Roussoella intermedia
CDS                     1..200
CDS                     269..440
CDS                     511..649
CDS                     716..825
SEQUENCE: 186
atgaagtaca tcctcatcgc cctcacatct gccatcctcg cctctgccgc ccctacaccg    60
gcgctcctcc cccgtgcacc accaaacatc ccttccaccg caacagcaaa gtcacagctt   120
gccgccttga ccgtcgcagc acaaggccct caagatggct attcccgtga cttgttccct   180
cactggatca cacagagcgg gtacgccgac gaatcccac aagatgtttg tcccaccgg    240
gcggatgctg acataggtac cgtcgcaggt cctgcaacac ccgcgaggta gtactcaagc   300
gtgacggcac caacgtcgtg caagactcct cttgtgctgc cacgtccggc acatgggttt   360
ctcccttcga cggtgccacc tggacagcc caagcgacgt cgacatcgat catctctgcc   420
ccttgagcaa tgcctggaag gttcgtccct aatcttttct ttctgtattc cgctctgggg   480
agtcaagaag acactaatag tacaccacag agcggcgccg cctcctggac gactgctcgc   540
cgccagtcct tcgccaacga cctcaccaac ccccagctcc tcgccgtcac cgacgaagtg   600
aaccagcta agggcgacaa gggccccgag gcctggaage ctccgctagg tcagttctct   660
tcctcctctc ttccaacatc tttcagtctc tagatggatg ctaacgacca cccagcaagc   720
taccactgca cctacgccaa gatgtgggtc aaggtcaaga gcacgtacag cctgaccatc   780
acgtcggctg agaagagcgc cttgacgact atgttgaaca cttgctag              828

SEQ ID NO: 187          moltype = AA  length = 207
FEATURE                 Location/Qualifiers
source                  1..207
                        mol_type = protein
                        organism = Roussoella intermedia
SEQUENCE: 187
MKYILIALTS AILASAAPTP ALLPRAPPNI PSTATAKSQL AALTVAAQGP QDGYSRDLFP    60
HWITQSGSCN TREVVLKRDG TNVVQDSSCA ATSGTWVSPF DGATWTAASD VDIDHLVPLS   120
NAWKSGAASW TTARRQSFAN DLTNPQLLAV TDEVNQAKGD KGPEAWKPPL ASYHCTYAKM   180
WVKVKSTYSL TITSAEKSAL TTMLNTC                                       207

SEQ ID NO: 188          moltype = AA  length = 191
FEATURE                 Location/Qualifiers
source                  1..191
                        mol_type = protein
                        organism = Roussoella intermedia
SEQUENCE: 188
APTPALLPRA PPNIPSTATA KSQLAALTVA AQGPQDGYSR DLFPHWITQS GSCNTREVVL    60
KRDGTNVVQD SSCAATSGTW VSPFDGATWT AASDVDIDHL VPLSNAWKSG AASWTTARRQ   120
SFANDLTNPQ LLAVTDEVNQ AKGDKGPEAW KPPLASYHCT YAKMWVKVKS TYSLTITSAE   180
KSALTTMLNT C                                                        191

SEQ ID NO: 189          moltype = DNA  length = 792
FEATURE                 Location/Qualifiers
sig_peptide             1..48
mat_peptide             49..789
source                  1..792
                        mol_type = genomic DNA
                        organism = Pleosporales sp.
CDS                     1..200
CDS                     271..442
CDS                     492..630
CDS                     680..789
SEQUENCE: 189
atgaagtaca ccatcctcgc tacggccttt gtggccctcg ctgcggccct cccgacacct    60
agtctggtca agcgaacacc gccaaacatc ccgtcgacca cctcggccaa gtctcttctt   120
gctggcttga ccgtcgccgc tcagggaccc caggatggct actcccgtga cttgttccct   180
cactggatca ctataagcgg gtaagcaagc ttcatctcca gtttcaatca tcaccagcat   240
tgggagcata ttctgacgag ggggacatag aacgtgcaac accgcgaga cggttctcaa    300
gcgcgacggt accaacgtcg taaccgactc cgcttgctcc tctacctccg gatcttggta   360
ctcgacctac gacggcgcta cctgaccgc cgcttctgac gtcgacattg accacgtcgt    420
tcctctctcg aatgcttgga aggtattgta ctcgtctatt tccctcaact tcccacgctg   480
acccagacca gtccggagcc gcgtcctgga ccaccgcccg ccgccagtct ttcgctaacg   540
acctgactaa ccctcaactg attgccgtga ccgacagcgt caaccagtcc aagggcgaca   600
agggccccga gtcctggaag cccccgctaa gtgagtcctg gtcaatagt ttcgtagtcc    660
```

-continued

```
tatgctgatg acaatatagc ctcgtaccac tgcacctacg caaagatgtg ggtcaaggtc   720
aaggacgtgt acagtctgac cgtcacgtct gccgagaagt ctgccttgac gaccatgttg   780
aacacctgct ga                                                       792

SEQ ID NO: 190          moltype = AA  length = 207
FEATURE                 Location/Qualifiers
source                  1..207
                        mol_type = protein
                        organism = Pleosporales sp.
SEQUENCE: 190
MKYTILATAF VALAAALPTP SLVKRTPPNI PSTTSAKSLL AGLTVAAQGP QDGYSRDLFP    60
HWITISGTCN TRETVLKRDG TNVVTDSACA STSGSWYSTY DGATWTAASD VDIDHVVPLS   120
NAWKSGAASW TTARRQSFAN DLTNPQLIAV TDSVNQSKGD KGPESWKPPL TSYHCTYAKM   180
WVKVKDVYSL TVTSAEKSAL TTMLNTC                                       207

SEQ ID NO: 191          moltype = AA  length = 191
FEATURE                 Location/Qualifiers
source                  1..191
                        mol_type = protein
                        organism = Pleosporales sp.
SEQUENCE: 191
LPTPSLVKRT PPNIPSTTSA KSLLAGLTVA AQGPQDGYSR DLFPHWITIS GTCNTRETVL    60
KRDGTNVVTD SACASTSGSW YSTYDGATWT AASDVDIDHV VPLSNAWKSG AASWTTARRQ   120
SFANDLTNPQ LIAVTDSVNQ SKGDKGPESW KPPLTSYHCT YAKMWVKVKD VYSLTVTSAE   180
KSALTTMLNT C                                                        191

SEQ ID NO: 192          moltype = DNA  length = 704
FEATURE                 Location/Qualifiers
sig_peptide             1..54
mat_peptide             55..701
source                  1..704
                        mol_type = genomic DNA
                        organism = Phaeosphaeria sp.
CDS                     1..381
CDS                     453..701
SEQUENCE: 192
atgaaatccg ccctccttct tgccatcgcc tcaacggcaa ccctcatctc tgccctccct    60
gcccctatcc acctcactgc tcgggcacca caaacatcc cgtccgcctc cgaagctcgc   120
actcaacttg ccggcctgac cgtcgcgct caaggcccgc aggatggcta ctcgcgcgac   180
ctcttcccgc actggatcac gcaatctggg acatgtaaca gcgagaaac cgtgctcaag   240
cgggacggca cgaacgtcgt tacgaactcc gcctgcgcga gcaccagtgg aagctggttc   300
agcccgtacg acggagcgac atggacagca gcgtctgacg tcgacattga ccatatggta   360
ccgttgagca atgcctggaa agtacgtctt cagccttcc ctttttccca ttccaatttc   420
ccctcttgta catccgctaa tcaacattgc agtccggtgc cgcgtcctgg accacgcc   480
gccgccaggc ctttgcaaac gacctgacta cccgcagct cctcgccgtc acggacaacg   540
tcaaccaagc aaaaggcgac aagggccccg aggactggaa accccgctt acaagctact   600
actgcacgta tgcgcggatg tgggtcaagg taaagagtg gtatgccctg acggtaacga   660
gcgcggagaa gagcgctttg acgagcatgt tgggcacttg ttga                   704

SEQ ID NO: 193          moltype = AA  length = 210
FEATURE                 Location/Qualifiers
source                  1..210
                        mol_type = protein
                        organism = Phaeosphaeria sp.
SEQUENCE: 193
MKSALLLAIA STATLISALP APIHLTARAP PNIPSASEAR TQLAGLTVAA QGPQDGYSRD    60
LFPHWITQSG TCNTRETVLK RDGTNVVTNS ACASTSGSWF SPYDGATWTA ASDVDIDHMV   120
PLSNAWKSGA ASWTTARRQA FANDLTNPQL LAVTDNVNQA KGDKGPEDWK PPLTSYYCTY   180
ARMWVKVKSV YALTVTSAEK SALTSMLGTC                                    210

SEQ ID NO: 194          moltype = AA  length = 192
FEATURE                 Location/Qualifiers
source                  1..192
                        mol_type = protein
                        organism = Phaeosphaeria sp.
SEQUENCE: 194
LPAPIHLTAR APPNIPSASE ARTQLAGLTV AAQGPQDGYS RDLFPHWITQ SGTCNTRETV    60
LKRDGTNVVT NSACASTSGS WFSPYDGATW TAASDVDIDH MVPLSNAWKS GAASWTTARR   120
QAFANDLTNP QLLAVTDNVN QAKGDKGPED WKPPLTSYYC TYARMWVKVK SVYALTVTSA   180
EKSALTSMLG TC                                                       192

SEQ ID NO: 195          moltype = DNA  length = 889
FEATURE                 Location/Qualifiers
sig_peptide             1..51
mat_peptide             52..886
source                  1..889
                        mol_type = genomic DNA
                        organism = Didymosphaeria futilis
CDS                     1..237
```

| | |
|---|---|
| CDS | 297..437 |
| CDS | 491..622 |
| CDS | 679..712 |
| CDS | 772..837 |
| CDS | 879..886 |

SEQUENCE: 195

```
atgaagtcca ctcttctcat tgctctgttc tctccagcct tagtggcagc cttgcccacg    60
cctaacaccc ttgaggctcg tgcaccccca acattcctt caacatcagc cgcccaatct    120
cagctttctg cattaacggt agctgctcag ggaccacaaa ggttactc tcgtgatctc    180
tttcctcact ggatcaccca gtctggaact tgcaacacaa gggagacagt cttgaaggtc    240
agtcgaaggt cccgatatga gtggcgtcta tttcatttga ataacgcagt atgcagcgcg    300
acggcacgaa cgttctaact gactctgcgt gtgcgtcaac ttctgggtca tggaagagtc    360
catatgacgg tgcaacgtgg actgctgcca gcgacgtcga catcgaccac gtcgtccat    420
tgagcaacgc ttggaaggtg cggaccgtac aaataagtta atagtgcttg tgtgtctaac    480
gaaagtacag tccggagcag caagctggac tactgctcgc cgccagtcat ttgccaacga    540
cctgaccaac ccacagctga ttgcagtaac agataatgtg aaccaagcta agggtgataa    600
gggacccgaa gactggaagc cagtacgttt caaatgtcct caggttcacg agacattggt    660
catactaacc ttcgtcagcc gctaacaagc tactactgca cctatgcaaa gagtaagtgc    720
tccatattac gttgacatac catttgactt cagttctaat tatgcggaca gtgtgggtta    780
aggtcaagag cgttgacagc ctgacaatta caagtgctga aaagagtgca ctgacgagta    840
tgttgaacac ctgttagttg gctctaatag gttgccagtg ttggcatag                889
```

| | | |
|---|---|---|
| SEQ ID NO: 196 | moltype = AA | length = 206 |
| FEATURE | Location/Qualifiers | |
| source | 1..206 | |
| | mol_type = protein | |
| | organism = Didymosphaeria futilis | |

SEQUENCE: 196

```
MKSTLLIALF SPALVAALPT PNTLEARAPP NIPSTSAAQS QLSALTVAAQ GPQTGYSRDL    60
FPHWITQSGT CNTRETVLKR DGTNVLTDSA CASTSGSWKS PYDGATWTAA SDVDIDHVVP   120
LSNAWKSGAA SWTTARRQSF ANDLTNPQLI AVTDNVNQAK GDKGPEDWKP PLTSYYCTYA   180
KMWVKVKSVY SLTITSAEKS ALTMLA                                        206
```

| | | |
|---|---|---|
| SEQ ID NO: 197 | moltype = AA | length = 189 |
| FEATURE | Location/Qualifiers | |
| source | 1..189 | |
| | mol_type = protein | |
| | organism = Didymosphaeria futilis | |

SEQUENCE: 197

```
LPTPNTLEAR APPNIPSTSA AQSQLSALTV AAQGPQTGYS RDLFPHWITQ SGTCNTRETV    60
LKRDGTNVLT DSACASTSGS WKSPYDGATW TAASDVDIDH VVPLSNAWKS GAASWTTARR   120
QSFANDLTNP QLIAVTDNVN QAKGDKGPED WKPPLTSYYC TYAKMWVKVK SVYSLTITSA   180
EKSALTMLA                                                           189
```

| | | |
|---|---|---|
| SEQ ID NO: 198 | moltype = | length = |
| SEQUENCE: 198 | | |
| 000 | | |

| | | |
|---|---|---|
| SEQ ID NO: 199 | moltype = | length = |
| SEQUENCE: 199 | | |
| 000 | | |

| | | |
|---|---|---|
| SEQ ID NO: 200 | moltype = | length = |
| SEQUENCE: 200 | | |
| 000 | | |

| | | |
|---|---|---|
| SEQ ID NO: 201 | moltype = | length = |
| SEQUENCE: 201 | | |
| 000 | | |

| | | |
|---|---|---|
| SEQ ID NO: 202 | moltype = | length = |
| SEQUENCE: 202 | | |
| 000 | | |

| | | |
|---|---|---|
| SEQ ID NO: 203 | moltype = | length = |
| SEQUENCE: 203 | | |
| 000 | | |

| | | |
|---|---|---|
| SEQ ID NO: 204 | moltype = AA | length = 7 |
| FEATURE | Location/Qualifiers | |
| REGION | 1..7 | |
| | note = Synthetic construct | |
| VARIANT | 1 | |
| | note = X=D, M or L | |
| VARIANT | 2 | |
| | note = X=S or T | |
| VARIANT | 7 | |
| | note = X=D or N | |
| source | 1..7 | |

```
                        mol_type = protein
                        organism = synthetic construct
SEQUENCE: 204
XXGYSRX                                                              7

SEQ ID NO: 205          moltype = AA  length = 8
FEATURE                 Location/Qualifiers
REGION                  1..8
                        note = Synthetic construct
VARIANT                 3
                        note = X=any amino acid
source                  1..8
                        mol_type = protein
                        organism = synthetic construct
SEQUENCE: 205
ASXNRSKG                                                             8

SEQ ID NO: 206          moltype = AA  length = 8
FEATURE                 Location/Qualifiers
REGION                  1..8
                        note = Synthetic construct
source                  1..8
                        mol_type = protein
                        organism = synthetic construct
VARIANT                 1
                        note = X=V or I
VARIANT                 4
                        note = X=S or A
SEQUENCE: 206
XPLXNAWK                                                             8

SEQ ID NO: 207          moltype = AA  length = 4
FEATURE                 Location/Qualifiers
REGION                  1..4
                        note = Synthetic construct
source                  1..4
                        mol_type = protein
                        organism = synthetic construct
SEQUENCE: 207
NPQL                                                                 4

SEQ ID NO: 208          moltype =     length =
SEQUENCE: 208
000

SEQ ID NO: 209          moltype =     length =
SEQUENCE: 209
000

SEQ ID NO: 210          moltype =     length =
SEQUENCE: 210
000
```

POLYPEPTIDES

CROSS-REFERENCE TO RELATED APPLICATIONS

This application is a divisional of U.S. application Ser. No. 17/157,137 filed on Jan. 25, 2021, now U.S. Pat. No. 11,613,741, which is a divisional of U.S. application Ser. No. 15/766,894 filed Apr. 9, 2018, now U.S. Pat. No. 10,954,497, which is a 35 U.S.C. 371 national application of international application no. PCT/EP2016/074079 filed Oct. 7, 2016, which claims priority or the benefit under 35 U.S.C. 119 of Danish application nos. PA 2015 00615, PA 2015 00617 and PA 2015 00618, all filed on Oct. 7, 2015. The content of each application is fully incorporated herein by reference.

REFERENCE TO A SEQUENCE LISTING

This application contains a Sequence Listing in computer readable form, which is incorporated herein by reference. The name of the file containing the Sequence Listing is SQ.XML, which was created on May 31, 2023 and has 321,271 bytes.

FIELD OF THE INVENTION

The present invention relates to new polypeptides having deoxyribonuclease (DNase) activity, nucleotides encoding the polypeptide, as well as methods of producing the polypeptides. The present invention also relates to detergent composition comprising a DNase, a laundering method and the use of DNase.

BACKGROUND OF THE INVENTION

Microorganisms generally live attached to surfaces in many natural, industrial, and medical environments, encapsulated by extracellular substances including biopolymers and macromolecules. The resulting layer of slime encapsulated microorganism is termed a biofilm. Biofilms are the predominant mode of growth of bacteria in the natural environment, and bacteria growing in biofilms exhibit distinct physiological properties. Compared to their planktonically grown counterparts, the bacteria in a biofilm are more resistant to antibiotics, UV irradiation, detergents and the host immune response.

A biofilm may include one or more microorganisms, including gram-positive and gram-negative bacteria, algae, protozoa, and/or yeast or filamentous fungi and viruses and/or bacteriophage. Examples of problematic biofilms are dental plaque, infections on medical implants, but also the initial fouling on ship hulls. Biofilms are attributed to the pathogenesis of many infections in humans and are a significant problem in industry in terms of biofouling of exposed surfaces, where biofilm colonization can form the base component of a localized ecosystem which can disrupt and interfere with industrial processes and components.

When laundry items like T-shirts or sportswear are used, they are exposed to bacteria from the body of the user and from the rest of the environment in which they are used. Some of these bacteria are capable of adhering to the laundry item and form a biofilm on the item. The presence of bacteria implies that the laundry items become sticky and therefore soil adheres to the sticky areas. This soil has shown difficult to remove by commercially available detergent compositions. Further, when very dirty laundry items are washed together with less dirty laundry items the dirt present in the wash liquor tend to stick to the biofilm. As a result hereof, the laundry item is more "soiled" after wash than before wash. Further, these bacteria are a source of bad odor, which develops after use of the laundry item. The bad odor (malodor) is difficult to remove and may remain even after wash. The reason for this bad odor is adhesion of bacteria to the textile surface. Because of the adhesion to the textile, the bacteria may remain even after wash, and continue to be a source of bad odor.

International patent applications WO 2011/098579 (University of Newcastle) and WO 2014/087011 (Novozymes A/S) relates to deoxyribonuclease compounds and methods for biofilm disruption and prevention.

SUMMARY OF THE INVENTION

The invention relates to novel polypeptides having DNase (deoxyribonuclease) activity and the polynucleotides encoding these.

One aspect of the invention relates to a composition comprising
  i. at least 0.002 ppm of a polypeptide having DNase activity, wherein the polypeptide comprises the motif HXXP, where H is histidine, P is proline and X is any amino acid, wherein the composition further comprises: one or more polyol(s), preferably selected from glycerol, (mono, di, or tri) propylene glycol, ethylene glycol, polyethylene glycol, sugar alcohols, sorbitol, mannitol, erythritol, dulcitol, inositol, xylitol and adonitol, and/or
  ii. optionally one or more enzyme, preferably selected from proteases, amylases or lipases,
  iii. optionally one or more surfactant, preferably selected from anionic and nonionic surfactants,
  iv. optionally one or more polymers.

Another aspect of the invention relates to a granule comprising
  i. a core comprising a polypeptide having DNase activity and optionally,
  ii. a coating consisting of one or more layer(s) surrounding the core.

In one aspect of the invention the granule comprises a polypeptide having DNase activity and wherein the polypeptide comprises one or more of the motifs selected from the motifs [T/D/S][G/N]PQL (SEQ ID NO: 198), [G/T]Y[D/S][R/K/L] (SEQ ID NO: 199), [E/D/H]H[I/V/L/F/M]X[P/A/S] (SEQ ID NO: 200), [F/L/Y/I]A[N/R]D[L/I/P/V] (SEQ ID NO: 201) and C[D/N]T[A/R] (SEQ ID NO: 202) and wherein the granule comprises a core comprising said polypeptide and a coating.

In one aspect the invention relates to a composition comprising a polypeptide having DNase activity, wherein the polypeptide comprises one or more of the motifs selected from the motifs [T/D/S][G/N]PQL (SEQ ID NO: 198), [G/T]Y[D/S][R/K/L] (SEQ ID NO: 199), [E/D/H]H[I/V/L/F/M]X[P/A/S] (SEQ ID NO: 200), [F/L/Y/I]A[N/R]D[L/I/P/V] (SEQ ID NO: 201) and C[D/N]T[A/R] (SEQ ID NO: 202).

In one aspect the invention relates to a composition, wherein the polypeptide having DNase activity belongs to the GYS clade, and comprises one or both of the motifs [D/M/L][S/T]GYSR[D/N](SEQ ID NO: 204) or ASXNRSKG (SEQ ID NO: 205).

In one aspect the composition comprises a polypeptide wherein the polypeptide has DNase activity, wherein the polypeptide comprises one or both of the motifs [D/M/L]

[S/T]GYSR[D/N] (SEQ ID NO: 204) or ASXNRSKG (SEQ ID NO: 205) and wherein the polypeptide comprises, consists essentially of or consists of an amino acid sequence selected from the group consisting of SEQ ID NO: 8, SEQ ID NO: 9, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 53, SEQ ID NO: 56, SEQ ID NO: 59, SEQ ID NO: 62, SEQ ID NO: 65, SEQ ID NO: 68, SEQ ID NO: 71, SEQ ID NO: 74, SEQ ID NO: 77 and SEQ ID NO: 80 or polypeptides having at least 80% sequence identity thereto.

In one aspect the composition comprises a polypeptide having DNase activity and which belongs to the NAWK clade and comprises one or both of the motifs [V/I]PL[S/A]NAWK (SEQ ID NO: 206) or NPQL (SEQ ID NO: 207).

In one aspect the composition comprises a polypeptide wherein the polypeptide has DNase activity, wherein the polypeptide comprises one or both of the motifs [V/I]PL[S/A]NAWK (SEQ ID NO: 206) or NPQL (SEQ ID NO: 207) and wherein the polypeptide comprises, consists essentially of or consists of an amino acid sequence selected from the group consisting of SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116 and SEQ ID NO: 119 or polypeptides having at least 80% sequence identity thereto.

In one aspect the composition comprises a polypeptide having DNase activity and which belongs to the KNAW clade and comprises one or both of the motifs P[Q/E]L[W/Y] (SEQ ID NO: 208) or [K/H/E]NAW (SEQ ID NO: 209).

In one aspect composition comprises a polypeptide wherein the polypeptide has DNase activity, comprises P[Q/E]L[W/Y] (SEQ ID NO: 208) or [K/H/E]NAW (SEQ ID NO: 209) and comprises, consists essentially of or consists of an amino acid sequence selected from the group consisting of SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155 and SEQ ID NO: 158 or polypeptides having at least 80% sequence identity thereto.

In one aspect the composition is a cleaning composition such as a laundry or dish wash composition.

One aspect of the invention relates to a polypeptide having DNase activity, wherein the polypeptide comprises the motif HXXP, where H is histidine and wherein P is proline and X is any amino acid.

In one aspect the polypeptide having DNase activity comprises one or more motifs selected from the group consisting of [T/D/S][G/N]PQL (SEQ ID NO: 198), [G/T]Y[D/S][R/K/L] (SEQ ID NO: 199), [E/D/H]H[I/V/L/F/M]X[P/A/S] (SEQ ID NO: 200), [F/L/Y/I]A[N/R]D[L/I/P/V] (SEQ ID NO: 201) and C[D/N]T[A/R] (SEQ ID NO: 202).

In one aspect of the invention the polypeptide having DNase activity belongs to the GYS clade and comprises one or both of the motifs [D/M/L][S/T]GYSR[D/N] (SEQ ID NO: 204) or ASXNRSKG (SEQ ID NO:205).

In one aspect the polypeptide is selected from the group consisting of the polypeptides shown in SEQ ID NO: 8, SEQ ID NO: 9, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 53, SEQ ID NO: 56, SEQ ID NO: 59, SEQ ID NO: 62, SEQ ID NO: 65, SEQ ID NO: 68, SEQ ID NO: 71, SEQ ID NO: 74, SEQ ID NO: 77 and SEQ ID NO: 80 or polypeptides having at least 98% sequence identity thereto.

In one aspect of the invention the polypeptide having DNase activity belongs to the NAWK clade and comprises one or both of the motifs [V/I]PL[S/A]NAWK (SEQ ID NO: 206) or NPQL (SEQ ID NO: 207).

In one aspect the polypeptide comprises any of the motifs [V/I]PL[S/A]NAWK (SEQ ID NO: 206) or NPQL (SEQ ID NO: 207) and is selected from the group consisting of the polypeptides shown in SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116 and SEQ ID NO: 119 and polypeptides having at least 95% sequence identity thereto.

In one aspect of the invention the polypeptide having DNase activity belongs to the KNAW clade and comprises one or both of the motifs P[Q/E]L[W/Y] (SEQ ID NO: 208) or [K/H/E]NAW (SEQ ID NO: 209).

In one aspect the polypeptide comprises the motif P[Q/E]L[W/Y] (SEQ ID NO: 208) or [K/H/E]NAW (SEQ ID NO: 209) and is selected from the group consisting of the polypeptides shown in SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155 and SEQ ID NO: 158 or polypeptides having at least 98% sequence identity thereto.

One aspect of the invention relates to a polynucleotide encoding a polypeptide of the invention. The invention further relates to a nucleic acid construct or expression vector comprising the polynucleotide. The invention further relates to a host cell comprising a polypeptide of the invention.

One aspect relates to the use of a polypeptide of the invention for reduction or removal of a biofilm from an item, such as textile, preferably is a cleaning process such as laundry.

One aspect relates to a method of producing the polypeptide of the invention, comprising:
(a) cultivating the recombinant host cell under conditions conducive for production of the polypeptide; and
(b) recovering the polypeptide.

The invention further relates to
(a) a polypeptide having at least 60% sequence identity to the mature polypeptide of SEQ ID NO: 2, 4 or 6;
(b) a polypeptide encoded by a polynucleotide having at least 60% sequence identity to the mature polypeptide coding sequence of SEQ ID NO: 1, 3 or 5;
(c) a variant of the mature polypeptide of SEQ ID NO: 2, 4 or 6 comprising a substitution, deletion, and/or insertion at one or more positions; and
(d) a fragment of the polypeptide of (a), (b) or (c), which has DNase activity.

In another aspect, the invention relates to detergent compositions comprising a polypeptide having DNase activity and preferably a detergent adjunct ingredient. One aspect of the invention relates to a composition comprising a polypeptide having DNase activity with at least 60% sequence identity to the mature polypeptide of SEQ ID NO: 2, 4 or 6 and a detergent adjunct.

The invention further relates to a cleaning or laundering method for cleaning or laundering an item comprising the steps of:

a. Exposing an item to a wash liquor comprising a polypeptide having DNase activity or a detergent composition comprising the polypeptide having DNase activity;
b. Completing at least one wash cycle; and
c. Optionally rinsing the item, wherein the item is a textile and wherein the polypeptide having DNase activity is a polypeptide with at least 60% sequence identity to the polypeptide of SEQ ID NO: 8, 9 or 10.

In addition, the invention relates to the use of DNases for preventing, reducing or removing the biofilm of an item.

The present invention further relates to nucleotides encoding the polypeptides and methods of producing the polypeptides.

Sequences

SEQ ID NO: 1 DNA sequence obtained from *Bacillus* sp-62451
SEQ ID NO: 2 is the polypeptide sequence derived from SEQ ID NO: 1
SEQ ID NO: 3 DNA sequence obtained from *Bacillus horikoshii*
SEQ ID NO: 4 is the polypeptide sequence derived from SEQ ID NO: 3
SEQ ID NO: 5 DNA sequence obtained from *Paenibacillus* sp-18057
SEQ ID NO: 6 is the polypeptide sequence derived from SEQ ID NO: 3
SEQ ID NO: 7 mature polypeptide Benzonase DNase (WO 2011/098579)
SEQ ID NO: 8 mature polypeptide of SEQ ID NO: 2 obtained from *Bacillus* sp-62451
SEQ ID NO: 9 mature polypeptide of SEQ ID NO: 4 obtained from *Bacillus horikoshii*
SEQ ID NO: 10 mature polypeptide of SEQ ID NO: 6 obtained from *Paenibacillus* sp-18057
SEQ ID NO: 11 mature polypeptide obtained from *Bacillus* sp-62520
SEQ ID NO: 12 mature polypeptide obtained from *Bacillus* sp-62520
SEQ ID NO: 13 mature polypeptide obtained from *Bacillus horikoshii*
SEQ ID NO: 14 mature polypeptide obtained from *Bacillus horikoshii*
SEQ ID NO: 15 mature polypeptide obtained from *Bacillus* sp-16840
SEQ ID NO: 16 mature polypeptide obtained from *Bacillus* sp-16840
SEQ ID NO: 17 mature polypeptide obtained from *Bacillus* sp-62668
SEQ ID NO: 18 mature polypeptide obtained from *Bacillus* sp-13395
SEQ ID NO: 19 mature polypeptide obtained from *Bacillus horneckiae*
SEQ ID NO: 20 mature polypeptide obtained from *Bacillus* sp-11238
SEQ ID NO: 21 mature polypeptide obtained from *Bacillus cibi*
SEQ ID NO: 22 mature polypeptide obtained from *Bacillus* sp-18318
SEQ ID NO: 23 mature polypeptide obtained from *Bacillus idriensis*
SEQ ID NO: 24 is *Bacillus clausii* secretion signal
SEQ ID NO: 25 DNA sequence obtained from *Bacillus* sp-62520
SEQ ID NO: 26 polypeptide sequence derived from SEQ ID NO: 25
SEQ ID NO: 27 DNA sequence obtained from *Bacillus* sp-62520
SEQ ID NO: 28 polypeptide sequence derived from SEQ ID NO: 27
SEQ ID NO: 29 DNA sequence obtained from *Bacillus horikoshii*
SEQ ID NO: 30 polypeptide sequence derived from SEQ ID NO: 29
SEQ ID NO: 31 DNA sequence obtained from *Bacillus horikoshii*
SEQ ID NO: 32 polypeptide sequence derived from SEQ ID NO: 31
SEQ ID NO: 33 DNA sequence obtained from *Bacillus* sp-16840
SEQ ID NO: 34 polypeptide sequence derived from SEQ ID NO: 33
SEQ ID NO: 35 DNA sequence obtained from *Bacillus* sp-16840
SEQ ID NO: 36 polypeptide sequence derived from SEQ ID NO: 35
SEQ ID NO: 37 DNA sequence obtained from *Bacillus* sp-62668
SEQ ID NO: 38 polypeptide sequence derived from SEQ ID NO: 37
SEQ ID NO: 39 DNA sequence obtained from *Bacillus* sp-13395
SEQ ID NO: 40 polypeptide sequence derived from SEQ ID NO: 39
SEQ ID NO: 41 DNA sequence obtained from *Bacillus horneckiae*
SEQ ID NO: 42 polypeptide sequence derived from SEQ ID NO: 41
SEQ ID NO: 43 DNA sequence obtained from *Bacillus* sp-11238
SEQ ID NO: 44 polypeptide sequence derived from SEQ ID NO: 43
SEQ ID NO: 45 DNA sequence obtained from *Bacillus cibi*
SEQ ID NO: 46 polypeptide sequence derived from SEQ ID NO: 45
SEQ ID NO: 47 DNA sequence obtained from *Bacillus* sp-18318
SEQ ID NO: 48 polypeptide sequence derived from SEQ ID NO: 47
SEQ ID NO: 49 DNA sequence obtained from *Bacillus idriensis*
SEQ ID NO: 50 polypeptide sequence derived from SEQ ID NO: 49
SEQ ID NO: 51 DNA sequence obtained from *Bacillus algicola*
SEQ ID NO: 52 polypeptide sequence derived from SEQ ID NO: 51
SEQ ID NO: 53 is the mature polypeptide obtained from *Bacillus algicola*
SEQ ID NO: 54 DNA sequence derived from Xanthan alkaline community J
SEQ ID NO: 55 polypeptide sequence derived from SEQ ID NO: 54
SEQ ID NO: 56 mature polypeptide obtained from Xanthan alkaline community J
SEQ ID NO: 57 DNA sequence obtained from *Bacillus vietnamensis*
SEQ ID NO: 58 polypeptide sequence derived from SEQ ID NO: 57
SEQ ID NO: 59 mature polypeptide obtained from *Bacillus vietnamensis*

SEQ ID NO: 60 DNA sequence obtained from *Bacillus hwajinpoensis*
SEQ ID NO: 61 polypeptide sequence derived from SEQ ID NO: 60
SEQ ID NO: 62 mature polypeptide obtained from *Bacillus hwajinpoensis*
SEQ ID NO: 63 DNA sequence obtained from *Paenibacillus mucilaginosus*
SEQ ID NO: 64 polypeptide sequence derived from SEQ ID NO: 63
SEQ ID NO: 65 mature polypeptide obtained from *Paenibacillus mucilaginosus*
SEQ ID NO: 66 DNA sequence obtained from *Bacillus indicus*
SEQ ID NO: 67 polypeptide sequence derived from SEQ ID NO: 66
SEQ ID NO: 68 mature polypeptide obtained from *Bacillus indicus*
SEQ ID NO: 69 DNA sequence obtained from *Bacillus marisflavi*
SEQ ID NO: 70 polypeptide sequence derived from SEQ ID NO: 69
SEQ ID NO: 71 Mature polypeptide obtained from *Bacillus marisflavi*
SEQ ID NO: 72 DNA sequence obtained from *Bacillus luciferensis*
SEQ ID NO: 73 polypeptide sequence derived from SEQ ID NO: 72
SEQ ID NO: 74 mature polypeptide obtained from *Bacillus luciferensis*
SEQ ID NO: 75 DNA sequence obtained from *Bacillus marisflavi*
SEQ ID NO: 76 polypeptide sequence derived from SEQ ID NO: 75
SEQ ID NO: 77 mature polypeptide obtained from *Bacillus marisflavi*
SEQ ID NO: 78 DNA sequence obtained from *Bacillus* sp. SA2-6
SEQ ID NO: 79 polypeptide sequence derived from SEQ ID NO: 78
SEQ ID NO: 80 mature polypeptide obtained from *Bacillus* sp. SA2-6
SEQ ID NO: 81 DNA sequence obtained from *Pyrenochaetopsis* sp.
SEQ ID NO: 82 polypeptide sequence derived from SEQ ID NO: 81
SEQ ID NO: 83 mature polypeptide obtained from *Pyrenochaetopsis* sp.
SEQ ID NO: 84 DNA sequence obtained from *Vibrissea flavovirens*
SEQ ID NO: 85 polypeptide sequence derived from SEQ ID NO: 84
SEQ ID NO: 86 mature polypeptide obtained from *Vibrissea flavovirens*
SEQ ID NO: 87 DNA sequence obtained from *Setosphaeria rostrate*
SEQ ID NO: 88 polypeptide sequence derived from SEQ ID NO: 87
SEQ ID NO: 89 mature polypeptide obtained from *Setosphaeria rostrate*
SEQ ID NO: 90 DNA sequence obtained from *Endophragmiella valdina*
SEQ ID NO: 91 polypeptide sequence derived from SEQ ID NO: 90
SEQ ID NO: 92 mature polypeptide obtained from *Endophragmiella valdina*
SEQ ID NO: 93 DNA sequence obtained from *Corynespora cassiicola*
SEQ ID NO: 94 polypeptide sequence derived from SEQ ID NO: 93
SEQ ID NO: 95 mature polypeptide obtained from *Corynespora cassiicola*
SEQ ID NO: 96 DNA sequence obtained from *Paraphoma* sp. XZ1965
SEQ ID NO: 97 polypeptide sequence derived from SEQ ID NO: 96
SEQ ID NO: 98 mature polypeptide obtained from *Paraphoma* sp. XZ1965
SEQ ID NO: 99 DNA sequence obtained from *Monilinia fructicola*
SEQ ID NO: 100 polypeptide sequence derived from SEQ ID NO: 99
SEQ ID NO: 101 mature polypeptide obtained from *Monilinia fructicola*
SEQ ID NO: 102 DNA sequence obtained from *Curvularia lunata*
SEQ ID NO: 103 polypeptide sequence derived from SEQ ID NO: 102
SEQ ID NO: 104 mature polypeptide obtained from *Curvularia lunata*
SEQ ID NO: 105 DNA sequence obtained from *Penicillium reticulisporum*
SEQ ID NO: 106 polypeptide sequence derived from SEQ ID NO: 105
SEQ ID NO: 107 mature polypeptide obtained from *Penicillium reticulisporum*
SEQ ID NO: 108 DNA sequence obtained from *Penicillium quercetorum*
SEQ ID NO: 109 polypeptide sequence derived from SEQ ID NO: 108
SEQ ID NO: 110 mature polypeptide obtained from *Penicillium quercetorum*
SEQ ID NO: 111 DNA sequence obtained from *Setophaeosphaeria* sp.
SEQ ID NO: 112 polypeptide sequence derived from SEQ ID NO: 111
SEQ ID NO: 113 mature polypeptide obtained from *Setophaeosphaeria* sp.
SEQ ID NO: 114 DNA sequence obtained from *Alternaria* sp. XZ2545
SEQ ID NO: 115 polypeptide sequence derived from SEQ ID NO: 114
SEQ ID NO: 116 mature polypeptide obtained from *Alternaria* sp. XZ2545
SEQ ID NO: 117 DNA sequence obtained from *Alternaria*
SEQ ID NO: 118 polypeptide sequence derived from SEQ ID NO: 117
SEQ ID NO: 119 mature polypeptide obtained from *Alternaria*
SEQ ID NO: 120 DNA sequence obtained from *Trichoderma reesei*
SEQ ID NO: 121 polypeptide sequence derived from SEQ ID NO: 121
SEQ ID NO: 122 mature polypeptide obtained from *Trichoderma reesei*
SEQ ID NO: 123 DNA sequence obtained from *Chaetomium thermophilum*
SEQ ID NO: 124 polypeptide sequence derived from SEQ ID NO: 123
SEQ ID NO: 125 mature polypeptide obtained from *Chaetomium thermophilum*

SEQ ID NO: 126 DNA sequence obtained from *Scytalidium thermophilum*
SEQ ID NO: 127 polypeptide sequence derived from SEQ ID NO: 126
SEQ ID NO: 128 mature polypeptide obtained from *Scytalidium thermophilum*
SEQ ID NO: 129 DNA sequence obtained from *Metapochonia suchlasporia*
SEQ ID NO: 130 polypeptide sequence derived from SEQ ID NO: 129
SEQ ID NO: 131 mature polypeptide obtained from *Metapochonia suchlasporia*
SEQ ID NO: 132 DNA sequence obtained from *Daldinia fissa*
SEQ ID NO: 133 polypeptide sequence derived from SEQ ID NO: 132
SEQ ID NO: 134 mature polypeptide obtained from *Daldinia fissa*
SEQ ID NO: 135 DNA sequence obtained from *Acremonium* sp. XZ2007
SEQ ID NO: 136 polypeptide sequence derived from SEQ ID NO: 135
SEQ ID NO: 137 mature polypeptide obtained from *Acremonium* sp. XZ2007
SEQ ID NO: 138 DNA sequence obtained from *Acremonium dichromosporum*
SEQ ID NO: 139 polypeptide sequence derived from SEQ ID NO: 138
SEQ ID NO: 140 mature polypeptide obtained from *Acremonium dichromosporum*
SEQ ID NO: 141 DNA sequence obtained from *Sarocladium* sp. XZ2014
SEQ ID NO: 142 polypeptide sequence derived from SEQ ID NO: 141
SEQ ID NO: 143 mature polypeptide obtained from *Sarocladium* sp. XZ2014
SEQ ID NO: 144 DNA sequence obtained from *Metarhizium* sp. HNA15-2
SEQ ID NO: 145 polypeptide sequence derived from SEQ ID NO: 144
SEQ ID NO: 146 mature polypeptide obtained from *Metarhizium* sp. HNA15-2
SEQ ID NO: 147 DNA sequence obtained from *Acremonium* sp. XZ2414
SEQ ID NO: 148 polypeptide sequence derived from SEQ ID NO: 147
SEQ ID NO: 149 mature polypeptide obtained from *Acremonium* sp. XZ2414
SEQ ID NO: 150 DNA sequence obtained from *Isaria tenuipes*
SEQ ID NO: 151 polypeptide sequence derived from SEQ ID NO: 150
SEQ ID NO: 152 mature polypeptide obtained from *Isaria tenuipes*
SEQ ID NO: 153 DNA sequence obtained from *Scytalidium circinatum*
SEQ ID NO: 154 polypeptide sequence derived from SEQ ID NO: 153
SEQ ID NO: 155 mature polypeptide obtained from *Scytalidium circinatum*
SEQ ID NO: 156 DNA sequence obtained from *Metarhizium lepidiotae*
SEQ ID NO: 157 polypeptide sequence derived from SEQ ID NO: 156
SEQ ID NO: 158 mature polypeptide obtained from *Metarhizium lepidiotae*
SEQ ID NO: 159 DNA sequence obtained from *Thermobispora bispora*
SEQ ID NO: 160 polypeptide sequence derived from SEQ ID NO: 159
SEQ ID NO: 161 mature polypeptide obtained from *Thermobispora bispora*
SEQ ID NO: 162 DNA sequence obtained from *Sporormia fimetaria*
SEQ ID NO: 163 polypeptide sequence derived from SEQ ID NO: 162
SEQ ID NO: 164 mature polypeptide obtained from *Sporormia fimetaria*
SEQ ID NO: 165 DNA sequence obtained from *Pycnidiophora cf. dispera*
SEQ ID NO: 166 polypeptide sequence derived from SEQ ID NO: 165
SEQ ID NO: 167 mature polypeptide obtained from *Pycnidiophora cf. dispera*
SEQ ID NO: 168 DNA sequence obtained from Xanthan alkaline community D
SEQ ID NO: 169 polypeptide sequence derived from SEQ ID NO: 168
SEQ ID NO: 170 mature polypeptide obtained from Xanthan alkaline community D
SEQ ID NO: 171 DNA sequence obtained from Xanthan alkaline community O
SEQ ID NO: 172 polypeptide sequence derived from SEQ ID NO: 171
SEQ ID NO: 173 mature polypeptide obtained from Xanthan alkaline community O
SEQ ID NO: 174 DNA sequence obtained from *Clavicipitaceae* sp-70249
SEQ ID NO: 175 polypeptide sequence derived from SEQ ID NO: 174
SEQ ID NO: 176 mature polypeptide obtained from 175 from *Clavicipitaceae* sp-70249
SEQ ID NO: 177 DNA sequence obtained from *Westerdykella* sp. AS85-2
SEQ ID NO: 178 polypeptide sequence derived from SEQ ID NO: 177
SEQ ID NO: 179 mature polypeptide obtained from *Westerdykella* sp. AS85-2
SEQ ID NO: 180 DNA sequence obtained from *Humicolopsis cephalosporioides*
SEQ ID NO: 181 polypeptide sequence derived from SEQ ID NO: 180
SEQ ID NO: 182 mature polypeptide obtained from *Humicolopsis cephalosporioides*
SEQ ID NO: 183 DNA sequence obtained from *Neosartorya massa*
SEQ ID NO: 184 polypeptide sequence derived from SEQ ID NO: 183
SEQ ID NO: 185 mature polypeptide obtained from *Neosartorya massa*
SEQ ID NO: 186 DNA sequence obtained from *Roussoella intermedia*
SEQ ID NO: 187 polypeptide sequence derived from SEQ ID NO: 186
SEQ ID NO: 188 mature polypeptide obtained from SEQ ID NO: 187
SEQ ID NO: 189 DNA sequence obtained from *Pleosporales*
SEQ ID NO: 190 polypeptide sequence derived from SEQ ID NO: 189
SEQ ID NO: 191 mature polypeptide obtained from *Pleosporales*

SEQ ID NO: 192 DNA sequence obtained from *Phaeosphaeria*
SEQ ID NO: 193 polypeptide sequence derived from SEQ ID NO: 192
SEQ ID NO: 194 mature polypeptide obtained from *Phaeosphaeria*
SEQ ID NO: 195 DNA sequence obtained from *Didymosphaeria futilis*
SEQ ID NO: 196 polypeptide sequence derived from SEQ ID NO: 195
SEQ ID NO: 197 mature polypeptide obtained from *Didymosphaeria futilis* motif
[T/D/S][G/N]PQL
SEQ ID NO: 198 motif
[G/T]Y[D/S][R/K/L]
SEQ ID NO: 199 motif
[E/D/H]H[I/V/L/F/M]X[P/A/S]
SEQ ID NO: 200 motif
[F/L/Y/I]A[N/R]D[L/I/P/V]
SEQ ID NO: 201 motif
C[D/N]T[A/R]
SEQ ID NO: 202 motif
[D/Q][I/V]DH
SEQ ID NO: 203 motif
[D/M/L][S/T]GYSR[D/N]
SEQ ID NO: 204 motif
ASXNRSKG
SEQ ID NO: 205 motif
[V/I]PL[S/A]NAWK
SEQ ID NO: 206 motif
NPQL
SEQ ID NO: 207 motif
P[Q/E]L[W/Y]
SEQ ID NO: 208 motif
[K/H/E]NAW
SEQ ID NO: 209

BRIEF DESCRIPTION OF THE FIGURES

FIGS. 1, 1A, 1B, 1C and 1D provides an alignment of the polypeptides of the invention comprised in the GYS clade.

FIGS. 2, 2A, 2B and 2C provides an alignment of the polypeptides of the invention comprised in the NAWK clade.

FIGS. 3, 3A, 3B and 3C provides an alignment of the polypeptides of the invention comprised in the KNAW clade.

DEFINITIONS

Figure 2A:
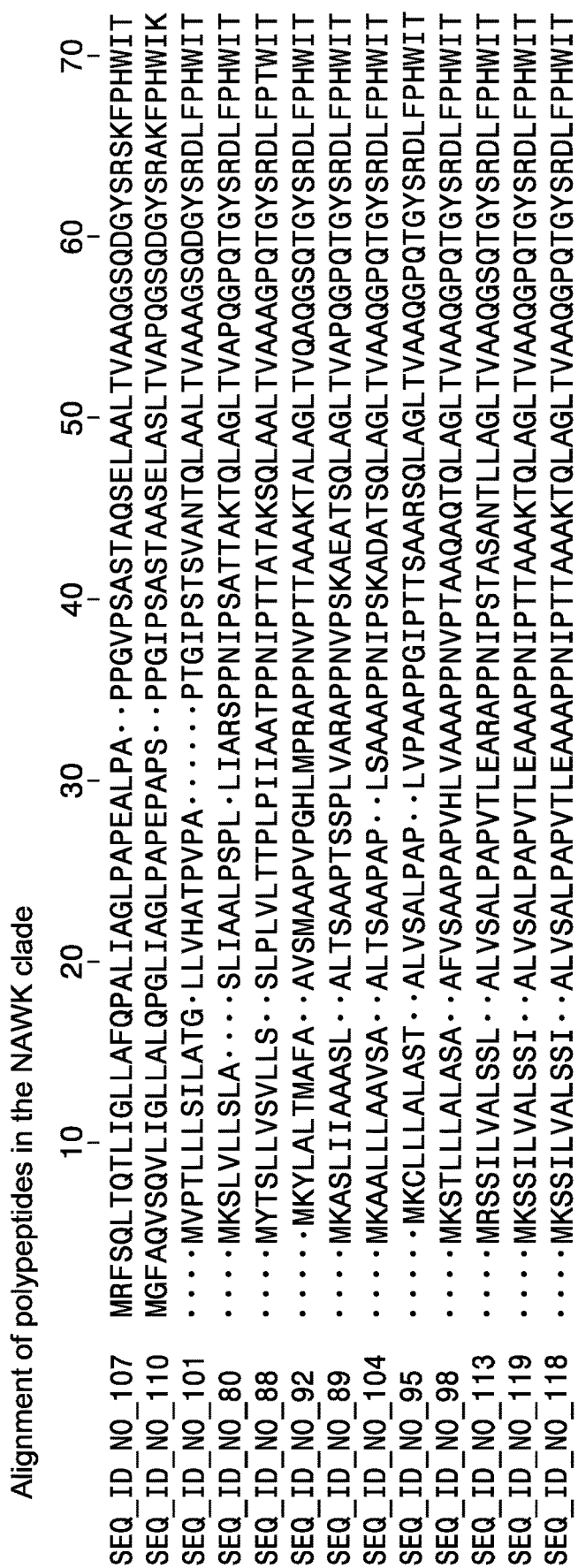
Figure 3A:
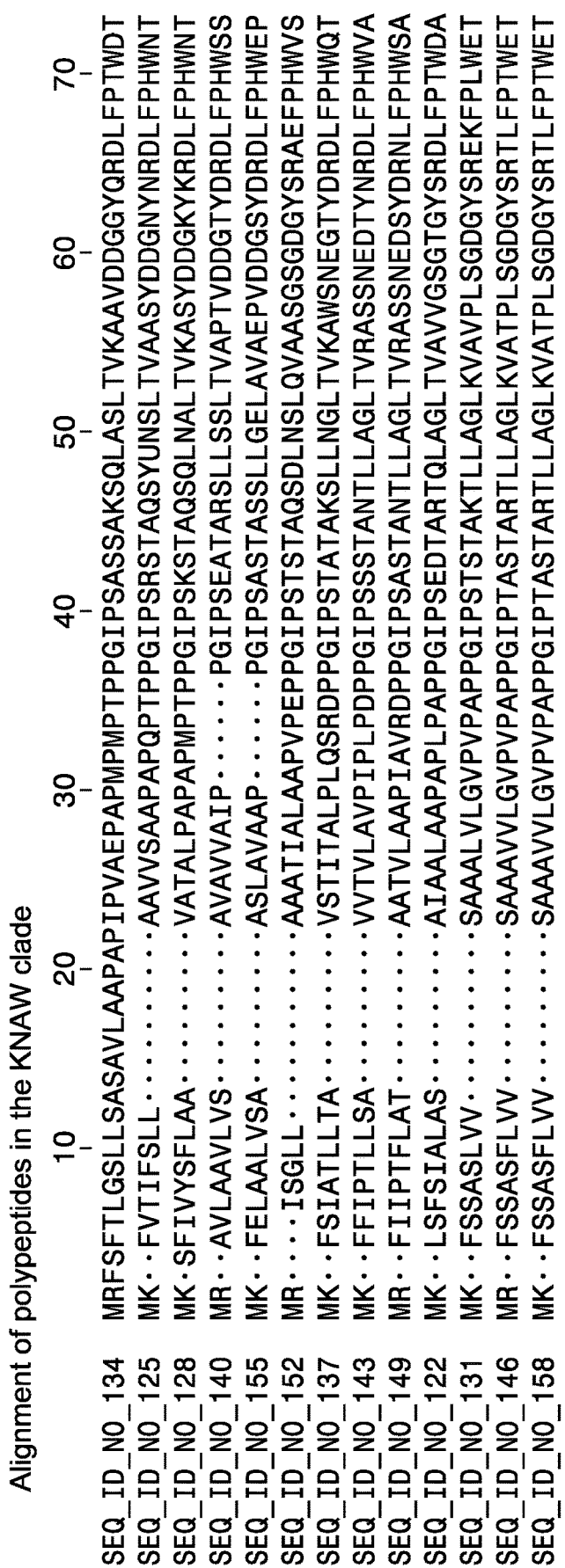

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Biofilm: A biofilm is any group of microorganisms in which cells stick to each other on a surface, such as a textile, dishware or hard surface. These adherent cells are frequently embedded within a self-produced matrix of extracellular polymeric substance (EPS). Biofilm EPS is a polymeric conglomeration generally composed of extracellular DNA, proteins, and polysaccharides. Biofilms may form on living or non-living surfaces. The microbial cells growing in a biofilm are physiologically distinct from planktonic cells of the same organism, which, by contrast, are single cells that may float or swim in a liquid medium. Bacteria living in a biofilm usually have significantly different properties from free-floating bacteria of the same species, as the dense and protected environment of the film allows them to cooperate and interact in various ways. One benefit of this environment is increased resistance to detergents and antibiotics, as the dense extracellular matrix and the outer layer of cells protect the interior of the community. On laundry biofilm producing bacteria can be found among the following species: *Acinetobacter* sp., *Aeromicrobium* sp., *Brevundimonas* sp., *Microbacterium* sp., *Micrococcus luteus*, *Pseudomonas* sp., *Staphylococcus epidermidis*, and *Stenotrophomonas* sp.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, synthetic DNA, or a combination thereof.

Color difference (L value): A Lab color space is a color-opponent space with dimension L for lightness. L value, L* represents the darkest black at L*=0, and the brightest white at L*=100. In the context of the present invention L value is also referred to as color difference.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Deep cleaning: By the term "deep cleaning" is meant disruption or removal of a biofilm or components of a biofilm such as polysaccharides, proteins, DNA, soil or other components present in the biofilm.

Detergent adjunct ingredient: The detergent adjunct ingredient is different to the DNase of this invention. The precise nature of these additional adjunct components, and levels of incorporation thereof, will depend on the physical form of the composition and the nature of the operation for which it is to be used. Suitable adjunct materials include, but are not limited to the components described below such as surfactants, builders, flocculating aid, chelating agents, dye transfer inhibitors, enzymes, enzyme stabilizers, enzyme inhibitors, catalytic materials, bleach activators, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, builders and co-builders, fabric huing agents, anti-foaming agents, dispersants, processing aids, and/or pigments.

Detergent Composition: The term "detergent composition" refers to compositions that find use in the removal of undesired compounds from items to be cleaned, such as textiles. The detergent composition may be used to, e.g., clean textiles for both household cleaning and industrial cleaning. The terms encompass any materials/compounds selected for the particular type of cleaning composition desired and the form of the product (e.g., liquid, gel, powder, granulate, paste, or spray compositions) and includes, but is not limited to, detergent compositions (e.g., liquid and/or solid laundry detergents and fine fabric detergents; fabric fresheners; fabric softeners; and textile and laundry pre-spotters/pretreatment. In addition to containing the enzyme of the invention, the detergent formulation may contain one or more additional enzymes (such as proteases, amylases, lipases, cutinases, cellulases, endoglucanases, xyloglucanases, pectinases, pectin lyases, xanthanases, peroxidases, haloperoxygenases, catalases and mannanases, or any mixture thereof), and/or detergent adjunct ingredients such as surfactants, builders, chelators or chelating agents, bleach system or bleach components, polymers, fabric conditioners, foam boosters, suds suppressors, dyes, perfume, tannish inhibitors, optical brighteners, bactericides, fungicides, soil suspending agents, anti-corrosion agents, enzyme inhibitors or stabilizers, enzyme activators, transferase(s), hydrolytic enzymes, oxido reductases, bluing agents and fluorescent dyes, antioxidants, and solubilizers.

DNase (deoxyribonuclease): The term "DNase" means a polypeptide with DNase activity that catalyzes the hydrolytic cleavage of phosphodiester linkages in the DNA backbone, thus, degrading DNA. The term "DNases" and the expression "a polypeptide with DNase activity" are used interchangeably throughout the application. For purposes of the present invention, DNase activity is determined according to the procedure described in the Assay I. In one aspect, the polypeptides of the present invention have at least 20%, e.g., at least 40%, at least 50%, at least 60%, at least 70%, at least 80%, at least 90%, at least 95%, or at least 100% of the DNase activity of the mature polypeptide of SEQ ID NO: 2, 4 or 6, preferable of SEQ ID NO: 2. In one embodiment, the polypeptides of the present invention have improved DNase activity, e.g., such that the DNase activity of the polypeptide is at least 105%, e.g., at least 110%, at least 120%, at least 130%, at least 140%, at least 160%, at least 170%, at least 180%, or at least 200% with reference to the DNase activity of the mature polypeptide of SEQ ID NO: 2, 4 or 6, preferably of SEQ ID NO: 2.

In a preferred embodiment, the DNase activity of the polypeptide is at least at least 20%, e.g., at least 40%, at least 50%, at least 60%, at least 70%, at least 80%, at least 90%, at least 95%, at least 100%, at least 105%, at least 110%, at least 120%, at least 130%, at least 140%, at least 160%, at least 170%, at least 180%, or at least 200% with reference to the DNase activity of the mature polypeptide of SEQ ID NO: 2 as determined according to the procedure described in the Assay I.

Enzyme Detergency benefit: The term "enzyme detergency benefit" is defined herein as the advantageous effect an enzyme may add to a detergent compared to the same detergent without the enzyme. Important detergency benefits which can be provided by enzymes are stain removal with no or very little visible soils afterwashing and/or cleaning, prevention or reduction of redeposition of soils released in the washing process (an effect that also is termed anti-redeposition), restoring fully or partly the whiteness of textiles which originally were white but after repeated use and wash have obtained a greyish or yellowish appearance (an effect that also is termed whitening). Textile care benefits, which are not directly related to catalytic stain removal or prevention of redeposition of soils, are also important for enzyme detergency benefits. Examples of such textile care benefits are prevention or reduction of dye transfer from one fabric to another fabric or another part of the same fabric (an effect that is also termed dye transfer inhibition or anti-backstaining), removal of protruding or broken fibers from a fabric surface to decrease pilling tendencies or remove already existing pills or fuzz (an effect that also is termed anti-pilling), improvement of the fabric-softness, colour clarification of the fabric and removal of particulate soils which are trapped in the fibers of the fabric or garment. Enzymatic bleaching is a further enzyme detergency benefit where the catalytic activity generally is used to catalyze the formation of bleaching components such as hydrogen peroxide or other peroxides.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Fragment: The term "fragment" means a polypeptide having one or more (e.g., several) amino acids absent from the amino and/or carboxyl terminus of a mature polypeptide or domain; wherein the fragment has DNase activity. In one aspect, a fragment contains at least 206 amino acid residues (e.g., amino acids 1 to 206 of SEQ ID NO: 2), at least 205 amino acid residues (e.g., amino acids 2 to 206 of SEQ ID NO: 2), or at least 204 amino acid residues (e.g., amino acids 3 to 206 of SEQ ID NO: 2). In one aspect, a fragment contains at least 206 amino acid residues (e.g., amino acids 1 to 206 of SEQ ID NO: 4), at least 205 amino acid residues (e.g., amino acids 4 to 206 of SEQ ID NO: 4), or at least 204 amino acid residues (e.g., amino acids 3 to 206 of SEQ ID NO: 4). In one aspect, a fragment contains at least 206 amino acid residues (e.g., amino acids 1 to 206 of SEQ ID NO: 6), at least 205 amino acid residues (e.g., amino acids 2 to 206 of SEQ ID NO: 6), or at least 204 amino acid residues (e.g., amino acids 3 to 206 of SEQ ID NO: 6).

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Improved wash performance: The term "improved wash performance" is defined herein as an enzyme displaying an increased wash performance in a detergent composition relative to the wash performance of same detergent composition without the enzyme, e.g., by increased stain removal or less redeposition. The term "improved wash performance" includes wash performance in laundry.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance). An isolated substance may be present in a fermentation broth sample; e.g., a host cell may be genetically modified to express the polypeptide of the invention. The fermentation broth from that host cell will comprise the isolated polypeptide.

Laundering: The term "laundering" relates to both household laundering and industrial laundering and means the process of treating textiles with a solution containing a cleaning or detergent composition of the present invention. The laundering process can for example be carried out using, e.g., a household or an industrial washing machine or can be carried out by hand.

Malodor: The term "malodor" means an odor which is not desired on clean items. The cleaned item should smell fresh and clean without malodors adhered to the item. One example of malodor is compounds with an unpleasant smell, which may be produced by microorganisms. Another example is unpleasant smells can be sweat or body odor adhered to an item which has been in contact with human or animal. Another example of malodor can be the odor from spices, which sticks to items for example curry or other exotic spices which smells strongly. One way of measuring the ability of an item to adhere malodor is by using Assay II disclosed herein.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 29 to 210 of SEQ ID NO: 2, amino acids 29 to 210 of SEQ ID NO: 4 or amino acids 23 to 202 of SEQ ID NO: 6 and amino acids 1 to 28 of SEQ ID NO: 2, amino acids 1 to 28 of SEQ ID NO: 4 and amino acids 1 to 22 of SEQ ID NO: 6 are signal peptides.

In one aspect, the mature polypeptide is amino acids 1 to 182 of SEQ ID NO: 26.

In one aspect, the mature polypeptide is amino acids 1 to 182 of SEQ ID NO: 28.

In one aspect, the mature polypeptide is amino acids 1 to 182 of SEQ ID NO: 30.

In one aspect, the mature polypeptide is amino acids 1 to 182 of SEQ ID NO: 32.

In one aspect, the mature polypeptide is amino acids 1 to 182 of SEQ ID NO: 34.

In one aspect, the mature polypeptide is amino acids 1 to 182 of SEQ ID NO: 36.

In one aspect, the mature polypeptide is amino acids 1 to 182 of SEQ ID NO: 38.

In one aspect, the mature polypeptide is amino acids 1 to 183 of SEQ ID NO: 40.

In one aspect, the mature polypeptide is amino acids 1 to 185 of SEQ ID NO: 42.

In one aspect, the mature polypeptide is amino acids 1 to 182 of SEQ ID NO: 44.

In one aspect, the mature polypeptide is amino acids 1 to 182 of SEQ ID NO: 46.

In one aspect, the mature polypeptide is amino acids 1 to 182 of SEQ ID NO: 48.

In one aspect, the mature polypeptide is amino acids 1 to 182 of SEQ ID NO: 50.

In one aspect, the mature polypeptide is amino acids 1 to 182 of SEQ ID NO: 52.

In one aspect, the mature polypeptide is amino acids 1 to 182 of SEQ ID NO: 55.

In one aspect, the mature polypeptide is amino acids 1 to 182 of SEQ ID NO: 58.

In one aspect, the mature polypeptide is amino acids 1 to 182 of SEQ ID NO: 61.

In one aspect, the mature polypeptide is amino acids 1 to 182 of SEQ ID NO: 64.

In one aspect, the mature polypeptide is amino acids 1 to 182 of SEQ ID NO: 67.

In one aspect, the mature polypeptide is amino acids 1 to 182 of SEQ ID NO: 70.

In one aspect, the mature polypeptide is amino acids 1 to 184 of SEQ ID NO: 73.

In one aspect, the mature polypeptide is amino acids 1 to 182 of SEQ ID NO: 76.

In one aspect, the mature polypeptide is amino acids 1 to 182 of SEQ ID NO: 79.

In one aspect, the mature polypeptide is amino acids 1 to 191 of SEQ ID NO: 82.

In one aspect, the mature polypeptide is amino acids 1 to 190 of SEQ ID NO: 85.

In one aspect, the mature polypeptide is amino acids 1 to 192 of SEQ ID NO: 88.

In one aspect, the mature polypeptide is amino acids 1 to 192 of SEQ ID NO: 91.

In one aspect, the mature polypeptide is amino acids 1 to 190 of SEQ ID NO: 94.

In one aspect, the mature polypeptide is amino acids 1 to 192 of SEQ ID NO: 97.

In one aspect, the mature polypeptide is amino acids 1 to 186 of SEQ ID NO: 100.

In one aspect, the mature polypeptide is amino acids 1 to 190 of SEQ ID NO: 103.

In one aspect, the mature polypeptide is amino acids 1 to 191 of SEQ ID NO: 106.

In one aspect, the mature polypeptide is amino acids 1 to 191 of SEQ ID NO: 109.

In one aspect, the mature polypeptide is amino acids 1 to 192 of SEQ ID NO: 112.

In one aspect, the mature polypeptide is amino acids 1 to 192 of SEQ ID NO: 115.

In one aspect, the mature polypeptide is amino acids 1 to 192 of SEQ ID NO: 118.

In one aspect, the mature polypeptide is amino acids 1 to 186 of SEQ ID NO: 121.

In one aspect, the mature polypeptide is amino acids 1 to 188 of SEQ ID NO: 124.

In one aspect, the mature polypeptide is amino acids 1 to 190 of SEQ ID NO: 127.

In one aspect, the mature polypeptide is amino acids 1 to 186 of SEQ ID NO: 130.

In one aspect, the mature polypeptide is amino acids 1 to 198 of SEQ ID NO: 133.

In one aspect, the mature polypeptide is amino acids 1 to 188 of SEQ ID NO: 136.

In one aspect, the mature polypeptide is amino acids 1 to 182 of SEQ ID NO: 139

In one aspect, the mature polypeptide is amino acids 1 to 188 of SEQ ID NO: 142.

In one aspect, the mature polypeptide is amino acids 1 to 186 of SEQ ID NO: 145.

In one aspect, the mature polypeptide is amino acids 1 to 188 of SEQ ID NO: 148.

In one aspect, the mature polypeptide is amino acids 1 to 186 of SEQ ID NO: 151.

In one aspect, the mature polypeptide is amino acids 1 to 184 of SEQ ID NO: 154.

In one aspect, the mature polypeptide is amino acids 1 to 186 of SEQ ID NO: 157.

In one aspect, the mature polypeptide is amino acids 1 to 226 of SEQ ID NO: 160.

In one aspect, the mature polypeptide is amino acids 1 to 191 of SEQ ID NO: 163.

In one aspect, the mature polypeptide is amino acids 1 to 193 of SEQ ID NO: 166.

In one aspect, the mature polypeptide is amino acids 1 to 199 of SEQ ID NO: 169.

In one aspect, the mature polypeptide is amino acids 1 to 194 of SEQ ID NO: 172.

In one aspect, the mature polypeptide is amino acids 1 to 186 of SEQ ID NO: 175.

In one aspect, the mature polypeptide is amino acids 1 to 187 of SEQ ID NO: 178.

In one aspect, the mature polypeptide is amino acids 1 to 194 of SEQ ID NO: 181.

In one aspect, the mature polypeptide is amino acids 1 to 190 of SEQ ID NO: 184.

In one aspect, the mature polypeptide is amino acids 1 to 191 of SEQ ID NO: 187.

In one aspect, the mature polypeptide is amino acids 1 to 191 of SEQ ID NO: 190.

In one aspect, the mature polypeptide is amino acids 1 to 192 of SEQ ID NO: 193.

In one aspect, the mature polypeptide is amino acids 1 to 189 of SEQ ID NO: 196.

It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide. The mature polypeptide of SEQ ID NO: 2 is SEQ ID NO: 8, the mature polypeptide of SEQ ID NO: 4 is SEQ ID NO: 9 and the mature polypeptide of SEQ ID NO: 6 is SEQ ID NO: 10.

Mature Polypeptide coding sequence: The term "mature polypeptide coding sequence" means a polynucleotide that encodes a mature polypeptide having DNase activity. In one aspect, the mature polypeptide coding sequences are nucleotides 85 to 630 of SEQ ID NO: 1, nucleotides 85 to 630 of SEQ ID NO: 3 and nucleotides 67 to 606 of SEQ ID NO: 5.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Pharmaceutical adjunct ingredient means any pharmaceutical excipient suitable for formulating the pharmaceutical compound.

Such excipients, carriers, vehicles etc. are well known to those of skill in the art and are described in text books such as Remington's Pharmaceutical Sciences, Mack Publishing Co., Easton, Pa., 1985.

Pharmaceutically acceptable excipients which are suitable for use in tablet formulations include, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. Tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

For hard gelatin capsule formulations, the active ingredient can be mixed with an inert solid diluent, for example, calcium carbonate, calcium phosphate or kaolin. For soft gelatin capsule formulations, the active ingredient can be mixed with water or an oil medium, for example peanut oil, liquid paraffin or olive oil.

Excipients suitable for the manufacture of aqueous suspensions include suspending agents, for example sodium carboxymethylcellulose, methylcellulose, hydropropyl methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters obtained from fatty acids and a hexitol such as polyoxyethylene sorbitol monooleate, or condensation products of ethylene oxide with partial esters obtained from fatty acids and hexitol anhydrides, for example polyethylene sorbitan monooleate.

Aqueous suspensions may also contain one or more preservatives, for example benzoates, such as ethyl, or n-propyl p-hydroxybenzoate, one or more colouring agents, one or more flavouring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin The oily suspensions may contain a thickening agent, for example beeswax, hard paraffin or cetyl alcohol. Sweetening agents and flavouring agents may be added. These compositions may be preserved by the addition of an antioxidant such as ascorbic acid.

Remission value: Wash performance is expressed as a Remission value of the stained swatches. After washing and rinsing the swatches were spread out flat and allowed to air dry at room temperature overnight. All washes swatches are evaluated the day after the wash. Light reflectance evaluations of the swatches were done using a Macbeth Color Eye 7000 reflectance spectrophotometer with very small aperture. The measurements were made without UV in the incident light and remission at 460 nm was extracted.

Sequence identity: The relatedness between two amino acid sequences or between two nucleotide sequences is described by the parameter "sequence identity". For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, Trends Genet. 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the-nobrief option) is used as the percent identity and is calculated as follows: (Identical Residues×100)/(Length of Alignment−Total Number of Gaps in Alignment). For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EM-BOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the-nobrief option) is used as the percent identity and is calculated as follows: (Identical Deoxyribonucleotides×100)/(Length of Alignment−Total Number of Gaps in Alignment).

Stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Subsequence: The term "subsequence" means a polynucleotide having one or more (e.g., several) nucleotides absent from the 5' and/or 3' end of a mature polypeptide coding sequence; wherein the subsequence encodes a fragment having DNase activity. In one aspect, a subsequence contains at least 550 nucleotides (e.g., nucleotides 85 to 630 of SEQ ID NO: 1, 3 or 5), at least 400 nucleotides (e.g., nucleotides 100 to 500 of SEQ ID NO: 1, 3 or 5), or at least 300 nucleotides (e.g., nucleotides 200 to 500 of SEQ ID NO: 1, 3 or 5).

Textile: The term "textile" means any textile material including yarns, yarn intermediates, fibers, non-woven materials, natural materials, synthetic materials, and any other textile material, fabrics made of these materials and products made from fabrics (e.g., garments and other articles). The textile or fabric may be in the form of knits, wovens, denims, non-wovens, felts, yarns, and towelling. The textile may be cellulose based such as natural cellulosics, including cotton, flax/linen, jute, ramie, sisal or coir or manmade cellulosics (e.g., originating from wood pulp) including viscose/rayon, cellulose acetate fibers (tricell), lyocell or blends thereof. The textile or fabric may also be non-cellulose based such as natural polyamides including wool, camel, cashmere, mohair, rabbit and silk or synthetic polymers such as nylon, aramid, polyester, acrylic, polypropylene and spandex/elastane, or blends thereof as well as blends of cellulose based and non-cellulose based fibers. Examples of blends are blends of cotton and/or rayon/viscose with one or more companion material such as wool, synthetic fibre (e.g., polyamide fibre, acrylic fibre, polyester fibre, polyvinyl chloride fibre, polyurethane fibre, polyurea fibre, aramid fibre), and/or cellulose-containing fibre (e.g., rayon/viscose, ramie, flax/linen, jute, cellulose acetate fibre, lyocell). Fabric may be conventional washable laundry, for example stained household laundry. When the term fabric or garment is used it is intended to include the broader term textiles as well. In the context of the present invention, the term "textile" also covers fabrics.

Variant: The term "variant" means a polypeptide having same enzyme activity as the parent enzyme, e.g., in the present context a variant of the invention have DNase activity, wherein the variant comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position. In the context of the present invention, a variant of an identified DNase has the enzymatic activity of the parent, i.e., the capacity of catalyzing the hydrolytic cleavage of phosphodiester linkages in the DNA backbone (deoxyribonuclease activity). In one embodiment, the deoxyribonuclease activity of the variant is increased with reference to the parent DNase, e.g., the mature polypeptide of SEQ ID NO: 2, 4 or 6. In one embodiment, the polypeptide has DNase activity and the variant has increased DNase activity compared to the parent DNase, e.g., the mature polypeptide of SEQ ID NO: 2, SEQ ID NO: 4, SEQ ID NO: 6, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 55, SEQ ID NO: 58, SEQ ID NO: 61, SEQ ID NO: 64, SEQ ID NO: 67, SEQ ID NO: 70, SEQ ID NO: 73, SEQ ID NO: 76, SEQ ID NO: 79, SEQ ID NO: 82, SEQ ID NO: 85, SEQ ID NO: 88, SEQ ID NO: 91, SEQ ID NO: 94, SEQ ID NO: 97, SEQ ID NO: 100, SEQ ID NO: 103, SEQ ID NO: 106, SEQ ID NO: 109, SEQ ID NO: 112, SEQ ID NO: 115, SEQ ID NO: 118, SEQ ID NO: 121, SEQ ID NO: 124, SEQ ID NO: 127, SEQ ID NO: 130, SEQ ID NO: 133, SEQ ID NO: 136, SEQ ID NO: 139, SEQ ID NO: 142, SEQ ID NO: 145, SEQ ID NO: 148, SEQ ID NO: 151, SEQ ID NO: 154, SEQ ID NO: 157, SEQ ID NO: 160, SEQ ID NO: 163, SEQ ID NO: 166, SEQ ID NO: 169, SEQ ID NO: 172, SEQ ID NO: 175, SEQ ID NO: 178, SEQ ID NO: 181, SEQ ID NO: 184, SEQ ID NO: 187, SEQ ID NO: 190, SEQ ID NO: 193 or SEQ ID NO: 196.

Wash cycle: The term "wash cycle" is defined herein as a washing operation wherein textiles are immersed in the wash liquor, mechanical action of some kind is applied to the textile in order to release stains and to facilitate flow of wash liquor in and out of the textile and finally the superfluous wash liquor is removed. After one or more wash cycles, the textile is generally rinsed and dried.

Wash liquor: The term "wash liquor" is defined herein as the solution or mixture of water and detergent components optionally including the enzyme of the invention.

Wash time: The term "wash time" is defined herein as the time it takes for the entire washing process; i.e., the time for the wash cycle(s) and rinse cycle(s) together.

Whiteness: The term "Whiteness" is defined herein as a broad term with different meanings in different regions and for different consumers. Loss of whiteness can, e.g., be due to greying, yellowing, or removal of optical brighteners/hueing agents. Greying and yellowing can be due to soil redeposition, body soils, colouring from, e.g., iron and copper ions or dye transfer. Whiteness might include one or several issues from the list below: colourant or dye effects; incomplete stain removal (e.g., body soils, sebum etc.); redeposition (greying, yellowing or other discolorations of the object) (removed soils reassociate with other parts of textile, soiled or unsoiled); chemical changes in textile during application; and clarification or brightening of colours.

Nomenclature

For purposes of the present invention, the nomenclature [E/Q] means that the amino acid at this position may be a glutamic acid (Glu, E) or a glutamine (Gln, Q). Likewise, the nomenclature [V/G/A/I] means that the amino acid at this position may be a valine (Val, V), glycine (Gly, G), alanine (Ala, A) or isoleucine (lie, 1), and so forth for other combinations as described herein. Unless otherwise limited further, the amino acid X is defined such that it may be any of the 20 natural amino acids.

DETAILED DESCRIPTION OF THE INVENTION

The present invention relates to novel polypeptides having deoxyribonuclease (DNase) activity which can be used for preventing, reducing or removing biofilm on items such as textiles and/or fabric. A polypeptide having DNase activity or a deoxyribonuclease (DNase) is any enzyme that catalyzes the hydrolytic cleavage of phosphodiester linkages in the DNA backbone, thus, degrading DNA. The two terms polypeptide having DNase activity and DNase are used interchangeably.

Polypeptides

Examples of polypeptides having DNase activity are polypeptides comprising the PFAM domain DUF1524 (http://pfam.xfam.org/), "The Pfam protein families database: towards a more sustainable future", Finn et al., 2016, *Nucleic Acids Research* Database Issue 44: D279-D285". The DUF1524 domain contains a conserved HXXP sequence motif commonly found in nucleases (Machnicka et al., 2015, "Phylogenomics and sequence-structure-function relationships in the GmrSD family of Type IV restriction enzymes", *BMC Bioinformaticsi* 16: 336). DUF means domain of unknown function, and the polypeptide families comprising, e.g., DUF have been collected together in the Pfam database. The Pfam data base provides sequence alignments and hidden Markov models that define the collected protein domains. A protein domain is a conserved part of a given protein sequence and (tertiary) structure that can evolve, function, and exist independently of the rest of the protein chain. Each domain forms a compact three-dimensional structure and often can be independently stable and folded. Many proteins consist of several structural domains. One domain may appear in a variety of different proteins.

A particular DUF may be identified using the prefix DUF followed by a number, e.g., 1524. The DUF1524 is a family of proteins all comprising the HXXP motif, where H is the amino acid histidine, P is the amino acid proline and X is any amino acid.

In one aspect of the invention the polypeptides of the present invention having DNase activity comprise the DUF1524 domain. Thus, according to one embodiment the invention relates to polypeptides having DNase activity, wherein the polypeptides comprise the DUF1524 domain and the invention relates to the use of such DNases, e.g., for preventing, reducing or removing biofilm on items such as textiles and/or fabric. The invention further relates to compositions comprising polypeptides having DNase activity, which comprises a DUF1524 domain, e.g., HXXP. Such compositions may be but is not limited to liquid or powder laundry compositions, tablets, unit dose, spray or soap bars.

In one embodiment the DNases of the invention comprise one or more DUF1524 domains, e.g., comprise one or both of the motifs [T/D/S][G/N]PQL (SEQ ID NO: 198) or [G/T]Y[D/S][R/K/L](SEQ ID NO: 199); where T is threonine, D is aspartic acid, S is serine, G is glycine, N is asparagine, P is proline, Q is glutamine, L is leucine, Y is tyrosine, R is arginine and K is lysine, i.e., the amino acids are listed in one letter code. The brackets indicate alternative amino acids within the bracket separated by vertical line or in some instances no line, e.g., [TDS]. Thus, [T/D/S][G/N]PQL means that either T, D or S could be in the first position and either G or N could be present in the second position followed by PQL. The motifs may then be either of TGPQL, TNPQL, DGPQL, DNPQL, SGPQL or SNPQL. For the motif [G/T]Y[D/S][R/K/L] the conservative amino acid is Y and G or T optional amino acids before and D or S optional amino acids after that position. The motif could then beGYD, TYD, GYSorTYS.

Another domain shared among polypeptides of the DUF1524 is [E/D/H]H[I/V/L/F/M]X[P/A/S](SEQ ID NO: 200), which is located at positions corresponding to positions 87 to 91 in *B. cibi* (SEQ ID NO: 21). H88 is a catalytic residue involved in the catalytic activity of DUF1524, and part of the HXXP motif. Modification of H88 to another amino acid will may result in the loss of catalytic activity.

Polypeptides having DNase activity and comprising these motifs have shown particularly good deep cleaning properties, i.e., the polypeptides of the invention having DNase activity are particularly effective in removing or reducing biofilm. One aspect of the invention relates to polypeptides having DNase activity, wherein the polypeptides comprises one or more of the motifs [E/D/H]H[I/V/L/F/M]X[P/A/S] (SEQ ID NO: 200), [T/D/S][G/N]PQL (SEQ ID NO: 198) and [G/T]Y[D/S][R/K/L] (SEQ ID NO: 199). One aspect of the invention relates to polypeptides having DNase activity, wherein the polypeptides comprises one or more of the motifs [E/D/H]H[I/V/L/F/M]X[P/A/S] (SEQ ID NO: 200), [T/D/S][G/N]PQL (SEQ ID NO: 198) and [G/T]Y[D/S][R/K/L] (SEQ ID NO: 199), with the proviso that the polypeptide is not a DNase comprising SEQ ID NO: 2 of WO 2015/155351.

One embodiment of the invention relates to DNases comprising the DUF1524 domain and one or more of the motifs SEQ ID NO: 198, SEQ ID NO: 199 or SEQ ID NO: 200, wherein the DNases have deep-cleaning properties, i.e., wherein the DNases effectively prevent, reduce or remove biofilm of an item such as a fabric, textile and/or hard surface.

As already described the polypeptides of the invention having DNase activity may comprise the structural domains of DUF1524. A further domain, preferably shared by the DNases of the invention, was identified. This domain has not been described previously, the domain is termed NUC1 and polypeptides of this domain are in addition to having DNase activity, characterized by comprising certain motifs, e.g., one or more of the motifs [F/L/Y/I]A[N/R]D[L/I/P/V] (SEQ ID NO: 201) or C[D/N]T[A/R] (SEQ ID NO: 202); as described above the letters indicate amino acids in one letter code thus, F is phenylalanine, L is leucine, A is alanine, N is asparagine, D is aspartic acid, I is isoleucine, V is valine, H is histidine, G is glycine, C cysteine, T is threonine, R is arginine and so forth. The brackets indicate that the amino acids within the bracket are alternatives.

One embodiment of the invention relates to polypeptides having DNase activity, wherein the polypeptides comprising one or both of the motifs [F/L/Y/I]A[N/R]D[L/I/P/V] (SEQ ID NO: 201) or C[D/N]T[A/R] (SEQ ID NO: Y). One embodiment of the invention relates to polypeptides having DNase activity, wherein the polypeptides comprise one or both of the motifs [F/L/Y/I]A[N/R]D[L/I/P/V](SEQ ID NO: 201) or C[D/N]T[A/R] (SEQ ID NO: 202), preferably where the motif [F/L/Y/I]A[N/R]D[L/I/P/V] (SEQ ID NO: 201) is located at positions corresponding to positions 110 to 114 of SEQ ID NO: 21 and/or where to motif C[D/N]T[A/R] is located at positions corresponding to positions 43 to 46 of SEQ ID NO: 21.

One embodiment of the invention relates to polypeptides having DNase activity, wherein the polypeptides comprise one or both of the motifs [F/L/Y/I]A[N/R]D[L/I/P/V] (SEQ ID NO: 201) or C[D/N]T[A/R] (SEQ ID NO: 202), with the proviso that the polypeptide is not a DNase comprising SEQ ID NO: 2 of WO 2015/155351, preferably the motif [F/L/Y/I]A[N/R]D[L/I/P/V] (SEQ ID NO: 201) is located at positions corresponding to positions 110 to 114 of SEQ ID NO: 21 and/or where to motif C[D/N]T[A/R] is located at positions corresponding to positions 43 to 46 of SEQ ID NO: 21.

The motifs and domains are defined cross-kingdom meaning that the domains and motifs comprise both fungal and bacterial DNases. It is well known that DNases belonging to different taxonomic may share common structural elements, which could be identified by comparing the primary structure, e.g., amino acid sequence and grouping the DNases according to sequence homology. However, common structural elements may also be identified by comparing the three dimensional (3D) structure of various DNases. Both approaches have been applied in the present invention.

The structural approach identified DNases, which have different taxonomy but share structural elements common for the identified group. The groups such as, e.g., a clade share common functionalities, which may be preference for certain biofilms etc.

From the NUC1 domain a sub-domain has been identified by the inventors and this domain is termed the NUC1_A domain. In addition to comprising any of the domains above the polypeptides having DNase activity belonging to the NUC1_A domain share the common motif [D/Q][I/V]DH (SEQ ID NO: 203), corresponding to amino acid 85 to 88 in the reference polypeptide (SEQ ID NO: 21). The D at the position corresponding to position 85 of SEQ ID NO: 21 is predicted to be involved in binding of catalytic metal ion cofactor, where the letters define amino acids as described above and the brackets indicate alternative amino acids. In one embodiment the invention relates to polypeptides comprising the motif [D/Q][I/V]DH (SEQ ID NO:203), wherein the polypeptides have DNase activity. In one embodiment the invention relates to polypeptides comprising the motif [D/Q][I/V]DH (SEQ ID NO:203), wherein the polypeptides have DNase activity, with the proviso that the polypeptide is not a DNase comprising SEQ ID NO: 2 of WO 2015/155351. One embodiment of the invention relates to polypeptides comprising one or more of the motifs selected from the motifs [E/D/H]H[I/V/L/F/M]X[P/A/S], [T/D/S][G/N]PQL, [G/T]Y[D/S][R/K/L], [F/L/Y/I]A[N/R]D[L/I/P/V], C[D/N]T[A/R] and [D/Q][I/V]DH, wherein the polypeptides have DNase activity. One embodiment of the invention relates to polypeptides comprising one or more of the motifs selected from the motifs [E/D/H]H[I/V/L/F/M]X[P/A/S], [T/D/S][G/N]PQL, [G/T]Y[D/S][R/K/L], [F/L/Y/I]A[N/R]D[L/I/P/V], C[D/N]T[A/R] and [D/Q][I/V]DH, wherein the polypeptides have DNase activity, with the proviso that the polypeptide is not a DNase comprising SEQ ID NO: 2 of WO 2015/155351.

Polypeptides having DNase activity and comprising one or more or all of the motifs, [E/D/H]H[I/V/L/F/M]X[P/A/S], [T/D/S][G/N]PQL, [G/T]Y[D/S][R/K/L], [F/L/Y/I]A[N/R]D[L/I/P/V], C[D/N]T[A/R] and [D/Q][I/V]DH effectively prevent, remove or reduce biofilm and the DNases are particularly useful in cleaning processes, such as laundry and dish wash. One aspect of the invention relates to a polypeptide having DNase activity, where the polypeptide is selected from the group consisting of polypeptides having the amino acid sequence shown in SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 53, SEQ ID NO: 56, SEQ ID NO: 59, SEQ ID NO: 62, SEQ ID NO: 68, SEQ ID NO: 71, SEQ ID NO: 74, SEQ ID NO: 77, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 164, SEQ ID NO: 167, SEQ ID NO: 170, SEQ ID NO: 173, SEQ ID NO: 176, SEQ ID NO: 179, SEQ ID NO: 182, SEQ ID NO: 185, SEQ ID NO: 188, SEQ ID NO: 191 and SEQ ID NO: 197 or polypeptides having at least 80% sequence identity, such as at least 85%, such as at least 90%, such as at least 95% or 100% sequence identity thereto, where the polypeptide further comprises one or more or all of the motifs [E/D/H]H[I/V/L/F/M]X[P/A/S], [T/D/S][G/N]PQL, [G/T]Y[D/S][R/K/L], [F/L/Y/I]A[N/R]D[L/I/P/V], C[D/N]T[A/R] and [D/Q][I/V]DH. The motifs are novel and have not previously been described. The DNases of the present invention therefore share a novel common inventive concept.

One aspect of the invention relates to a polypeptide having DNase activity, wherein the polypeptide comprises one or more or all of the motifs [E/D/H]H[I/V/L/F/M]X[P/A/S], [T/D/S][G/N]PQL, [G/T]Y[D/S][R/K/L], [F/L/Y/I]A[N/R]D[L/I/P/V], C[D/N]T[A/R] or [D/Q][I/V]DH, wherein the polypeptide is selected from the group consisting of a) a polypeptide having at least 84% sequence identity to the polypeptide of SEQ ID NO: 8,
b) a polypeptide having at least 94% sequence identity to the polypeptide of SEQ ID NO: 9,
c) a polypeptide having at least 92% sequence identity to the polypeptide of SEQ ID NO: 11,
d) a polypeptide having at least 92% sequence identity to the polypeptide of SEQ ID NO: 12,
e) a polypeptide having at least 97% sequence identity to the polypeptide of SEQ ID NO: 13,
f) a polypeptide having at least 96% sequence identity to the polypeptide of SEQ ID NO: 14,
g) a polypeptide having at least 90% sequence identity to the polypeptide of SEQ ID NO: 15,
h) a polypeptide having at least 88% sequence identity to the polypeptide of SEQ ID NO: 16,
i) a polypeptide having at least 93% sequence identity to the polypeptide of SEQ ID NO: 17,
j) a polypeptide having at least 90% sequence identity to the polypeptide of SEQ ID NO: 18,
k) a polypeptide having at least 89% sequence identity to the polypeptide of SEQ ID NO: 19,
l) a polypeptide having at least 90% sequence identity to the polypeptide of SEQ ID NO: 20,
m) a polypeptide having at least 93% sequence identity to the polypeptide of SEQ ID NO: 21,
n) a polypeptide having at least 90% sequence identity to the polypeptide of SEQ ID NO: 22,
o) a polypeptide having at least 93% sequence identity to the polypeptide of SEQ ID NO: 23,
p) a polypeptide having at least 85% sequence identity to the polypeptide of SEQ ID NO: 53,
q) a polypeptide having at least 98% sequence identity to the polypeptide of SEQ ID NO: 56,
r) a polypeptide having at least 94% sequence identity to the polypeptide of SEQ ID NO: 59,
s) a polypeptide having at least 85% sequence identity to the polypeptide of SEQ ID NO: 62,
t) a polypeptide having at least 97% sequence identity to the polypeptide of SEQ ID NO: 68,
u) a polypeptide having at least 99% sequence identity to the polypeptide of SEQ ID NO: 71,
v) a polypeptide having at least 91% sequence identity to the polypeptide of SEQ ID NO: 74,
w) a polypeptide having at least 98% sequence identity to the polypeptide of SEQ ID NO: 77,
x) a polypeptide having at least 81% sequence identity to the polypeptide of SEQ ID NO: 83,
y) a polypeptide having at least 89% sequence identity to the polypeptide of SEQ ID NO: 86,
z) a polypeptide having at least 99% sequence identity to the polypeptide of SEQ ID NO: 89,
aa) a polypeptide having at least 91% sequence identity to the polypeptide of SEQ ID NO: 92,
bb) a polypeptide having at least 90% sequence identity to the polypeptide of SEQ ID NO: 95,
cc) a polypeptide having at least 91% sequence identity to the polypeptide of SEQ ID NO: 98,
dd) a polypeptide having at least 92% sequence identity to the polypeptide of SEQ ID NO: 104,
ee) a polypeptide having at least 90% sequence identity to the polypeptide of SEQ ID NO: 107.
ff) a polypeptide having at least 91.5% sequence identity to the polypeptide of SEQ ID NO: 110.
gg) a polypeptide having at least 93% sequence identity to the polypeptide of SEQ ID NO: 113,
hh) a polypeptide having at least 96% sequence identity to the polypeptide of SEQ ID NO: 116,
ii) a polypeptide having at least 99.5% sequence identity to the polypeptide of SEQ ID NO: 119,
jj) a polypeptide having at least 99.5% sequence identity to the polypeptide of SEQ ID NO: 128,
kk) a polypeptide having at least 93% sequence identity to the polypeptide of SEQ ID NO: 131,
ll) a polypeptide having at least 79% sequence identity to the polypeptide of SEQ ID NO: 134,
mm) a polypeptide having at least 72% sequence identity to the polypeptide of SEQ ID NO: 137,
nn) a polypeptide having at least 77% sequence identity to the polypeptide of SEQ ID NO: 140,
oo) a polypeptide having at least 74% sequence identity to the polypeptide of SEQ ID NO: 143,
pp) a polypeptide having at least 97% sequence identity to the polypeptide of SEQ ID NO: 146,
qq) a polypeptide having at least 71% sequence identity to the polypeptide of SEQ ID NO: 149,
rr) a polypeptide having at least 96% sequence identity to the polypeptide of SEQ ID NO: 152,
ss) a polypeptide having at least 72% sequence identity to the polypeptide of SEQ ID NO: 155,
tt) a polypeptide having at least 93% sequence identity to the polypeptide of SEQ ID NO: 158,
uu) a polypeptide having at least 85% sequence identity to the polypeptide of SEQ ID NO: 164,
vv) a polypeptide having at least 88% sequence identity to the polypeptide of SEQ ID NO: 167,
ww) a polypeptide having at least 87% sequence identity to the polypeptide of SEQ ID NO: 176,
xx) a polypeptide having at least 81% sequence identity to the polypeptide of SEQ ID NO: 179,
yy) a polypeptide having at least 89% sequence identity to the polypeptide of SEQ ID NO: 182,
zz) a polypeptide having at least 96% sequence identity to the polypeptide of SEQ ID NO: 185,
aaa) a polypeptide having at least 88% sequence identity to the polypeptide of SEQ ID NO: 188,
bbb) a polypeptide having at least 87% sequence identity to the polypeptide of SEQ ID NO: 191,
ccc) a polypeptide having at least 94% sequence identity to the polypeptide of SEQ ID NO: 194, and ddd) a polypeptide having at least 90% sequence identity to the polypeptide of SEQ ID NO: 197.

The NUC_1A domain is identified for the first time in the present invention and described above. The domain may be further divided into different clades. A clade is a group of polypeptides clustered together on the basis of homologous features traced to a common ancestor. Polypeptide clades can be visualized as phylogenetic trees and a clade is a group of polypeptides that consists of a common ancestor and all its lineal descendants. Example 11 describes generation of phylogenetic trees.

The clade of GYS or the GYS-clade is a group of DNases all related to the same ancestor, which share common properties. The hereto unknown clade comprises polypeptides forming a group within a domain, e.g., NUC1_A of the phylogenetic tree, which share common properties and are more closely related than other polypeptides in the domain.

The polypeptides of the GYS clade share the conservative motifs [D/M/L][S/T]GYSR[D/N](SEQ ID NO: 204) or ASXNRSKG (SEQ ID NO:205), where the letters are the amino acids (one letter code), X is any amino acid and the brackets means that the amino acids are alternative. In addition, the polypeptides of the GYS-clade may comprise any of the motifs [E/D/H]H[I/V/L/F/M]X[P/A/S], [T/D/S][G/N]PQL, [G/T]Y[D/S][R/K/L], [F/L/Y/I]A[N/R]D[L/I/P/V], C[D/N]T[A/R] and [D/Q][I/V]DH.

One aspect of the invention relates to polypeptides of the GYS clade comprising one or more of the motifs [D/M/L][S/T]GYSR[D/N] (SEQ ID NO: 204) or ASXNRSKG (SEQ ID NO:205), wherein the polypeptides have DNase activity. In one aspect the ASXNRSKG motif correspond to pos 125 to 133 of SEQ ID NO: 21. In one aspect the [D/M/L][S/T]GYSR[D/N] motif correspond to positions 26 to 32 of SEQ ID NO: 21.

The GYS clade comprises polypeptides having DNase activity shown in SEQ ID NO: 8, SEQ ID NO: 9, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 53, SEQ ID NO: 56, SEQ ID NO: 59, SEQ ID NO: 62, SEQ ID NO: 65, SEQ ID NO: 68, SEQ ID NO: 71, SEQ ID NO: 74, SEQ ID NO: 77 and SEQ ID NO: 80.

The polypeptides having DNase activity shown in SEQ ID NO: 65 and SEQ ID NO: 80 are public sequences, with UniProt accession numbers (H6NAU2 and A0A0M2T1U6).

One aspect of the invention relates to a polypeptide of the GYS clade comprising one or both of the motifs [D/M/L][S/T]GYSR[D/N] (SEQ ID NO: 204) or ASXNRSKG (SEQ ID NO:205), wherein the polypeptide has DNase activity and wherein the polypeptide is selected from any of the polypeptides shown in SEQ ID NO: 8, SEQ ID NO: 9, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 53, SEQ ID NO: 56, SEQ ID NO: 59, SEQ ID NO: 62, SEQ ID NO: 68, SEQ ID NO: 71, SEQ ID NO: 74 and SEQ ID NO: 77 or variant hereof having 1-25, such as 1-20, such as 1-15, such as 1-10, such as 1-5 amino acid alterations, e.g., substitutions.

One aspect of the invention relates to a polypeptide of the GYS clade comprising one or both of the motifs [D/M/L][S/T]GYSR[D/N] or ASXNRSKG and further comprises one or more of the motifs [E/D/H]H[I/V/L/F/M]X[P/A/S], [T/D/S][G/N]PQL, [G/T]Y[D/S][R/K/L], [F/L/Y/I]A[N/R]D[L/I/P/V], C[D/N]T[A/R] and [D/Q][I/V]DH, wherein the polypeptide has DNase activity and wherein the polypeptide is selected from any of the polypeptides shown in SEQ ID NO: 8, SEQ ID NO: 9, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 53, SEQ ID NO: 56, SEQ ID NO: 59, SEQ ID NO: 62, SEQ ID NO: 68, SEQ ID NO: 71, SEQ ID NO: 74 and SEQ ID NO: 77 or variant hereof having 1-25, such as 1-20, such as 1-15, such as 1-10, such as 1-5 amino acid alterations, e.g., substitutions.

One embodiment of the invention relates to a polypeptide of the GYS clade having DNase activity and comprising one or more of the motifs [D/M/L][S/T]GYSR[D/N] (SEQ ID NO: 204), ASXNRSKG (SEQ ID NO: 205), with the proviso that the polypeptide is not the polypeptides shown in SEQ ID NO: 65 or SEQ ID NO: 80.

One embodiment of the invention relates to a polypeptide of the GYS clade having DNase activity, wherein the polypeptide comprise one or both of the motifs [D/M/L][S/T]GYSR[D/N] (SEQ ID NO: 204) or ASXNRSKG (SEQ ID NO: 205) and wherein the polypeptide is selected from the polypeptides:

a) a polypeptide having at least 84% sequence identity to the polypeptide shown in SEQ ID NO: 8,
b) a polypeptide having at least 94% sequence identity to the polypeptide shown in SEQ ID NO: 9,
c) a polypeptide having at least 92% sequence identity to the polypeptide shown in SEQ ID NO: 11,
d) a polypeptide having at least 92% sequence identity to the polypeptide shown in SEQ ID NO: 12,
e) a polypeptide having at least 97% sequence identity to the polypeptide shown in SEQ ID NO: 13,
f) a polypeptide having at least 96% sequence identity to the polypeptide shown in SEQ ID NO: 14,
g) a polypeptide having at least 90% sequence identity to the polypeptide shown in SEQ ID NO: 15,
h) a polypeptide having at least 88% sequence identity to the polypeptide shown in SEQ ID NO: 16,
i) a polypeptide having at least 93% sequence identity to the polypeptide shown in SEQ ID NO: 17,
j) a polypeptide having at least 90% sequence identity to the polypeptide shown in SEQ ID NO: 18,
k) a polypeptide having at least 89% sequence identity to the polypeptide shown in SEQ ID NO: 19,
l) a polypeptide having at least 90% sequence identity to the polypeptide shown in SEQ ID NO: 20,
m) a polypeptide having at least 93% sequence identity to the polypeptide shown in SEQ ID NO: 21,
n) a polypeptide having at least 90% sequence identity to the polypeptide shown in SEQ ID NO: 22,
o) a polypeptide having at least 93% sequence identity to the polypeptide shown in SEQ ID NO: 23,
p) a polypeptide having at least 85% sequence identity to the polypeptide shown in SEQ ID NO: 53,
q) a polypeptide having at least 98% sequence identity to the polypeptide shown in SEQ ID NO: 56,
r) a polypeptide having at least 94% sequence identity to the polypeptide shown in SEQ ID NO: 59,
s) a polypeptide having at least 85% sequence identity to the polypeptide shown in SEQ ID NO: 62,
t) a polypeptide having at least 97% sequence identity to the polypeptide shown in SEQ ID NO: 68,
u) a polypeptide having at least 99% sequence identity to the polypeptide shown in SEQ ID NO: 71,
v) a polypeptide having at least 91% sequence identity to the polypeptide shown in SEQ ID NO: 74, and w) a polypeptide having at least 98% sequence identity to the polypeptide shown in SEQ ID NO: 77.

One embodiment of the invention relates to a polypeptide of the GYS clade having DNase activity and comprising one or more of the motifs [D/M/L][S/T]GYSR[D/N] (SEQ ID NO: 204) or ASXNRSKG (SEQ ID NO: 205), wherein the polypeptide has DNase activity and is selected from the group consisting of SEQ ID NO: 8, SEQ ID NO: 9, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 53, SEQ ID NO: 56, SEQ ID NO: 59, SEQ ID NO: 62, SEQ ID NO: 68, SEQ ID NO: 71, SEQ ID NO: 74 and SEQ ID NO: 77 or a polypeptide having at least 99% sequence identity thereto.

One embodiment of the invention relates to a polypeptide of the GYS clade comprising one or both of the motifs [D/M/L][S/T]GYSR[D/N] (SEQ ID NO: 204) or ASXNR-SKG (SEQ ID NO: 205), wherein the polypeptide has DNase activity and wherein the polypeptide is the polypeptide shown in SEQ ID NO: 8 or a polypeptide having at least 84%, such as at least 85%, such as at least 90%, such as at least 95% or such as 100% sequence identity thereto.

One embodiment of the invention relates to a polypeptide of the GYS clade comprising one or both of the motifs [D/M/L][S/T]GYSR[D/N] (SEQ ID NO: 204) or ASXNR-SKG (SEQ ID NO: 205), wherein the polypeptide has DNase activity and wherein the polypeptide is shown in SEQ ID NO: 9 or a polypeptide having at least 94%, such as at least 95% or 100% sequence identity thereto.

One embodiment of the invention relates to a polypeptide of the GYS clade comprising one or both of the motifs [D/M/L][S/T]GYSR[D/N] (SEQ ID NO: 204) or ASXNR-SKG (SEQ ID NO:205), wherein the polypeptide has DNase activity and wherein the polypeptide is the polypeptide in SEQ ID NO: 11 or a polypeptide having at least 92% such as at least 95%, at least 96%, at least 98% or 100% sequence identity thereto.

One embodiment of the invention relates to a polypeptide of the GYS clade comprising one or both of the motifs [D/M/L][S/T]GYSR[D/N] (SEQ ID NO: 204) or ASXNR-SKG (SEQ ID NO: 205), wherein the polypeptide has DNase activity and wherein the polypeptide is the polypeptide shown in SEQ ID NO: 12 or a polypeptide having at least 92%, such as at least 95%, at least 97%, at least 98% or 100% sequence identity thereto.

One embodiment of the invention relates to a polypeptide of the GYS clade comprising one or both of the motifs [D/M/L][S/T]GYSR[D/N] (SEQ ID NO: 204) or ASXNR-SKG (SEQ ID NO: 205), wherein the polypeptide has DNase activity and wherein the polypeptide is the polypeptide shown in SEQ ID NO: 13 or a polypeptide having at least 97%, such as at least 98%, at least 99% or 100% sequence identity thereto.

One embodiment of the invention relates to a polypeptide of the GYS clade comprising one or both of the motifs [D/M/L][S/T]GYSR[D/N] (SEQ ID NO: 204) or ASXNR-SKG (SEQ ID NO: 205), wherein the polypeptide has DNase activity and wherein the polypeptide is the polypeptide shown in SEQ ID NO: 14 or a polypeptide having at least 96%, such as at least 97%, at least 98%, at least 99% or 100% sequence identity thereto.

One embodiment of the invention relates to a polypeptide of the GYS clade comprising one or both of the motifs [D/M/L][S/T]GYSR[D/N] (SEQ ID NO: 204) or ASXNR-SKG (SEQ ID NO: 205), wherein the polypeptide has DNase activity and wherein the polypeptide is the polypeptide shown in SEQ ID NO: 15 or a polypeptide having at least 90%, such as at least 93%, at least 95%, at least 97% or 100% sequence identity thereto.

One embodiment of the invention relates to a polypeptide of the GYS clade comprising one or both of the motifs [D/M/L][S/T]GYSR[D/N] (SEQ ID NO: 204); or ASXNR-SKG (SEQ ID NO: 205), wherein the polypeptide has DNase activity and wherein the polypeptide is the polypeptide shown in SEQ ID NO: 16 or a polypeptide having at least 88%, such as at least 90%, at least 93%, at least 95%, at least 98% or 100% sequence identity thereto.

One embodiment of the invention relates to a polypeptide of the GYS clade comprising one or both of the motifs [D/M/L][S/T]GYSR[D/N] (SEQ ID NO: 204) or ASXNR-SKG (SEQ ID NO: 205), wherein the polypeptide has DNase activity and wherein the polypeptide is the polypeptide shown in SEQ ID NO: 17 or a polypeptide having at least 93%, such as at least 95%, at least 96%, at least 97%, at least 98% or 100% sequence identity thereto.

One embodiment of the invention relates to a polypeptide of the GYS clade comprising one or both of the motifs [D/M/L][S/T]GYSR[D/N] (SEQ ID NO: 204) or ASXNR-SKG (SEQ ID NO: 205), wherein the polypeptide has DNase activity and wherein the polypeptide is the polypeptide shown in SEQ ID NO: 18 or a polypeptide having at least 90%, such as at least 91%, at least 93%, at least 95%, at least 98% or 100% sequence identity thereto.

One embodiment of the invention relates to a polypeptide of the GYS clade comprising one or both of the motifs [D/M/L][S/T]GYSR[D/N] (SEQ ID NO: 204) or ASXNR-SKG (SEQ ID NO:21), wherein the polypeptide has DNase activity and wherein the polypeptide is the polypeptide shown in SEQ ID NO: 19 or a polypeptide having at least 89%, such as at least 90%, at least 93%, at least 95%, at least 98% or 100% sequence identity thereto.

One embodiment of the invention relates to a polypeptide of the GYS clade comprising one or both of the motifs [D/M/L][S/T]GYSR[D/N] (SEQ ID NO: 204) or ASXNR-SKG (SEQ ID NO: 205), wherein the polypeptide has DNase activity and wherein the polypeptide is the polypeptide shown in SEQ ID NO: 20 or a polypeptide having at least 90%, such as at least 91%, at least 93%, at least 95%, at least 98% or 100% sequence identity thereto.

One embodiment of the invention relates to a polypeptide of the GYS clade comprising one or both of the motifs [D/M/L][S/T]GYSR[D/N] (SEQ ID NO: 204) or ASXNR-SKG (SEQ ID NO: 205), wherein the polypeptide has DNase activity and wherein the polypeptide is the polypeptide shown in SEQ ID NO: 21 or a polypeptide having at least 93%, such as at least 94%, at least 95%, at least 96%, at least 97%, at least 98% or 100% sequence identity thereto.

One embodiment of the invention relates to a polypeptide of the GYS clade comprising one or both of the motifs [D/M/L][S/T]GYSR[D/N] (SEQ ID NO: 204) or ASXNR-SKG (SEQ ID NO: 205), wherein the polypeptide has DNase activity and wherein the polypeptide is the polypeptide shown in SEQ ID NO: 22 or a polypeptide having at least 90%, such as at least 93%, at least 94%, at least 95%, at least 96%, at least 97%, at least 98% or 100% sequence identity thereto.

One embodiment of the invention relates to a polypeptide of the GYS clade comprising one or both of the motifs [D/M/L][S/T]GYSR[D/N] (SEQ ID NO: 204) or ASXNR-SKG (SEQ ID NO: 205), wherein the polypeptide has DNase activity and wherein the polypeptide is the polypeptide shown in SEQ ID NO: 23 or a polypeptide having at least 93%, such as at least 94%, at least 95%, at least 96%, at least 97%, at least 98%, at least 99% or 100% sequence identity thereto.

One embodiment of the invention relates to a polypeptide of the GYS clade comprising one or both of the motifs [D/M/L][S/T]GYSR[D/N] (SEQ ID NO: 204) or ASXNR-SKG (SEQ ID NO: 205), wherein the polypeptides has DNase activity and wherein the polypeptide is the polypeptide shown in SEQ ID NO: 53 or a polypeptide having at least 85%, such as at least 90%, at least 93%, at least 95%, at least 96%, at least 97%, at least 98% or 100% sequence identity thereto.

One embodiment of the invention relates to a polypeptide of the GYS clade comprising one or both of the motifs [D/M/L][S/T]GYSR[D/N] (SEQ ID NO: 204) or ASXNR-SKG (SEQ ID NO: 205), wherein the polypeptides has DNase activity and wherein the polypeptide is the polypeptide shown in SEQ ID NO: 56 or a polypeptide having at least 98%, such as at least 99% or 100% sequence identity thereto.

One embodiment of the invention relates to a polypeptide of the GYS clade comprising one or both of the motifs [D/M/L][S/T]GYSR[D/N] (SEQ ID NO: 204) or ASXNR-SKG (SEQ ID NO: 205), wherein the polypeptides has DNase activity and wherein the polypeptide is the polypeptide shown in SEQ ID NO: 59 or a polypeptide having at least 94%, such as at least 95%, at least 96%, at least 97%, at least 98% or 100% sequence identity thereto.

One embodiment of the invention relates to a polypeptide of the GYS clade comprising one or more of the motifs [D/M/L][S/T]GYSR[D/N] (SEQ ID NO: 204); or ASXNR-SKG (SEQ ID NO: 205), wherein the polypeptide has DNase activity and wherein the polypeptide is the polypeptide shown in SEQ ID NO: 62 or a polypeptide having at least 85%, such as at least 90%, at least 95%, at least 95%, at least 96%, at least 97%, at least 98% or 100% sequence identity thereto.

One embodiment of the invention relates to a polypeptide of the GYS clade comprising one or more of the motifs [D/M/L][S/T]GYSR[D/N] (SEQ ID NO: 204) or ASXNR-SKG (SEQ ID NO: 205), wherein the polypeptide has DNase activity and wherein the polypeptide is the polypeptide shown in SEQ ID NO: 68 or a polypeptide having at least 97%, such as at least 98% or 100% sequence identity thereto.

One embodiment of the invention relates to a polypeptide of the GYS clade comprising one or more of the motifs [D/M/L][S/T]GYSR[D/N] (SEQ ID NO: 204) or ASXNR-SKG (SEQ ID NO: 205), wherein the polypeptide has DNase activity and wherein the polypeptide is the polypeptide shown in SEQ ID NO: 71 or a polypeptide having at least 99% or 100% sequence identity thereto.

One embodiment of the invention relates to a polypeptide of the GYS clade comprising one or more of the motifs [D/M/L][S/T]GYSR[D/N] (SEQ ID NO: 204) or ASXNR-SKG (SEQ ID NO: 205), wherein the polypeptide has DNase activity and wherein the polypeptide is the polypeptide shown in SEQ ID NO: 74 or a polypeptide having at least 91%, such as at least 93%, at least 94%, at least 95%, at least 96%, at least 97%, at least 98% or 100% sequence identity thereto.

One embodiment of the invention relates to a polypeptide of the GYS clade comprising one or more of the motifs [D/M/L][S/T]GYSR[D/N] (SEQ ID NO: 204) or ASXNR-SKG (SEQ ID NO: 205), wherein the polypeptide has DNase activity and wherein the polypeptide is the polypeptide shown in SEQ ID NO: 77 or a polypeptide having at least 98%, such as at least 99% or 100% sequence identity thereto.

Another distinguishable clade is the NAWK-clade. The clade of NAWK or the NAWK-clade is a group of DNases all related to the same ancestor which share common properties. The hereto unknown clade comprises polypeptides forming a group within a domain, e.g., NUC1_A of the phylogenetic tree, which may share common properties and are more closely related than other polypeptides in the domain.

The polypeptides of the NAWK-clade share the conservative motifs [V/I]PL[S/A]NAWK (SEQ ID NO: 206), or NPQL (SEQ ID NO: 207), where the letters are the amino acid (one letter code) and the amino acids in the brackets are alternatives. In addition, the polypeptides of the NAWK-clade may comprise any of the motifs [E/D/H]H[I/V/L/F/M]X[P/A/S], [T/D/S][G/N]PQL, [G/T]Y[D/S][R/K/L], [F/L/Y/I]A[N/R]D[L/I/P/V], C[D/N]T[A/R] and [D/Q][I/V]DH.

One aspect of the invention relates to polypeptides of the NAWK-clade comprising one or more of the motifs [V/I]PL[S/A]NAWK (SEQ ID NO: 206) or NPQL (SEQ ID NO: 207), wherein the polypeptides have DNase activity. In one aspect the [VI]PL[S/A]NAWK motif correspond to pos 87 to 94 of SEQ ID NO: 68. In one aspect the NPQL motif correspond to positions 114 to 117 of SEQ ID NO: 68.

The NAWK clade comprises polypeptides having DNase activity shown in SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116 and SEQ ID NO: 119.

The polypeptide shown in SEQ ID NO: 119 share 99.48% sequence identity with the polypeptide with a UniProt sequence having accession number A0A178DM75.

One aspect of the invention relates to a polypeptide of the NAWK clade comprising one or both of the motifs [V/I]PL[S/A]NAWK (SEQ ID NO: 206) or NPQL (SEQ ID NO: 207), wherein the polypeptide has DNase activity and wherein the polypeptide is selected from any of the polypeptides shown in SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116 and SEQ ID NO: 119 or a variant hereof having 1-25, such as 1-20, such as 1-15, such as 1-10, such as 1-5 amino acid alterations, e.g., substitutions.

One aspect of the invention relates to a polypeptide of the NAWK clade comprising one or both of the motifs [V/I]PL[S/A]NAWK (SEQ ID NO: 206) or NPQL (SEQ ID NO: 207) and further comprises one or more of the motifs [E/D/H]H[I/V/L/F/M]X[P/A/S], [T/D/S][G/N]PQL, [G/T]Y[D/S][R/K/L], [F/L/Y/I]A[N/R]D[L/I/P/V], C[D/N]T[A/R] and [D/Q][I/V]DH, wherein the polypeptide has DNase activity and wherein the polypeptide is selected from any of the polypeptides shown in SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116 and SEQ ID NO: 119 or a variant hereof having 1-25, such as 1-20, such as 1-15, such as 1-10, such as 1-5 amino acid alterations, e.g., substitutions.

One embodiment of the invention relates to a polypeptide of the NAWK clade having DNase activity and comprising one or more of the motifs [V/I]PL[S/A]NAWK (SEQ ID NO: 206), NPQL (SEQ ID NO: 207), with the proviso that the polypeptide is not the polypeptide shown in SEQ ID NO: 119.

One embodiment of the invention relates to a polypeptide of the NAWK-clade having DNase activity and where the polypeptide comprise one or both of the motifs [V/I]PL[S/A]NAWK (SEQ ID NO: 206) or NPQL (SEQ ID NO: 207), wherein the polypeptide is selected from the polypeptides:
 a) a polypeptide having at least 81% sequence identity to the polypeptide shown in SEQ ID NO: 83,
 b) a polypeptide having at least 88.5% sequence identity to the polypeptide shown in SEQ ID NO: 86
 c) a polypeptide having at least 99% sequence identity to the polypeptide shown in SEQ ID NO: 89
 d) a polypeptide having at least 91% sequence identity to the polypeptide shown in SEQ ID NO: 92,
 e) a polypeptide having at least 90% sequence identity to the polypeptide shown in SEQ ID NO: 95,
 f) a polypeptide having at least 91% sequence identity to the polypeptide shown in SEQ ID NO: 98,
 g) a polypeptide having at least 89% sequence identity to the polypeptide shown in SEQ ID NO: 101,
 h) a polypeptide having at least 92% sequence identity to the polypeptide shown in SEQ ID NO: 104,
 i) a polypeptide having at least 90% sequence identity to the polypeptide shown in SEQ ID NO: 107
 j) a polypeptide having at least 91.5% sequence identity to the polypeptide shown in SEQ ID NO: 110,
 k) a polypeptide having at least 93% sequence identity to the polypeptide shown in SEQ ID NO: 113, and
 l) a polypeptide having at least 96% sequence identity to the polypeptide shown in SEQ ID NO: 116, One embodiment of the invention relates to polypeptides of the NAWK clade comprising one or both of the motifs [V/I]PL[S/A]NAWK (SEQ ID NO: 206) or NPQL (SEQ ID NO: 207), wherein the polypeptides have DNase activity and wherein the polypeptide is selected from the group consisting of SEQ ID NO: 83, SEQ ID NO: 86, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113 and SEQ ID NO: 116 or polypeptides having at least 96% sequence identity thereto.

One embodiment of the invention relates to a polypeptide of the NAWK-clade comprising one or both of the motifs [V/I]PL[S/A]NAWK (SEQ ID NO: 206), NPQL (SEQ ID NO: 207), wherein the polypeptide has DNase activity and wherein the polypeptide is the polypeptide shown in SEQ ID NO: 83 or polypeptides having at least 81%, such as at least 83%, such as at least 85%, such as at least 87%, such as at least 90%, such as at least 93%, such as at least 95%, such as at least 97%, such as at least 98%, such as at least 99% or 100% sequence identity thereto.

One embodiment of the invention relates to a polypeptide of the NAWK clade comprising one or both of the motifs [V/I]PL[S/A]NAWK (SEQ ID NO: 206) or NPQL (SEQ ID NO: 207), wherein the polypeptide has DNase activity and wherein the polypeptide is the polypeptide shown in SEQ ID NO: 86 or polypeptides having at least 88.5%, such as at least 90%, such as at least 93%, such as at least 95%, such as at least 97%, such as at least 98%, such as at least 99% or 100% sequence identity thereto.

One embodiment of the invention relates to a polypeptide of the NAWK clade comprising one or both of the motifs [V/I]PL[S/A]NAWK (SEQ ID NO: 206) or NPQL (SEQ ID NO: 207), wherein the polypeptide has DNase activity and wherein the polypeptide is the polypeptide shown in SEQ ID NO: 89 or polypeptides having at least 99% or 100% sequence identity thereto.

One embodiment of the invention relates to a polypeptide of the NAWK clade comprising one or both of the motifs [V/I]PL[S/A]NAWK (SEQ ID NO: 206) or NPQL (SEQ ID NO: 207), wherein the polypeptide has DNase activity and wherein the polypeptide is the polypeptide shown in SEQ ID NO: 92 or polypeptides having at least 91%, such as at least 92%, such as at least 93%, such as at least 95%, such as at least 97%, such as at least 98%, such as at least 99% or 100% sequence identity thereto.

One embodiment of the invention relates to a polypeptide of the NAWK clade comprising one or both of the motifs [V/I]PL[S/A]NAWK (SEQ ID NO: 206), NPQL (SEQ ID NO: 207), wherein the polypeptide has DNase activity and wherein the polypeptide is the polypeptide shown in SEQ ID NO: 95 or polypeptides having at least 90%, such as at least 92%, at least 93%, at least 95%, at least 97%, at least 98%, at least 99% or 100% sequence identity thereto.

One embodiment of the invention relates to a polypeptide of the NAWK clade comprising one or both of the motifs [V/I]PL[S/A]NAWK (SEQ ID NO: 206) or NPQL (SEQ ID NO: 207), wherein the polypeptide has DNase activity and wherein the polypeptide is the polypeptide shown in SEQ ID NO: 98 or polypeptides having at least 91%, such as at least 92%, at least 93%, at least 95%, at least 97%, at least 98%, at least 99% or 100% sequence identity thereto.

One embodiment of the invention relates to a polypeptide of the NAWK clade comprising one or both of the motifs [V/I]PL[S/A]NAWK (SEQ ID NO: 206) or NPQL (SEQ ID NO: 207), wherein the polypeptide has DNase activity and wherein the polypeptide is the polypeptide shown in SEQ ID NO: 101 or polypeptides having at least 89%, such as at least 90%, at least 93%, at least 95%, at least 97%, at least 98%, at least 99% or 100% sequence identity thereto.

One embodiment of the invention relates to a polypeptide of the NAWK clade comprising one or more of the motifs [V/I]PL[S/A]NAWK (SEQ ID NO: 68) or NPQL (SEQ ID NO: 207), wherein the polypeptide has DNase activity and wherein the polypeptide is the polypeptide shown in SEQ ID NO: 104 or polypeptides having at least 92%, such as at least 93%, at least 95%, at least 97%, at least 98%, at least 99% or 100% sequence identity thereto.

One embodiment of the invention relates to a polypeptide of the NAWK clade comprising one or both of the motifs [V/I]PL[S/A]NAWK (SEQ ID NO: 206) or NPQL (SEQ ID NO: 207), wherein the polypeptide has DNase activity and wherein the polypeptide is the polypeptide shown in SEQ ID NO: 107 or polypeptides having at least 90%, such as at least 92%, at least 93%, at least 95%, at least 97%, at least 98%, at least 99% or 100% sequence identity thereto.

One embodiment of the invention relates to a polypeptide of the NAWK clade comprising one or both of the motifs [V/I]PL[S/A]NAWK (SEQ ID NO: 206) or NPQL (SEQ ID NO: 207), wherein the polypeptide has DNase activity and wherein the polypeptide is the polypeptide shown in SEQ ID NO: 110 or polypeptides having at least 91.5%, such as at least 92%, at least 93%, at least 95%, at least 97%, at least 98%, at least 99% or 100% sequence identity thereto.

One embodiment of the invention relates to a polypeptide of the NAWK clade comprising one or both of the motifs [V/I]PL[S/A]NAWK (SEQ ID NO: 206) or NPQL (SEQ ID NO: 207), wherein the polypeptide has DNase activity and wherein the polypeptide is the polypeptide shown in SEQ ID NO: 113 or polypeptides having at least 93%, such as at least 94%, at least 95%, at least 97%, at least 98%, at least 99% or 100% sequence identity thereto.

One embodiment of the invention relates to a polypeptide of the NAWK clade comprising one or both of the motifs [V/I]PL[S/A]NAWK (SEQ ID NO: 206) or NPQL (SEQ ID NO: 207), wherein the polypeptide has DNase activity and wherein the polypeptide is the polypeptide shown in SEQ ID NO: 116 or polypeptides having at least 96%, such as at least 97%, at least 98%, at least 99% or 100% sequence identity thereto.

One embodiment of the invention relates to a polypeptide of the NAWK clade comprising one or both of the motifs [V/I]PL[S/A]NAWK (SEQ ID NO: 206) or NPQL (SEQ ID NO: 207), wherein the polypeptide having DNase activity and wherein the polypeptide comprises or consists of the polypeptide shown in SEQ ID NO: 119.

A third distinguished clade is the KNAW clade. The clade of KNAW or the KNAW clade is a group of DNases all related to the same ancestor which share common properties. The hereto unknown clade comprises polypeptides forming a group within a domain, e.g., NUC1_A of the phylogenetic tree, which may share common properties and are more closely related than other polypeptides in the domain.

The polypeptides of the KNAW-clade share the conservative motifs P[Q/E]L[W/Y] (SEQ ID NO: 208) and [K/H/E]NAW (SEQ ID NO:209), where the letters are the amino acid (one letter code) and the amino acids in the brackets are alternatives. In addition, the polypeptides of the KNAW-clade may comprise any of the motifs [E/D/H]H[I/V/L/F/M]X[P/A/S], [T/D/S][G/N]PQL, [G/T]Y[D/S][R/K/L], [F/L/Y/I]A[N/R]D[L/I/P/V], C[D/N]T[A/R] or [D/Q][I/V]DH.

One aspect of the invention relates to polypeptides of the KNAW clade where the polypeptides comprise one or both of the motifs P[Q/E]L[W/Y] (SEQ ID NO: 208) and/or [K/H/E]NAW (SEQ ID NO: 209), wherein the polypeptides have DNase activity.

The KNAW clade comprises polypeptides having DNase activity shown in SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155 and SEQ ID NO: 158.

The polypeptides shown in SEQ ID NO: 122 and SEQ ID NO: 125 are public sequences.

One aspect of the invention relates to a polypeptide of the KNAW-clade comprising one or both of the motifs P[Q/E]L[W/Y] (SEQ ID NO: 208) or [K/H/E]NAW (SEQ ID NO: 209), wherein the polypeptide has DNase activity and wherein the polypeptide is selected from any of the polypeptides shown in SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155 and SEQ ID NO: 158 or variant hereof having 1-25, such as 1-20, such as 1-15, such as 1-10, such as 1-5 amino acid alterations, e.g., substitutions.

One aspect of the invention relates to a polypeptide of the KNAW-clade comprising one or both of the motifs P[Q/E]L[W/Y] (SEQ ID NO: 208) or [K/H/E]NAW (SEQ ID NO: 209) and further comprises one or more of the motifs [E/D/H]H[I/V/L/F/M]X[P/A/S], [T/D/S][G/N]PQL, [G/T]Y[D/S][R/K/L], [F/L/Y/I]A[N/R]D[L/I/P/V], C[D/N]T[A/R] and [D/Q][I/V]DH, wherein the polypeptide has DNase activity and wherein the polypeptide is selected from any of the polypeptides shown in SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155 and SEQ ID NO: 158 or variant hereof having 1-25, such as 1-20, such as 1-15, such as 1-10, such as 1-5 amino acid alterations, e.g., substitutions.

One embodiment of the invention relates to a polypeptide of the KNAW clade having DNase activity and where the polypeptide comprises one or both of the motifs P[Q/E]L[W/Y] (SEQ ID NO: 208) or [K/H/E]NAW (SEQ ID NO: 209), with the proviso that the polypeptide is not the polypeptides shown in SEQ ID NO: 122 and SEQ ID NO: 125 and with the proviso that the polypeptide is not the *Trichoderma harzianum* DNase shown in SEQ ID NO: 2 of WO 2015/155351.

One embodiment of the invention relates to a polypeptide of the KNAW clade having DNase activity and where the polypeptide comprise one or both of the motifs P[Q/E]L[W/Y] (SEQ ID NO: 208) or [K/H/E]NAW (SEQ ID NO: 209), and wherein the polypeptide is selected from the polypeptides:

a) a polypeptide having at least 99.5% sequence identity to the polypeptide shown in SEQ ID NO: 128,
b) a polypeptide having at least 93% sequence identity to the polypeptide shown in SEQ ID NO: 131,
c) a polypeptide having at least 79% sequence identity to the polypeptide shown in SEQ ID NO: 134,
d) a polypeptide having at least 72% sequence identity to the polypeptide shown in SEQ ID NO: 137,
e) a polypeptide having at least 77% sequence identity to the polypeptide shown in SEQ ID NO: 140
f) a polypeptide having at least 74% sequence identity to the polypeptide shown in SEQ ID NO: 143,
g) a polypeptide having at least 97% sequence identity to the polypeptide shown in SEQ ID NO: 146,
h) a polypeptide having at least 71% sequence identity to the polypeptide shown in SEQ ID NO: 149,
i) a polypeptide having at least 96% sequence identity to the polypeptide shown in SEQ ID NO: 152,
j) a polypeptide having at least 72% sequence identity to the polypeptide shown in SEQ ID NO: 155, and
k) a polypeptide having at least 98% sequence identity to the polypeptide shown in SEQ ID NO: 158.

One embodiment of the invention relates to a polypeptide of the KNAW clade comprising one or both of the motifs P[Q/E]L[W/Y] (SEQ ID NO: 208) or [K/H/E]NAW (SEQ ID NO: 209), wherein the polypeptide having DNase activity is selected from the group consisting of SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155 and SEQ ID NO: 158 or polypeptides having at least 98% sequence identity thereto.

One embodiment of the invention relates to a polypeptide of the KNAW clade comprising one or both of the motifs P[Q/E]L[W/Y] (SEQ ID NO: 208) or [K/H/E]NAW (SEQ ID NO: 209), wherein the polypeptide has DNase activity and wherein the polypeptide is the polypeptide shown in SEQ ID NO: 128 or polypeptides having at least 99.5% or 100% sequence identity thereto.

One embodiment of the invention relates to a polypeptide of the KNAW clade comprising one or both of the motifs P[Q/E]L[W/Y] (SEQ ID NO: 208) or [K/H/E]NAW (SEQ ID NO: 209), wherein the polypeptide has DNase activity and wherein the polypeptide is the polypeptide shown in SEQ ID NO: 131 or polypeptides having at least 93%, such as at least 94%, at least 95%, at least 98%, at least 99% or 100% sequence identity thereto.

One embodiment of the invention relates to a polypeptide of the KNAW clade comprising one or both of the motifs P[Q/E]L[W/Y] (SEQ ID NO: 208) or [K/H/E]NAW (SEQ ID NO: 209), wherein the polypeptide has DNase activity and wherein the polypeptide is the polypeptide shown in SEQ ID NO: 134 or polypeptides having at least 79%, such as at least 80%, at least 85%, at least 86%, at least 88%, at least 90%, at least 93%, at least 95%, at least 98%, at least 99% or 100% sequence identity thereto.

One embodiment of the invention relates to a polypeptide of the KNAW clade comprising one or both of the motifs P[Q/E]L[W/Y] (SEQ ID NO: 208) or [K/H/E]NAW (SEQ ID NO: 209), wherein the polypeptide has DNase activity and wherein the polypeptide is the polypeptide shown in SEQ ID NO: 137 or polypeptides having at least 72%, such as at least 75%, at least 80%, at least 85%, at least 86%, at least 88%, at least 90%, at least 93%, at least 95%, at least 98%, at least 99% or 100% sequence identity thereto.

One embodiment of the invention relates to a polypeptide of the KNAW clade comprising one or both of the motifs P[Q/E]L[W/Y] (SEQ ID NO: 208) or [K/H/E]NAW (SEQ ID NO: 209), wherein the polypeptide has DNase activity and wherein the polypeptide is the polypeptide shown in SEQ ID NO: 140 or polypeptides having at least 77%, such as at least 80%, at least 85%, at least 86%, at least 88%, at least 90%, at least 93%, at least 95%, at least 98%, at least 99% or 100% sequence identity thereto.

One embodiment of the invention relates to a polypeptide of the KNAW clade comprising one or both of the motifs P[Q/E]L[W/Y] (SEQ ID NO: 208) or [K/H/E]NAW (SEQ ID NO: 209), wherein the polypeptide has DNase activity and wherein the polypeptide is the polypeptide shown in SEQ ID NO: 143 or polypeptides having at least 74%, such as at least 80%, at least 85%, at least 86%, at least 88%, at least 90%, at least 93%, at least 95%, at least 98%, at least 99% or 100% sequence identity thereto.

One embodiment of the invention relates to a polypeptide of the KNAW clade comprising one or both of the motifs P[Q/E]L[W/Y] (SEQ ID NO: 208) or [K/H/E]NAW (SEQ ID NO: 209), wherein the polypeptide has DNase activity and wherein the polypeptide is the polypeptide shown in SEQ ID NO: 146 or polypeptides having at least 97%, such as at least 98%, at least 99% or 100% sequence identity thereto.

One embodiment of the invention relates to a polypeptide of the KNAW clade comprising one or both of the motifs P[Q/E]L[W/Y] (SEQ ID NO: 208) or [K/H/E]NAW (SEQ ID NO: 209), wherein the polypeptide has DNase activity and wherein the polypeptide is the polypeptide shown in SEQ ID NO: 149 or polypeptides having at least 71%, such as at least 75%, at least 80%, at least 85%, at least 86%, at least 88%, at least 90%, at least 93%, at least 95%, at least 98%, at least 99% or 100% sequence identity thereto.

One embodiment of the invention relates to a polypeptide of the KNAW clade comprising one or both of the motifs P[Q/E]L[W/Y] (SEQ ID NO: 208) or [K/H/E]NAW (SEQ ID NO: 209), wherein the polypeptide has DNase activity and wherein the polypeptide is the polypeptide shown in SEQ ID NO: 152 or polypeptides having at least 96%, such as at least 97%, at least 98%, at least 99% or 100% sequence identity thereto.

One embodiment of the invention relates to a polypeptide of the KNAW clade comprising one or both of the motifs P[Q/E]L[W/Y] (SEQ ID NO: 208) or [K/H/E]NAW (SEQ ID NO: 209), wherein the polypeptide has DNase activity and wherein the polypeptide is the polypeptide shown in SEQ ID NO: 155 or polypeptides having at least 72%, such as at least 75%, at least 80%, at least 85%, at least 86%, at least 88%, at least 90%, at least 93%, at least 95%, at least 98%, at least 99% or 100% sequence identity thereto.

One embodiment of the invention relates to a polypeptide of the KNAW clade comprising one or both of the motifs P[Q/E]L[W/Y] (SEQ ID NO: 208) or [K/H/E]NAW (SEQ ID NO: 209), wherein the polypeptide has DNase activity and wherein the polypeptide is the polypeptide shown in SEQ ID NO: 158 or polypeptides having at least 98%, such as at least 99% or 100% sequence identity thereto.

One embodiment of the invention relates to a polypeptide having DNase activity, wherein the polypeptide is selected from the group consisting of:
 a) a polypeptide having at least 84% sequence identity to the polypeptide shown in SEQ ID NO: 8,
 b) a polypeptide having at least 94% sequence identity to the polypeptide shown in SEQ ID NO: 9,
 c) a polypeptide having at least 92% sequence identity to the polypeptide shown in SEQ ID NO: 11,
 d) a polypeptide having at least 92% sequence identity to the polypeptide shown in SEQ ID NO: 12,
 e) a polypeptide having at least 97% sequence identity to the polypeptide shown in SEQ ID NO: 13,
 f) a polypeptide having at least 96% sequence identity to the polypeptide shown in SEQ ID NO: 14,
 g) a polypeptide having at least 90% sequence identity to the polypeptide shown in SEQ ID NO: 15,
 h) a polypeptide having at least 88% sequence identity to the polypeptide shown in SEQ ID NO: 16,
 i) a polypeptide having at least 93% sequence identity to the polypeptide shown in SEQ ID NO: 17,
 j) a polypeptide having at least 90% sequence identity to the polypeptide shown in SEQ ID NO: 18,
 k) a polypeptide having at least 89% sequence identity to the polypeptide shown in SEQ ID NO: 19,
 l) a polypeptide having at least 90% sequence identity to the polypeptide shown in SEQ ID NO: 20,
 m) a polypeptide having at least 93% sequence identity to the polypeptide shown in SEQ ID NO: 21,
 n) a polypeptide having at least 90% sequence identity to the polypeptide shown in SEQ ID NO: 22,
 o) a polypeptide having at least 93% sequence identity to the polypeptide shown in SEQ ID NO: 23,
 p) a polypeptide having at least 85% sequence identity to the polypeptide shown in SEQ ID NO: 53,
 q) a polypeptide having at least 98% sequence identity to the polypeptide shown in SEQ ID NO: 56,
 r) a polypeptide having at least 94% sequence identity to the polypeptide shown in SEQ ID NO: 59,
 s) a polypeptide having at least 85% sequence identity to the polypeptide shown in SEQ ID NO: 62,
 t) a polypeptide having at least 97% sequence identity to the polypeptide shown in SEQ ID NO: 68,
 u) a polypeptide having at least 99% sequence identity to the polypeptide shown in SEQ ID NO: 71,
 v) a polypeptide having at least 91% sequence identity to the polypeptide shown in SEQ ID NO: 74,
 w) a polypeptide having at least 98% sequence identity to the polypeptide shown in SEQ ID NO: 77,
 x) a polypeptide having at least 81% sequence identity to the polypeptide shown in SEQ ID NO: 83,
 y) a polypeptide having at least 89% sequence identity to the polypeptide shown in SEQ ID NO: 86,
 z) a polypeptide having at least 99% sequence identity to the polypeptide shown in SEQ ID NO: 89,
 aa) a polypeptide having at least 91% sequence identity to the polypeptide shown in SEQ ID NO: 92, bb) a polypeptide having at least 90% sequence identity to the polypeptide shown in SEQ ID NO: 95,
cc) a polypeptide having at least 91% sequence identity to the polypeptide shown in SEQ ID NO: 98,
dd) a polypeptide having at least 92% sequence identity to the polypeptide shown in SEQ ID NO: 104,
ee) a polypeptide having at least 90% sequence identity to the polypeptide shown in SEQ ID NO: 107.
ff) a polypeptide having at least 91.5% sequence identity to the polypeptide shown in SEQ ID NO: 110.
gg) a polypeptide having at least 93% sequence identity to the polypeptide shown in SEQ ID NO: 113,
hh) a polypeptide having at least 96% sequence identity to the polypeptide shown in SEQ ID NO: 116,
ii) a polypeptide having at least 99.5% sequence identity to the polypeptide shown in SEQ ID NO: 119,
jj) a polypeptide having at least 99.5% sequence identity to the polypeptide shown in SEQ ID NO: 128,
kk) a polypeptide having at least 93% sequence identity to the polypeptide shown in SEQ ID NO: 131,
ll) a polypeptide having at least 79% sequence identity to the polypeptide shown in SEQ ID NO: 134,
mm) a polypeptide having at least 72% sequence identity to the polypeptide shown in SEQ ID NO: 137,
nn) a polypeptide having at least 77% sequence identity to the polypeptide shown in SEQ ID NO: 140,
oo) a polypeptide having at least 74% sequence identity to the polypeptide shown in SEQ ID NO: 143,
pp) a polypeptide having at least 97% sequence identity to the polypeptide shown in SEQ ID NO: 146,
qq) a polypeptide having at least 71% sequence identity to the polypeptide shown in SEQ ID NO: 149,
rr) a polypeptide having at least 96% sequence identity to the polypeptide shown in SEQ ID NO: 152,
ss) a polypeptide having at least 72% sequence identity to the polypeptide shown in SEQ ID NO: 155,
tt) a polypeptide having at least 93% sequence identity to the polypeptide shown in SEQ ID NO: 158,
uu) a polypeptide having at least 85% sequence identity to the polypeptide shown in SEQ ID NO: 164,
vv) a polypeptide having at least 88% sequence identity to the polypeptide shown in SEQ ID NO: 167
ww) a polypeptide having at least 99.8% sequence identity to the polypeptide shown in SEQ ID NO: 170,
xx) a polypeptide having at least 97% sequence identity to the polypeptide shown in SEQ ID NO: 173,
yy) a polypeptide having at least 87% sequence identity to the polypeptide shown in SEQ ID NO: 176
zz) a polypeptide having at least 81% sequence identity to the polypeptide shown in SEQ ID NO: 179,
aaa) a polypeptide having at least 89% sequence identity to the polypeptide shown in SEQ ID NO: 182,
bbb) a polypeptide having at least 96% sequence identity to the polypeptide shown in SEQ ID NO: 185,
ccc) a polypeptide having at least 88% sequence identity to the polypeptide shown in SEQ ID NO: 188,
ddd) a polypeptide having at least 87% sequence identity to the polypeptide shown in SEQ ID NO: 191,
eee) a polypeptide having at least 94% sequence identity to the polypeptide shown in SEQ ID NO: 194,
fff) a polypeptide having at least 90% sequence identity to the polypeptide shown in SEQ ID NO: 197, and optionally
ggg) one or more of the motifs [E/D/H]H[I/V/L/F/M]X [P/A/S], [T/D/S][G/N]PQL, [G/T]Y[D/S][R/K/L], [F/L/Y/I]A[N/R]D[L/I/P/V] or C[D/N]T[A/R] and [D/Q][I/V]DH.

In one aspect of the invention, the DNase is obtainable from *Bacillus* sp-62451, *Bacillus horikoshii* or *Paenibacillus* sp-18057. The DNase of the present invention includes the mature polypeptide of SEQ ID NO: 2, 4 or 6 or polypeptides having a sequence identity to the mature polypeptides of SEQ ID NO: 2, 4 or 6 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% and wherein the polypeptides have DNase activity.

The group of DNases comprised in the GYS-clade as described above share similar structural and functional properties as described above, e.g., common motifs. The DNases of the GYS-clade are preferably obtained from *Bacillus* genus. The individual DNases in the GYS group are described in detail below.

The DNase may be obtained from *Bacillus*, preferably *Bacillus* sp. sp-62451 The DNase may be a polypeptide comprising the mature polypeptide of SEQ ID NO: 2 or a polypeptide closely related hereto such as a polypeptide having at least 60%, such as at least 70%, at least 75%, at least 80%, at least 85%, at least 90% or at least 95% sequence identity thereto. A DNase according to the invention may be obtained from *Bacillus*, such as *Bacillus* sp. sp-62451 and comprise a polypeptide having at least 60%, e.g., at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 8. The polypeptides comprising SEQ ID NO: 21 (mature polypeptide obtained from *Bacillus cibi*), SEQ ID NO: 22 (mature polypeptide obtained from *Bacillus* sp-18318) and SEQ ID NO: 23 (mature polypeptide obtained from *Bacillus idriensis*) are homologue polypeptides with, e.g., at least 80% sequence identity to SEQ ID NO: 8.

The polypeptides comprising SEQ ID NO: 21 (mature polypeptide obtained from *Bacillus cibi*), SEQ ID NO: 22 (mature polypeptide obtained from *Bacillus* sp-18318) and SEQ ID NO: 23 (mature polypeptide obtained from *Bacillus idriensis*) are also useful for preventing or removing biofilm on items such as textiles and/or fabric as shown in example 2. The DNase may be a polypeptide comprising the mature polypeptide shown in SEQ ID NO: 21 or a polypeptide closely related hereto. Thus, one aspect of the invention relates to a DNase having at least 60%, e.g., at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 21, preferably obtained from *Bacillus cibi*. The DNase may be a polypeptide comprising the mature polypeptide shown in SEQ ID NO: 22 or a polypeptide closely related hereto. One aspect of the invention relates to a DNase having at least 60%, e.g., at least 65%, at least 70%, at least 75%, at least 76%, at least 77%, at least 78%, at least 79%, at least 80%, at least 81%, at least 82%, at least 83%, at least, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 22, preferably obtained from *Bacillus* sp-18318. The DNase may be a polypeptide comprising the mature polypeptide shown in SEQ ID NO: 23 or a polypeptide closely related hereto. One aspect of the invention relates to a DNase having at least 60%, e.g., at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 23, preferably obtained from *Bacillus idriensis*.

The DNase may be obtained from *Bacillus*, preferably *Bacillus horikoshii*. The DNase may be a polypeptide comprising the mature polypeptide of SEQ ID NO: 4 or a polypeptide closely related hereto such as a polypeptide having at least 60% such as at least 70%, at least 75%, at least 80%, at least 85%, at least 90% or such as at least 95% sequence identity thereto. A DNase according to the invention may be obtained from *Bacillus* such as *Bacillus horikoshii* and comprise a polypeptide having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 9. The homologue polypeptides comprised in SEQ ID NO: 11 (mature polypeptide obtained from *Bacillus* sp-62520), SEQ ID NO: 12 (mature polypeptide obtained from *Bacillus* sp-62520), SEQ ID NO: 13 (mature polypeptide obtained from *Bacillus horikoshii*), SEQ ID NO: 14 (mature polypeptide obtained from *Bacillus horikoshii*), SEQ ID NO: 15 (mature polypeptide obtained from *Bacillus* sp-16840), SEQ ID NO: 16 (mature polypeptide obtained from *Bacillus* sp-16840), SEQ ID NO: 17 (mature polypeptide obtained from *Bacillus* sp-62668), SEQ ID NO: 18 (mature polypeptide obtained from *Bacillus* sp-13395), SEQ ID NO: 19 (mature polypeptide obtained from *Bacillus* horneckiae) or SEQ ID NO: 20 (mature polypeptide obtained from *Bacillus* sp-11238) are homologue polypeptides within at least 80% sequence identity to SEQ ID NO: 9. The polypeptides comprising SEQ ID NO: 11 (mature polypeptide obtained from *Bacillus* sp-62520), SEQ ID NO: 12 (mature polypeptide obtained from *Bacillus* sp-62520), SEQ ID NO: 13 (mature polypeptide obtained from *Bacillus horikoshii*), SEQ ID NO: 14 (mature polypeptide obtained from *Bacillus horikoshii*), SEQ ID NO: 15 (mature polypeptide obtained from *Bacillus* sp-16840), SEQ ID NO: 16 (mature polypeptide obtained from *Bacillus* sp-16840), SEQ ID NO: 17 (mature polypeptide obtained from *Bacillus* sp-62668), SEQ ID NO: 18 (mature polypeptide obtained from *Bacillus* sp-13395), SEQ ID NO: 19 (mature polypeptide obtained from *Bacillus* horneckiae) or SEQ ID NO: 20 (mature polypeptide obtained from *Bacillus* sp-11238) are also useful for preventing or removing biofilm on items such as textiles and/or fabric as shown in example 2. The DNase may be a polypeptide comprising the mature polypeptide shown in SEQ ID NO: 11 or a polypeptide closely related hereto. Thus, one aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 11, preferably obtained from *Bacillus* sp-62520. The DNase may be a polypeptide comprising the mature polypeptide shown in SEQ ID NO: 12 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 12, preferably obtained from *Bacillus* sp-62520. The DNase may be a polypeptide comprising the mature polypeptide shown in SEQ ID NO: 13 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 13, preferably obtained from *Bacillus horikoshii*. The DNase may be a polypeptide comprising the mature polypeptide shown in SEQ ID NO: 14 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 14, preferably obtained from *Bacillus horikoshii*. The DNase may be a polypeptide comprising the mature polypeptide shown in SEQ ID NO: 15 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 15, preferably obtained from *Bacillus* sp-16840. The DNase may be a polypeptide comprising the mature polypeptide shown in SEQ ID NO: 16 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 16, preferably obtained from *Bacillus* sp-16840. The DNase may be a polypeptide comprising the mature polypeptide shown in SEQ ID NO: 17 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 17, preferably obtained from *Bacillus* sp-62668. The DNase may be a polypeptide comprising the mature polypeptide shown in SEQ ID NO: 18 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 18, preferably obtained from *Bacillus* sp-13395. The DNase may be a polypeptide comprising the mature polypeptide shown in SEQ ID NO: 19 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 19, preferably obtained from *Bacillus horneckiae*.

The DNase may be a polypeptide comprising the mature polypeptide shown in SEQ ID NO: 20 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 20, preferably obtained from *Bacillus* sp-11238.

The DNase may be a polypeptide comprising the mature polypeptide shown in SEQ ID NO: 53 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 53, preferably obtained from *Bacillus algicola*.

The DNase may be a polypeptide comprising the mature polypeptide shown in SEQ ID NO: 56 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 56, preferably obtained from Xanthan community J.

The DNase may be a polypeptide comprising the mature polypeptide shown in SEQ ID NO: 59 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 59, preferably obtained from *Bacillus vietnamensis*.

The DNase may be a polypeptide comprising the mature polypeptide shown in SEQ ID NO: 62 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 62, preferably obtained from *Bacillus hwajinpoensis*.

The DNase may be a polypeptide comprising the mature polypeptide shown in SEQ ID NO: 68 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 68, preferably obtained from *Bacillus indicus*.

The DNase may be a polypeptide comprising the mature polypeptide shown in SEQ ID NO: 71 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 71, preferably obtained from *Bacillus marisflavi*.

The DNase may be a polypeptide comprising the mature polypeptide shown in SEQ ID NO: 74 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 74, preferably obtained from *Bacillus luciferensis*.

The DNase may be a polypeptide comprising the mature polypeptide shown in SEQ ID NO: 77 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 77, preferably obtained from *Bacillus marisflavi*.

The group of DNases comprised in the NAWK-clade as described above share similar structural and functional properties as described above, e.g., common motifs. The DNases of the NAWK-clade may be obtained from any of the genus and species listed below. The individual DNases in the NAWK group are described in detail below.

The DNase may be a polypeptide comprising the mature polypeptide shown in SEQ ID NO: 83 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 83, preferably obtained from *Pyrenochaetopsis* sp.

The DNase may be a polypeptide comprising the mature polypeptide shown in SEQ ID NO: 86 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 86, preferably obtained from *Vibrissea flavovirens*.

The DNase may be a polypeptide comprising the mature polypeptide shown in SEQ ID NO: 89 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 89, preferably obtained from *Setosphaeria rostrate*.

The DNase may be a polypeptide comprising the mature polypeptide shown in SEQ ID NO: 92 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 92, preferably obtained from *Endophragmiella valdina*.

The DNase may be a polypeptide comprising the mature polypeptide shown in SEQ ID NO: 95 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 95, preferably obtained from *Corynespora cassiicola*.

The DNase may be a polypeptide comprising the mature polypeptide shown in SEQ ID NO: 98 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 98, preferably obtained from *Paraphoma* sp. XZ1965.

The DNase may be a polypeptide comprising the mature polypeptide shown in SEQ ID NO: 101 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 101, preferably obtained from *Monilinia fructicola*.

The DNase may be a polypeptide comprising the mature polypeptide shown in SEQ ID NO: 104 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 104, preferably obtained from *Curvularia lunata*.

The DNase may be a polypeptide comprising the mature polypeptide shown in SEQ ID NO: 107 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 107, preferably obtained from *Penicillium reticulisporum*.

The DNase may be a polypeptide comprising the mature polypeptide shown in SEQ ID NO: 110 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 110, preferably obtained from *Penicillium quercetorum*.

The DNase may be a polypeptide comprising the mature polypeptide shown in SEQ ID NO: 113 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 113, preferably obtained from *Setophaeosphaeria* sp.

The DNase may be a polypeptide comprising the mature polypeptide shown in SEQ ID NO: 116 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 116, preferably obtained from *Alternaria* sp. XZ2545.

The DNase may be a polypeptide comprising the mature polypeptide shown in SEQ ID NO: 119 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 119, preferably obtained from *Alternaria* sp.

The group of DNases comprised in the KNAW-clade as described above share similar structural and functional properties as described above, e.g., common motifs. The DNases of the NAWK clade are preferably obtained from any of the genus and species listed below. The individual DNases in the NAWK group are described in detail below.

The DNase may be a polypeptide comprising the mature polypeptide shown in SEQ ID NO: 128 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 128, preferably obtained from *Scytalidium thermophilum*.

The DNase may be a polypeptide comprising the mature polypeptide shown in SEQ ID NO: 131 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 131, preferably obtained from *Metapochonia suchlasporia*.

The DNase may be a polypeptide comprising the mature polypeptide shown in SEQ ID NO: 134 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 134, preferably obtained from *Daldinia fissa*.

The DNase may be a polypeptide comprising the mature polypeptide shown in SEQ ID NO: 137 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 137, preferably obtained from *Acremonium* sp. XZ2007.

The DNase may be a polypeptide comprising the mature polypeptide shown in SEQ ID NO: 140 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 140, preferably obtained from *Acremonium dichromosporum*.

The DNase may be a polypeptide comprising the mature polypeptide shown in SEQ ID NO: 143 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 143, preferably obtained from *Sarocladium* sp. XZ2014.

The DNase may be a polypeptide comprising the mature polypeptide shown in SEQ ID NO: 146 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 146, preferably obtained from *Metarhizium* sp. HNA15-2.

The DNase may be a polypeptide comprising the mature polypeptide shown in SEQ ID NO: 149 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 149, preferably obtained from *Acremonium* sp. XZ2414.

The DNase may be a polypeptide comprising the mature polypeptide shown in SEQ ID NO: 152 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 152, preferably obtained from *Isaria tenuipes*.

The DNase may be a polypeptide comprising the mature polypeptide shown in SEQ ID NO: 155 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 155, preferably obtained from *Scytalidium circinatum*.

The DNase may be a polypeptide comprising the mature polypeptide shown in SEQ ID NO: 158 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 158, preferably obtained from *Metarhizium lepidiotae*.

The polypeptides having DNase activity listed below are also useful for deep cleaning, e.g., for preventing, reducing or removing biofilm, e.g., on fabric, e.g., textiles, such as cotton and polyester. The polypeptides having DNase activity listed below comprise the NUC1 and NUC1_A domain and the NUC1 and NUC1_A motifs and have similarity with the polypeptides belonging to either of the clades GYS, NAWK and KNAW, which also comprise the NUC1 and NUC1_A domains and motifs.

The DNase may be a polypeptide comprising the mature polypeptide shown in SEQ ID NO: 164 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 164, preferably obtained from *Sporormia fimetaria*.

The DNase may be a polypeptide comprising the mature polypeptide shown in SEQ ID NO: 167 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 167, preferably obtained from *Pycnidiophora cf. dispera*.

The DNase may be a polypeptide comprising the mature polypeptide shown in SEQ ID NO: 170 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 170, preferably obtained from Xanthan alkaline community D.

The DNase may be a polypeptide comprising the mature polypeptide shown in SEQ ID NO: 173 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 173, preferably obtained from Xanthan alkaline community O.

The DNase may be a polypeptide comprising the mature polypeptide shown in SEQ ID NO: 176 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 176, preferably obtained from *Clavicipitaceae* sp-70249.

The DNase may be a polypeptide comprising the mature polypeptide shown in SEQ ID NO: 179 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 179, preferably obtained from *Westerdykella* sp. AS85-2.

The DNase may be a polypeptide comprising the mature polypeptide shown in SEQ ID NO: 182 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 182, preferably obtained from *Humicolopsis cephalosporioides*.

The DNase may be a polypeptide comprising the mature polypeptide shown in SEQ ID NO: 185 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 185, preferably obtained from *Neosartorya massa*.

The DNase may be a polypeptide comprising the mature polypeptide shown in SEQ ID NO: 188 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 188, preferably obtained from *Roussoella intermedia*.

The DNase may be a polypeptide comprising the mature polypeptide shown in SEQ ID NO: 191 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 191, preferably obtained from *Pleosporales*.

The DNase may be a polypeptide comprising the mature polypeptide shown in SEQ ID NO: 194 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 194, preferably obtained from *Phaeosphaeria* sp.

The DNase may be a polypeptide comprising the mature polypeptide shown in SEQ ID NO: 197 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 197, preferably obtained from *Didymosphaeria futilis*.

The DNase may be obtained from *Paenibacillus* preferably *Paenibacillus* sp-18057. The DNase may be a polypeptide comprising the mature polypeptide of SEQ ID NO: 6 or a polypeptide closely related hereto. A DNase according to the invention may be obtained from *Paenibacillus* sp-18057 and comprise a polypeptide having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 10.

In one aspect of the invention, the polypeptide having DNase activity is obtained from *Bacillus*, in particular from *Bacillus* sp-62451. In one aspect of the invention the polypeptide having DNase activity is obtained from *Bacillus*, in particular from *Bacillus horikoshii*. In one aspect of the invention the polypeptide having DNase activity is obtained from *Bacillus*, in particular from *Bacillus* sp-62520. In one aspect of the invention the polypeptide having DNase activity is obtained from *Bacillus*, in particular from *Bacillus* sp-16840. In one aspect of the invention the polypeptide having DNase activity is obtained from *Bacillus*, in particular from *Bacillus* sp-62668. In one aspect of the invention the polypeptide having DNase activity is obtained from *Bacillus*, in particular from *Bacillus* sp-13395. In one aspect of the invention the polypeptide having DNase activity is obtained from *Bacillus*, in particular from *Bacillus* sp-11238. In one aspect of the invention the polypeptide having DNase activity is obtained from *Bacillus*, in particular from *Bacillus cibi*. In one aspect of the invention the polypeptide having DNase activity is obtained from *Bacil-*

*lus*, in particular from *Bacillus* sp-18318. In one aspect of the invention the polypeptide having DNase activity is obtained from *Bacillus*, in particular from *Bacillus idriensis*. In one aspect of the invention the polypeptide having DNase activity is obtained from *Vibrissea flavovirens* and comprises or consists of the polypeptide shown in SEQ ID NO: 86. In one aspect of the invention the polypeptide having DNase activity is obtained from *Acremonium dichromosporum* and comprises or consists of the polypeptide shown in SEQ ID NO: 140. In one aspect of the invention the polypeptide having DNase activity is obtained from *Clavicipitaceae* sp-70249 and comprises or consists of the polypeptide shown in SEQ ID NO: 176. In one aspect of the invention the polypeptide having DNase activity is obtained from *Penicillium reticulisporum* and comprises or consists of the polypeptide shown in SEQ ID NO: 107. In one aspect of the invention the polypeptide having DNase activity is obtained from *Pycnidiophora cf. dispera* and comprises or consists of the polypeptide shown in SEQ ID NO: 167. In one aspect of the invention the polypeptide having DNase activity is obtained from *Metapochonia suchlasporia* and comprises or consists of the polypeptide shown in SEQ ID NO: 131. In one aspect of the invention the polypeptide having DNase activity is obtained from *Acremonium* sp. XZ2007 and comprises or consists of the polypeptide shown in SEQ ID NO: 137. In one aspect of the invention the polypeptide having DNase activity is obtained from *Setosphaeria rostrata* and comprises or consists of the polypeptide shown in SEQ ID NO: 89. In one aspect of the invention the polypeptide having DNase activity is obtained from *Sarocladium* sp. XZ2014 and comprises or consists of the polypeptide shown in SEQ ID NO: 143. In one aspect of the invention the polypeptide having DNase activity is obtained from *Metarhizium* sp. HNA 15-2 and comprises or consists of the polypeptide shown in SEQ ID NO: 146. In one aspect of the invention the polypeptide having DNase activity is obtained from *Endophragmiella valdina* and comprises or consists of the polypeptide shown in SEQ ID NO: 92. In one aspect of the invention the polypeptide having DNase activity is obtained from *Humicolopsis cephalosporioides* and comprises or consists of the polypeptide shown in SEQ ID NO: 182. In one aspect of the invention the polypeptide having DNase activity is obtained from *Corynespora cassiicola* and comprises or consists of the polypeptide shown in SEQ ID NO: 95. In one aspect of the invention the polypeptide having DNase activity is obtained from *Paraphoma* sp. XZ1965 and comprises or consists of the polypeptide shown in SEQ ID NO: 98. In one aspect of the invention the polypeptide having DNase activity is obtained from *Curvularia lunata* and comprises or consists of the polypeptide shown in SEQ ID NO: 104. In one aspect of the invention the polypeptide having DNase activity is obtained from *Acremonium* sp. XZ2414 and comprises or consists of the polypeptide shown in SEQ ID NO: 149. In one aspect of the invention the polypeptide having DNase activity is obtained from *Isaria tenuipes* and comprises or consists of the polypeptide shown in SEQ ID NO: 152. In one aspect of the invention the polypeptide having DNase activity is obtained from *Roussoella intermedia* and comprises or consists of the polypeptide shown in SEQ ID NO: 188. In one aspect of the invention the polypeptide having DNase activity is obtained from *Scytalidium circinatum* and comprises or consists of the polypeptide shown in SEQ ID NO: 155. In one aspect of the invention the polypeptide having DNase activity is obtained from *Setophaeosphaeria* sp. and comprises or consists of the polypeptide shown in SEQ ID NO: 158. In one aspect of the invention the polypeptide having DNase activity is obtained from *Alternaria* sp. XZ2545 and comprises or consists of the polypeptide shown in SEQ ID NO: 116. In one aspect of the invention the polypeptide having DNase activity is obtained from *Alternaria* sp. and comprises or consists of the polypeptide shown in SEQ ID NO: 119. In one aspect of the invention the polypeptide having DNase activity is obtained from *Metarhizium lepidiotae* and comprises or consists of the polypeptide shown in SEQ ID NO: 158. In one aspect of the invention the polypeptide having DNase activity is obtained from *Pleosporales* and comprises or consists of the polypeptide shown in SEQ ID NO: 191. In one aspect of the invention the polypeptide having DNase activity is obtained from *Phaeosphaeria* sp. and comprises or consists of the polypeptide shown in SEQ ID NO: 194. In one aspect of the invention the polypeptide having DNase activity is obtained from *Didymosphaeria futilis* and comprises or consists of the polypeptide shown in SEQ ID NO: 197. In one aspect of the invention the polypeptide having DNase activity is obtained from *Bacillus vietnamensis* and comprises or consists of the polypeptide shown in SEQ ID NO: 59. In one aspect of the invention the polypeptide having DNase activity is obtained from *Bacillus hwajinpoensis* and comprises or consists of the polypeptide shown in SEQ ID NO: 62. In one aspect of the invention the polypeptide having DNase activity is obtained from Xanthan alkaline community J and comprises or consists of the polypeptide shown in SEQ ID NO: 56. In one aspect of the invention the polypeptide having DNase activity is obtained from *Bacillus indicus* and comprises or consists of the polypeptide shown in SEQ ID NO: 68. In one aspect of the invention the polypeptide having DNase activity is obtained from *Bacillus marisflavi* and comprises or consists of the polypeptide shown in SEQ ID NO: 71. In one aspect of the invention the polypeptide having DNase activity is obtained from *Bacillus luciferensis* and comprises or consists of the polypeptide shown in SEQ ID NO: 74. In one aspect of the invention the polypeptide having DNase activity is obtained from *Bacillus marisflavi* and comprises or consists of the polypeptide shown in SEQ ID NO: 77. In one aspect of the invention the polypeptide having DNase activity is obtained from *Sporormia fimetaria* and comprises or consists of the polypeptide shown in SEQ ID NO: 164. In one aspect of the invention the polypeptide having DNase activity is obtained from *Daldinia fissa* and comprises or consists of the polypeptide shown in SEQ ID NO. 134. In one aspect of the invention the polypeptide having DNase activity is obtained from *Pyrenochaetopsis* sp. and comprises or consists of the polypeptide shown in SEQ ID NO: 83. In one aspect of the invention the polypeptide having DNase activity is obtained from *Westerdykella* sp. AS85-2 and comprises or consists of the polypeptide shown in SEQ ID NO: 179. In one aspect of the invention the polypeptide having DNase activity is obtained from *Monilinia fructicola* and comprises or consists of the polypeptide shown in SEQ ID NO: 101. In one aspect of the invention the polypeptide having DNase activity is obtained from *Neosartorya massa* and comprises or consists of the polypeptide shown in SEQ ID NO: 185. In one aspect of the invention the polypeptide having DNase activity is obtained from *Penicillium quercetorum* and comprises or consists of the polypeptide shown in SEQ ID NO: 110. In one aspect of the invention the polypeptide having DNase activity is obtained from Xanthan alkaline community D and comprises or consists of the polypeptide shown in SEQ ID NO: 170. In one aspect of the invention the polypeptide having DNase activity is obtained from *Bacillus algicola* and comprises or consists of the polypeptide shown in SEQ ID NO: 53. In one aspect of the invention the polypeptide having DNase activity is obtained from Xanthan alkaline community O and comprises or consists of the polypeptide shown in SEQ ID NO: 173. In one aspect of the invention the polypeptide having DNase activity is obtained from *Scytalidium thermophilum* and comprises or consists of the polypeptide shown in SEQ ID NO: 128.

In one aspect of the invention the polypeptide having DNase activity is obtained from *Paenibacillus*, in particular from *Paenibacillus* sp-18057. In one aspect of the invention the polypeptide having DNase activity is obtained from *Bacillus* and comprises the mature polypeptide of SEQ ID NOS 2, 4 or 6, i.e., the mature polypeptides with SEQ ID NOS 8, 9 or 10. In a preferred aspect of the invention the DNase is obtained from *Bacillus* sp-62451 and comprises the polypeptide sequence with SEQ ID NO: 8. In a preferred aspect of the invention the DNase is obtained from *Bacillus horikoshii* and comprises the polypeptide sequence with SEQ ID NO: 9. In a preferred aspect of the invention the DNase is obtained from *Paenibacillus* sp-18057 and comprises any of the polypeptide sequence with SEQ ID NO: 10. In a preferred aspect of the invention the DNase is obtained from *Bacillus* sp-62520 and comprises the polypeptide sequence with SEQ ID NO: 11. In a preferred aspect of the invention the DNase is obtained from *Bacillus* sp-62520 and comprises the polypeptide sequence with SEQ ID NO: 12. In a preferred aspect of the invention the DNase is obtained from *Bacillus horikoshii* and comprises the polypeptide sequence with SEQ ID NO: 13. In a preferred aspect of the invention the DNase is obtained from *Bacillus horikoshii* and comprises the polypeptide sequence with SEQ ID NO: 14. In a preferred aspect of the invention the DNase is obtained from *Bacillus* sp-16840 and comprises the polypeptide sequence with SEQ ID NO: 15. In a preferred aspect of the invention the DNase is obtained from *Bacillus* sp-16840 and comprises the polypeptide sequence with SEQ ID NO: 16. In a preferred aspect of the invention the DNase is obtained from *Bacillus* sp-62668 and comprises the polypeptide sequence with SEQ ID NO: 17. In a preferred aspect of the invention the DNase is obtained from *Bacillus* sp-13395 and comprises the polypeptide sequence with SEQ ID NO: 18. In a preferred aspect of the invention the DNase is obtained from *Bacillus horneckiae* and comprises the polypeptide sequence with SEQ ID NO: 19. In a preferred aspect of the invention the DNase is obtained from *Bacillus* sp-11238 and comprises the polypeptide sequence with SEQ ID NO: 20. In a preferred aspect of the invention the DNase is obtained from *Bacillus cibi* and comprises the polypeptide sequence with SEQ ID NO: 21. In a preferred aspect of the invention the DNase is obtained from *Bacillus* sp-18318 and comprises the polypeptide sequence with SEQ ID NO: 22. In a preferred aspect of the invention the DNase is obtained from *Bacillus idriensis* and comprises the polypeptide sequence with SEQ ID NO: 23.

In a preferred aspect of the invention the DNase is obtained from *Bacillus* sp-62451 and consists of the polypeptide sequence with SEQ ID NO: 8. In another preferred aspect of the invention the DNase is obtained from *Bacillus horikoshii* and consists of the polypeptide sequence with SEQ ID NO: 9. In another preferred aspect of the invention the DNase is obtained from *Paenibacillus* sp-18057 and consists of the polypeptide sequence with SEQ ID NO: 10. In a preferred aspect of the invention the DNase is obtained from *Bacillus* sp-62520 and consists of the polypeptide sequence with SEQ ID NO: 11. In a preferred aspect of the invention the DNase is obtained from *Bacillus* sp-62520 and consists of the polypeptide sequence with SEQ ID NO: 12. In a preferred aspect of the invention the DNase is obtained from *Bacillus horikoshii* and consists of the polypeptide sequence with SEQ ID NO: 13. In a preferred aspect of the invention the DNase is obtained from *Bacillus horikoshii* and consists of the polypeptide sequence with SEQ ID NO: 14. In a preferred aspect of the invention the DNase is obtained from *Bacillus* sp-16840 and consists of the polypeptide sequence with SEQ ID NO: 15. In a preferred aspect of the invention the DNase is obtained from *Bacillus* sp-16840 and consists of the polypeptide sequence with SEQ ID NO: 16. In a preferred aspect of the invention the DNase is obtained from *Bacillus* sp-62668 and consists of the polypeptide sequence with SEQ ID NO: 17. In a preferred aspect of the invention the DNase is obtained from *Bacillus* sp-13395 and consists of the polypeptide sequence with SEQ ID NO: 18. In a preferred aspect of the invention the DNase is obtained from *Bacillus horneckiae* and consists of the polypeptide sequence with SEQ ID NO: 19. In a preferred aspect of the invention the DNase is obtained from *Bacillus* sp-11238 and consists of the polypeptide sequence with SEQ ID NO: 20. In a preferred aspect of the invention the DNase is obtained from *Bacillus cibi* and consists of the polypeptide sequence with SEQ ID NO: 21. In a preferred aspect of the invention the DNase is obtained from *Bacillus* sp-18318 and consists of the polypeptide sequence with SEQ ID NO: 22. In a preferred aspect of the invention the DNase is obtained from *Bacillus idriensis* and consists of the polypeptide sequence with SEQ ID NO: 23.

Biofilm can develop on textile when microorganisms are present on an item and stick together on the item. Some microorganisms tend to adhere to the surface of items such as textiles. Some microorganisms adhere to such surfaces and form a biofilm on the surface. The biofilm may be sticky and the adhered microorganisms and/or the biofilm may be difficult to remove. Furthermore, the biofilm adhere soil due to the sticky nature of the biofilm. The commercial laundry detergent compositions available on the marked do not remove such adhered microorganisms, microorganism parts or biofilm.

The present invention relates to polypeptides having DNase activity and the use of such polypeptides for preventing, reducing or removing a biofilm from an item, such as textiles. In one embodiment of the invention the polypeptide having DNase activity is used for preventing, reducing or removing the stickiness of an item. In one embodiment of the invention, the polypeptide having DNase activity improves whiteness of an item, such as a textile. In one embodiment the polypeptide of the invention having DNase activity helps maintaining the colour on textiles. When textiles are repeatedly washed the colours tend to be less bright. In one embodiment a polypeptide of the invention having DNase has an improved effect of maintaining the colour of coloured textiles even after repeated washes. In one embodiment the polypeptide of the invention also reduced the colouring of non-coloured part of the same or additional textile present in the wash.

The polypeptide having DNase activity can further be used for pretreating stains on textile such as textile with a pronounced amount of biofilm adhered to the textile.

The polypeptide having DNase activity can further be used for preventing, reducing or removing static electricity from an item on which static electricity may accumulate, such item maybe a textile or a hard surface. The polypeptide having DNase activity can further be used for preventing, reducing and/or removing a biofilm from an item, such item may be a hard surface, e.g., dishes, cutlery, porcelain, china, crockery etc. Thus, in some aspect the polypeptide having DNase activity may be used in an ADW (Automatic dishwash) process.

Additionally, the invention relates to the use of a polypeptide having DNase activity for preventing, reducing or removing redeposition of soil during a wash cycle. When the polypeptide is used for example in the laundering of textile, the polypeptide hinders deposition of soil present in the wash liquor to deposit on the textile.

Further, the invention concerns the use of a polypeptide having DNase activity for preventing, reducing or removing the adherence of soil to an item. In one embodiment, the item is textile. When the soil does not adhere to the item, the item appears cleaner. Thus, the invention further relates to the use of a polypeptide having DNase activity for maintaining or improving the whiteness of the item.

When items like T-shirts or sportswear are used, they are exposed to bacteria from the body of the user and from the rest of the environment in which they are used. This may cause malodor on the item even after the item is washed. The present invention relates to removal or reduction of malodor on textile. The malodor may be caused by bacteria producing compounds with an unpleasant smell. One example of such unpleasant smelling compounds is E-2-nonenal. The malodor can be present on newly washed textile which is still wet or the malodor can be present on newly washed textile, which has subsequently been dried. The malodor may also be present on textile, which has been stored for some time after wash. The present invention concerns the reduction or removal of malodor such as E-2-nonenal from wet or dry textile.

The polypeptides of the invention having DNase activity, i.e., the DNases of the invention have very good cleaning performance in powder and liquid detergents. Examples of beneficial effects of the DNases with SEQ ID NO: 8, 9 and 10 and homologue DNases, e.g., polypeptides having DNases activity and having a polypeptide sequence shown in SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 53, SEQ ID NO: 56, SEQ ID NO: 59, SEQ ID NO: 62, SEQ ID NO: 65, SEQ ID NO: 68, SEQ ID NO: 71, SEQ ID NO: 74, SEQ ID NO: 77, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 161, SEQ ID NO: 164, SEQ ID NO: 167, SEQ ID NO: 170, SEQ ID NO: 173, SEQ ID NO: 176, SEQ ID NO: 179, SEQ ID NO: 182, SEQ ID NO: 185, SEQ ID NO: 188, SEQ ID NO: 191, SEQ ID NO: 194 and SEQ ID NO: 197. The deep-cleaning effect is shown in examples 2 and 3 one effect is preventing laundry in becoming grey and removal of malodor. The polypeptides comprising SEQ ID NO: 8, 9 and 10 are novel polypeptides having DNase activity which have deep cleaning effect in powder detergents and liquid detergents. The polypeptides comprising SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 53, SEQ ID NO: 56, SEQ ID NO: 59, SEQ ID NO: 62, SEQ ID NO: 65, SEQ ID NO: 68, SEQ ID NO: 71, SEQ ID NO: 74, SEQ ID NO: 77, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 104, SEQ ID NO: 107, SEQ ID NO: 110, SEQ ID NO: 113, SEQ ID NO: 116, SEQ ID NO: 119, SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 158, SEQ ID NO: 161, SEQ ID NO: 164, SEQ ID NO: 167, SEQ ID NO: 170, SEQ ID NO: 176, SEQ ID NO: 179, SEQ ID NO: 185, SEQ ID NO: 188, SEQ ID NO: 191 and SEQ ID NO: 197, are also polypeptides having DNase activity which have deep cleaning effect in powder detergents and liquid detergents.

Benzonase (SIGMA-E1014) SEQ ID NO: 7) is a commercially available DNase. The inventors show that this DNase has also has a deep cleaning effect as could be seen in example 2 The deep cleaning helps preventing greyness of laundry and removing of odor of laundry Yet another embodiment relates to the use of a DNase, selected from the group consisting of SEQ ID NO: 7, 8, 9 and 10 for reducing malodor from laundry and/or textile. Another embodiment relates to the use of a DNase, selected from the group consisting of SEQ ID NO: 7, 8, 9 and 10 for reducing malodor from laundry and/or textile, for anti-redeposition and for maintaining or improving the whiteness of a textile.

Some aspect of the invention relates to the use of a polypeptide having DNase activity, for prevention, reduction or removing a biofilm from an item, wherein the polypeptide having DNase activity comprises the HXXP motif and wherein H is the amino acid histidine, P is the amino acid proline and X is any amino acid. The item is preferably a fabric, e.g., textile, e.g., cotton and/or polyester.

Some aspect of the invention relates to the use of a polypeptide having DNase activity, for prevention, reduction or removing a biofilm from an item, wherein the polypeptide having DNase activity comprises one or more of the motifs [E/D/H]H[I/V/L/F/M]X[P/A/S], [T/D/S][G/N]PQL, [G/T]Y[D/S][R/K/L]. The item is preferably a fabric, e.g., textile, e.g., cotton and/or polyester.

Some aspect of the invention relates to the use of a polypeptide having DNase activity, for prevention, reduction or removing a biofilm from an item, wherein the polypeptide having DNase activity comprises one or both of the motifs [F/L/Y/I]A[N/R]D[L/I/P/V] or C[D/N]T[A/R]. The item is preferably a fabric, e.g., textile, e.g., cotton and/or polyester.

Some aspect of the invention relates to the use of a polypeptide having DNase activity, for prevention, reduction or removing a biofilm from an item, wherein the polypeptide having DNase activity belongs to the GYS clade and comprises one or both of the motifs [D/M/L][S/T]GYSR[D/N](SEQ ID NO: 204) or ASXNRSKG (SEQ ID NO: 205). The item is preferably a fabric, e.g., textile, e.g., cotton and/or polyester.

Some aspect of the invention relates to the use of a polypeptide having DNase activity, for prevention, reduction or removing a biofilm from an item, wherein the polypeptide having DNase activity belongs to the GYS clade and comprises a polypeptide selected from the polypeptides shown in SEQ ID NO: 8, SEQ ID NO: 9, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 53, SEQ ID NO: 56, SEQ ID NO: 59, SEQ ID NO: 62, SEQ ID NO: 65, SEQ ID NO: 68, SEQ ID NO: 71, SEQ ID NO: 74, SEQ ID NO: 77 and SEQ ID NO: 80 or polypeptides having at least 80%, such as at least 85%, such as at least 90%, such as at least 95% or 100% sequence identity thereto. The item is preferably a fabric, e.g., textile, e.g., cotton and/or polyester.

Some aspect of the invention relates to the use of a polypeptide having DNase activity, for prevention, reduction or removing a biofilm from an item, wherein the polypeptide having DNase activity belongs to the NAWK clade and comprises one or both of the motifs [V/I]PL[S/A]NAWK (SEQ ID NO: 206) or NPQL (SEQ ID NO: 207). The item is preferably a fabric, e.g., textile, e.g., cotton and/or polyester.

Some aspect of the invention relates to the use of a polypeptide having DNase activity, for prevention, reduction or removing a biofilm from an item, wherein the polypeptide having DNase activity belongs to the NAWK clade and comprises a polypeptide selected from the polypeptides shown in SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116 and SEQ ID NO: 119 or polypeptides having at least 80%, such as at least 85%, such as at least 90%, such as at least 95% or 100% sequence identity thereto. The item is preferably a fabric, e.g., textile, e.g., cotton and/or polyester.

Some aspect of the invention relates to the use of a polypeptide having DNase activity, for prevention, reduction or removing a biofilm from an item, wherein the polypeptide having DNase activity belongs to the KNAW clade and comprises one or both of the motifs P[Q/E]L[W/Y] (SEQ ID NO: 208) or [K/H/E]NAW (SEQ ID NO: 209). The item is preferably a fabric, e.g., textile, e.g., cotton and/or polyester.

Some aspect of the invention relates to the use of a polypeptide having DNase activity, for prevention, reduction or removing a biofilm from an item, wherein the polypeptide having DNase activity belongs to the KNAW clade and comprises a polypeptide selected from the polypeptides shown in SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155 and SEQ ID NO: 158 or polypeptides having at least 80%, such as at least 85%, at least 90%, at least 95% or 100% sequence identity thereto. The item is preferably a fabric, e.g., textile, e.g., cotton and/or polyester.

Some aspect of the invention relates to the use of a polypeptide having DNase activity, for prevention, reduction or removing a biofilm from an item, wherein the polypeptide having DNase activity comprises the polypeptide shown in SEQ ID NO: 161, SEQ ID NO: 164, SEQ ID NO: 167, SEQ ID NO: 170, SEQ ID NO: 173, SEQ ID NO: 176, SEQ ID NO: 179, SEQ ID NO: 182, SEQ ID NO: 185, SEQ ID NO: 188, SEQ ID NO: 191, SEQ ID NO: 194 and SEQ ID NO: 197 or polypeptides having at least 80%, such as at least 85%, such as at least 90%, such as at least 95% or 100% sequence identity thereto. The item is preferably a fabric, e.g., textile, e.g., cotton and/or polyester.

Some aspect of the invention relates to the use of a polypeptide having DNase activity and comprising the amino acid sequence shown in SEQ ID NO: 11 or a polypeptide having at least 80% sequence identity thereto for reducing malodor from laundry and/or textile, for anti-redeposition and for maintaining or improving the whiteness of a textile.

Some aspect of the invention relates to the use of a polypeptide having DNase activity and comprising the amino acid sequence shown in SEQ ID NO: 12 or a polypeptide having at least 80% sequence identity thereto for reducing malodor from laundry and/or textile, for anti-redeposition and for maintaining or improving the whiteness of a textile.

Some aspect of the invention relates to the use of a polypeptide having DNase activity and comprising the amino acid sequence shown in SEQ ID NO: 13 or a polypeptide having at least 80% sequence identity thereto for reducing malodor from laundry and/or textile, for anti-redeposition and for maintaining or improving the whiteness of a textile.

Some aspect of the invention relates to the use of a polypeptide having DNase activity and comprising the amino acid sequence shown in SEQ ID NO: 14 or a polypeptide having at least 80% sequence identity thereto for reducing malodor from laundry and/or textile, for anti-redeposition and for maintaining or improving the whiteness of a textile.

Some aspect of the invention relates to the use of a polypeptide having DNase activity and comprising the amino acid sequence shown in SEQ ID NO: 15 or a polypeptide having at least 80% sequence identity thereto for reducing malodor from laundry and/or textile, for anti-redeposition and for maintaining or improving the whiteness of a textile.

Some aspect of the invention relates to the use of a polypeptide having DNase activity and comprising the amino acid sequence shown in SEQ ID NO: 16 or a polypeptide having at least 80% sequence identity thereto for reducing malodor from laundry and/or textile, for anti-redeposition and for maintaining or improving the whiteness of a textile.

Some aspect of the invention relates to the use of a polypeptide having DNase activity and comprising the amino acid sequence shown in SEQ ID NO: 17 or a polypeptide having at least 80% sequence identity thereto for reducing malodor from laundry and/or textile, for anti-redeposition and for maintaining or improving the whiteness of a textile.

Some aspect of the invention relates to the use of a polypeptide having DNase activity and comprising the amino acid sequence shown in SEQ ID NO: 18 or a polypeptide having at least 80% sequence identity thereto for reducing malodor from laundry and/or textile, for anti-redeposition and for maintaining or improving the whiteness of a textile.

Some aspect of the invention relates to the use of a polypeptide having DNase activity and comprising the amino acid sequence shown in SEQ ID NO: 19 or a polypeptide having at least 80% sequence identity thereto for reducing malodor from laundry and/or textile, for anti-redeposition and for maintaining or improving the whiteness of a textile.

Some aspect of the invention relates to the use of a polypeptide having DNase activity and comprising the amino acid sequence shown in SEQ ID NO: 20 or a polypeptide having at least 80% sequence identity thereto for reducing malodor from laundry and/or textile, for anti-redeposition and for maintaining or improving the whiteness of a textile.

Some aspect of the invention relates to the use of a polypeptide having DNase activity and comprising the amino acid sequence shown in SEQ ID NO: 21 or a polypeptide having at least 80% sequence identity thereto for reducing malodor from laundry and/or textile, for anti-redeposition and for maintaining or improving the whiteness of a textile.

Some aspect of the invention relates to the use of a polypeptide having DNase activity and comprising the amino acid sequence shown in SEQ ID NO: 22 or a polypeptide having at least 80% sequence identity thereto for reducing malodor from laundry and/or textile, for anti-redeposition and for maintaining or improving the whiteness of a textile.

Some aspect of the invention relates to the use of a polypeptide having DNase activity and comprising the amino acid sequence shown in SEQ ID NO: 23 or a polypeptide having at least 80% sequence identity thereto for reducing malodor from laundry and/or textile, for anti-redeposition and for maintaining or improving the whiteness of a textile.

Some aspect of the invention relates to the use of a polypeptide having DNase activity and comprising the amino acid sequence shown in SEQ ID NO: 53 or a polypeptide having at least 80% sequence identity thereto for reducing malodor from laundry and/or textile, for anti-redeposition and for maintaining or improving the whiteness of a textile.

Some aspect of the invention relates to the use of a polypeptide having DNase activity and comprising the amino acid sequence shown in SEQ ID NO: 56 or a polypeptide having at least 80% sequence identity thereto for reducing malodor from laundry and/or textile, for anti-redeposition and for maintaining or improving the whiteness of a textile.

Some aspect of the invention relates to the use of a polypeptide having DNase activity and comprising the amino acid sequence shown in SEQ ID NO: 59 or a polypeptide having at least 80% sequence identity thereto for reducing malodor from laundry and/or textile, for anti-redeposition and for maintaining or improving the whiteness of a textile.

Some aspect of the invention relates to the use of a polypeptide having DNase activity and comprising the amino acid sequence shown in SEQ ID NO: 62 or a polypeptide having at least 80% sequence identity thereto for reducing malodor from laundry and/or textile, for anti-redeposition and for maintaining or improving the whiteness of a textile.

Some aspect of the invention relates to the use of a polypeptide having DNase activity and comprising the amino acid sequence shown in SEQ ID NO: 65 or a polypeptide having at least 80% sequence identity thereto for reducing malodor from laundry and/or textile, for anti-redeposition and for maintaining or improving the whiteness of a textile.

Some aspect of the invention relates to the use of a polypeptide having DNase activity and comprising the amino acid sequence shown in SEQ ID NO: 68 or a polypeptide having at least 80% sequence identity thereto for reducing malodor from laundry and/or textile, for anti-redeposition and for maintaining or improving the whiteness of a textile.

Some aspect of the invention relates to the use of a polypeptide having DNase activity and comprising the amino acid sequence shown in SEQ ID NO: 71 or a polypeptide having at least 80% sequence identity thereto for reducing malodor from laundry and/or textile, for anti-redeposition and for maintaining or improving the whiteness of a textile.

Some aspect of the invention relates to the use of a polypeptide having DNase activity and comprising the amino acid sequence shown in SEQ ID NO: 74 or a polypeptide having at least 80% sequence identity thereto for reducing malodor from laundry and/or textile, for anti-redeposition and for maintaining or improving the whiteness of a textile.

Some aspect of the invention relates to the use of a polypeptide having DNase activity and comprising the amino acid sequence shown in SEQ ID NO: 77 or a polypeptide having at least 80% sequence identity thereto for reducing malodor from laundry and/or textile, for anti-redeposition and for maintaining or improving the whiteness of a textile.

Some aspect of the invention relates to the use of a polypeptide having DNase activity and comprising the amino acid sequence shown in SEQ ID NO: 80 or a polypeptide having at least 80% sequence identity thereto for reducing malodor from laundry and/or textile, for anti-redeposition and for maintaining or improving the whiteness of a textile.

Some aspect of the invention relates to the use of a polypeptide having DNase activity and comprising the amino acid sequence shown in SEQ ID NO: 83 or a polypeptide having at least 80% sequence identity thereto for reducing malodor from laundry and/or textile, for anti-redeposition and for maintaining or improving the whiteness of a textile.

Some aspect of the invention relates to the use of a polypeptide having DNase activity and comprising the amino acid sequence shown in SEQ ID NO: 86 or a polypeptide having at least 80% sequence identity thereto for reducing malodor from laundry and/or textile, for anti-redeposition and for maintaining or improving the whiteness of a textile.

Some aspect of the invention relates to the use of a polypeptide having DNase activity and comprising the amino acid sequence shown in SEQ ID NO: 89 or a polypeptide having at least 80% sequence identity thereto for reducing malodor from laundry and/or textile, for anti-redeposition and for maintaining or improving the whiteness of a textile.

Some aspect of the invention relates to the use of a polypeptide having DNase activity and comprising the amino acid sequence shown in SEQ ID NO: 92 or a polypeptide having at least 80% sequence identity thereto for reducing malodor from laundry and/or textile, for anti-redeposition and for maintaining or improving the whiteness of a textile.

Some aspect of the invention relates to the use of a polypeptide having DNase activity and comprising the amino acid sequence shown in SEQ ID NO: 95 or a polypeptide having at least 80% sequence identity thereto for reducing malodor from laundry and/or textile, for anti-redeposition and for maintaining or improving the whiteness of a textile.

Some aspect of the invention relates to the use of a polypeptide having DNase activity and comprising the amino acid sequence shown in SEQ ID NO: 98 or a polypeptide having at least 80% sequence identity thereto for reducing malodor from laundry and/or textile, for anti-redeposition and for maintaining or improving the whiteness of a textile.

Some aspect of the invention relates to the use of a polypeptide having DNase activity and comprising the amino acid sequence shown in SEQ ID NO: 101 or a polypeptide having at least 80% sequence identity thereto for reducing malodor from laundry and/or textile, for anti-redeposition and for maintaining or improving the whiteness of a textile.

Some aspect of the invention relates to the use of a polypeptide having DNase activity and comprising the amino acid sequence shown in SEQ ID NO: 104 or a polypeptide having at least 80% sequence identity thereto for reducing malodor from laundry and/or textile, for anti-redeposition and for maintaining or improving the whiteness of a textile.

Some aspect of the invention relates to the use of a polypeptide having DNase activity and comprising the amino acid sequence shown in SEQ ID NO: 107 or a polypeptide having at least 80% sequence identity thereto for reducing malodor from laundry and/or textile, for anti-redeposition and for maintaining or improving the whiteness of a textile.

Some aspect of the invention relates to the use of a polypeptide having DNase activity and comprising the amino acid sequence shown in SEQ ID NO: 110 or a polypeptide having at least 80% sequence identity thereto for reducing malodor from laundry and/or textile, for anti-redeposition and for maintaining or improving the whiteness of a textile.

Some aspect of the invention relates to the use of a polypeptide having DNase activity and comprising the amino acid sequence shown in SEQ ID NO: 113 or a polypeptide having at least 80% sequence identity thereto for reducing malodor from laundry and/or textile, for anti-redeposition and for maintaining or improving the whiteness of a textile.

Some aspect of the invention relates to the use of a polypeptide having DNase activity and comprising the amino acid sequence shown in SEQ ID NO: 116 or a polypeptide having at least 80% sequence identity thereto for reducing malodor from laundry and/or textile, for anti-redeposition and for maintaining or improving the whiteness of a textile.

Some aspect of the invention relates to the use of a polypeptide having DNase activity and comprising the amino acid sequence shown in SEQ ID NO: 119 or a polypeptide having at least 80% sequence identity thereto for reducing malodor from laundry and/or textile, for anti-redeposition and for maintaining or improving the whiteness of a textile.

Some aspect of the invention relates to the use of a polypeptide having DNase activity and comprising the amino acid sequence shown in SEQ ID NO: 122 or a polypeptide having at least 80% sequence identity thereto for reducing malodor from laundry and/or textile, for anti-redeposition and for maintaining or improving the whiteness of a textile.

Some aspect of the invention relates to the use of a polypeptide having DNase activity and comprising the amino acid sequence shown in SEQ ID NO: 125 or a polypeptide having at least 80% sequence identity thereto for reducing malodor from laundry and/or textile, for anti-redeposition and for maintaining or improving the whiteness of a textile.

Some aspect of the invention relates to the use of a polypeptide having DNase activity and comprising the amino acid sequence shown in SEQ ID NO: 128 or a polypeptide having at least 80% sequence identity thereto for reducing malodor from laundry and/or textile, for anti-redeposition and for maintaining or improving the whiteness of a textile.

Some aspect of the invention relates to the use of a polypeptide having DNase activity and comprising the amino acid sequence shown in SEQ ID NO: 131 or a polypeptide having at least 80% sequence identity thereto for reducing malodor from laundry and/or textile, for anti-redeposition and for maintaining or improving the whiteness of a textile.

Some aspect of the invention relates to the use of a polypeptide having DNase activity and comprising the amino acid sequence shown in SEQ ID NO 134 or a polypeptide having at least 80% sequence identity thereto for reducing malodor from laundry and/or textile, for anti-redeposition and for maintaining or improving the whiteness of a textile.

Some aspect of the invention relates to the use of a polypeptide having DNase activity and comprising the amino acid sequence shown in SEQ ID NO: 137 or a polypeptide having at least 80% sequence identity thereto for reducing malodor from laundry and/or textile, for anti-redeposition and for maintaining or improving the whiteness of a textile.

Some aspect of the invention relates to the use of a polypeptide having DNase activity and comprising the amino acid sequence shown in SEQ ID NO: 140 or a polypeptide having at least 80% sequence identity thereto for reducing malodor from laundry and/or textile, for anti-redeposition and for maintaining or improving the whiteness of a textile.

Some aspect of the invention relates to the use of a polypeptide having DNase activity and comprising the amino acid sequence shown in SEQ ID NO: 143 or a polypeptide having at least 80% sequence identity thereto for reducing malodor from laundry and/or textile, for anti-redeposition and for maintaining or improving the whiteness of a textile.

Some aspect of the invention relates to the use of a polypeptide having DNase activity and comprising the amino acid sequence shown in SEQ ID NO: 146 or a polypeptide having at least 80% sequence identity thereto for reducing malodor from laundry and/or textile, for anti-redeposition and for maintaining or improving the whiteness of a textile.

Some aspect of the invention relates to the use of a polypeptide having DNase activity and comprising the amino acid sequence shown in SEQ ID NO: 149 or a polypeptide having at least 80% sequence identity thereto for reducing malodor from laundry and/or textile, for anti-redeposition and for maintaining or improving the whiteness of a textile.

Some aspect of the invention relates to the use of a polypeptide having DNase activity and comprising the amino acid sequence shown in SEQ ID NO: 152 or a polypeptide having at least 80% sequence identity thereto for reducing malodor from laundry and/or textile, for anti-redeposition and for maintaining or improving the whiteness of a textile.

Some aspect of the invention relates to the use of a polypeptide having DNase activity and comprising the amino acid sequence shown in SEQ ID NO: 155 or a polypeptide having at least 80% sequence identity thereto for reducing malodor from laundry and/or textile, for anti-redeposition and for maintaining or improving the whiteness of a textile.

Some aspect of the invention relates to the use of a polypeptide having DNase activity and comprising the amino acid sequence shown in SEQ ID NO: 158 or a polypeptide having at least 80% sequence identity thereto for reducing malodor from laundry and/or textile, for anti-redeposition and for maintaining or improving the whiteness of a textile.

Some aspect of the invention relates to the use of a polypeptide having DNase activity and comprising the amino acid sequence shown in SEQ ID NO: 161 or a polypeptide having at least 80% sequence identity thereto for reducing malodor from laundry and/or textile, for anti-redeposition and for maintaining or improving the whiteness of a textile.

Some aspect of the invention relates to the use of a polypeptide having DNase activity and comprising the amino acid sequence shown in SEQ ID NO: 164 or a polypeptide having at least 80% sequence identity thereto for reducing malodor from laundry and/or textile, for anti-redeposition and for maintaining or improving the whiteness of a textile.

Some aspect of the invention relates to the use of a polypeptide having DNase activity and comprising the amino acid sequence shown in SEQ ID NO: 167 or a polypeptide having at least 80% sequence identity thereto for reducing malodor from laundry and/or textile, for anti-redeposition and for maintaining or improving the whiteness of a textile.

Some aspect of the invention relates to the use of a polypeptide having DNase activity and comprising the amino acid sequence shown in SEQ ID NO: 170 or a polypeptide having at least 80% sequence identity thereto for reducing malodor from laundry and/or textile, for anti-redeposition and for maintaining or improving the whiteness of a textile.

Some aspect of the invention relates to the use of a polypeptide having DNase activity and comprising the amino acid sequence shown in SEQ ID NO: 173 or a polypeptide having at least 80% sequence identity thereto for reducing malodor from laundry and/or textile, for anti-redeposition and for maintaining or improving the whiteness of a textile.

Some aspect of the invention relates to the use of a polypeptide having DNase activity and comprising the amino acid sequence shown in SEQ ID NO: 176 or a polypeptide having at least 80% sequence identity thereto for reducing malodor from laundry and/or textile, for anti-redeposition and for maintaining or improving the whiteness of a textile.

Some aspect of the invention relates to the use of a polypeptide having DNase activity and comprising the amino acid sequence shown in SEQ ID NO: 179 or a polypeptide having at least 80% sequence identity thereto for reducing malodor from laundry and/or textile, for anti-redeposition and for maintaining or improving the whiteness of a textile.

Some aspect of the invention relates to the use of a polypeptide having DNase activity and comprising the amino acid sequence shown in SEQ ID NO: 182 or a polypeptide having at least 80% sequence identity thereto for reducing malodor from laundry and/or textile, for anti-redeposition and for maintaining or improving the whiteness of a textile.

Some aspect of the invention relates to the use of a polypeptide having DNase activity and comprising the amino acid sequence shown in SEQ ID NO: 185 or a polypeptide having at least 80% sequence identity thereto for reducing malodor from laundry and/or textile, for anti-redeposition and for maintaining or improving the whiteness of a textile.

Some aspect of the invention relates to the use of a polypeptide having DNase activity and comprising the amino acid sequence shown in SEQ ID NO: 188 or a polypeptide having at least 80% sequence identity thereto for reducing malodor from laundry and/or textile, for anti-redeposition and for maintaining or improving the whiteness of a textile.

Some aspect of the invention relates to the use of a polypeptide having DNase activity and comprising the amino acid sequence shown in SEQ ID NO: 191 or a polypeptide having at least 80% sequence identity thereto for reducing malodor from laundry and/or textile, for anti-redeposition and for maintaining or improving the whiteness of a textile.

Some aspect of the invention relates to the use of a polypeptide having DNase activity and comprising the amino acid sequence shown in SEQ ID NO: 194 or a polypeptide having at least 80% sequence identity thereto for reducing malodor from laundry and/or textile, for anti-redeposition and for maintaining or improving the whiteness of a textile.

Some aspect of the invention relates to the use of a polypeptide having DNase activity and comprising the amino acid sequence shown in SEQ ID NO: 197 or a polypeptide having at least 80% sequence identity thereto for reducing malodor from laundry and/or textile, for anti-redeposition and for maintaining or improving the whiteness of a textile.

A particular preferred aspect of the invention relates to DNases from the genus of *Bacillus*, e.g., a *Bacillus* DNase, preferably a *Bacillus* sp. sp-62451 or a DNase selected from the group consisting DNases closely related hereto, e.g., *Bacillus cibi*, *Bacillus* sp-18318 and *Bacillus idriensis* having at least 80% sequence identity the polypeptide having the amino acid sequence shown in SEQ ID NO: 8 (*Bacillus* sp. sp-62451). A preferred aspect of the invention relates to the use of a DNase obtained from *Bacillus*, such as *Bacillus* sp. sp-62451 comprising a polypeptide having at least 60%, e.g., at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 8 for reducing malodor from laundry and/or textile, for anti-redeposition and for maintaining or improving the whiteness of a textile. A preferred aspect of the invention relates to the use of a DNase obtained from *Bacillus*, such as *Bacillus cibi* comprising a polypeptide having at least 60%, e.g., at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 21 for reducing malodor from laundry and/or textile, for anti-redeposition and for maintaining or improving the whiteness of a textile.

A preferred aspect of the invention relates to the use of a DNase obtained from *Bacillus*, such as *Bacillus* sp-18318 comprising a polypeptide having at least 60%, e.g., at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 22 for reducing malodor from laundry and/or textile, for anti-redeposition and for maintaining or improving the whiteness of a textile. A preferred aspect of the invention relates to the use of a DNase obtained from *Bacillus*, such as *Bacillus idriensis* comprising a polypeptide having at least 60%, e.g., at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 23 for reducing malodor from laundry and/or textile, for anti-redeposition and for maintaining or improving the whiteness of a textile.

As stated above the DNase polypeptides of the invention have particularly deep cleaning powers, e.g., the DNases of the invention are particularly effective in disruption or removal of a biofilm or components of a biofilm such as polysaccharides, proteins, DNA, soil or other components present in the biofilm. Thus, the DNase polypeptides of the invention are particularly effective in preventing, reducing or removing a biofilm from items such as textiles and hard surfaces.

The polypeptide having DNase activity is preferably obtained from *Bacillus* sp. or *Paenibacillus*. The invention relates to polypeptides having a sequence identity to any of the mature polypeptides of SEQ ID NO: 2, 4 or 6 of at least 60% which have DNase activity and wherein the polypeptides are used for preventing, reducing or removing a biofilm from an item. The invention further relates to polypeptides having a sequence identity to any of the mature polypeptides of SEQ ID NO: 2, 4 or 6 of at least 60%, e.g., at least 70%, 80% or 90%, which have DNase activity and wherein the polypeptides are usable for preventing, reducing or removing a biofilm from an item. The invention further relates to polypeptides having a sequence identity to any of the polypeptides of SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22 or SEQ ID NO: 23 of at least 60%, e.g., at least 70%, 80% or 90%, which have DNase activity and wherein the polypeptides are useable for preventing, reducing or removing a biofilm from an item.

In an embodiment, the present invention relates to a polypeptide having a sequence identity to the polypeptide of SEQ ID NO: 8 of at least 60%, which has DNase activity and wherein the polypeptide is used for preventing, reducing or removing a biofilm from an item.

In an embodiment, the present invention relates to a polypeptide having a sequence identity to the polypeptide of SEQ ID NO: 9 of at least 60%, which has DNase activity and wherein the polypeptide is used for preventing, reducing or removing a biofilm from an item.

In an embodiment, the present invention relates to a polypeptide having a sequence identity to the polypeptide of SEQ ID NO: 10 of at least 60%, which has DNase activity and wherein the polypeptide is used for preventing, reducing or removing a biofilm from an item.

In an embodiment, the present invention relates to a polypeptide having a sequence identity to the polypeptide of SEQ ID NO: 11 of at least 60%, which has DNase activity and wherein the polypeptide is used for preventing, reducing or removing a biofilm from an item.

In an embodiment, the present invention relates to a polypeptide having a sequence identity to the polypeptide of SEQ ID NO: 12 of at least 60%, which has DNase activity and wherein the polypeptide is used for preventing, reducing or removing a biofilm from an item.

In an embodiment, the present invention relates to a polypeptide having a sequence identity to the polypeptide of SEQ ID NO: 13 of at least 60%, which has DNase activity and wherein the polypeptide is used for preventing, reducing or removing a biofilm from an item.

In an embodiment, the present invention relates to a polypeptide having a sequence identity to the polypeptide of SEQ ID NO: 14 of at least 60%, which has DNase activity and wherein the polypeptide is used for preventing, reducing or removing a biofilm from an item.

In an embodiment, the present invention relates to a polypeptide having a sequence identity to the polypeptide of SEQ ID NO: 15 of at least 60%, which has DNase activity and wherein the polypeptide is used for preventing, reducing or removing a biofilm from an item.

In an embodiment, the present invention relates to a polypeptide having a sequence identity to the polypeptide of SEQ ID NO: 16 of at least 60%, which has DNase activity and wherein the polypeptide is used for preventing, reducing or removing a biofilm from an item.

In an embodiment, the present invention relates to a polypeptide having a sequence identity to the polypeptide of SEQ ID NO: 17 of at least 60%, which has DNase activity and wherein the polypeptide is used for preventing, reducing or removing a biofilm from an item.

In an embodiment, the present invention relates to a polypeptide having a sequence identity to the polypeptide of SEQ ID NO: 18 of at least 60%, which has DNase activity and wherein the polypeptide is used for preventing, reducing or removing a biofilm from an item.

In an embodiment, the present invention relates to a polypeptide having a sequence identity to the polypeptide of SEQ ID NO: 19 of at least 60%, which has DNase activity and wherein the polypeptide is used for preventing, reducing or removing a biofilm from an item.

In an embodiment, the present invention relates to a polypeptide having a sequence identity to the polypeptide of SEQ ID NO: 20 of at least 60%, which has DNase activity and wherein the polypeptide is used for preventing, reducing or removing a biofilm from an item.

In an embodiment, the present invention relates to a polypeptide having a sequence identity to the polypeptide of SEQ ID NO: 21 of at least 60%, which has DNase activity and wherein the polypeptide is used for preventing, reducing or removing a biofilm from an item.

In an embodiment, the present invention relates to a polypeptide having a sequence identity to the polypeptide of SEQ ID NO: 22 of at least 60%, which has DNase activity and wherein the polypeptide is used for preventing, reducing or removing a biofilm from an item.

In an embodiment, the present invention relates to a polypeptide having a sequence identity to the polypeptide of SEQ ID NO: 23 of at least 60%, which has DNase activity and wherein the polypeptide is used for preventing, reducing or removing a biofilm from an item.

In an embodiment, the present invention relates to a polypeptide having a sequence identity to the polypeptide of SEQ ID NO: 8 of at least 70%, which has DNase activity and wherein the polypeptide is used for preventing, reducing or removing a biofilm from an item.

In an embodiment, the present invention relates to a polypeptide having a sequence identity to the polypeptide of SEQ ID NO: 9 of at least 70%, which has DNase activity and wherein the polypeptide is used for preventing, reducing or removing a biofilm from an item.

In an embodiment, the present invention relates to a polypeptide having a sequence identity to the polypeptide of SEQ ID NO: 10 of at least 70%, which has DNase activity and wherein the polypeptide is used for preventing, reducing or removing a biofilm from an item.

In an embodiment, the present invention relates to a polypeptide having a sequence identity to the polypeptide of SEQ ID NO: 11 of at least 70%, which has DNase activity and wherein the polypeptide is used for preventing, reducing or removing a biofilm from an item.

In an embodiment, the present invention relates to a polypeptide having a sequence identity to the polypeptide of SEQ ID NO: 12 of at least 70%, which has DNase activity and wherein the polypeptide is used for preventing, reducing or removing a biofilm from an item.

In an embodiment, the present invention relates to a polypeptide having a sequence identity to the polypeptide of SEQ ID NO: 13 of at least 70%, which has DNase activity and wherein the polypeptide is used for preventing, reducing or removing a biofilm from an item.

In an embodiment, the present invention relates to a polypeptide having a sequence identity to the polypeptide of SEQ ID NO: 14 of at least 70%, which has DNase activity and wherein the polypeptide is used for preventing, reducing or removing a biofilm from an item.

In an embodiment, the present invention relates to a polypeptide having a sequence identity to the polypeptide of SEQ ID NO: 15 of at least 70%, which has DNase activity and wherein the polypeptide is used for preventing, reducing or removing a biofilm from an item.

In an embodiment, the present invention relates to a polypeptide having a sequence identity to the polypeptide of SEQ ID NO: 16 of at least 70%, which has DNase activity and wherein the polypeptide is used for preventing, reducing or removing a biofilm from an item.

In an embodiment, the present invention relates to a polypeptide having a sequence identity to the polypeptide of SEQ ID NO: 17 of at least 70%, which has DNase activity and wherein the polypeptide is used for preventing, reducing or removing a biofilm from an item.

In an embodiment, the present invention relates to a polypeptide having a sequence identity to the polypeptide of SEQ ID NO: 18 of at least 70%, which has DNase activity and wherein the polypeptide is used for preventing, reducing or removing a biofilm from an item.

In an embodiment, the present invention relates to a polypeptide having a sequence identity to the polypeptide of SEQ ID NO: 19 of at least 70%, which has DNase activity and wherein the polypeptide is used for preventing, reducing or removing a biofilm from an item.

In an embodiment, the present invention relates to a polypeptide having a sequence identity to the polypeptide of SEQ ID NO: 20 of at least 70%, which has DNase activity and wherein the polypeptide is used for preventing, reducing or removing a biofilm from an item.

In an embodiment, the present invention relates to a polypeptide having a sequence identity to the polypeptide of SEQ ID NO: 21 of at least 70%, which has DNase activity and wherein the polypeptide is used for preventing, reducing or removing a biofilm from an item.

In an embodiment, the present invention relates to a polypeptide having a sequence identity to the polypeptide of SEQ ID NO: 22 of at least 70%, which has DNase activity and wherein the polypeptide is used for preventing, reducing or removing a biofilm from an item.

In an embodiment, the present invention relates to a polypeptide having a sequence identity to the polypeptide of SEQ ID NO: 23 of at least 70%, which has DNase activity and wherein the polypeptide is used for preventing, reducing or removing a biofilm from an item.

In an embodiment, the present invention relates to a polypeptide having a sequence identity to the polypeptide of SEQ ID NO: 8 of at least 80%, which has DNase activity and wherein the polypeptide is used for preventing, reducing or removing a biofilm from an item.

In an embodiment, the present invention relates to a polypeptide having a sequence identity to the polypeptide of SEQ ID NO: 9 of at least 80%, which has DNase activity and wherein the polypeptide is used for preventing, reducing or removing a biofilm from an item.

In an embodiment, the present invention relates to a polypeptide having a sequence identity to the polypeptide of SEQ ID NO: 10 of at least 80%, which has DNase activity and wherein the polypeptide is used for preventing, reducing or removing a biofilm from an item.

In an embodiment, the present invention relates to a polypeptide having a sequence identity to the polypeptide of SEQ ID NO: 11 of at least 80%, which has DNase activity and wherein the polypeptide is used for preventing, reducing or removing a biofilm from an item.

In an embodiment, the present invention relates to a polypeptide having a sequence identity to the polypeptide of SEQ ID NO: 12 of at least 80%, which has DNase activity and wherein the polypeptide is used for preventing, reducing or removing a biofilm from an item.

In an embodiment, the present invention relates to a polypeptide having a sequence identity to the polypeptide of SEQ ID NO: 13 of at least 80%, which has DNase activity and wherein the polypeptide is used for preventing, reducing or removing a biofilm from an item.

In an embodiment, the present invention relates to a polypeptide having a sequence identity to the polypeptide of SEQ ID NO: 14 of at least 80%, which has DNase activity and wherein the polypeptide is used for preventing, reducing or removing a biofilm from an item.

In an embodiment, the present invention relates to a polypeptide having a sequence identity to the polypeptide of SEQ ID NO: 15 of at least 80%, which has DNase activity and wherein the polypeptide is used for preventing, reducing or removing a biofilm from an item.

In an embodiment, the present invention relates to a polypeptide having a sequence identity to the polypeptide of SEQ ID NO: 16 of at least 80%, which has DNase activity and wherein the polypeptide is used for preventing, reducing or removing a biofilm from an item.

In an embodiment, the present invention relates to a polypeptide having a sequence identity to the polypeptide of SEQ ID NO: 17 of at least 80%, which has DNase activity and wherein the polypeptide is used for preventing, reducing or removing a biofilm from an item.

In an embodiment, the present invention relates to a polypeptide having a sequence identity to the polypeptide of SEQ ID NO: 18 of at least 80%, which has DNase activity and wherein the polypeptide is used for preventing, reducing or removing a biofilm from an item.

In an embodiment, the present invention relates to a polypeptide having a sequence identity to the polypeptide of SEQ ID NO: 19 of at least 80%, which has DNase activity and wherein the polypeptide is used for preventing, reducing or removing a biofilm from an item.

In an embodiment, the present invention relates to a polypeptide having a sequence identity to the polypeptide of SEQ ID NO: 20 of at least 80%, which has DNase activity and wherein the polypeptide is used for preventing, reducing or removing a biofilm from an item.

In an embodiment, the present invention relates to a polypeptide having a sequence identity to the polypeptide of SEQ ID NO: 21 of at least 80%, which has DNase activity and wherein the polypeptide is used for preventing, reducing or removing a biofilm from an item.

In an embodiment, the present invention relates to a polypeptide having a sequence identity to the polypeptide of SEQ ID NO: 22 of at least 80%, which has DNase activity and wherein the polypeptide is used for preventing, reducing or removing a biofilm from an item.

In an embodiment, the present invention relates to a polypeptide having a sequence identity to the polypeptide of SEQ ID NO: 23 of at least 80%, which has DNase activity and wherein the polypeptide is used for preventing, reducing or removing a biofilm from an item.

In an embodiment, the present invention relates to a polypeptide having a sequence identity to the polypeptide of SEQ ID NO: 8 of at least 85%, which has DNase activity and wherein the polypeptide is used for preventing, reducing or removing a biofilm from an item.

In an embodiment, the present invention relates to a polypeptide having a sequence identity to the polypeptide of SEQ ID NO: 9 of at least 85%, which has DNase activity and wherein the polypeptide is used for preventing, reducing or removing a biofilm from an item.

In an embodiment, the present invention relates to a polypeptide having a sequence identity to the polypeptide of SEQ ID NO: 10 of at least 85%, which has DNase activity and wherein the polypeptide is used for preventing, reducing or removing a biofilm from an item.

In an embodiment, the present invention relates to a polypeptide having a sequence identity to the polypeptide of SEQ ID NO: 11 of at least 85%, which has DNase activity and wherein the polypeptide is used for preventing, reducing or removing a biofilm from an item.

In an embodiment, the present invention relates to a polypeptide having a sequence identity to the polypeptide of SEQ ID NO: 12 of at least 85%, which has DNase activity and wherein the polypeptide is used for preventing, reducing or removing a biofilm from an item.

In an embodiment, the present invention relates to a polypeptide having a sequence identity to the polypeptide of SEQ ID NO: 13 of at least 85%, which has DNase activity and wherein the polypeptide is used for preventing, reducing or removing a biofilm from an item.

In an embodiment, the present invention relates to a polypeptide having a sequence identity to the polypeptide of SEQ ID NO: 14 of at least 85%, which has DNase activity and wherein the polypeptide is used for preventing, reducing or removing a biofilm from an item.

In an embodiment, the present invention relates to a polypeptide having a sequence identity to the polypeptide of SEQ ID NO: 15 of at least 85%, which has DNase activity and wherein the polypeptide is used for preventing, reducing or removing a biofilm from an item.

In an embodiment, the present invention relates to a polypeptide having a sequence identity to the polypeptide of SEQ ID NO: 16 of at least 85%, which has DNase activity and wherein the polypeptide is used for preventing, reducing or removing a biofilm from an item.

In an embodiment, the present invention relates to a polypeptide having a sequence identity to the polypeptide of SEQ ID NO: 17 of at least 85%, which has DNase activity and wherein the polypeptide is used for preventing, reducing or removing a biofilm from an item.

In an embodiment, the present invention relates to a polypeptide having a sequence identity to the polypeptide of SEQ ID NO: 18 of at least 85%, which has DNase activity and wherein the polypeptide is used for preventing, reducing or removing a biofilm from an item.

In an embodiment, the present invention relates to a polypeptide having a sequence identity to the polypeptide of SEQ ID NO: 19 of at least 85%, which has DNase activity and wherein the polypeptide is used for preventing, reducing or removing a biofilm from an item.

In an embodiment, the present invention relates to a polypeptide having a sequence identity to the polypeptide of SEQ ID NO: 20 of at least 85%, which has DNase activity and wherein the polypeptide is used for preventing, reducing or removing a biofilm from an item.

In an embodiment, the present invention relates to a polypeptide having a sequence identity to the polypeptide of SEQ ID NO: 21 of at least 85%, which has DNase activity and wherein the polypeptide is used for preventing, reducing or removing a biofilm from an item.

In an embodiment, the present invention relates to a polypeptide having a sequence identity to the polypeptide of SEQ ID NO: 22 of at least 85%, which has DNase activity and wherein the polypeptide is used for preventing, reducing or removing a biofilm from an item.

In an embodiment, the present invention relates to a polypeptide having a sequence identity to the polypeptide of SEQ ID NO: 23 of at least 85%, which has DNase activity and wherein the polypeptide is used for preventing, reducing or removing a biofilm from an item.

In an embodiment, the present invention relates to a polypeptide having a sequence identity to the polypeptide of SEQ ID NO: 8 of at least 90%, which has DNase activity and wherein the polypeptide is used for preventing, reducing or removing a biofilm from an item.

In an embodiment, the present invention relates to a polypeptide having a sequence identity to the polypeptide of SEQ ID NO: 9 of at least 90%, which has DNase activity and wherein the polypeptide is used for preventing, reducing or removing a biofilm from an item.

In an embodiment, the present invention relates to a polypeptide having a sequence identity to the polypeptide of SEQ ID NO: 10 of at least 90%, which has DNase activity and wherein the polypeptide is used for preventing, reducing or removing a biofilm from an item.

In an embodiment, the present invention relates to a polypeptide having a sequence identity to the polypeptide of SEQ ID NO: 11 of at least 90%, which has DNase activity and wherein the polypeptide is used for preventing, reducing or removing a biofilm from an item.

In an embodiment, the present invention relates to a polypeptide having a sequence identity to the polypeptide of SEQ ID NO: 12 of at least 90%, which has DNase activity and wherein the polypeptide is used for preventing, reducing or removing a biofilm from an item.

In an embodiment, the present invention relates to a polypeptide having a sequence identity to the polypeptide of SEQ ID NO: 13 of at least 90%, which has DNase activity and wherein the polypeptide is used for preventing, reducing or removing a biofilm from an item.

In an embodiment, the present invention relates to a polypeptide having a sequence identity to the polypeptide of SEQ ID NO: 14 of at least 90%, which has DNase activity and wherein the polypeptide is used for preventing, reducing or removing a biofilm from an item.

In an embodiment, the present invention relates to a polypeptide having a sequence identity to the polypeptide of SEQ ID NO: 15 of at least 90%, which has DNase activity and wherein the polypeptide is used for preventing, reducing or removing a biofilm from an item.

In an embodiment, the present invention relates to a polypeptide having a sequence identity to the polypeptide of SEQ ID NO: 16 of at least 90%, which has DNase activity and wherein the polypeptide is used for preventing, reducing or removing a biofilm from an item.

In an embodiment, the present invention relates to a polypeptide having a sequence identity to the polypeptide of SEQ ID NO: 17 of at least 90%, which has DNase activity and wherein the polypeptide is used for preventing, reducing or removing a biofilm from an item.

In an embodiment, the present invention relates to a polypeptide having a sequence identity to the polypeptide of SEQ ID NO: 18 of at least 90%, which has DNase activity and wherein the polypeptide is used for preventing, reducing or removing a biofilm from an item.

In an embodiment, the present invention relates to a polypeptide having a sequence identity to the polypeptide of SEQ ID NO: 19 of at least 90%, which has DNase activity and wherein the polypeptide is used for preventing, reducing or removing a biofilm from an item.

In an embodiment, the present invention relates to a polypeptide having a sequence identity to the polypeptide of SEQ ID NO: 20 of at least 90%, which has DNase activity and wherein the polypeptide is used for preventing, reducing or removing a biofilm from an item.

In an embodiment, the present invention relates to a polypeptide having a sequence identity to the polypeptide of SEQ ID NO: 21 of at least 90%, which has DNase activity and wherein the polypeptide is used for preventing, reducing or removing a biofilm from an item.

In an embodiment, the present invention relates to a polypeptide having a sequence identity to the polypeptide of SEQ ID NO: 22 of at least 90%, which has DNase activity and wherein the polypeptide is used for preventing, reducing or removing a biofilm from an item.

In an embodiment, the present invention relates to a polypeptide having a sequence identity to the polypeptide of SEQ ID NO: 23 of at least 90%, which has DNase activity and wherein the polypeptide is used for preventing, reducing or removing a biofilm from an item.

In an embodiment, the present invention relates to a polypeptide having a sequence identity to the polypeptide of SEQ ID NO: 8 of at least 95%, which has DNase activity and wherein the polypeptide is used for preventing, reducing or removing a biofilm from an item.

In an embodiment, the present invention relates to a polypeptide having a sequence identity to the polypeptide of SEQ ID NO: 9 of at least 95%, which has DNase activity and wherein the polypeptide is used for preventing, reducing or removing a biofilm from an item.

In an embodiment, the present invention relates to a polypeptide having a sequence identity to the polypeptide of SEQ ID NO: 10 of at least 95%, which has DNase activity and wherein the polypeptide is used for preventing, reducing or removing a biofilm from an item.

In an embodiment, the present invention relates to a polypeptide having a sequence identity to the polypeptide of SEQ ID NO: 11 of at least 95%, which has DNase activity and wherein the polypeptide is used for preventing, reducing or removing a biofilm from an item.

In an embodiment, the present invention relates to a polypeptide having a sequence identity to the polypeptide of SEQ ID NO: 12 of at least 95%, which has DNase activity and wherein the polypeptide is used for preventing, reducing or removing a biofilm from an item.

In an embodiment, the present invention relates to a polypeptide having a sequence identity to the polypeptide of SEQ ID NO: 13 of at least 95%, which has DNase activity and wherein the polypeptide is used for preventing, reducing or removing a biofilm from an item.

In an embodiment, the present invention relates to a polypeptide having a sequence identity to the polypeptide of SEQ ID NO: 14 of at least 95%, which has DNase activity and wherein the polypeptide is used for preventing, reducing or removing a biofilm from an item.

In an embodiment, the present invention relates to a polypeptide having a sequence identity to the polypeptide of SEQ ID NO: 15 of at least 95%, which has DNase activity and wherein the polypeptide is used for preventing, reducing or removing a biofilm from an item.

In an embodiment, the present invention relates to a polypeptide having a sequence identity to the polypeptide of SEQ ID NO: 16 of at least 95%, which has DNase activity and wherein the polypeptide is used for preventing, reducing or removing a biofilm from an item.

In an embodiment, the present invention relates to a polypeptide having a sequence identity to the polypeptide of SEQ ID NO: 17 of at least 95%, which has DNase activity and wherein the polypeptide is used for preventing, reducing or removing a biofilm from an item.

In an embodiment, the present invention relates to a polypeptide having a sequence identity to the polypeptide of SEQ ID NO: 18 of at least 95%, which has DNase activity and wherein the polypeptide is used for preventing, reducing or removing a biofilm from an item.

In an embodiment, the present invention relates to a polypeptide having a sequence identity to the polypeptide of SEQ ID NO: 19 of at least 95%, which has DNase activity and wherein the polypeptide is used for preventing, reducing or removing a biofilm from an item.

In an embodiment, the present invention relates to a polypeptide having a sequence identity to the polypeptide of SEQ ID NO: 20 of at least 95%, which has DNase activity and wherein the polypeptide is used for preventing, reducing or removing a biofilm from an item.

In an embodiment, the present invention relates to a polypeptide having a sequence identity to the polypeptide of SEQ ID NO: 21 of at least 95%, which has DNase activity and wherein the polypeptide is used for preventing, reducing or removing a biofilm from an item.

In an embodiment, the present invention relates to a polypeptide having a sequence identity to the polypeptide of SEQ ID NO: 22 of at least 95%, which has DNase activity and wherein the polypeptide is used for preventing, reducing or removing a biofilm from an item.

In an embodiment, the present invention relates to a polypeptide having a sequence identity to the polypeptide of SEQ ID NO: 23 of at least 95%, which has DNase activity and wherein the polypeptide is used for preventing, reducing or removing a biofilm from an item.

The preferred polypeptides of the present invention are DNases from *Bacillus* sp-62451 (SEQ ID NO: 8 or the mature polypeptide of SEQ ID NO: 2) and closely related polypeptides having at least 80% sequence identity to the mature polypeptide with SEQ ID NO: 8. The homologue polypeptides also claimed are *Bacillus cibi*, SEQ ID NO: 21,

*Bacillus* sp-18318 SEQ ID NO: 22 and *Bacillus idriensis* SEQ ID NO: 23 as well as DNases having at least 80% sequence identity thereto.

The preferred polypeptides of the present invention are DNases from *Bacillus horikoshii* (SEQ ID NO: 9, or the mature polypeptide of SEQ ID NO: 4) and closely related polypeptides having at least 80% sequence identity to the mature polypeptide with SEQ ID NO: 9. The homologue polypeptides also claimed are *Bacillus* sp-62520 SEQ ID NO: 11, *Bacillus* sp-62520 SEQ ID NO: 12, *Bacillus horikoshii* SEQ ID NO: 13, *Bacillus horikoshii* SEQ ID NO: 14, *Bacillus* sp-16840 SEQ ID NO: 15, *Bacillus* sp-16840 SEQ ID NO: 16, *Bacillus* sp-62668 SEQ ID NO: 17, *Bacillus* sp-13395 SEQ ID NO: 18, *Bacillus horneckiae* SEQ ID NO: 19, *Bacillus* sp-11238 SEQ ID NO: 20 as well as DNases having at least 80% sequence identity thereto.

The preferred polypeptides of the present invention are DNases from *Paenibacillus* sp-18057 (SEQ ID NO: 10, or the mature polypeptide of SEQ ID NO: 6) and closely related polypeptides having at least 80% sequence identity to the mature polypeptide with SEQ ID NO: 10.

The deep cleaning effect of the polypeptides having DNases activity with SEQ ID NO: 8, 9 and 10 and homologue polypeptides having at least 80% identity to SEQ ID NO: 8, 9 and 10 is shown in Example 2.

The term "deep cleaning" means disruption or removal of a biofilm or components of a biofilm such as polysaccharides, proteins, DNA, soil or other components present in the biofilm.

A polypeptide of the present invention preferably comprises or consists of the amino acid sequence of any of the amino acid sequence shown in SEQ ID NO: 8, 9 or 10 or an allelic variant thereof; or is a fragment thereof having DNase activity. In another aspect, the polypeptide comprises or consists of the mature polypeptide of any of the polypeptides having the amino acid sequence shown in SEQ ID NO: 2, 4 or 6. A polypeptide of the present invention preferably comprises or consists of the amino acid sequence of any of the amino acid sequences shown in SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 53, SEQ ID NO: 56, SEQ ID NO: 59, SEQ ID NO: 62, SEQ ID NO: 65, SEQ ID NO: 68, SEQ ID NO: 71, SEQ ID NO: 74, SEQ ID NO: 77, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 161, SEQ ID NO: 164, SEQ ID NO: 167, SEQ ID NO: 170, SEQ ID NO: 173, SEQ ID NO: 176, SEQ ID NO: 179, SEQ ID NO: 182, SEQ ID NO: 185, SEQ ID NO: 188, SEQ ID NO: 191, SEQ ID NO: 194 or SEQ ID NO: 197 or an allelic variant thereof; or is a fragment thereof having DNase activity. In another aspect, the polypeptide comprises or consists of the mature polypeptide of any of the polypeptides having the amino acid sequences shown in SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23 SEQ ID NO: 53, SEQ ID NO: 56, SEQ ID NO: 59, SEQ ID NO: 62, SEQ ID NO: 65, SEQ ID NO: 68, SEQ ID NO: 71, SEQ ID NO: 74, SEQ ID NO: 77, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 161, SEQ ID NO: 164, SEQ ID NO: 167, SEQ ID NO: 170, SEQ ID NO: 173, SEQ ID NO: 176, SEQ ID NO: 179, SEQ ID NO: 182, SEQ ID NO: 185, SEQ ID NO: 188, SEQ ID NO: 191, SEQ ID NO: 194 or SEQ ID NO: 197.

In an embodiment, the polypeptide has been isolated.

In another embodiment, the present invention relates to variants of the mature polypeptide of SEQ ID NO: 2, 4 or 6 or any of the homologue polypeptides having the amino acid sequence shown in SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 53, SEQ ID NO: 56, SEQ ID NO: 59, SEQ ID NO: 62, SEQ ID NO: 65, SEQ ID NO: 68, SEQ ID NO: 71, SEQ ID NO: 74, SEQ ID NO: 77, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 161, SEQ ID NO: 164, SEQ ID NO: 167, SEQ ID NO: 170, SEQ ID NO: 173, SEQ ID NO: 176, SEQ ID NO: 179, SEQ ID NO: 182, SEQ ID NO: 185, SEQ ID NO: 188, SEQ ID NO: 191, SEQ ID NO: 194 or SEQ ID NO: 197, comprising a substitution, deletion, and/or insertion at one or more (e.g., several) positions. In an embodiment, the number of amino acid substitutions, deletions and/or insertions introduced into the mature polypeptide of SEQ ID NO: 2, 4 or 6 is up to 10, e.g., 1, 2, 3, 4, 5, 6, 7, 8, 9, or 10.

In another embodiment, the present invention relates to variants of the mature polypeptide of SEQ ID NO: 8 comprising a substitution, deletion, and/or insertion at one or more (e.g., several) positions. In an embodiment, the number of amino acid substitutions, deletions and/or insertions introduced into the polypeptide of SEQ ID NO: 8 is up to 10, e.g., 1, 2, 3, 4, 5, 6, 7, 8, 9, or 10.

In another embodiment, the present invention relates to variants of the mature polypeptide of SEQ ID NO: 9 comprising a substitution, deletion, and/or insertion at one or more (e.g., several) positions. In an embodiment, the number of amino acid substitutions, deletions and/or insertions introduced into the polypeptide of SEQ ID NO: 9 is up to 10, e.g., 1, 2, 3, 4, 5, 6, 7, 8, 9, or 10.

In another embodiment, the present invention relates to variants of the mature polypeptide of SEQ ID NO: 10 comprising a substitution, deletion, and/or insertion at one or more (e.g., several) positions. In an embodiment, the number of amino acid substitutions, deletions and/or insertions introduced into the polypeptide of SEQ ID NO: 10 is up to 10, e.g., 1, 2, 3, 4, 5, 6, 7, 8, 9, or 10.

In another embodiment, the present invention relates to variants of the mature polypeptide of SEQ ID NO: 11 comprising a substitution, deletion, and/or insertion at one or more (e.g., several) positions. In an embodiment, the number of amino acid substitutions, deletions and/or insertions introduced into the polypeptide of SEQ ID NO: 11 is up to 10, e.g., 1, 2, 3, 4, 5, 6, 7, 8, 9, or 10.

In another embodiment, the present invention relates to variants of the mature polypeptide of SEQ ID NO: 12 comprising a substitution, deletion, and/or insertion at one or more (e.g., several) positions. In an embodiment, the number of amino acid substitutions, deletions and/or insertions introduced into the polypeptide of SEQ ID NO: 12 is up to 10, e.g., 1, 2, 3, 4, 5, 6, 7, 8, 9, or 10.

In another embodiment, the present invention relates to variants of the mature polypeptide of SEQ ID NO: 13 comprising a substitution, deletion, and/or insertion at one or more (e.g., several) positions. In an embodiment, the number of amino acid substitutions, deletions and/or insertions introduced into the polypeptide of SEQ ID NO: 13 is up to 10, e.g., 1, 2, 3, 4, 5, 6, 7, 8, 9, or 10.

In another embodiment, the present invention relates to variants of the mature polypeptide of SEQ ID NO: 14 comprising a substitution, deletion, and/or insertion at one or more (e.g., several) positions. In an embodiment, the number of amino acid substitutions, deletions and/or insertions introduced into the polypeptide of SEQ ID NO: 14 is up to 10, e.g., 1, 2, 3, 4, 5, 6, 7, 8, 9, or 10.

In another embodiment, the present invention relates to variants of the mature polypeptide of SEQ ID NO: 15 comprising a substitution, deletion, and/or insertion at one or more (e.g., several) positions. In an embodiment, the number of amino acid substitutions, deletions and/or insertions introduced into the polypeptide of SEQ ID NO: 15 is up to 10, e.g., 1, 2, 3, 4, 5, 6, 7, 8, 9, or 10.

In another embodiment, the present invention relates to variants of the mature polypeptide of SEQ ID NO: 16 comprising a substitution, deletion, and/or insertion at one or more (e.g., several) positions. In an embodiment, the number of amino acid substitutions, deletions and/or insertions introduced into the polypeptide of SEQ ID NO: 16 is up to 10, e.g., 1, 2, 3, 4, 5, 6, 7, 8, 9, or 10.

In another embodiment, the present invention relates to variants of the mature polypeptide of SEQ ID NO: 17 comprising a substitution, deletion, and/or insertion at one or more (e.g., several) positions. In an embodiment, the number of amino acid substitutions, deletions and/or insertions introduced into the polypeptide of SEQ ID NO: 17 is up to 10, e.g., 1, 2, 3, 4, 5, 6, 7, 8, 9, or 10.

In another embodiment, the present invention relates to variants of the mature polypeptide of SEQ ID NO: 18 comprising a substitution, deletion, and/or insertion at one or more (e.g., several) positions. In an embodiment, the number of amino acid substitutions, deletions and/or insertions introduced into the polypeptide of SEQ ID NO: 18 is up to 10, e.g., 1, 2, 3, 4, 5, 6, 7, 8, 9, or 10.

In another embodiment, the present invention relates to variants of the mature polypeptide of SEQ ID NO: 19 comprising a substitution, deletion, and/or insertion at one or more (e.g., several) positions. In an embodiment, the number of amino acid substitutions, deletions and/or insertions introduced into the polypeptide of SEQ ID NO: 19 is up to 10, e.g., 1, 2, 3, 4, 5, 6, 7, 8, 9, or 10.

In another embodiment, the present invention relates to variants of the mature polypeptide of SEQ ID NO: 20 comprising a substitution, deletion, and/or insertion at one or more (e.g., several) positions. In an embodiment, the number of amino acid substitutions, deletions and/or insertions introduced into the polypeptide of SEQ ID NO: 20 is up to 10, e.g., 1, 2, 3, 4, 5, 6, 7, 8, 9, or 10.

In another embodiment, the present invention relates to variants of the mature polypeptide of SEQ ID NO: 21 comprising a substitution, deletion, and/or insertion at one or more (e.g., several) positions. In an embodiment, the number of amino acid substitutions, deletions and/or insertions introduced into the polypeptide of SEQ ID NO: 21 is up to 10, e.g., 1, 2, 3, 4, 5, 6, 7, 8, 9, or 10.

In another embodiment, the present invention relates to variants of the mature polypeptide of SEQ ID NO: 22 comprising a substitution, deletion, and/or insertion at one or more (e.g., several) positions. In an embodiment, the number of amino acid substitutions, deletions and/or insertions introduced into the polypeptide of SEQ ID NO: 22 is up to 10, e.g., 1, 2, 3, 4, 5, 6, 7, 8, 9, or 10.

In another embodiment, the present invention relates to variants of the mature polypeptide of SEQ ID NO: 23 comprising a substitution, deletion, and/or insertion at one or more (e.g., several) positions. In an embodiment, the number of amino acid substitutions, deletions and/or insertions introduced into the polypeptide of SEQ ID NO: 23 is up to 10, e.g., 1, 2, 3, 4, 5, 6, 7, 8, 9, or 10.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for DNase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labelling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. Use of a polypeptide having DNase activity 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Polynucleotides

The present invention also relates to polynucleotides encoding a polypeptide, as described herein. In an embodiment, the polynucleotide encoding the polypeptide of the present invention has been isolated. In another embodiment, the polynucleotide encoding a polypeptide of the present invention comprises or consists of the polynucleotide sequence set forth in SEQ ID NO: 1, 3 or 5.

In another embodiment, the present invention relates to an isolated polypeptide having DNase activity encoded by a polynucleotide that hybridizes under low stringency conditions with (i) the mature polypeptide coding sequence of SEQ ID NO: 1, 3 or 5 or (ii) the full-length complement of (i) (Sambrook et al., 1989, Molecular Cloning, A Laboratory Manual, 2d edition, Cold Spring Harbor, New York). In an embodiment, the polypeptide has been isolated.

In another embodiment, the present invention relates to an isolated polypeptide having DNase activity encoded by a polynucleotide that hybridizes under low-medium stringency conditions with (i) the mature polypeptide coding sequence of SEQ ID NO: 1, 3 or 5 or (ii) the full-length complement of (i). In an embodiment, the polypeptide has been isolated.

In another embodiment, the present invention relates to an isolated polypeptide having DNase activity encoded by a polynucleotide that hybridizes under medium stringency conditions with (i) the mature polypeptide coding sequence of SEQ ID NO: 1, 3 or 5 or (ii) the full-length complement of (i). In an embodiment, the polypeptide has been isolated.

In another embodiment, the present invention relates to an isolated polypeptide having DNase activity encoded by a polynucleotide that hybridizes under medium-high stringency conditions with (i) the mature polypeptide coding sequence of SEQ ID NO: 1, 3 or 5 or (ii) the full-length complement of (i). In an embodiment, the polypeptide has been isolated.

In another embodiment, the present invention relates to an isolated polypeptide having DNase activity encoded by a polynucleotide that hybridizes under high stringency conditions with (i) the mature polypeptide coding sequence of SEQ ID NO: 1, 3 or 5 or (ii) the full-length complement of (i). In an embodiment, the polypeptide has been isolated.

In another embodiment, the present invention relates to an isolated polypeptide having DNase activity encoded by a polynucleotide that hybridizes under very high stringency conditions with (i) the mature polypeptide coding sequence of SEQ ID NO: 1, 3 or 5 or (ii) the full-length complement of (i). In an embodiment, the polypeptide has been isolated.

The polynucleotide of SEQ ID NO: 1, 3 or 5 or a subsequence thereof, as well as the polypeptides of SEQ ID NO: 2, 4 or 6 or a fragment thereof or the polypeptide of SEQ ID NO: 8, 9 or 10 or a fragment thereof, may be used to design nucleic acid probes to identify and clone DNA encoding polypeptides having DNase activity from strains of different genera or species according to methods well known in the art. In particular, such probes can be used for hybridization with the genomic DNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides or at least 600 nucleotides in length. Both DNA and RNA probes can be used. The probes are typically labelled for detecting the corresponding gene (for example, with $^{32}$P, $^{3}$H, $^{35}$S, biotin, or avidin). Such probes are encompassed by the present invention.

A genomic DNA or cDNA (when polypeptides comprises introns) library prepared from such other strains may be screened for DNA that hybridizes with the probes described above and encodes a polypeptide having DNase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1, 3 or 5 or a subsequence thereof, the carrier material is used in a Southern blot.

For purposes of the present invention, hybridization indicates that the polynucleotide hybridizes to a labelled nucleic acid probe corresponding to (i) SEQ ID NO: 1, 3 or 5; (ii) the mature polypeptide coding sequence of SEQ ID NO: 1, 3 or 5; (iii) the full-length complement thereof; or (iv) a subsequence thereof; under very low, low stringency conditions, low-medium stringency conditions, medium stringency conditions, medium-high stringency conditions, high stringency conditions to very high stringency conditions. Molecules to which the nucleic acid probe hybridizes under these conditions can be detected using, for example, X-ray film or any other detection means known in the art.

In another embodiment, the present invention relates to a polypeptide having DNase activity encoded by a polynucleotide having a sequence identity to the mature polypeptide coding sequence of SEQ ID NO: 1, 3 or 5 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polypeptide has been isolated.

In another embodiment, the present invention relates to a polypeptide having DNase activity encoded by a polynucleotide having a sequence identity to the mature polypeptide coding sequence of SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 54, SEQ ID NO: 57, SEQ ID NO: 60, SEQ ID NO: 63, SEQ ID NO: 66, SEQ ID NO: 69, SEQ ID NO: 72, SEQ ID NO: 75, SEQ ID NO: 78, SEQ ID NO: 81, SEQ ID NO: 84, SEQ ID NO: 87, SEQ ID NO: 90, SEQ ID NO: 93, SEQ ID NO: 96, SEQ ID NO: 99, SEQ ID NO: 102, SEQ ID NO: 105, SEQ ID NO: 108, SEQ ID NO: 111, SEQ ID NO: 114, SEQ ID NO: 117, SEQ ID NO: 120, SEQ ID NO: 123, SEQ ID NO: 126, SEQ ID NO: 129, SEQ ID NO: 132, SEQ ID NO: 135, SEQ ID NO: 138, SEQ ID NO: 141, SEQ ID NO: 144, SEQ ID NO: 147, SEQ ID NO: 150, SEQ ID NO: 153, SEQ ID NO: 156, SEQ ID NO: 159, SEQ ID NO: 162, SEQ ID NO: 165, SEQ ID NO: 168, SEQ ID NO: 171, SEQ ID NO: 174, SEQ ID NO: 177, SEQ ID NO: 180, SEQ ID NO: 183, SEQ ID NO: 186, SEQ ID NO: 189, SEQ ID NO: 192, SEQ ID NO: 195 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polypeptide has been isolated.

The techniques used to isolate or clone a polynucleotide are known in the art and include isolation from genomic DNA, or a combination thereof. The cloning of the polynucleotides from genomic DNA can be effected, e.g., by using the well-known polymerase chain reaction (PCR) or antibody screening of expression libraries to detect cloned DNA fragments with shared structural features. See, e.g., Innis et al., 1990, PCR: A Guide to Methods and Application, Academic Press, New York. Other nucleic acid amplification procedures such as ligase chain reaction (LCR), ligation activated transcription (LAT) and polynucleotide-based amplification (NASBA) may be used.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variants may be constructed on the basis of the mature polypeptide coding sequence of SEQ ID NO: 1, 3 or 5 or, e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, Protein Expression and Purification 2: 95-107.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the Bacillus amyloliquefaciens alpha-amylase gene (amyQ), Bacillus licheniformis alpha-amylase gene (amyL), Bacillus licheniformis penicillinase gene (penP), Bacillus stearothermophilus maltogenic amylase gene (amyM), Bacillus subtilis levansucrase gene (sacB), Bacillus subtilis xylA and xylB genes, Bacillus thuringiensis cryIIIA gene (Agaisse and Lereclus, 1994, Molecular Microbiology 13: 97-107), E. coli lac operon, E. coli trc promoter (Egon et al., 1988, Gene 69: 301-315), Streptomyces coelicolor agarase gene (dagA), and prokaryotic beta-lactamase gene (Villa-Kamaroff et al., 1978, Proc. Natl. Acad. Sci. USA 75: 3727-3731), as well as the tac promoter (DeBoer et al., 1983, Proc. Natl. Acad. Sci. USA 80: 21-25). Further promoters are described in "Useful proteins from recombinant bacteria" in Gilbert et al., 1980, Scientific American 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for Aspergillus nidulans acetamidase, Aspergillus niger neutral alpha-amylase, Aspergillus niger acid stable alpha-amylase, Aspergillus niger or Aspergillus awamori glucoamylase (glaA), Aspergillus oryzae TAKA amylase, Aspergillus oryzae alkaline protease, Aspergillus oryzae triose phosphate isomerase, Fusarium oxysporum trypsin-like protease (WO 96/00787), Fusarium venenatum amyloglucosidase (WO 00/56900), Fusarium venenatum Daria (WO 00/56900), Fusarium venenatum Quinn (WO 00/56900), Rhizomucor miehei lipase, Rhizomucor miehei aspartic proteinase, Trichoderma reesei beta-glucosidase, Trichoderma reesei cellobiohydrolase I, Trichoderma reesei cellobiohydrolase II, Trichoderma reesei endoglucanase I, Trichoderma reesei endoglucanase II, Trichoderma reesei endoglucanase Ill, Trichoderma reesei endoglucanase V, Trichoderma reesei xylanase I, Trichoderma reesei xylanase II, Trichoderma reesei xylanase Ill, Trichoderma reesei beta-xylosidase, and Trichoderma reesei translation elongation factor, as well as the NA2-tpi promoter (a modified promoter from an Aspergillus neutral alpha-amylase gene in which the untranslated leader has been replaced by an untranslated leader from an Aspergillus triose phosphate isomerase gene; non-limiting examples include modified promoters from an Aspergillus niger neutral alpha-amylase gene in which the untranslated leader has been replaced by an untranslated leader from an Aspergillus nidulans or Aspergillus oryzae triose phosphate isomerase gene); and mutant, truncated, and hybrid promoters thereof. Other promoters are described in U.S. Pat. No. 6,011,147.

In a yeast host, useful promoters are obtained from the genes for Saccharomyces cerevisiae enolase (ENO-1), Saccharomyces cerevisiae galactokinase (GAL1), Saccharomyces cerevisiae alcohol dehydrogenase/glyceraldehyde-3-phosphate dehydrogenase (ADH1, ADH2/GAP), Saccharomyces cerevisiae triose phosphate isomerase (TPI), Saccharomyces cerevisiae metallothionein (CUP1), and Saccharomyces cerevisiae 3-phosphoglycerate kinase. Other useful promoters for yeast host cells are described by Romanos et al., 1992, Yeast 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for Bacillus clausii alkaline protease (aprH), Bacillus licheniformis alpha-amylase (amyL), and Escherichia coli ribosomal RNA (rrnB).

Preferred terminators for filamentous fungal host cells are obtained from the genes for Aspergillus nidulans acetamidase, Aspergillus nidulans anthranilate synthase, Aspergillus niger glucoamylase, Aspergillus niger alpha-glucosidase, Aspergillus oryzae TAKA amylase, Fusarium oxysporum trypsin-like protease, Trichoderma reesei beta-glucosidase, Trichoderma reesei cellobiohydrolase I, Trichoderma reesei cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase Ill, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cry/I/A gene (WO 94/25612) and a *Bacillus subtilis* SP82 gene (Hue et al., 1995, Journal of Bacteriology 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence; a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, Microbiological Reviews 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression. The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosylaminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is an hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMß1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol. (Praha)* 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., *In,* *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, Passmore, and Davenport, editors, *Soc. App. Bacteriol. Symposium Series No. 9*, 1980).

The yeast host cell may be a *Candida, Hansenula, Kluyveromyces, Pichia, Saccharomyces, Schizosaccharomyces*, or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se.

Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising (a) cultivating a cell, which in its wild-type form produces the polypeptide, under conditions conducive for production of the polypeptide; and optionally, (b) recovering the polypeptide. In one aspect, the cell is a *Bacillus* sp. or *Paenibacillus* cell. In another aspect, the cell is a *Bacillus* sp. 6245, *Bacillus horikoshii* or *Paenibacillus* sp-18057 cell.

The present invention also relates to methods of producing a polypeptide of the present invention, comprising (a) cultivating a recombinant host cell of the present invention under conditions conducive for production of the polypeptide; and optionally, (b) recovering the polypeptide.

One aspect of the invention relates to a method of producing a polypeptide, wherein the polypeptide is selected from the group consisting of polypeptides in shown in SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 53, SEQ ID NO: 56, SEQ ID NO: 59, SEQ ID NO: 62, SEQ ID NO: 65, SEQ ID NO: 68, SEQ ID NO: 71, SEQ ID NO: 74, SEQ ID NO: 77, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 161, SEQ ID NO: 164, SEQ ID NO: 167, SEQ ID NO: 170, SEQ ID NO: 173, SEQ ID NO: 176, SEQ ID NO: 179, SEQ ID NO: 182, SEQ ID NO: 185, SEQ ID NO: 188, SEQ ID NO: 191, SEQ ID NO: 194 and SEQ ID NO: 197, wherein the polypeptide has DNase activity (a) cultivating the recombinant host cell under conditions conducive for production of the polypeptide; and (b) recovering the polypeptide.

In one aspect, the cell is a *Bacillus* or *Aspergillus* or any of the host cells mentioned in the section "Host cells".

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, a fermentation broth comprising the polypeptide is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

In one embodiment, the invention further comprises producing the polypeptide by cultivating the recombinant host cell further comprising a polynucleotide encoding a second polypeptide of interest; preferably an enzyme of interest; more preferably a secreted enzyme of interest; even more preferably a hydrolase, isomerase, ligase, lyase, oxidoreductase, or a transferase; and most preferably the secreted enzyme is an alpha-galactosidase, alpha-glucosidase, aminopeptidase, amylase, asparaginase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, green fluorescent protein, glucano-transferase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or a xylanase.

In one embodiment, the second polypeptide of interest is heterologous or homologous to the host cell.

In one embodiment, the recombinant host cell is a fungal host cell; preferably a filamentous fungal host cell; more preferably an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell; most preferably an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium luc-*

*knowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

In one embodiment, the recombinant host cell is a bacterial host cell; preferably a prokaryotic host cell; more preferably a Gram-positive host cell; even more preferably a *Bacillus, Clostridium, Enterococcus, Geobacillus, Lactobacillus, Lactococcus, Oceanobacillus, Staphylococcus, Streptococcus,* or *Streptomyces* host cell; and most preferably a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* and *Bacillus thuringiensis* host cell.

In one embodiment, a method of producing the second polypeptide of interest comprises cultivating the host cell under conditions conducive for production of the second polypeptide of interest.

In one embodiment, the method further comprises recovering the second polypeptide of interest.

Fermentation Broth Formulations or Cell Compositions

The present invention also relates to a fermentation broth formulation or a cell composition comprising a polypeptide of the present invention. The fermentation broth product further comprises additional ingredients used in the fermentation process, such as, for example, cells (including, the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells are removed by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed whole broth or composition may contain the unfractionated contents of the fermentation materials derived at the end of the fermentation. Typically, the cell-killed whole broth or composition contains the spent culture medium and cell debris present after the microbial cells are grown to saturation, incubated under carbon-limiting conditions to allow protein synthesis. In some embodiments, the cell-killed whole broth or composition contains the spent cell culture medium, extracellular enzymes, and killed bacterial cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Compositions

The present invention relates to compositions comprising a DNase according to the invention.

Some aspect of the invention relates to a composition comprising at least 0.02 ppm of a polypeptide having DNase activity, wherein the polypeptide comprises the motif HXXP, where H is histidine and where P is proline and X is any amino acid.

The amount of DNase is preferably at least 0.02 ppm but may be at least 0.00008, at least 0.0001, at least 0.0002 at least 0.0005, at least 0.0008, at least 0.001, at least 0.002, at least 0.005, at least 0.008, at least 0.01, at least 0.02, at least 0.05, at least 0.08, at least 0.1, at least 0.2, at least 0.5 or at least 0.5 ppm enzyme protein per gram composition. The amount of DNase is preferably at least 0.02 ppm but may be from 0.00008 to 100, in the range of 0.0001-100, in the range of 0.0002-100, in the range of 0.0004-100, in the range of 0.0008-100, in the range of 0.001-100 ppm enzyme protein, 0.01-100 ppm enzyme protein, 0.01-50 ppm enzyme protein, preferably 0.05-50 ppm enzyme protein, preferably 0.02-50 ppm enzyme protein, 0.015-50 ppm enzyme protein, preferably 0.01-50 ppm enzyme protein, preferably 0.1-50 ppm enzyme protein, preferably 0.2-50 ppm enzyme protein, preferably 0.1-30 ppm enzyme protein, preferably 0.5-20 ppm enzyme protein or preferably 0.5-10 ppm enzyme protein per gram composition.

Some aspect of the invention relates to a composition comprising a polypeptide having DNase activity, wherein the polypeptide having DNase activity comprises one or more of the motifs [E/D/H]H[I/V/L/F/M]X[P/A/S], [T/D/S][G/N]PQL, [G/T]Y[D/S][R/K/L], [F/L/Y/I]A[N/R]D[L/I/P/V], C[D/N]T[A/R] and [D/Q][I/V]DH. Preferably the amount of DNase is at least 0.02 ppm but may be at least 0.00008, at least 0.0001, at least 0.0002 at least 0.0005, at least 0.0008, at least 0.001, at least 0.002, at least 0.005, at least 0.008, at least 0.01, at least 0.02, at least 0.05, at least 0.08, at least 0.1, at least 0.2, at least 0.5 or at least 0.5 ppm enzyme protein per gram composition Some aspect of the invention relates to a composition comprising a polypeptide having DNase activity, wherein the polypeptide having DNase activity comprises one or more of the motifs [E/D/H]H[I/V/L/F/M]X[P/A/S], [T/D/S][G/N]PQL, [G/T]Y[D/S][R/K/L], [F/L/Y/I]A[N/R]D[L/I/P/V], C[D/N]T[A/R] and [D/Q][I/V]DH, with the proviso that the polypeptide is not the *Trichoderma harzianum* DNase shown in SEQ ID NO: 2 of WO 2015/155351. Preferably the amount of DNase is at least 0.02 ppm but may be at least 0.00008, at least 0.0001, at least 0.0002 at least 0.0005, at least 0.0008, at least 0.001, at least 0.002, at least 0.005, at least 0.008, at least 0.01, at least 0.02, at least 0.05, at least 0.08, at least 0.1, at least 0.2, at least 0.5 or at least 0.5 ppm enzyme protein per gram composition. In some aspects the motif [G/T]Y[D/S][R/K/L][RKL] corresponding to pos 28 to 31 of SEQ ID NO: 21. In some aspects the motif [E/D/H]H[I/V/L/F/M]X[P/A/S] corresponds to positions corresponding to positions 87 to 91 in *B. cibi* (SEQ ID NO: 21).

Some aspects of the invention relates to a composition comprising a polypeptide having DNase activity, wherein the polypeptide having DNase activity comprises one, two, three or all of the motifs [E/D/H]H[I/V/L/F/M]X[P/A/S], [T/D/S][G/N]PQL, [G/T]Y[D/S][R/K/L], [F/L/Y/I]A[N/R]D[L/I/P/V], C[D/N]T[A/R] and [D/Q][I/V]DH. Preferably the amount of DNase is at least 0.02 ppm but may be at least 0.00008, at least 0.0001, at least 0.0002 at least 0.0005, at least 0.0008, at least 0.001, at least 0.002, at least 0.005, at least 0.008, at least 0.01, at least 0.02, at least 0.05, at least 0.08, at least 0.1, at least 0.2, at least 0.5 or at least 0.5 ppm enzyme protein per gram composition. In some aspects the motif [F/L/Y/I]A[N/R]D[L/I/P/V] (SEQ ID NO: 201) corresponding to positions 110 to 114 of SEQ ID NO: 21.

Some aspects of the invention relates to a composition comprising a polypeptide having DNase activity, wherein the polypeptide having DNase activity comprises the motif one, two, three or all of the motifs [E/D/H]H[I/V/L/F/M]X[P/A/S], [T/D/S][G/N]PQL, [G/T]Y[D/S][R/K/L], [F/L/Y/I]A[N/R]D[L/I/P/V], C[D/N]T[A/R] and [D/Q][I/V]DH, wherein the amino acids in brackets are alternatives. Preferably the amount of DNase is at least 0.02 ppm but may be at least 0.00008, at least 0.0001, at least 0.0002 at least 0.0005, at least 0.0008, at least 0.001, at least 0.002, at least 0.005, at least 0.008, at least 0.01, at least 0.02, at least 0.05, at least 0.08, at least 0.1, at least 0.2, at least 0.5 or at least 0.5 ppm enzyme protein per gram composition with the proviso that the polypeptide is not the *Trichoderma harzianum* DNase shown in SEQ ID NO: 2 of WO 2015/155351.

Some aspects of the invention relates to a composition comprising a polypeptide having DNase activity, wherein the polypeptide having DNase activity belongs to the GYS-clade, comprises one or more of the motifs selected from the motifs [D/M/L][S/T]GYSR[D/N] (SEQ ID NO: 204) or ASXNRSKG (SEQ ID NO: 205).

Some aspects of the invention relates to a composition comprising a polypeptide having DNase activity, wherein the polypeptide having DNase activity belongs to the GYS clade, comprises one or both of the motifs selected from the motifs [D/M/L][S/T]GYSR[D/N] (SEQ ID NO: 204) or ASXNRSKG (SEQ ID NO: 205), wherein the polypeptide having DNase activity is selected from the group consisting of the polypeptides shown in SEQ ID NO: 8, SEQ ID NO: 9, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 53, SEQ ID NO: 56, SEQ ID NO: 59, SEQ ID NO: 62, SEQ ID NO: 65, SEQ ID NO: 68, SEQ ID NO: 71, SEQ ID NO: 74, SEQ ID NO: 77 and SEQ ID NO: 80 or polypeptides having at least 80%, such as at least 85%, such as at least 90%, such as at least 95% or 100% sequence identity thereto.

Some aspects of the invention relates to a composition comprising a polypeptide having DNase activity, wherein the polypeptide having DNase activity belongs to the NAWK-clade, and where the polypeptide comprises one or both of the motifs selected from [V/I]PL[S/A]NAWK (SEQ ID NO: 206) or NPQL (SEQ ID NO: 207).

Some aspects of the invention relates to a composition comprising a polypeptide having DNase activity, wherein the polypeptide having DNase activity belongs to the NAWK clade, and wherein the polypeptide comprises one or both of the motifs selected from the motifs [V/I]PL[S/A]NAWK (SEQ ID NO: 206) or NPQL (SEQ ID NO: 207), wherein the amino acids in brackets are alternatives, wherein X is any amino acid and wherein the polypeptide having DNase activity is selected from the polypeptide shown in SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116 and SEQ ID NO: 119 or polypeptides having at least 80%, such as at least 85%, such as at least 90%, such as at least 95% or 100% sequence identity thereto.

Some aspects of the invention relates to a composition comprising a polypeptide having DNase activity, wherein the polypeptide having DNase activity belongs to the KNAW clade, wherein the polypeptide comprises one or both of the motifs P[Q/E]L[W/Y] (SEQ ID NO: 208) or [K/H/E]NAW (SEQ ID NO: 209), wherein amino acid in brackets are alternatives and wherein the polypeptide having DNase activity is selected from the group consisting of SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155 and SEQ ID NO: 158 or polypeptides having at least 80% such as at least 85%, such as at least 90%, such as at least 95% or 100% sequence identity thereto.

Some aspects of the invention relates to a composition comprising a polypeptide having DNase activity, wherein the polypeptide having DNase activity belongs to the KNAW clade, wherein the polypeptide comprises one or both of the motifs P[Q/E]L[W/Y] (SEQ ID NO: 208) or [K/H/E]NAW (SEQ ID NO: 209), wherein amino acid in brackets are alternatives and wherein the polypeptide having DNase activity is selected from the group consisting of SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155 and SEQ ID NO: 158 or polypeptides having at least 80% such as at least 85%, such as at least 90%, such as at least 95% or 100% sequence identity thereto, with the proviso that the polypeptide is not the *Trichoderma harzianum* DNase shown in SEQ ID NO: 2 of WO 2015/155351.

Some aspects of the invention relates to a composition comprising a polypeptide having DNase activity, wherein the polypeptide comprises one or more motifs selected from the motifs [E/D/H]H[I/V/L/F/M]X[P/A/S], [T/D/S][G/N]PQL, [G/T]Y[D/S][R/K/L], [F/L/Y/I]A[N/R]D[L/I/P/V], C[D/N]T[A/R] and [D/Q][I/V]DH, wherein amino acid in brackets are alternatives and wherein the polypeptide having DNase activity is selected from the group consisting of SEQ ID NO: 161, SEQ ID NO: 164, SEQ ID NO: 167, SEQ ID NO: 170, SEQ ID NO: 173, SEQ ID NO: 176, SEQ ID NO: 179, SEQ ID NO: 182, SEQ ID NO: 185, SEQ ID NO: 188, SEQ ID NO: 191, SEQ ID NO: 194 and SEQ ID NO: 197 or polypeptides having at least 80% such as at least 85%, such as at least 90%, such as at least 95% or 100% sequence identity thereto.

Some aspects of the invention relate to a composition comprising a polypeptide having DNase activity, wherein the polypeptide having DNase activity is selected from the group consisting of:

a) a polypeptide having at least 70%, at least 80%, at least 85%, at least 90%, at least 95%, at least 98%, at least 99% or 100% sequence identity to the polypeptide of SEQ ID NO: 8, b) a polypeptide having at least 70%, at least 80%, at least 85%, at least 90%, at least 95%, at least 98%, at least 99% or 100% sequence identity to the polypeptide of SEQ ID NO: 9, c) a polypeptide having at least 70%, at least 80%, at least 85%, at least 90%, at least 95%, at least 98%, at least 99% or 100% sequence identity to the polypeptide of SEQ ID NO: 11, d) a polypeptide having at least 70%, at least 80%, at least 85%, at least 90%, at least 95%, at least 98%, at least 99% or 100% sequence identity to the polypeptide of SEQ ID NO: 12, e) a polypeptide having at least 70%, at least 80%, at least 85%, at least 90%, at least 95%, at least 98%, at least 99% or 100% sequence identity to the polypeptide of SEQ ID NO: 13, f) a polypeptide having at least 70%, at least 80%, at least 85%, at least 90%, at least 95%, at least 98%, at least 99% or 100% sequence identity to the polypeptide of SEQ ID NO: 14, g) a polypeptide having at least 70%, at least 80%, at least 85%, at least 90%, at least 95%, at least 98%, at least 99% or 100% sequence identity to the polypeptide of SEQ ID NO: 15, h) a polypeptide having at least 70%, at least 80%, at least 85%, at least 90%, at least 95%, at least 98%, at least 99% or 100% sequence identity to the polypeptide of SEQ ID NO: 16, i) a polypeptide having at least 70%, at least 80%, at least 85%, at least 90%, at least 95%, at least 98%, at least 99% or 100% sequence identity to the polypeptide of SEQ ID NO: 17, j) a polypeptide having at least 70%, at least 80%, at least 85%, at least 90%, at least 95%, at least 98%, at least 99% or 100% sequence identity to the polypeptide of SEQ ID NO: 18, k) a polypeptide having at least 70%, at least 80%, at least 85%, at least 90%, at least 95%, at least 98%, at least 99% or 100% sequence identity to the polypeptide of SEQ ID NO: 19, l) a polypeptide having at least 70%, at least 80%, at least 85%, at least 90%, at least 95%, at least 98%, at least 99% or 100% sequence identity to the polypeptide of SEQ ID NO: 20, m) a polypeptide having at least 70%, at least 80%, at least 85%, at least 90%, at least 95%, at least 98%, at least 99% or 100% sequence identity to the polypeptide of SEQ ID NO: 21, n) a polypeptide having at least 70%, at least 80%, at least 85%, at least 90%, at least 95%, at least 98%, at least 99% or 100% sequence identity to the polypeptide of SEQ ID NO: 22, o) a polypeptide having at least 70%, at least 80%, at least 85%, at least 90%, at least 95%, at least 98%, at least 99% or 100% sequence identity to the polypeptide of SEQ ID NO: 23, p) a polypeptide having at least 70%, at least 80%, at least 85%, at least 90%, at least 95%, at least 98%, at least 99% or 100% sequence identity to the polypeptide of SEQ ID NO: 53, q) a polypeptide having at least 70%, at least 80%, at least 85%, at least 90%, at least 95%, at least 98%, at least 99% or 100% sequence identity to the polypeptide of SEQ ID NO: 56, r) a polypeptide having at least 70%, at least 80%, at least 85%, at least 90%, at least 95%, at least 98%, at least 99% or 100% sequence identity to the polypeptide of SEQ ID NO: 59, s) a polypeptide having at least 70%, at least 80%, at least 85%, at least 90%, at least 95%, at least 98%, at least 99% or 100% sequence identity to the polypeptide of SEQ ID NO: 62, t) a polypeptide having at least 70%, at least 80%, at least 85%, at least 90%, at least 95%, at least 98%, at least 99% or 100% sequence identity to the polypeptide of SEQ ID NO: 65, u) a polypeptide having at least 70%, at least 80%, at least 85%, at least 90%, at least 95%, at least 98%, at least 99% or 100% sequence identity to the polypeptide of SEQ ID NO: 68, v) a polypeptide having at least 70%, at least 80%, at least 85%, at least 90%, at least 95%, at least 98%, at least 99% or 100% sequence identity to the polypeptide of SEQ ID NO: 71, w) a polypeptide having at least 70%, at least 80%, at least 85%, at least 90%, at least 95%, at least 98%, at least 99% or 100% sequence identity to the polypeptide of SEQ ID NO: 74, x) a polypeptide having at least 70%, at least 80%, at least 85%, at least 90%, at least 95%, at least 98%, at least 99% or 100% sequence identity to the polypeptide of SEQ ID NO: 77, y) a polypeptide having at least 70%, at least 80%, at least 85%, at least 90%, at least 95%, at least 98%, at least 99% or 100% sequence identity to the polypeptide of SEQ ID NO: 80, z) a polypeptide having at least 70%, at least 80%, at least 85%, at least 90%, at least 95%, at least 98%, at least 99% or 100% sequence identity to the polypeptide of SEQ ID NO: 83, aa) a polypeptide having at least 70%, at least 80%, at least 85%, at least 90%, at least 95%, at least 98%, at least 99% or 100% sequence identity to the polypeptide of SEQ ID NO: 86, bb) a polypeptide having at least 70%, at least 80%, at least 85%, at least 90%, at least 95%, at least 98%, at least 99% or 100% sequence identity to the polypeptide of SEQ ID NO: 89, cc) a polypeptide having at least 70%, at least 80%, at least 85%, at least 90%, at least 95%, at least 98%, at least 99% or 100% sequence identity to the polypeptide of SEQ ID NO: 92, dd) a polypeptide having at least 70%, at least 80%, at least 85%, at least 90%, at least 95%, at least 98%, at least 99% or 100% sequence identity to the polypeptide of SEQ ID NO: 95, ee) a polypeptide having at least 70%, at least 80%, at least 85%, at least 90%, at least 95%, at least 98%, at least 99% or 100% sequence identity to the polypeptide of SEQ ID NO: 98, ff) a polypeptide having at least 70%, at least 80%, at least 85%, at least 90%, at least 95%, at least 98%, at least 99% or 100% sequence identity to the polypeptide of SEQ ID NO: 101, gg) a polypeptide having at least 70%, at least 80%, at least 85%, at least 90%, at least 95%, at least 98%, at least 99% or 100% sequence identity to the polypeptide of SEQ ID NO: 104, hh) a polypeptide having at least 70%, at least 80%, at least 85%, at least 90%, at least 95%, at least 98%, at least 99% or 100% sequence identity to the polypeptide of SEQ ID NO: 107, ii) a polypeptide having at least 70%, at least 80%, at least 85%, at least 90%, at least 95%, at least 98%, at least 99% or 100% sequence identity to the polypeptide of SEQ ID NO: 110, jj) a polypeptide having at least 70%, at least 80%, at least 85%, at least 90%, at least 95%, at least 98%, at least 99% or 100% sequence identity to the polypeptide of SEQ ID NO: 113, kk) a polypeptide having at least 70%, at least 80%, at least 85%, at least 90%, at least 95%, at least 98%, at least 99% or 100% sequence identity to the polypeptide of SEQ ID NO: 116, ll) a polypeptide having at least 70%, at least 80%, at least 85%, at least 90%, at least 95%, at least 98%, at least 99% or 100% sequence identity to the polypeptide of SEQ ID NO: 119, mm) a polypeptide having at least 70%, at least 80%, at least 85%, at least 90%, at least 95%, at least 98%, at least 99% or 100% sequence identity to the polypeptide of SEQ ID NO: 122, nn) a polypeptide having at least 70%, at least 80%, at least 85%, at least 90%, at least 95%, at least 98%, at least 99% or 100% sequence identity to the polypeptide of SEQ ID NO: 125, oo) a polypeptide having at least 70%, at least 80%, at least 85%, at least 90%, at least 95%, at least 98%, at least 99% or 100% sequence identity to the polypeptide of SEQ ID NO: 128, pp) a polypeptide having at least 70%, at least 80%, at least 85%, at least 90%, at least 95%, at least 98%, at least 99% or 100% sequence identity to the polypeptide of SEQ ID NO: 131, qq) a polypeptide having at least 70%, at least 80%, at least 85%, at least 90%, at least 95%, at least 98%, at least 99% or 100% sequence identity to the polypeptide of SEQ ID NO: 134, rr) a polypeptide having at least 70%, at least 80%, at least 85%, at least 90%, at least 95%, at least 98%, at least 99% or 100% sequence identity to the polypeptide of SEQ ID NO: 137, ss) a polypeptide having at least 70%, at least 80%, at least 85%, at least 90%, at least 95%, at least 98%, at least 99% or 100% sequence identity to the polypeptide of SEQ ID NO: 140, tt) a polypeptide having at least 70%, at least 80%, at least 85%, at least 90%, at least 95%, at least 98%, at least 99% or 100% sequence identity to the polypeptide of SEQ ID NO: 143, uu) a polypeptide having at least 70%, at least 80%, at least 85%, at least 90%, at least 95%, at least 98%, at least 99% or 100% sequence identity to the polypeptide of SEQ ID NO: 146, vv) a polypeptide having at least 70%, at least 80%, at least 85%, at least 90%, at least 95%, at least 98%, at least 99% or 100% sequence identity to the polypeptide of SEQ ID NO: 149, ww) a polypeptide having at least 70%, at least 80%, at least 85%, at least 90%, at least 95%, at least 98%, at least 99% or 100% sequence identity to the polypeptide of SEQ ID NO: 152, xx) a polypeptide having at least 70%, at least 80%, at least 85%, at least 90%, at least 95%, at least 98%, at least 99% or 100% sequence identity to the polypeptide of SEQ ID NO: 155, yy) a polypeptide having at least 70%, at least 80%, at least 85%, at least 90%, at least 95%, at least 98%, at least 99% or 100% sequence identity to the polypeptide of SEQ ID NO: 158, zz) a polypeptide having at least 70%, at least 80%, at least 85%, at least 90%, at least 95%, at least 98%, at least 99% or 100% sequence identity to the polypeptide of SEQ ID NO: 161, aaa) a polypeptide having at least 70%, at least 80%, at least 85%, at least 90%, at least 95%, at least 98%, at least 99% or 100% sequence identity to the polypeptide of SEQ ID NO: 164, bbb) a polypeptide having at least 70%, at least 80%, at least 85%, at least 90%, at least 95%, at least 98%, at least 99% or 100% sequence identity to the polypeptide of SEQ ID NO: 167, ccc) a polypeptide having at least 70%, at least 80%, at least 85%, at least 90%, at least 95%, at least 98%, at least 99% or 100% sequence identity to the polypeptide of SEQ ID NO: 170, ddd) a polypeptide having at least 70%, at least 80%, at least 85%, at least 90%, at least 95%, at least 98%, at least 99% or 100% sequence identity to the polypeptide of SEQ ID NO: 173, eee) a polypeptide having at least 70%, at least 80%, at least 85%, at least 90%, at least 95%, at least 98%, at least 99% or 100% sequence identity to the polypeptide of SEQ ID NO: 176, fff) a polypeptide having at least 70%, at least 80%, at least 85%, at least 90%, at least 95%, at least 98%, at least 99% or 100% sequence identity to the polypeptide of SEQ ID NO: 179, ggg) a polypeptide having at least 70%, at least 80%, at least 85%, at least 90%, at least 95%, at least 98%, at least 99% or 100% sequence identity to the polypeptide of SEQ ID NO: 182, hhh) a polypeptide having at least 70%, at least 80%, at least 85%, at least 90%, at least 95%, at least 98%, at least 99% or 100% sequence identity to the polypeptide of SEQ ID NO: 185,
iii) a polypeptide having at least 70%, at least 80%, at least 85%, at least 90%, at least 95%, at least 98%, at least 99% or 100% sequence identity to the polypeptide of SEQ ID NO: 188,
jjj) a polypeptide having at least 70%, at least 80%, at least 85%, at least 90%, at least 95%, at least 98%, at least 99% or 100% sequence identity to the polypeptide of SEQ ID NO: 191,
kkk) a polypeptide having at least 70%, at least 80%, at least 85%, at least 90%, at least 95%, at least 98%, at least 99% or 100% sequence identity to the polypeptide of SEQ ID NO: 194,
lll) a polypeptide having at least 70%, at least 80%, at least 85%, at least 90%, at least 95%, at least 98%, at least 99% or 100% sequence identity to the polypeptide of SEQ ID NO: 197,
optionally the polypeptide comprises one or more of the motifs [E/D/H]H[I/V/L/F/M]X[P/A/S], [T/D/S][G/N]PQL, [G/T]Y[D/S][R/K/L], [F/L/Y/I]A[N/R]D[L/I/P/V], C[D/N]T[A/R] and [D/Q][I/V]DH and optionally the composition comprises one or more of the following;
i. one or more polyol(s), preferably selected from glycerol, (mono, di, or tri) propylene glycol, ethylene glycol, polyethylene glycol, sugar alcohols, sorbitol, mannitol, erythritol, dulcitol, inositol, xylitol and adonitol,
ii. optionally one or more enzymes, preferably selected from proteases, amylases or lipases,
iii. optionally one or more surfactants, preferably selected from anionic and nonionic surfactants,
iv. optionally one or more polymers.

A polyol (or polyhydric alcohol) used according to the invention is an alcohol with two or more hydroxyl groups, for example alcohols with many hydroxyl groups. The polyol typically includes less than 10 carbons, such as 9, 8, 7, 6, 5, 4, or 3 carbons. The molecular weight is typically less than 500 g/mol, such as 400 g/mol or 300 g/mol. Examples of suitable polyols include, but are not limited to, glycerol, (mono, di, or tri) propylene glycol, ethylene glycol, polyethylene glycol (for example PEG 200-PEG 800), sugar alcohols, sorbitol, mannitol, erythritol, dulcitol, inositol, xylitol and adonitol.

The present invention further concerns a detergent composition comprising a polypeptide having DNase activity and preferably a detergent adjunct ingredient. The detergent composition can be used for preventing, reducing or removing biofilm from an item, for preventing, reducing or removing the stickiness of an item, for pretreating stains on the item, for preventing, reducing or removing redeposition of soil during a wash cycle, for reducing or removing adherence of soil to an item, for maintaining or improving the whiteness of an item and for preventing, reducing or removing malodor from an item, such as E-2-nonenal as described in Assay II. The detergent compositions comprising the polypeptides of the present invention overcomes the problems of the prior art.

The polypeptides of the invention having DNase activity are useful in powder and liquid detergent and show high performance in both types of detergents. This is surprising since the composition and condition of such detergents are very diverse and it shows the broad performance range of the polypeptides of the invention.

In one embodiment of the invention, the detergent composition comprises a DNase, selected from the group consisting of SEQ ID NO: 7, 8, 9 and 10, or a DNase having at least 60%, e.g., at least 70%, 80%, or 90% sequence identity thereto and a detergent adjunct.

In one embodiment of the invention, the detergent composition comprises a DNase, selected from the group consisting of SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 53, SEQ ID NO: 56, SEQ ID NO: 59, SEQ ID NO: 62, SEQ ID NO: 65, SEQ ID NO: 68, SEQ ID NO: 71, SEQ ID NO: 74, SEQ ID NO: 77, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 161, SEQ ID NO: 164, SEQ ID NO: 167, SEQ ID NO: 170, SEQ ID NO: 173, SEQ ID NO: 176, SEQ ID NO: 179, SEQ ID NO: 182, SEQ ID NO: 185, SEQ ID NO: 188, SEQ ID NO: 191, SEQ ID NO: 194 and SEQ ID NO: 197 or a DNase having at least 75%, e.g., at least 80%, at least 85%, at least 90%, at least 95%, at least 98%, or at least 99% sequence identity thereto and a detergent adjunct.

In one embodiment of the invention, the detergent adjunct ingredient is selected from the group consisting of surfactants, builders, flocculating aid, chelating agents, dye transfer inhibitors, enzymes, enzyme stabilizers, enzyme inhibitors, catalytic materials, bleach activators, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, builders and co-builders, fabric hueing agents, anti-foaming agents, dispersants, processing aids, and/or pigments.

The detergent adjunct ingredient may preferably be a surfactant. One advantage of including a surfactant in a detergent composition comprising a DNase is that the wash performance is improved. In one embodiment, the detergent adjunct ingredient is a builder. In another embodiment, the detergent adjunct is a clay soil removal/anti-redeposition agent.

In one embodiment, detergent adjunct ingredient is an enzyme. The detergent composition may in addition to a DNase of the invention comprise one or more enzymes, as specified below. The one or more enzymes may be selected from the group consisting of proteases, lipases, cutinases, amylases, carbohydrases, cellulases, pectinases, mannanases, arabinases, galactanases, xylanases and oxidases. Specific enzymes suitable for the detergent compositions of the invention are described below.

In one embodiment, the detergent composition is capable of reducing adhesion of bacteria selected from the group consisting of *Acinetobacter* sp., *Aeromicrobium* sp., *Brevundimonas* sp., *Microbacterium* sp., *Micrococcus luteus*, *Pseudomonas* sp., *Staphylococcus epidermidis*, and *Stenotrophomonas* sp. to a surface, or releasing the bacteria from a surface to which they adhere.

Biofilm growth in laundry items may originate from many organisms as described previously. One particular abundant bacterium in biofilm originates from *Brevundimonas*. The DNases of the invention are particularly effective in reducing the growth of the bacterium and reducing the malodor, stickiness and re-deposition coursed by these bacteria. One embodiment of the invention relates to the use of a DNase, selected from the group consisting of SEQ ID NO: 7, 8, 9 and 10 or a DNase having at least 60%, e.g., at least 70%, 80%, or 90% sequence identity thereto in reduction of malodor and reducing stickiness and re-deposition. One embodiment relates to the use in laundering of a DNase, selected from the group consisting of SEQ ID NO: 7, 8, 9 and 10 or a DNase having at least 60%, e.g., at least 70%, 80% or 90% sequence identity thereto, wherein the DNase reducing adhesion of bacteria, e.g., from *Brevundimonas*.

One embodiment of the invention relates to the use of a DNase, selected from the group consisting of SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 53, SEQ ID NO: 56, SEQ ID NO: 59, SEQ ID NO: 62, SEQ ID NO: 65, SEQ ID NO: 68, SEQ ID NO: 71, SEQ ID NO: 74, SEQ ID NO: 77, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 161, SEQ ID NO: 164, SEQ ID NO: 167, SEQ ID NO: 170, SEQ ID NO: 173, SEQ ID NO: 176, SEQ ID NO: 179, SEQ ID NO: 182, SEQ ID NO: 185, SEQ ID NO: 188, SEQ ID NO: 191, SEQ ID NO: 194 and SEQ ID NO: 197, or a DNase having at least 70%, e.g., at least 80%, at least 85%, at least 90% or 100% sequence identity thereto for reduction of malodor, stickiness and/or re-deposition. One embodiment relates to the use in laundering of a DNase, selected from the group consisting of SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 53, SEQ ID NO: 56, SEQ ID NO: 59, SEQ ID NO: 62, SEQ ID NO: 65, SEQ ID NO: 68, SEQ ID NO: 71, SEQ ID NO: 74, SEQ ID NO: 77, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 161, SEQ ID NO: 164, SEQ ID NO: 167, SEQ ID NO: 170, SEQ ID NO: 173, SEQ ID NO: 176, SEQ ID NO: 179, SEQ ID NO: 182, SEQ ID NO: 185, SEQ ID NO: 188, SEQ ID NO: 191, SEQ ID NO: 194 and SEQ ID NO: 197 or a DNase having at least 70%, e.g., at least 80%, at least 85%, at least 90% or 100% sequence identity thereto, wherein the DNase reducing adhesion of bacteria, e.g., from *Brevundimonas*.

In one embodiment of the invention, the surface is a textile surface. The textile can be made of cotton, Cotton/Polyester, Polyester, Polyamide, Polyacryl and/or silk.

One embodiment relates to a method for laundering a textile comprising the steps of:
a) Contacting the textile with a wash liquor comprising a DNase selected from the group consisting of the polypeptides having the amino acids sequence shown in SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 53, SEQ ID NO: 56, SEQ ID NO: 59, SEQ ID NO: 62, SEQ ID NO: 65, SEQ ID NO: 68, SEQ ID NO: 71, SEQ ID NO: 74, SEQ ID NO: 77, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 161, SEQ ID NO: 164, SEQ ID NO: 167, SEQ ID NO: 170, SEQ ID NO: 173, SEQ ID NO: 176, SEQ ID NO: 179, SEQ ID NO: 182, SEQ ID NO: 185, SEQ ID NO: 188, SEQ ID NO: 191, SEQ ID NO: 194 and SEQ ID NO: 197 or a DNase having at least 70%, e.g., at least 80%, at least 85%, at least 90% or 100% sequence identity thereto and a surfactant; and
b) optionally rinsing the textile,
wherein the textile comprises at least 20% polyester.

The detergent composition may be formulated as a bar, a homogenous tablet, and a tablet having two or more layers, a pouch having one or more compartments, a regular or compact powder, a granule, a paste, a gel, or a regular, compact or concentrated liquid. The detergent composition can be a liquid detergent, a powder detergent or a granule detergent.

The DNases of the invention are suitable for use in cleaning processes such as laundry. The invention further relates a method for laundering an item, which method comprises the steps of:
a. Exposing an item to a wash liquor comprising a polypeptide selected from the group consisting of polypeptides comprising SEQ ID NOS 7, 8, 9 and 10 or a DNase having at least 70%, e.g., at least 80%, at least 85%, at least 90% or 100% sequence identity thereto which have DNase activity or a detergent composition comprising the polypeptide;
b. Completing at least one wash cycle; and
c. Optionally rinsing the item, wherein the item is a textile.

The invention further relates a method for laundering an item, which method comprises the steps of:
a. Exposing an item to a wash liquor comprising a polypeptide selected from the group consisting of polypeptides having the amino acid sequence shown in SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23 SEQ ID NO: 53, SEQ ID NO: 56, SEQ ID NO: 59, SEQ ID NO: 62, SEQ ID NO: 65, SEQ ID NO: 68, SEQ ID NO: 71, SEQ ID NO: 74, SEQ ID NO: 77, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 161, SEQ ID NO: 164, SEQ ID NO: 167, SEQ ID NO: 170, SEQ ID NO: 173, SEQ ID NO: 176, SEQ ID NO: 179, SEQ ID NO: 182, SEQ ID NO: 185, SEQ ID NO: 188, SEQ ID NO: 191, SEQ ID NO: 194 and SEQ ID NO: 197 or a DNase having at least 70%, e.g., at least 80%, at least 85%, at least 90% or 100% sequence identity thereto, which have DNase activity or a detergent composition comprising the polypeptide;

b. Completing at least one wash cycle; and
c. Optionally rinsing the item, wherein the item is a textile.

The pH of the liquid solution is in the range of 1 to 11, such as in the range 5.5 to 11, such as in the range of 7 to 9, in the range of 7 to 8 or in the range of 7 to 8.5.

The wash liquor may have a temperature in the range of 5° C. to 95° C., or in the range of 10° C. to 80° C., in the range of 10° C. to 70° C., in the range of 10° C. to 60° C., in the range of 10° C. to 50° C., in the range of 15° C. to 40° C. or in the range of 20° C. to 30° C. In one embodiment the temperature of the wash liquor is 30° C.

In one embodiment of the invention, the method for laundering an item further comprises draining of the wash liquor or part of the wash liquor after completion of a wash cycle. The wash liquor can then be re-used in a subsequent wash cycle or in a subsequent rinse cycle. The item may be exposed to the wash liquor during a first and optionally a second or a third wash cycle. In one embodiment the item is rinsed after being exposed to the wash liquor. The item can be rinsed with water or with water comprising a conditioner.

The invention further concerns an item washed according to the inventive method.

The detergent composition comprising a polypeptide selected from the group consisting of polypeptides comprising SEQ ID NO: 7, 8, 9 and 10 or a DNase having at least 60%, e.g., at least 70%, 80% or 90% sequence identity thereto having DNase activity can be used for releasing or removing a biofilm or preventing biofilm formation.

The detergent composition comprising a polypeptide selected from the group consisting of polypeptides having the amino acid sequence shown in SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 53, SEQ ID NO: 56, SEQ ID NO: 59, SEQ ID NO: 62, SEQ ID NO: 65, SEQ ID NO: 68, SEQ ID NO: 71, SEQ ID NO: 74, SEQ ID NO: 77, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 161, SEQ ID NO: 164, SEQ ID NO: 167, SEQ ID NO: 170, SEQ ID NO: 173, SEQ ID NO: 176, SEQ ID NO: 179, SEQ ID NO: 182, SEQ ID NO: 185, SEQ ID NO: 188, SEQ ID NO: 191, SEQ ID NO: 194 and SEQ ID NO: 197 or a DNase having at least 70%, e.g., at least 80%, at least 85%, at least 90% or 100% sequence identity thereto, which have DNase activity, may be used for releasing or removing a biofilm or preventing biofilm formation.

The DNases of the invention may be added to a wash liquor.

Thus, one embodiment of the invention relates to a detergent composition comprising one or more anionic surfactants; an enzyme selected from the group consisting of: a protease, a lipase, a cutinase, an amylase, a carbohydrase, a cellulase, a pectinase, a mannanase, an arabinase, a galactanase, a xylanase, and an oxidase; and a DNase, selected from the group consisting of SEQ ID NO: 7, SEQ ID NO: 8, SEQ ID NO: 9, SEQ ID NO 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 53, SEQ ID NO: 56, SEQ ID NO: 59, SEQ ID NO: 62, SEQ ID NO: 65, SEQ ID NO: 68, SEQ ID NO: 71, SEQ ID NO: 74, SEQ ID NO: 77, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 161, SEQ ID NO: 164, SEQ ID NO: 167, SEQ ID NO: 170, SEQ ID NO: 173, SEQ ID NO: 176, SEQ ID NO: 179, SEQ ID NO: 182, SEQ ID NO: 185, SEQ ID NO: 188, SEQ ID NO: 191, SEQ ID NO: 194 and SEQ ID NO: 197 or a DNase having at least 70%, e.g., at least 80%, at least 85%, at least 90% or 100% sequence identity thereto.

One embodiment further relates to a washing method for textile comprising:
a. exposing a textile to a wash liquor comprising a DNase or a detergent composition comprising at least one of the DNases,
b. completing at least one wash cycle; and
c. optionally rinsing the textile,
wherein the DNase is selected from the group consisting of SEQ ID NO: 7, 8, 9 and 10 or a DNase having at least 60%, e.g., at least 70%, 80% or 90% sequence identity thereto.

One embodiment further relates to a washing method for textile comprising:
a. exposing a textile to a wash liquor comprising a DNase or a detergent composition comprising at least one of the DNases,
b. completing at least one wash cycle; and
c. optionally rinsing the textile,
wherein the DNase is selected from the group consisting of SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23 and SEQ ID NO: 53, SEQ ID NO: 56, SEQ ID NO: 59, SEQ ID NO: 62, SEQ ID NO: 65, SEQ ID NO: 68, SEQ ID NO: 71, SEQ ID NO: 74, SEQ ID NO: 77, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 161, SEQ ID NO: 164, SEQ ID NO: 167, SEQ ID NO: 170, SEQ ID NO: 173, SEQ ID NO: 176, SEQ ID NO: 179, SEQ ID NO: 182, SEQ ID NO: 185, SEQ ID NO: 188, SEQ ID NO: 191, SEQ ID NO: 194 and SEQ ID NO: 197 or a DNase having at least 70%, e.g., at least 80%, at least 85%, at least 90% or 100% sequence identity thereto.

Another embodiment relates to a textile washed according to the inventive method.

The concentration of the DNase in the wash liquor is typically in the range of 0.00004-100 ppm enzyme protein, such as in the range of 0.00008-100, in the range of 0.0001-100, in the range of 0.0002-100, in the range of 0.0004-100, in the range of 0.0008-100, in the range of 0.001-100 ppm enzyme protein, 0.01-100 ppm enzyme protein, preferably 0.05-50 ppm enzyme protein, more preferably 0.1-50 ppm enzyme protein, more preferably 0.1-30 ppm enzyme protein, more preferably 0.5-20 ppm enzyme protein, and most preferably 0.5-10 ppm enzyme protein.

The DNase of the present invention may be added to a detergent composition in an amount corresponding to at least 0.002 mg of DNase protein, such as at least 0.004 mg of DNase protein, at least 0.006 mg of DNase protein, at least 0.008 mg of DNase protein, at least 0.01 mg of DNase protein, at least 0.1 mg of protein, preferably at least 1 mg of protein, more preferably at least 10 mg of protein, even more preferably at least 15 mg of protein, most preferably at least 20 mg of protein, and even most preferably at least 25 mg of protein. Thus, the detergent composition may comprise at least 0.00008% DNase protein, preferably at least 0.002%, 0.003%, 0.004%, 0.005%, 0.006%, 0.008%, 0.01%, 0.02%, 0.03%, 0.05%, 0.1%, 0.2%, 0.3%, 0.4%, 0.6%, 0.7%, 0.8%, 0.9% or 1.0% of DNase protein.

Enzymes, e.g., protease present in a detergent of the invention may be stabilized using conventional stabilizing agents, e.g., a polyol such as propylene glycol or glycerol, a sugar or sugar alcohol, different salts such as NaCl or KCl. A polyol (or polyhydric alcohol) used according to the invention is an alcohol with two or more hydroxyl groups, for example alcohols with many hydroxyl groups. The polyol typically includes less than 10 carbons, such as 9, 8, 7, 6, 5, 4, or 3 carbons. The molecular weight is typically less than 500 g/mol, such as 400 g/mol or 300 g/mol. Examples of suitable polyols include, but are not limited to, glycerol, (mono, di, or tri) propylene glycol, ethylene glycol, polyethylene glycol (for example PEG 200-PEG 800), sugar alcohols, sorbitol, mannitol, erythritol, dulcitol, inositol, xylitol and adonitol. DNases present in the detergent of the invention may be stabilized by lactic acid, formic acid, boric acid, or a boric acid derivative, e.g., an aromatic borate ester, or a phenyl boronic acid derivative such as 4-formylphenyl boronic acid, or a peptide aldehyde such as di-, tri- or tetrapeptide aldehydes or aldehyde analogues (either of the form B1-B⁰-R wherein, R is H, CH3, CX3, CHX2, or CH2X (X=halogen), B⁰ is a single amino acid residue (preferably with an optionally substituted aliphatic or aromatic side chain); and 1 consists of one or more amino acid residues (preferably one, two or three), optionally comprising an N-terminal protection group, or as described in WO 2009/118375, WO 98/13459) or a protease inhibitor of the protein type such as RASI, BASI, WASI (bifunctional alpha-amylase/subtilisin inhibitors of rice, barley and wheat) or C12 or SSI. The composition may be formulated as described in, e.g., WO 92/19709, WO 92/19708 and U.S. Pat. No. 6,472,364. In some embodiments, the enzymes employed herein are stabilized by the presence of water-soluble sources of zinc (II), calcium (II) and/or magnesium (II) ions in the finished compositions that provide such ions to the enzymes, as well as other metal ions (e.g., barium (II), scandium (II), iron (II), manganese (II), aluminum (III), Tin (II), cobalt (II), copper (II), Nickel (II), and oxovanadium (IV)).

In one embodiment, the polypeptides are stabilized using peptide aldehydes or ketones Suitable peptide aldehydes are described in WO 94/04651, WO 95/25791, WO 98/13458, WO 98/13459, WO 98/13460, WO 98/13461, WO 98/13462, WO 2007/141736, WO 2007/145963, WO 2009/118375, WO 2010/055052 and WO 2011/036153. A polypeptide of the present invention may also be incorporated in the detergent formulations disclosed in WO 97/07202, which is hereby incorporated by reference.

In another embodiment, the polypeptides are stabilized using a phenyl boronic acid derivative is 4-formylphenyl-boronic acid (4-FPBA) with the following formula:

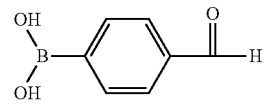

The detergent compositions may comprise two or more stabilizing agents, e.g., such as those selected from the group consisting of propylene glycol, glycerol, 4-formylphenyl boronic acid and borate.

The detergent compositions may comprise two or more stabilizing agents, e.g., such as those selected from the group consisting of propylene glycol, glycerol, 4-formylphenyl boronic acid and borate.

The stabilizing agent(s) is preferably present in the detergent composition in a quantity of from 0.001 to about 5.0 wt %, from 0.01 to about 2.0 wt %, from 0.1 to about 3 wt % or from 0.5 to about 1.5 wt %.

Liquid Detergent Compositions

The DNases of the invention may also be formulated in liquid laundry compositions such as a liquid laundry compositions composition comprising:
   a) at least 0.002 mg, preferably at least 0.005 mg of active DNase protein per litre detergent wherein the DNase is a polypeptide selected from a list consisting of SEQ ID NO: 7, SEQ ID NO: 8, SEQ ID NO: 9 and SEQ ID NO: 10 or a DNase having at least 70%, e.g., at least 80%, at least 85%, at least 90% or 100% sequence identity thereto,
   b) 2 wt % to 60 wt % of at least one surfactant, and/or
   c) 5 wt % to 50 wt % of at least one builder The DNases of the invention may also be formulated in liquid laundry compositions such as a liquid laundry compositions composition comprising:
   a) at least 0.002 ppm active DNase, wherein the DNase is selected from a polypeptide comprising SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 53, SEQ ID NO: 56, SEQ ID NO: 59, SEQ ID NO: 62, SEQ ID NO: 65, SEQ ID NO: 68, SEQ ID NO: 71, SEQ ID NO: 74, SEQ ID NO: 77, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 161, SEQ ID NO: 164, SEQ ID NO: 167, SEQ ID NO: 170, SEQ ID NO: 173, SEQ ID NO: 176, SEQ ID NO: 179, SEQ ID NO: 182, SEQ ID NO: 185, SEQ ID NO: 188, SEQ ID NO: 191, SEQ ID NO: 194 and SEQ ID NO: 197 or a DNase having at least 70%, e.g., at least 80% at least 85% at least 90% or 100% sequence identity thereto, b) 2 wt % to 60 wt % of one or more surfactants, and/or c) 5 wt % to 50 wt % of one or more builders.

One aspect of the invention relates to a liquid laundry compositions composition comprising:

a) at least 0.002 ppm active DNase, wherein the DNase is selected from a polypeptide comprising SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 53, SEQ ID NO: 56, SEQ ID NO: 59, SEQ ID NO: 62, SEQ ID NO: 65, SEQ ID NO: 68, SEQ ID NO: 71, SEQ ID NO: 74, SEQ ID NO: 77, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 161, SEQ ID NO: 164, SEQ ID NO: 167, SEQ ID NO: 170, SEQ ID NO: 173, SEQ ID NO: 176, SEQ ID NO: 179, SEQ ID NO: 182, SEQ ID NO: 185, SEQ ID NO: 188, SEQ ID NO: 191, SEQ ID NO: 194 and SEQ ID NO: 197 or a DNase having at least 70%, e.g., at least 80% at least 85%, at least 90% or 100% sequence identity thereto, b) 2 wt % to 60 wt % of one or more surfactants, and/or c) 5 wt % to 50 wt % of one or more builders, provided that the polypeptide is not the *Trichoderma harzianum* DNase shown in SEQ ID NO: 2 of WO 2015/155351.

The surfactant may be selected among nonionic, anionic and/or amphoteric surfactants as described above, preferably anionic or nonionic surfactants but also amphoteric surfactants may be used. In general, bleach-stable surfactants are preferred. Preferred anionic surfactants are sulphate surfactants and in particular alkyl ether sulphates, especially C-9-15 alcohol ethersulfates, C12-15 primary alcohol ethoxylate, C8-C16 ester sulphates and C10-C14 ester sulphates, such as mono dodecyl ester sulphates Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diyl-bis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or salt of fatty acids (soap), and combinations thereof.

The anionic surfactants are preferably added to the detergent in the form of salts. Suitable cations in these salts are alkali metal ions, such as sodium, potassium and lithium and ammonium salts, for example (2-hydroxyethyl)ammonium, bis(2-hydroxyethyl)ammonium and tris(2-hydroxyethyl) ammonium salts. Non-limiting examples of nonionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides, FAGA), as well as products available under the trade names SPAN and TWEEN, and combinations thereof. Commercially available nonionic surfactants include Plurafac™, Lutensol™ and Pluronic™ range from BASF, Dehypon™ series from Cognis and Genapol™ series from Clariant.

The builder is preferably selected among phosphates, sodium citrate builders, sodium carbonate, sodium silicate, sodium aluminosilicate (zeolite). Suitable builders are alkali metal or ammonium phosphates, polyphosphates, phosphonates, polyphosphates, carbonates, bicarbonates, borates, citrates, and polycarboxylates. Citrate builders, e.g., citric acid and soluble salts thereof (particularly sodium salt), are polycarboxylate builders. Citrates can be used in combination with zeolite, silicates like the BRITESIL types, and/or layered silicate builders. The builder is preferably added in an amount of about 0-65% by weight, such as about 5% to about 50% by weight. In a laundry detergent, the level of builder is typically about 40-65% by weight, particularly about 50-65% by weight, particularly from 20% to 50% by weight. The builder and/or co-builder may particularly be a chelating agent that forms water-soluble complexes with Ca and Mg. Any builder and/or co-builder known in the art for use in cleaning detergents may be utilized. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), and (carboxymethyl) inulin (CMI), and combinations thereof. Further non-limiting examples of builders include citrate, chelators such as aminocarboxylates, aminopolycarboxylates and phosphonates, and alkyl- or alkenylsuccinic acid. Additional specific examples include 2,2',2"-nitrilotriacetic acid (NTA), ethylenediaminetetraacetic acid (EDTA), diethylenetriaminepentaacetic acid (DTPA), iminodisuccinic acid (IDS), ethylenediamine-N,N'-disuccinic acid (EDDS), methylglycine-N,N-diaceticacid (MGDA), glutamic acid-N,N-diacetic acid (GLDA), 1-hydroxyethane-1,1-diphosphonicacid, N-(2-hydroxyethyl)iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(sulfomethyl)aspartic acid (SMAS), N-(2-sulfoethyl)-aspartic acid (SEAS), N-(sulfomethylglutamic acid (SMGL), N-(2-sulfoethyl)-glutamicacid (SEGL), N-methyliminodiacetic acid (MIDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and N'-(2-hydroxyethyl)ethylenediamine-N,N,N'-triacetic acid (HEDTA), diethanolglycine (DEG), and combinations and salts thereof.

Phosphonates suitable for use herein include 1-hydroxyethane-1,1-diphosphonic acid (HEDP), ethylenediaminetetrakis(methylenephosphonic acid) (EDTMPA), diethylenetriaminepentakis(methylenephosphonic acid) (DTMPA or DTPMPA or DTPMP), nitrilotris(methylenephosphonic acid) (ATMP or NTMP), 2-phosphonobutane-1,2,4-tricarboxylic acid (PBTC), hexamethylenediaminetetrakis(methylenephosphonic acid) (HDTMP).

The composition may also contain 0-50% by weight, such as about 5% to about 30%, of a detergent co-builder.

The detergent composition may include a co-builder alone, or in combination with a builder, for example a zeolite builder. Non-limiting examples of co-builders include homopolymers of polyacrylates or copolymers thereof, such as poly(acrylic acid) (PAA) or copoly(acrylic acid/maleic acid) (PAA/PMA) or polyaspartic acid.

Further exemplary builders and/or co-builders are described in, e.g., WO 2009/102854, U.S. Pat. No. 5,977,053.

In one preferred embodiment, the builder is a non-phosphorus based builder such as citric acid and/or methylglycine-N,N-diacetic acid (MGDA) and/or glutamic-N,N-diacetic acid (GLDA) and/or salts thereof.

The laundry composition may also be phosphate free in the instance the preferred builders includes citrate and/or methylglycine-N,N-diacetic acid (MGDA) and/or glutamic-N,N-diacetic acid (GLDA) and/or salts thereof.

One embodiment of the invention concerns a liquid laundry compositions composition comprising:
- a) at least 0.002 ppm active DNase, wherein the DNase is selected from a polypeptide comprising SEQ ID NO: 7, SEQ ID NO: 8, SEQ ID NO: 9, SEQ ID NO: 10 or DNases having at least 60%, e.g., at least 70%, 80%, or 90% sequence identity thereto,
- b) 1% to 15% by weight of one or more surfactant wherein the surfactant is LAS, AEOS and/or SLES, and/or
- c) 5% to 50% by weight of one or more builder selected from HEDP, DTMPA or DTPMPA.

One embodiment of the invention concerns a liquid laundry compositions composition comprising:
- a) at least 0.002 ppm active DNase, wherein the DNase is selected from a polypeptide comprising SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 53, SEQ ID NO: 56, SEQ ID NO: 59, SEQ ID NO: 62, SEQ ID NO: 65, SEQ ID NO: 68, SEQ ID NO: 71, SEQ ID NO: 74, SEQ ID NO: 77, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 161, SEQ ID NO: 164, SEQ ID NO: 167, SEQ ID NO: 170, SEQ ID NO: 173, SEQ ID NO: 176, SEQ ID NO: 179, SEQ ID NO: 182, SEQ ID NO: 185, SEQ ID NO: 188, SEQ ID NO: 191, SEQ ID NO: 194 and SEQ ID NO: 197 or DNases having at least 60%, e.g., at least 70%, 80% or 90% sequence identity thereto,
- b) 1% to 15% by weight of at least one surfactant wherein the surfactant is LAS, AEOS and/or SLES, and/or
- c) 5% to 50% by weight of at least one builder selected from HEDP, DTMPA or DTPMPA.

The liquid detergent composition may typically contain at least 20% by weight and up to 95% water, such as up to 70% water, up to 50% water, up to 40% water, up to 30% water, or up to 20% water. Other types of liquids, including without limitation, alkanols, amines, diols, ethers and polyols may be included in an aqueous liquid detergent. An aqueous liquid detergent may contain from 0-30% organic solvent. A liquid detergent may even be non-aqueous, wherein the water content is below 10%, preferably below 5%.

Powder Compositions

The detergent composition may also be formulated into a granular detergent for laundry or dish wash. One embodiment of the invention concerns a granular detergent composition comprising
- a) at least 0.002 ppm active DNase, wherein the DNase is selected from a polypeptide comprising SEQ ID NO: 7, SEQ ID NO: 8, SEQ ID NO: 9, SEQ ID NO: 10, or a DNase having at least 60%, e.g., at least 70%, 80%, or 90% sequence identity thereto,
- b) 5 wt % to 50 wt % anionic surfactant, and/or
- c) 1 wt % to 8 wt % nonionic surfactant, and/or
- d) 5 wt % to 40 wt % builder such as carbonates, zeolites, phosphate builder, calcium sequestering builders or complexing agents.

One embodiment of the invention concerns a granular detergent composition comprising
- a) at least 0.002 ppm active DNase, wherein the DNase is selected from a polypeptide comprising SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 53, SEQ ID NO: 56, SEQ ID NO: 59, SEQ ID NO: 62, SEQ ID NO: 65, SEQ ID NO: 68, SEQ ID NO: 71, SEQ ID NO: 74, SEQ ID NO: 77, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 161, SEQ ID NO: 164, SEQ ID NO: 167, SEQ ID NO: 170, SEQ ID NO: 173, SEQ ID NO: 176, SEQ ID NO: 179, SEQ ID NO: 182, SEQ ID NO: 185, SEQ ID NO: 188, SEQ ID NO: 191, SEQ ID NO: 194 and SEQ ID NO: 197 or a DNase having at least 60%, e.g., at least 70%, 80% or 90% sequence identity thereto,
- b) 5 wt % to 50 wt % anionic surfactant and/or
- c) 1 wt % to 8 wt % nonionic surfactant, and/or
- d) 5 wt % to 40 wt % builder such as carbonates, zeolites, phosphate builder, calcium sequestering builders or complexing agents.

The surfactant may be selected among nonionic, anionic and/or amphoteric surfactants as described above, preferably anionic or nonionic surfactants but also amphoteric surfactants may be used. In general, bleach-stable surfactants are preferred. Preferred anionic surfactants are sulphate surfactants and in particular alkyl ether sulphates, especially C-9-15 alcohol ethersulfates, C12-15 primary alcohol ethoxylate, C8-C16 ester sulphates and C10-C14 ester sulphates, such as mono dodecyl ester sulphates Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diyl-bis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or salt of fatty acids (soap), and combinations thereof.

The anionic surfactants are preferably added to the detergent in the form of salts. Suitable cations in these salts are alkali metal ions, such as sodium, potassium and lithium and ammonium salts, for example (2-hydroxyethyl)ammonium, bis(2-hydroxyethyl)ammonium and tris(2-hydroxyethyl) ammonium salts.

Non-limiting examples of nonionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides, FAGA), as well as products available under the trade names SPAN and TWEEN, and combinations thereof.

Commercially available nonionic surfactants include Plurafac™, Lutensol™ and Pluronic™ range from BASF, Dehypon™ series from Cognis and Genapol™ series from Clariant.

The builder may be non-phosphate such as citrate preferably as a sodium salt and/or a zeolite. Phosphonate builder may be any of those described above.

The builder is preferably selected among phosphates and sodium citrate builders, sodium carbonate, sodium silicate, sodium aluminosilicate (zeolite) as described above. Suitable builders are described above and include alkali metal or ammonium phosphates, polyphosphates, phosphonates, polyphosphonates, carbonates, bicarbonates, borates, polyhydroxysulfonates, polyacetates, carboxylates, citrates, and polycarboxylates. Citrate builders, e.g., citric acid and soluble salts thereof (particularly sodium salt), are polycarboxylate builders. The builder is preferably added in an amount of about 0-65% by weight, such as about 5% to about 50% by weight, such as 5 to 40% by weight, such as 10 to 40% by weight, such as 10 to 30% by weight, such as 15 to 20% by weight or such as 20 to 40% by weight. The builder may be a phosphonate builder including 1-hydroxyethane-1,1-diphosphonic acid (HEDP), ethylenediaminetetra (methylenephosphonic acid) (EDTMPA), diethylentriaminepentakis (methylenephosphonic acid) (DTMPA or DTPMPA), diethylenetriamine penta (methylenephosphonic acid) (DTPMP), aminotris(methylenephosphonic acid) (ATMP), 2-phosphonobutane-1,2,4-tricarboxylic acid (PBTC) and hexamethylenediaminetetra (methylenephosphonic acid) (HDTMP). Preferred phosphonates include 1-hydroxyethane-1,1-diphosphonic acid (HEDP) and/or diethylenetriaminepentakis (methylenephosphonic acid) (DTMPA or DTPMPA). The phosphonate is preferably added in an amount of about in a level of from about 0.01% to about 10% by weight, preferably from 0.1% to about 5% by weight, more preferably from 0.5% to 3% by weight of the composition.

The laundry composition may also be phosphate free in the instance the preferred builders include citrate, carbonates and/or sodium aluminosilicate (zeolite).

The detergent may contain 0-30% by weight, such as about 1% to about 20%, of a bleaching system. Any bleaching system comprising components known in the art for use in cleaning detergents may be utilized. Suitable bleaching system components include sources of hydrogen peroxide; sources of peracids; and bleach catalysts or boosters.

Sources of hydrogen peroxide: Suitable sources of hydrogen peroxide are inorganic persalts, including alkali metal salts such as sodium percarbonate and sodium perborates (usually mono- or tetrahydrate), and hydrogen peroxide-urea (1/1).

Sources of peracids: Peracids may be (a) incorporated directly as preformed peracids or (b) formed in situ in the wash liquor from hydrogen peroxide and a bleach activator (perhydrolysis) or (c) formed in situ in the wash liquor from hydrogen peroxide and a perhydrolase and a suitable substrate for the latter, e.g., an ester.

a) Suitable preformed peracids include, but are not limited to, peroxycarboxylic acids such as peroxybenzoic acid and its ring-substituted derivatives, peroxy-α-naphthoic acid, peroxyphthalic acid, peroxylauric acid, peroxystearic acid, ε-phthalimidoperoxycaproic acid [phthalimidoperoxyhexanoic acid (PAP)], and o-carboxybenzamidoperoxycaproic acid; aliphatic and aromatic diperoxydicarboxylic acids such as diperoxydodecanedioic acid, diperoxyazelaic acid, diperoxysebacic acid, diperoxybrassylic acid, 2-decyl-diperoxybutanedioic acid, and diperoxyphthalic, -isophthalic and -terephthalic acids; perimidic acids; peroxymonosulfuric acid; peroxydisulfuric acid; peroxyphosphoric acid; peroxysilicic acid; and mixtures of said compounds. It is understood that the peracids mentioned may in some cases be best added as suitable salts, such as alkali metal salts (e.g., Oxone®) or alkaline earth-metal salts.

b) Suitable bleach activators include those belonging to the class of esters, amides, imides, nitriles or anhydrides and, where applicable, salts thereof. Suitable examples are tetraacetylethylenediamine (TAED), sodium 4-[(3,5,5-trimethylhexanoyl)oxy]benzene-1-sulfonate (ISONOBS), sodium 4-(dodecanoyloxy)benzene-1-sulfonate (LOBS), sodium 4-(decanoyloxy) benzene-1-sulfonate, 4-(decanoyloxy)benzoic acid (DOBA), sodium 4-(nonanoyloxy)benzene-1-sulfonate (NOBS), and/or those disclosed in WO 98/17767. A particular family of bleach activators of interest was disclosed in EP 624154 and particularly preferred in that family is acetyl triethyl citrate (ATC). ATC or a short chain triglyceride like triacetin has the advantage that they are environmentally friendly. Furthermore, acetyl triethyl citrate and triacetin have good hydrolytical stability in the product upon storage and are efficient bleach activators. Finally, ATC is multifunctional, as the citrate released in the perhydrolysis reaction may function as a builder.

Bleach catalysts and boosters: The bleaching system may also include a bleach catalyst or booster. Some non-limiting examples of bleach catalysts that may be used in the compositions of the present invention include manganese oxalate, manganese acetate, manganese-collagen, cobalt-amine catalysts and manganese triazacyclononane (Mn-TACN) catalysts; particularly preferred are complexes of manganese with 1,4,7-trimethyl-1,4,7-triazacyclononane (Me3-TACN) or 1,2,4,7-tetramethyl-1,4,7-triazacyclononane (Me4-TACN), in particular Me3-TACN, such as the dinuclear manganese complex [(Me3-TACN)Mn(O)3Mn(Me3-TACN)](PF6)2, and [2,2',2"-nitrilotris(ethane-1,2-diylazanylylidene-κN-methanylylidene)triphenolato-κ3O] manganese(III). The bleach catalysts may also be other metal compounds, such as iron or cobalt complexes.

In some embodiments, where a source of a peracid is included, an organic bleach catalyst or bleach booster may be used having one of the following formulae:

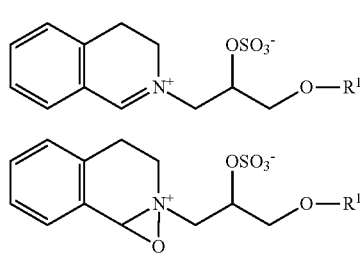

(iii) and mixtures thereof;

wherein each R1 is independently a branched alkyl group containing from 9 to 24 carbons or linear alkyl group containing from 11 to 24 carbons, preferably each R1 is independently a branched alkyl group containing from 9 to 18 carbons or linear alkyl group containing from 11 to 18 carbons, more preferably each R1 is independently selected from the group consisting of 2-propylheptyl, 2-butyloctyl, 2-pentylnonyl, 2-hexyldecyl, dodecyl, tetradecyl, hexadecyl, octadecyl, isononyl, isodecyl, isotridecyl and isopentadecyl.

Other exemplary bleaching systems are described, e.g., in WO 2007/087258, WO 2007/087244, WO 2007/087259, EP 1867708 (Vitamin K) and WO 2007/087242. Suitable photobleaches may for example be sulfonated zinc or aluminium phthalocyanines.

According to one embodiment and any of the previous embodiments the invention also relates to a cleaning composition comprising:
a) at least 0.002 mg, preferably at least 0.005 mg of active DNase per gram of composition wherein the DNase is selected from a polypeptide comprising SEQ ID NO: 7, SEQ ID NO: 8, SEQ ID NO: 9 and SEQ ID NO: 10 or a DNase having at least 60%, e.g., at least 70%, 80% or 90% sequence identity thereto,
b) 10-50 wt % builder and/or
c) at least one bleach component, wherein the bleach is a peroxide and the bleach catalyst is a manganese compound.

According to one embodiment and any of the previous embodiments the invention also relates to a cleaning composition comprising:
a) at least 0.002 ppm active DNase, wherein the DNase is selected from a polypeptide comprising SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 53, SEQ ID NO: 56, SEQ ID NO: 59, SEQ ID NO: 62, SEQ ID NO: 65, SEQ ID NO: 68, SEQ ID NO: 71, SEQ ID NO: 74, SEQ ID NO: 77, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 161, SEQ ID NO: 164, SEQ ID NO: 167, SEQ ID NO: 170, SEQ ID NO: 173, SEQ ID NO: 176, SEQ ID NO: 179, SEQ ID NO: 182, SEQ ID NO: 185, SEQ ID NO: 188, SEQ ID NO: 191, SEQ ID NO: 194 and SEQ ID NO: 197 or a DNase having at least 60%, e.g., at least 70%, 80% or 90% sequence identity thereto,
b) 5-50 wt % builder and/or
c) at least one bleach component, wherein the bleach is a peroxide and the bleach catalyst is a manganese compound.

The oxygen bleach is preferably percarbonate and the manganese catalyst preferably 1,4,7-trimethyl-1,4,7-triazacyclononane or manganese (III) acetate tetrahydrate.

According to one embodiment and any of the previous embodiments the invention also relates to a cleaning composition comprising:
a) at least 0.002 ppm active DNase, wherein the DNase is selected from a polypeptide comprising SEQ ID NO: 7, SEQ ID NO: 8, SEQ ID NO: 9 and SEQ ID NO: 10 or a DNase having at least 60%, e.g., at least 70%, 80% or 90% sequence identity thereto,
b) 10-50 wt % builder selected from citric acid, methyl glycine-N,N-diacetic acid (MGDA) and/or glutamic-N,N-diacetic acid (GLDA) and mixtures thereof, and/or
c) at least one bleach component, wherein the bleach is an oxygen bleach and the bleach catalyst is a manganese compound.

According to one embodiment and any of the previous embodiments the invention also relates to a cleaning composition comprising:
a) at least 0.002 ppm active DNase, wherein the DNase is selected from a polypeptide comprising SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 53, SEQ ID NO: 56, SEQ ID NO: 59, SEQ ID NO: 62, SEQ ID NO: 65, SEQ ID NO: 68, SEQ ID NO: 71, SEQ ID NO: 74, SEQ ID NO: 77, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 161, SEQ ID NO: 164, SEQ ID NO: 167, SEQ ID NO: 170, SEQ ID NO: 173, SEQ ID NO: 176, SEQ ID NO: 179, SEQ ID NO: 182, SEQ ID NO: 185, SEQ ID NO: 188, SEQ ID NO: 191, SEQ ID NO: 194 and SEQ ID NO: 197 or a DNase having at least 60%, e.g., at least 70%, 80% or 90% sequence identity thereto, b) 10-50 wt % builder selected from citric acid, methyl glycine-N,N-diacetic acid (MGDA) and/or glutamic-N,N-diacetic acid (GLDA) and mixtures thereof, and/or c) at least one bleach component, wherein the bleach is an oxygen bleach and the bleach catalyst is a manganese compound.

The oxygen bleach is preferably percarbonate and the manganese catalyst preferably 1,4,7-trimethyl-1,4,7-triaza-cyclo-nonane or manganese (II) acetate tetrahydrate.

According to one embodiment and any of the previous embodiments the invention also relates to a cleaning composition comprising:

a) at least 0.002 ppm active DNase, wherein the DNase is selected from a polypeptide comprising SEQ ID NO: 7, SEQ ID NO: 8, SEQ ID NO: 9 and SEQ ID NO: 10 or a DNase having at least 60%, e.g., at least 70%, 80% or 90% sequence identity thereto, b) 10-50 wt % builder selected from citric acid, methyl glycine-N,N-diacetic acid (MGDA) and/or glutamic-N,N-diacetic acid (GLDA) and mixtures thereof, and/or c) 0.1-40 wt %, preferably from 0.5-30 wt %, of bleaching components, wherein the bleach components are a peroxide, preferably percabonate and a metal-containing bleach catalyst preferably 1,4,7-trimethyl-1,4,7-triazacyclononane or manganese (II) acetate tetrahydrate (MnTACN).

According to one embodiment and any of the previous embodiments the invention also relates to a cleaning composition comprising:

a) at least 0.002 ppm active DNase, wherein the DNase is selected from a polypeptide comprising SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 53, SEQ ID NO: 56, SEQ ID NO: 59, SEQ ID NO: 62, SEQ ID NO: 65, SEQ ID NO: 68, SEQ ID NO: 71, SEQ ID NO: 74, SEQ ID NO: 77, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 161, SEQ ID NO: 164, SEQ ID NO: 167, SEQ ID NO: 170, SEQ ID NO: 173, SEQ ID NO: 176, SEQ ID NO: 179, SEQ ID NO: 182, SEQ ID NO: 185, SEQ ID NO: 188, SEQ ID NO: 191, SEQ ID NO: 194 and SEQ ID NO: 197 or a DNase having at least 60%, e.g., at least 70%, 80% or 90% sequence identity thereto, b) 10-50 wt % builder selected from citric acid, methyl glycine-N,N-diacetic acid (MGDA) and/or glutamic-N,N-diacetic acid (GLDA) and mixtures thereof, and/or c) 0.1-40 wt %, preferably from 0.5-30 wt %, of bleaching components, wherein the bleach components are a peroxide, preferably percabonate and a metal-containing bleach catalyst preferably 1,4,7-trimethyl-1,4,7-triazacyclononane or manganese (II) acetate tetrahydrate (MnTACN).

The choice of detergent components may include, for textile care, the consideration of the type of textile to be cleaned, the type and/or degree of soiling, the temperature at which cleaning is to take place, and the formulation of the detergent product. Although components mentioned below are categorized by general header according to a particular functionality, this is not to be construed as a limitation, as a component may comprise additional functionalities as will be appreciated by the skilled artisan, including the exemplary non-limiting components set forth below.

Hydrotropes

The cleaning composition may contain 0-10% by weight, for example 0-5% by weight, such as about 0.5 to about 5%, or about 3% to about 5%, of a hydrotrope. Any hydrotrope known in the art for use in detergents may be utilized. Non-limiting examples of hydrotropes include sodium benzenesulfonate, sodium p-toluene sulfonate (STS), sodium xylene sulfonate (SXS), sodium cumene sulfonate (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

Polymers

The cleaning composition may contain 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide antiredeposition, fibre protection, soil release, dye transfer inhibition, grease cleaning and/or anti-foaming properties. Some polymers may have more than one of the above-mentioned properties and/or more than one of the below-mentioned motifs. Exemplary polymers include (carboxymethyl)cellulose (CMC), poly(vinyl alcohol) (PVA), poly(vinylpyrrolidone) (PVP), poly(ethyleneglycol) or poly(ethylene oxide) (PEG), ethoxylated poly(ethyleneimine), carboxymethyl inulin (CMI), and polycarboxylates such as PAA, PAA/PMA, polyaspartic acid, and lauryl methacrylate/acrylic acid copolymers, hydrophobically modified CMC (HM-CMC) and silicones, copolymers of terephthalic acid and oligomeric glycols, copolymers of poly(ethylene terephthalate) and poly(oxyethene terephthalate) (PET-POET), PVP, poly(vinylimidazole) (PVI), poly(vinylpyridine-N-oxide) (PVPO or PVPNO) and polyvinylpyrrolidone-vinylimidazole (PVPVI). Further exemplary polymers include sulfonated polycarboxylates, polyethylene oxide and polypropylene oxide (PEO-PPO) and diquaternium ethoxy sulfate. Other exemplary polymers are disclosed in, e.g., WO 2006/130575. Salts of the above-mentioned polymers are also contemplated.

Fabric Hueing Agents

The cleaning compositions of the present invention may also include fabric hueing agents such as dyes or pigments, which when formulated in detergent compositions can deposit onto a fabric when said fabric is contacted with a wash liquor comprising said detergent compositions and thus, altering the tint of said fabric through absorption/ reflection of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO 2005/003274, WO 2005/003275, WO 2005/003276 and EP 1876226 (hereby incorporated by reference). The detergent composition preferably comprises from about 0.00003 wt % to about 0.2 wt %, from about 0.00008 wt % to about 0.05 wt %, or even from about 0.0001 wt % to about 0.04 wt % fabric hueing agent. The composition may comprise from 0.0001 wt % to 0.2 wt % fabric hueing agent, this may be especially preferred when the composition is in the form of a unit dose pouch. Suitable hueing agents are also disclosed in, e.g., WO 2007/087257 and WO 2007/087243.

Enzymes

The cleaning compositions of the invention may comprise one or more additional enzymes such as a protease, lipase, cutinase, an amylase, carbohydrase, cellulase, pectinase, mannanase, arabinase, galactanase, xylanase, oxidase, e.g., a laccase, and/or peroxidase.

In general, the properties of the selected enzyme(s) should be compatible with the selected detergent, (i.e., pH-optimum, compatibility with other enzymatic and non-enzymatic ingredients, etc.), and the enzyme(s) should be present in effective amounts.

Cellulases

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and WO 99/01544.

Other cellulases are endo-beta-1,4-glucanase enzyme having a sequence of at least 97% identity to the amino acid sequence of position 1 to position 773 of SEQ ID NO:2 of WO 2002/099091 or a family 44 xyloglucanase, which a xyloglucanase enzyme having a sequence of at least 60% identity to positions 40-559 of SEQ ID NO: 2 of WO 2001/062903.

Commercially available cellulases include Celluzyme™, and Carezyme™ (Novozymes A/S) Carezyme Premium™ (Novozymes A/S), Celluclean™ (Novozymes A/S), Celluclean Classic™ (Novozymes A/S), Cellusoft™ (Novozymes A/S), Whitezyme™ (Novozymes A/S), Clazinase™, and Puradax HA™ (Genencor International Inc.), and KAC-500(B)™ (Kao Corporation).

Proteases

Suitable proteases include those of bacterial, fungal, plant, viral or animal origin, e.g., vegetable or microbial origin. Microbial origin is preferred. Chemically modified or protein engineered mutants are included. It may be an alkaline protease, such as a serine protease or a metalloprotease. A serine protease may for example be of the S1 family, such as trypsin, or the S8 family such as subtilisin. A metalloproteases protease may for example be a thermolysin from, e.g., family M4 or other metalloprotease such as those from M5, M7 or M8 families.

The term "subtilases" refers to a sub-group of serine protease according to Siezen et al., 1991, *Protein Engng.* 4: 719-737 and Siezen et al., 1997, *Protein Science* 6: 501-523. Serine proteases are a subgroup of proteases characterized by having a serine in the active site, which forms a covalent adduct with the substrate. The subtilases may be divided into 6 sub-divisions, i.e., the Subtilisin family, the Thermitase family, the Proteinase K family, the Lantibiotic peptidase family, the Kexin family and the Pyrolysin family.

Examples of subtilases are those obtained from *Bacillus* such as *Bacillus lentus, B. alkalophilus, B. subtilis, B. amyloliquefaciens, Bacillus pumilus* and *Bacillus gibsonii* described in; U.S. Pat. No. 7,262,042 and WO 2009/021867, and subtilisin *lentus*, subtilisin Novo, subtilisin Carlsberg, *Bacillus licheniformis*, subtilisin BPN', subtilisin 309, subtilisin 147 and subtilisin 168 described in WO 89/06279 and protease PD138 described in (WO 93/18140). Other useful proteases may be those described in WO 92/175177, WO 01/16285, WO 02/026024 and WO 02/016547. Examples of trypsin-like proteases are trypsin (e.g., of porcine or bovine origin) and the *Fusarium* protease described in WO 89/06270, WO 94/25583 and WO 2005/040372, and the chymotrypsin proteases obtained from *Cellulomonas* described in WO 2005/052161 and WO 2005/052146.

A further preferred protease is the alkaline protease from *Bacillus lentus* DSM 5483, as described for example in WO 95/23221, and variants thereof which are described in WO 92/21760, WO 95/23221, EP 1921147 and EP 1921148.

Examples of metalloproteases are the neutral metalloprotease as described in WO 2007/044993 (Genencor Int.) such as those obtained from *Bacillus amyloliquefaciens*.

Examples of useful proteases are the variants described in: WO 92/19729, WO 96/34946, WO 98/20115, WO 98/20116, WO 99/11768, WO 01/44452, WO 03/06602, WO 2004/03186, WO 2004/041979, WO 2007/006305, WO 2011/036263, WO 2011/036264, especially the variants with substitutions in one or more of the following positions: 3, 4, 9, 15, 27, 36, 57, 68, 76, 87, 95, 96, 97, 98, 99, 100, 101, 102, 103, 104, 106, 118, 120, 123, 128, 129, 130, 160, 167, 170, 194, 195, 199, 205, 206, 217, 218, 222, 224, 232, 235, 236, 245, 248, 252 and 274 using subtilisin BPN' numbering. More preferred the subtilase variants may comprise the mutations: S3T, V4I, S9R, A15T, K27R, *36D, V68A, N76D, N87S,R, *97E, A98S, S99G,D,A, S99AD, S101G, M,R S103A, V104I,Y,N, S106A, G118V,R, H120D,N, N123S, S128L, P129Q, S130A, G160D, Y167A, R170S, A194P, G195E, V199M, V205I, L217D, N218D, M222S, A232V, K235L, Q236H, Q245R, N252K, T274A (using BPN' numbering).

Specific examples of useful proteases are the variants described in: WO 92/19729, WO 96/034946, WO 98/20115, WO 98/20116, WO 99/11768, WO 01/44452, WO 03/006602, WO 2004/03186, WO 2004/041979, WO 2007/006305, WO 2011/036263, WO 2011/036264, especially the variants with substitutions in one or more of the following positions: 3, 4, 9, 15, 24, 27, 42, 55, 59, 60, 66, 74, 85, 96, 97, 98, 99, 100, 101, 102, 104, 116, 118, 121, 126, 127, 128, 154, 156, 157, 158, 161, 164, 176, 179, 182, 185, 188, 189, 193,198, 199, 200, 203, 206, 211, 212, 216, 218, 226, 229, 230, 239, 246, 255, 256, 268 and 269 wherein the positions correspond to the positions of the *Bacillus lentus* protease shown in SEQ ID NO: 1 of WO 2016/001449. More preferred the subtilase variants may comprise the mutations: S3T, V4I, S9R, S9E, A15T, S24G, S24R, K27R, N42R, S55P, G59E, G59D, N60D, N60E, V66A, N74D, N85S, N85R, G96S, G96A, S97G, S97D, S97A, S97SD, S99E, S99D, S99G, S99M, S99N, S99R, S99H, S101A, V102I, V102Y, V102N, S104A, G116V, G116R, H118D, H118N, N120S, S126L, P127Q, S128A, S154D, A156E, G157D, G157P, S158E, Y161A, R164S, Q176E, N179E, S182E, Q185N, A188P, G189E, V193M, N198D, V199I, Y203W, S206G, L211Q, L211D, N212D, N212S, M216S, A226V, K229L, Q230H, Q239R, N246K, N255W, N255D, N255E, L256E, L256D T268A, R269H. The protease variants are preferably variants of the *Bacillus lentus* protease (Savinase®) shown in SEQ ID NO: 1 of WO 2016/001449, the *Bacillus amylolichenifaciens* protease (BPN') shown in SEQ ID NO: 2 of WO 2016/001449. The protease variants preferably have at least 80% sequence identity to SEQ ID NO: 1 or SEQ ID NO: 2 of WO 2016/001449.

Or a protease selected from a protease variant comprising a substitution at one or more positions corresponding to positions 171, 173, 175, 179, or 180 of SEQ ID NO: 1 of WO 2004/067737, wherein said protease variant has a sequence identity of at least 75% but less than 100% to SEQ ID NO: 1 of WO 2004/067737.

Suitable commercially available protease enzymes include those sold under the trade names Alcalase®, Duralase™, Durazym™, Relase®, Relase® Ultra, Savinase®, Savinase® Ultra, Primase®, Polarzyme®, Kannase®, Liquanase®, Liquanase® Ultra, Ovozyme®, Coronase®, Coronase® Ultra, Blaze, Blaze Evity® 100T, Blaze Evity® 125T, Blaze Evity® 150T, Neutrase®, Everlase® and Esperase® (Novozymes A/S), those sold under the tradename Maxatase®, Maxacal®, Maxapem®, Purafect®, Purafect Prime®, Preferenz™, Purafect MA®, Purafect Ox®, Purafect OxP®, Puramax®, Properase®, Effectenz™, FN2®, FN3®, FN4®, Excellase®, Excellenz P1000™, Excellenz P1250™, Eraser®, Preferenz P100™ Purafect Prime®, Preferenz P110™ Effectenz P1000™, Purafect™, Effectenz P1050™, Purafect Ox@™, Effectenz P2000™, Purafast®, Properase®, Opticlean® and Optimase® (Danisco/DuPont), Axapem™ (Gist-Brocades N.V.), BLAP (sequence shown in FIG. 29 of U.S. Pat. No. 5,352,604) and variants hereof (Henkel AG) and KAP (*Bacillus alkalophilus* subtilisin) from Kao.

Some aspect of the invention relates to a composition, such as a detergent, e.g., cleaning composition comprising a polypeptide having DNase activity, wherein the polypeptide having DNase activity is selected from the group consisting of the polypeptides shown in: SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 53, SEQ ID NO: 56, SEQ ID NO: 59, SEQ ID NO: 62, SEQ ID NO: 65, SEQ ID NO: 68, SEQ ID NO: 71, SEQ ID NO: 74, SEQ ID NO: 77, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 161, SEQ ID NO: 164, SEQ ID NO: 167, SEQ ID NO: 170, SEQ ID NO: 173, SEQ ID NO: 176, SEQ ID NO: 179, SEQ ID NO: 182, SEQ ID NO: 185, SEQ ID NO: 188, SEQ ID NO: 191, SEQ ID NO: 194 and SEQ ID NO: 197 or polypeptides having at least 60%, e.g., at least 70%, 80% or 90% sequence identity thereto, wherein the composition further comprises: at least 0.01 ppm of one or more protease variant comprising a substitution in one or more of the following positions: 3, 4, 9, 15, 24, 27, 42, 55, 59, 60, 66, 74, 85, 96, 97, 98, 99, 100, 101, 102, 104, 116, 118, 121, 126, 127, 128, 154, 156, 157, 158, 161, 164, 176, 179, 182, 185, 188, 189, 193, 198, 199, 200, 203, 206, 211, 212, 216, 218, 226, 229, 230, 239, 246, 255, 256, 268 and 269, wherein the positions correspond to the positions of the protease shown in SEQ ID NO: 1 of WO 2011/036263.

Lipases and Cutinases

Suitable lipases and cutinases include those of bacterial or fungal origin. Chemically modified or protein engineered mutant enzymes are included. Examples include lipase from *Thermomyces*, e.g., from T. *lanuginosus* (previously named *Humicola lanuginosa*) as described in EP 258068 and EP 305216, cutinase from *Humicola*, e.g., *H. insolens* (WO 96/13580), lipase from strains of *Pseudomonas* (some of these now renamed to *Burkholderia*), e.g., *P. alcaligenes* or *P. pseudoalcaligenes* (EP 218272), *P. cepacia* (EP 331376), *P.* sp. strain SD705 (WO 95/06720 & WO 96/27002), *P. wisconsinensis* (WO 96/12012), GDSL-type *Streptomyces* lipases (WO 2010/065455), cutinase from *Magnaporthe grisea* (WO 2010/107560), cutinase from *Pseudomonas mendocina* (U.S. Pat. No. 5,389,536), lipase from *Thermobifida fusca* (WO 2011/084412), *Geobacillus stearothermophilus* lipase (WO 2011/084417), lipase from *Bacillus subtilis* (WO 2011/084599), and lipase from *Streptomyces griseus* (WO 2011/150157) and *S. pristinaespiralis* (WO 2012/137147).

Other examples are lipase variants such as those described in EP 407225, WO 92/05249, WO 94/01541, WO 94/25578, WO 95/14783, WO 95/30744, WO 95/35381, WO 95/22615, WO 96/00292, WO 97/04079, WO 97/07202, WO 00/34450, WO 00/60063, WO 01/92502, WO 2007/87508 and WO 2009/109500.

Preferred commercial lipase products include Lipolase™, Lipex™; Lipolex™ and Lipoclean™ (Novozymes A/S), Lumafast (originally from Genencor) and Lipomax (originally from Gist-Brocades).

Still other examples are lipases sometimes referred to as acyltransferases or perhydrolases, e.g., acyltransferases with homology to *Candida antarctica* lipase A (WO 2010/111143), acyltransferase from *Mycobacterium smegmatis* (WO 2005/056782), perhydrolases from the CE 7 family (WO 2009/067279), and variants of the *M. smegmatis* perhydrolase in particular the S54V variant used in the commercial product Gentle Power Bleach from Huntsman Textile Effects Pte Ltd (WO 2010/100028).

Some aspect of the invention relates to a composition, such as a detergent, e.g., cleaning composition comprising a polypeptide having DNase activity, wherein the polypeptide having DNase activity is selected from the group consisting of the polypeptides shown in: SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 53, SEQ ID NO: 56, SEQ ID NO: 59, SEQ ID NO: 62, SEQ ID NO: 65, SEQ ID NO: 68, SEQ ID NO: 71, SEQ ID NO: 74, SEQ ID NO: 77, SEQ ID NO: 80, SEQ ID NO: 83, SEQ ID NO: 86, SEQ ID NO: 89, SEQ ID NO:

92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 161, SEQ ID NO: 164, SEQ ID NO: 167, SEQ ID NO: 170, SEQ ID NO: 173, SEQ ID NO: 176, SEQ ID NO: 179, SEQ ID NO: 182, SEQ ID NO: 185, SEQ ID NO: 188, SEQ ID NO: 191, SEQ ID NO: 194 and SEQ ID NO: 197, or polypeptides having at least 60%, e.g., at least 70%, 80% or 90% sequence identity thereto, wherein the composition further comprises:

a) at least 0.01 ppm one or more lipase.

Amylases

Suitable amylases which can be used together with the DNases of the invention may be an alpha-amylase or a glucoamylase and may be of bacterial or fungal origin. Chemically modified or protein engineered mutants are included. Amylases include, for example, alpha-amylases obtained from Bacillus, e.g., a special strain of Bacillus licheniformis, described in more detail in GB 1,296,839.

Suitable amylases include amylases having SEQ ID NO: 2 in WO 95/10603 or variants having 90% sequence identity to SEQ ID NO: 3 thereof. Preferred variants are described in WO 94/02597, WO 94/18314, WO 97/43424 and SEQ ID NO: 4 of WO 99/19467, such as variants with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444.

Different suitable amylases include amylases having SEQ ID NO: 6 in WO 02/10355 or variants thereof having 90% sequence identity to SEQ ID NO: 6. Preferred variants of SEQ ID NO: 6 are those having a deletion in positions 181 and 182 and a substitution in position 193.

Other amylases which are suitable are hybrid alpha-amylase comprising residues 1-33 of the alpha-amylase obtained from B. amyloliquefaciens shown in SEQ ID NO: 6 of WO 2006/066594 and residues 36-483 of the B. licheniformis alpha-amylase shown in SEQ ID NO: 4 of WO 2006/066594 or variants having 90% sequence identity thereof. Preferred variants of this hybrid alpha-amylase are those having a substitution, a deletion or an insertion in one of more of the following positions: G48, T49, G107, H156, A181, N190, M197, I201, A209 and Q264. Most preferred variants of the hybrid alpha-amylase comprising residues 1-33 of the alpha-amylase obtained from B. amyloliquefaciens shown in SEQ ID NO: 6 of WO 2006/066594 and residues 36-483 of SEQ ID NO: 4 are those having the substitutions:

M197T;
H156Y+A181T+N190F+A209V+Q264S; or
G48A+T491+G107A+H156Y+A181T+N190F+I201F+ A209V+Q264S.

Further amylases which are suitable are amylases having SEQ ID NO: 6 in WO 99/19467 or variants thereof having 90% sequence identity to SEQ ID NO: 6. Preferred variants of SEQ ID NO: 6 are those having a substitution, a deletion or an insertion in one or more of the following positions: R181, G182, H183, G184, N195, I206, E212, E216 and K269. Particularly preferred amylases are those having deletion in positions R181 and G182, or positions H183 and G184.

Additional amylases which can be used are those having SEQ ID NO: 1, SEQ ID NO: 3, SEQ ID NO: 2 or SEQ ID NO: 7 of WO 96/23873 or variants thereof having 90% sequence identity to SEQ ID NO: 1, SEQ ID NO: 2, SEQ ID NO: 3 or SEQ ID NO: 7. Preferred variants of SEQ ID NO: 1, SEQ ID NO: 2, SEQ ID NO: 3 or SEQ ID NO: 7 are those having a substitution, a deletion or an insertion in one or more of the following positions: 140, 181, 182, 183, 184, 195, 206, 212, 243, 260, 269, 304 and 476, using SEQ ID 2 of WO 96/23873 for numbering. More preferred variants are those having a deletion in two positions selected from 181, 182, 183 and 184, such as 181 and 182, 182 and 183, or positions 183 and 184. Most preferred amylase variants of SEQ ID NO: 1, SEQ ID NO: 2 or SEQ ID NO: 7 are those having a deletion in positions 183 and 184 and a substitution in one or more of positions 140, 195, 206, 243, 260, 304 and 476.

Other amylases which can be used are amylases having SEQ ID NO: 2 of WO 2008/153815, SEQ ID NO: 10 in WO 01/66712 or variants thereof having 90% sequence identity to SEQ ID NO: 2 of WO 2008/153815 or 90% sequence identity to SEQ ID NO: 10 in WO 01/66712. Preferred variants of SEQ ID NO: 10 in WO 01/66712 are those having a substitution, a deletion or an insertion in one of more of the following positions: 176, 177, 178, 179, 190, 201, 207, 211 and 264.

Further suitable amylases are amylases having SEQ ID NO: 2 of WO 2009/061380 or variants having 90% sequence identity to SEQ ID NO: 2 thereof. Preferred variants of SEQ ID NO: 2 are those having a truncation of the C-terminus and/or a substitution, a deletion or an insertion in one of more of the following positions: Q87, Q98, S125, N128, T131, T165, K178, R180, S181, T182, G183, M201, F202, N225, S243, N272, N282, Y305, R309, D319, Q320, Q359, K444 and G475. More preferred variants of SEQ ID NO: 2 are those having the substitution in one of more of the following positions: Q87E,R, Q98R, S125A, N128C, T1311, T1651, K178L, T182G, M201L, F202Y, N225E,R, N272E,R, S243Q,A,E,D, Y305R, R309A, Q320R, Q359E, K444E and G475K and/or deletion in position R180 and/or S181 or of T182 and/or G183. Most preferred amylase variants of SEQ ID NO: 2 are those having the substitutions:

N128C+K178L+T182G+Y305R+G475K;
N128C+K178L+T182G+F202Y+Y305R+D319T+ G475K;
S125A+N128C+K178L+T182G+Y305R+G475K; or
S125A+N128C+T1311+T1651+K178L+T182G+ Y305R+G475K, wherein the variants are C-terminally truncated and optionally further comprises a substitution at position 243 and/or a deletion at position 180 and/or position 181.

Other suitable amylases are the alpha-amylase having SEQ ID NO: 12 in WO 01/66712 or a variant having at least 90% sequence identity to SEQ ID NO: 12. Preferred amylase variants are those having a substitution, a deletion or an insertion in one of more of the following positions of SEQ ID NO: 12 in WO 01/66712: R28, R118, N174; R181, G182, D183, G184, G186, W189, N195, M202, Y298, N299, K302, S303, N306, R310, N314; R320, H324, E345, Y396, R400, W439, R444, N445, K446, Q449, R458, N471, N484. Particular preferred amylases include variants having a deletion of D183 and G184 and having the substitutions R118K, N195F, R320K and R458K, and a variant additionally having substitutions in one or more position selected from the group: M9, G149, G182, G186, M202, T257, Y295, N299, M323, E345 and A339, most preferred a variant that additionally has substitutions in all these positions.

Other examples are amylase variants such as those described in WO 2011/098531, WO 2013/001078 and WO 2013/001087.

Commercially available amylases are Duramyl™, Termamyl™, Fungamyl™, Stainzyme™ Stainzyme Plus™, Natalase™, Liquozyme X and BAN™ (from Novozymes A/S), and Rapidase™ Purastar™/Effectenz™, Powerase and Preferenz S100 (from Genencor International Inc./DuPont).

Some aspect of the invention relates to a composition, such as a detergent, e.g., cleaning composition comprising a polypeptide having DNase activity, wherein the polypeptide having DNase activity is selected from the group consisting of the polypeptides shown in: SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 53, SEQ ID NO: 56, SEQ ID NO: 59, SEQ ID NO: 62, SEQ ID NO: 65, SEQ ID NO: 68, SEQ ID NO: 71, SEQ ID NO: 74, SEQ ID NO: 77, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 161, SEQ ID NO: 164, SEQ ID NO: 167, SEQ ID NO: 170, SEQ ID NO: 173, SEQ ID NO: 176, SEQ ID NO: 179, SEQ ID NO: 182, SEQ ID NO: 185, SEQ ID NO: 188, SEQ ID NO: 191, SEQ ID NO: 194 and SEQ ID NO: 197, or polypeptides having at least 60%, e.g., at least 70%, 80% or 90% sequence identity thereto, wherein the composition further comprises:
  a) at least 0.01 ppm of one or more amylase variant, wherein the variant comprises:
    (i) one or more substitutions in the following positions: 9, 26, 30, 33, 82, 37, 106, 118, 128, 133, 149, 150, 160, 178, 182, 186, 193, 195, 202, 203, 214, 231, 256, 257, 258, 269, 270, 272, 283, 295, 296, 298, 299, 303, 304, 305, 311, 314, 315, 318, 319, 320, 323, 339, 345, 361, 378, 383, 419, 421, 437, 441, 444, 445, 446, 447, 450, 458, 461, 471, 482, 484, wherein the positions corresponds to positions of SEQ ID NO: 2 of WO 00/60060;
    (ii) exhibiting at least 90 percent identity with SEQ ID NO: 2 of WO 96/23873, with deletions in the 183 and 184 positions; or
    (iii) variants exhibiting at least 95 percent identity with SEQ ID NO: 3 of WO 2008/112459, comprising mutations in one or more of the following positions M202, M208, S255, R172 and/or M261.

Peroxidases/Oxidases

A peroxidase according to the invention is a peroxidase enzyme comprised by the enzyme classification EC 1.11.1.7, as set out by the Nomenclature Committee of the International Union of Biochemistry and Molecular Biology (IUBMB), or any fragment obtained therefrom, exhibiting peroxidase activity.

Suitable peroxidases include those of plant, bacterial or fungal origin. Chemically modified or protein engineered mutants are included. Examples of useful peroxidases include peroxidases from *Coprinopsis*, e.g., from *C. cinerea* (EP 179,486), and variants thereof as those described in WO 93/24618, WO 95/10602, and WO 98/15257.

A peroxidase according to the invention also includes a haloperoxidase enzyme, such as chloroperoxidase, bromoperoxidase and compounds exhibiting chloroperoxidase or bromoperoxidase activity. Haloperoxidases are classified according to their specificity for halide ions. Chloroperoxidases (E.C. 1.11.1.10) catalyze formation of hypochlorite from chloride ions.

In an embodiment, the haloperoxidase of the invention is a chloroperoxidase. Preferably, the haloperoxidase is a vanadium haloperoxidase, i.e., a vanadate-containing haloperoxidase. In a preferred method of the present invention the vanadate-containing haloperoxidase is combined with a source of chloride ion.

Haloperoxidases have been isolated from many different fungi, in particular from the fungus group dematiaceous hyphomycetes, such as *Caldariomyces*, e.g., *C. fumago*, *Alternaria*, *Curvularia*, e.g., *C. verruculosa* and *C. inaequalis*, *Drechslera*, *Ulocladium* and *Botrytis*.

Haloperoxidases have also been isolated from bacteria such as *Pseudomonas*, e.g., *P. pyrrocinia* and *Streptomyces*, e.g., *S. aureofaciens*.

In a preferred embodiment, the haloperoxidase is derivable from *Curvularia* sp., in particular *Curvularia verruculosa* or *Curvularia inaequalis*, such as *C. inaequalis* CBS 102.42 as described in WO 95/27046; or *C. verruculosa* CBS 147.63 or *C. verruculosa* CBS 444.70 as described in WO 97/04102; or from *Drechslera hartlebii* as described in WO 01/79459, *Dendryphiella salina* as described in WO 01/79458, *Phaeotrichoconis crotalarie* as described in WO 01/79461, or *Geniculosporium* sp. as described in WO 01/79460.

An oxidase according to the invention include, in particular, any laccase enzyme comprised by the enzyme classification EC 1.10.3.2, or any fragment obtained therefrom exhibiting laccase activity, or a compound exhibiting a similar activity, such as a catechol oxidase (EC 1.10.3.1), an o-aminophenol oxidase (EC 1.10.3.4), or a bilirubin oxidase (EC 1.3.3.5).

Preferred laccase enzymes are enzymes of microbial origin. The enzymes may be obtained from plants, bacteria or fungi (including filamentous fungi and yeasts).

Suitable examples from fungi include a laccase derivable from a strain of *Aspergillus*, *Neurospora*, e.g., *N. crassa*, *Podospora*, *Botrytis*, *Collybia*, *Fomes*, *Lentinus*, *Pleurotus*, *Trametes*, e.g., *T. villosa* and *T. versicolor*, *Rhizoctonia*, e.g., *R. solani*, *Coprinopsis*, e.g., *C. cinerea*, *C. comatus*, *C. friesii*, and *C. plicatilis*, *Psathyrella*, e.g., *P. condelleana*, *Panaeolus*, e.g., *P. papilionaceus*, *Myceliophthora*, e.g., *M. thermophila*, *Schytalidium*, e.g., *S. thermophilum*, *Polyporus*, e.g., *P. pinsitus*, *Phlebia*, e.g., *P. radiata* (WO 92/01046), or *Coriolus*, e.g., *C. hirsutus* (JP 2238885).

Suitable examples from bacteria include a laccase derivable from a strain of *Bacillus*.

A laccase obtained from *Coprinopsis* or *Myceliophthora* is preferred; in particular a laccase obtained from *Coprinopsis cinerea*, as disclosed in WO 97/08325; or from *Myceliophthora thermophila*, as disclosed in WO 95/33836.

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, for example, as a granulate, liquid, slurry, etc. Preferred detergent additive formulations are granulates, in particular non-dusting granulates, liquids, in particular stabilized liquids, or slurries.

Other Materials

Any detergent components known in the art for use in the cleaning composition of the invention may also be utilized. Other optional detergent components include anti-corrosion agents, anti-shrink agents, anti-soil redeposition agents, anti-wrinkling agents, bactericides, binders, corrosion inhibitors, disintegrants/disintegration agents, dyes, enzyme stabilizers (including boric acid, borates, CMC, and/or polyols such as propylene glycol), fabric conditioners including clays, fillers/processing aids, fluorescent whitening agents/optical brighteners, foam boosters, foam (suds) regulators, perfumes, soil-suspending agents, softeners, suds suppressors, tarnish inhibitors, and wicking agents, either alone or in combination. Any ingredient known in the art for use in detergents may be utilized. The choice of such ingredients is well within the skill of the artisan.

Dispersants

The cleaning compositions of the present invention can also contain dispersants. In particular, powdered detergents may comprise dispersants. Suitable water-soluble organic materials include the homo- or co-polymeric acids or their salts, in which the polycarboxylic acid comprises at least two carboxyl radicals separated from each other by not more than two carbon atoms. Suitable dispersants are for example described in Powdered Detergents, Surfactant science series volume 71, Marcel Dekker, Inc.

Dye Transfer Inhibiting Agents

The cleaning compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Fluorescent Whitening Agents

The cleaning compositions of the present invention will preferably also contain additional components that may tint articles being cleaned, such as a fluorescent whitening agent or optical brightener. Where present the brightener is preferably at a level of about 0.01% to about 0.5%. Any fluorescent whitening agent suitable for use in a laundry detergent composition may be used in the composition of the present invention. The most commonly used fluorescent whitening agents are those belonging to the classes of diaminostilbene-sulfonic acid derivatives, diarylpyrazoline derivatives and bisphenyl-distyryl derivatives. Examples of the diaminostilbene-sulfonic acid derivative type of fluorescent whitening agents include the sodium salts of: 4,4'-bis-(2-diethanolamino-4-anilino-s-triazin-6-ylamino) stilbene-2,2'-disulfonate, 4,4'-bis-(2,4-dianilino-s-triazin-6-ylamino) stilbene-2.2'-disulfonate, 4,4'-bis-(2-anilino-4-(N-methyl-N-2-hydroxy-ethylamino)-s-triazin-6-ylamino) stilbene-2,2'-disulfonate, 4,4'-bis-(4-phenyl-1,2,3-triazol-2-yl)stilbene-2,2'-disulfonate and sodium 5-(2H-naphtho[1,2-d][1,2,3]triazol-2-yl)-2-[(E)-2-phenylvinyl]benzenesulfonate.

Preferred fluorescent whitening agents are Tinopal DMS and Tinopal CBS available from Ciba-Geigy AG, Basel, Switzerland. Tinopal DMS is the disodium salt of 4,4'-bis-(2-morpholino-4-anilino-s-triazin-6-ylamino) stilbene-2,2'-disulfonate. Tinopal CBS is the disodium salt of 2,2'-bis-(phenyl-styryl)-disulfonate. Also preferred are fluorescent whitening agents is the commercially available Parawhite KX, supplied by Paramount Minerals and Chemicals, Mumbai, India. Tinopal CBS-X is a 4.4'-bis-(sulfostyryl)-biphenyl disodium salt also known as Disodium Distyrylbiphenyl Disulfonate. Other fluorescers suitable for use in the invention include the 1-3-diaryl pyrazolines and the 7-alkylaminocoumarins.

Suitable fluorescent brightener levels include lower levels of from about 0.01, from 0.05, from about 0.1 or even from about 0.2 wt % to upper levels of 0.5 or even 0.75 wt %.

Soil Release Polymers

The cleaning compositions of the present invention may also include one or more soil release polymers which aid the removal of soils from fabrics such as cotton and polyester based fabrics, in particular the removal of hydrophobic soils from polyester based fabrics. The soil release polymers may for example be nonionic or anionic terephthalte based polymers, polyvinyl caprolactam and related copolymers, vinyl graft copolymers, polyester polyamides see for example Chapter 7 in Powdered Detergents, Surfactant science series volume 71, Marcel Dekker, Inc. Another type of soil release polymers are amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087523 (hereby incorporated by reference). Furthermore, random graft co-polymers are suitable soil release polymers. Suitable graft co-polymers are described in more detail in WO 2007/138054, WO 2006/108856 and WO 2006/113314 (hereby incorporated by reference). Other soil release polymers are substituted polysaccharide structures especially substituted cellulosic structures such as modified cellulose deriviatives such as those described in EP 1867808 or WO 2003/040279 (both are hereby incorporated by reference). Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof.

Anti-Redeposition Agents

The cleaning compositions of the present invention may also include one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose based polymers described under soil release polymers above may also function as anti-redeposition agents.

Rheology Modifiers

The cleaning compositions of the present invention may also include one or more rheology modifiers, structurants or thickeners, as distinct from viscosity reducing agents. The rheology modifiers are selected from the group consisting of non-polymeric crystalline, hydroxy-functional materials, polymeric rheology modifiers which impart shear thinning characteristics to the aqueous liquid matrix of a liquid detergent composition. The rheology and viscosity of the detergent can be modified and adjusted by methods known in the art, for example as shown in EP 2169040.

Other suitable adjunct materials include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, solvents, and structurants for liquid detergents and/or structure elasticizing agents.

Anti-Parasitic/Viral Compounds

The cleaning composition may further comprise an anti-parasitic compound which can be one or more of a benzazole, such as albendazole, mebendazole and tiabendazole; an azole, such as metronidazole and tinidazole; a macrocycle, such as amphotericin B, rifampin and ivermectin; pyrantel pamoate; diethylcarbamazine; niclosamide; praziquantel; melarsopro; and eflornithine.

The antiviral compound can be one or more of a nucleoside analog reverse transcriptase inhibitor, such as acyclovir, didanosine, stavudine, zidovudine, lamivudine, abacavir, emtricitabine and entecavir; an uncoating inhibitor such as amantadine, rimantadine and pleconaril; a protease inhibitor such as saquinavir, ritonavir, indinavir, nelfinavir and amprenavir; zanamivir; oseltamivir; and rifampin. The antibacterial compound can be one or more of an aminoglycoside such as gentamicin, kanamycin and streptomycin; a beta-lactam such as penicillin, ampicillin and imipenem; a cephalosporin such as ceftazidime, a quinolone such as ciprofloxacin; a macrolide such as azithromycin, clarithromycin, dirithromycin, erythromycin, roxithromycin and telithromycin; an oxazolidinone such as linezolid; an ansamycin such as rifamycin; a sulphonamide; a tetracycline such as doxycycline; a glycopeptide such as vancomycin; sulfisoxazole, trimethoprim, novobiocin, daptomycin and linezolid.

The antifungal compound can be one or more of an azole, such as miconazole, ketoconazole, clotrimazole, econazole, omoconazole, bifonazole, butoconazole, fenticonazole, isoconazole, sertaconazole, sulconazole, tioconazole, fluconazole, itraconazole, isavuconazole, ravuconazole, posaconazole, voriconazole, terconazole and abafungin; a macrocycle, such as natamycin, rimocidin, filipin, nystatin, amphotericin B, candicin, hamycin; an allyl amine such as terbinafine, naftifine and butenafine; an echinocandin such as andidulafungin, caspofungin and micafungin; or others such as polygodial, ciclopirox, tolnaftate, benzoic acid, undecylenic acid, flucytosine and griseofulvin.

Formulation of DNases in Microcapsule

The DNases of the invention may be formulated in microcapsules or in liquid detergents comprising microcapsules. A liquid cleaning composition of the invention may comprise a surfactant and a detergent builder in a total concentration of at least 3% by weight, and an enzyme, which may be a DNase, containing microcapsule, wherein the membrane of the microcapsule is produced by cross-linking of a polybranched polyamine having a molecular weight of more than 1 kDa. Encapsulating of enzymes such as DNases in a microcapsule with a semipermeable membrane having a water activity inside these capsules (prior to addition to the liquid detergent) higher than in the liquid detergent, the capsules will undergo a (partly) collapse when added to the detergent (water is oozing out), thus, leaving a more concentrated and more viscous enzyme containing interior in the capsules. The collapse of the membrane may also result in a reduced permeability.

This can be further utilized by addition of stabilizers/polymers, especially ones that are not permeable through the membrane. The collapse and resulting increase in viscosity will reduce/hinder the diffusion of hostile components (e.g., surfactants or sequestrants) into the capsules, and thus, increase the storage stability of enzymes such as DNases in the liquid detergent. Components in the liquid detergent that are sensitive to the enzyme (e.g., components that act as substrate for the enzyme) are also protected against degradation by the enzyme. During wash the liquid detergent is diluted by water, thus, increasing the water activity. Water will now diffuse into the capsules (osmosis). The capsules will swell and the membrane will either become permeable to the enzyme so they can leave the capsules, or simply burst and in this way releasing the enzyme. The concept is very efficient in stabilizing the enzymes such as the DNases of the invention against hostile components in liquid detergent, and vice versa also protects enzyme sensitive components in the liquid detergent from enzymes.

Examples of detergent components which are sensitive to, and can be degraded by, enzymes include (relevant enzyme in parenthesis): xanthan gum (xanthanase), polymers with ester bonds (lipase), hydrogenated castor oil (lipase), perfume (lipase), methyl ester sulfonate surfactants (lipase), cellulose and cellulose derivatives (e.g., CMC) (cellulase), and dextrin and cyclodextrin (amylase).

Also, sensitive detergent ingredients can be encapsulated, and thus, stabilized, in the microcapsules of the invention. Sensitive detergent ingredients are prone to degradation during storage. Such detergent ingredients include bleaching compounds, bleach activators, perfumes, polymers, builder, surfactants, etc.

Generally, the microcapsules can be used to separate incompatible components/compounds in detergents.

Addition of the microcapsules to detergents can be used to influence the visual appearance of the detergent product, such as an opacifying effect (small microcapsules) or an effect of distinctly visible particles (large microcapsules). The microcapsules may also be colored.

The microcapsules can be used to reduce the enzyme dust levels during handling and processing of enzyme products.

Unless otherwise indicated, all percentages are indicated as percent by weight (% w/w) throughout the application.

Microcapsule: The microcapsules are typically produced by forming water droplets into a continuum that is non-miscible with water—i.e., typically by preparing a water-in-oil emulsion—and subsequently formation of the membrane by interfacial polymerization via addition of a cross-linking agent. After eventual curing the capsules can be harvested and further rinsed and formulated by methods known in the art. The capsule formulation is subsequently added to the detergent.

The payload, the major membrane constituents and eventual additional component that are to be encapsulated are found in the water phase. In the continuum is found components that stabilize the water droplets towards coalescence (emulsifiers, emulsion stabilizers, surfactants etc.) and the crosslinking agent is also added via the continuum.

The emulsion can be prepared be any methods known in the art, e.g., by mechanical agitation, dripping processes, membrane emulsification, microfluidics, sonication etc. In some cases simple mixing of the phases automatically will result in an emulsion, often referred to as self-emulsification. Using methods resulting in a narrow size distribution is an advantage.

The cross-linking agent(s) is typically subsequently added to the emulsion, either directly or more typically by preparing a solution of the crosslinking agent in a solvent which is soluble in the continuous phase. The emulsion and cross-linking agent or solution hereof can be mixed by conventional methods used in the art, e.g., by simple mixing or by carefully controlling the flows of the emulsion and the cross-linking agent solution through an in-line mixer.

In some cases, curing of the capsules is needed to complete the membrane formation. Curing is often simple stirring of the capsules for some time to allow the interfacial polymerization reaction to end. In other cases, the membrane formation can be stopped by addition of reaction quencher.

The capsules may be post modified, e.g., by reacting components onto the membrane to hinder or reduce flocculation of the particles in the detergent as described in WO 99/01534.

The produced capsules can be isolated or concentrated by methods known in the art, e.g., by filtration, centrifugation, distillation or decantation of the capsule dispersion.

The resulting capsules can be further formulated, e.g., by addition of surfactants to give the product the desired properties for storage, transport and later handling and addition to the detergent. Other microcapsule formulation agents include rheology modifiers, biocides (e.g., Proxel), acid/base for adjustment of pH (which will also adjust inside the microcapsules), and water for adjustment of water activity.

The capsule forming process may include the following steps:
Preparation of the initial water and oil phase(s),
Forming a water-in-oil emulsion,
Membrane formation by interfacial polymerization,
Optional post modification,
Optional isolation and/or formulation,
Addition to detergent.

The process can be either a batch process or a continuous or semi-continuous process.

A microcapsule may be a small aqueous sphere with a uniform membrane around it. The material inside the microcapsule is referred to as the core, internal phase, or fill, whereas the membrane is sometimes called a shell, coating, or wall. The microcapsules typically have diameters between 0.5 µm and 2 millimeters. Preferably, the mean diameter of the microcapsules is in the range of 1 µm to 1000 µm, more preferably in the range of 5 µm to 500 µm, even more preferably in the range of 10 µm to 500 µm, even more preferably in the range of 50 µm to 500 µm, and most preferably in the range of 50 µm to 200 µm. Alternatively, the diameter of the microcapsules is in the range of 0.5 µm to 30 µm; or in the range of 1 µm to 25 µm. The diameter of the microcapsule is measured in the oil phase after polymerization is complete. The diameter of the capsule may change depending on the water activity of the surrounding chemical environment.

Microencapsulation of enzymes may be carried out by interfacial polymerization, wherein the two reactants in a polymerization reaction meet at an interface and react rapidly. The basis of this method is a reaction of a polyamine with an acid derivative, usually an acid halide, acting as a crosslinking agent. The polyamine is preferably substantially water-soluble (when in free base form). Under the right conditions, thin flexible membranes form rapidly at the interface. One way of carrying out the polymerization is to use an aqueous solution of the enzyme and the polyamine, which are emulsified with a non-aqueous solvent (and an emulsifier), and a solution containing the acid derivative is added. An alkaline agent may be present in the enzyme solution to neutralize the acid formed during the reaction. Polymer (polyamide) membranes form instantly at the interface of the emulsion droplets. The polymer membrane of the microcapsule is typically of a cationic nature, and thus, bind/complex with compounds of an anionic nature.

The diameter of the microcapsules is determined by the size of the emulsion droplets, which is controlled, for example by the stirring rate.

Emulsion: An emulsion is a temporary or permanent dispersion of one liquid phase within a second liquid phase. The second liquid is generally referred to as the continuous phase. Surfactants are commonly used to aid in the formation and stabilization of emulsions. Not all surfactants are equally able to stabilize an emulsion. The type and amount of a surfactant needs to be selected for optimum emulsion utility especially with regard to preparation and physical stability of the emulsion, and stability during dilution and further processing. Physical stability refers to maintaining an emulsion in a dispersion form. Processes such as coalescence, aggregation, adsorption to container walls, sedimentation and creaming, are forms of physical instability, and should be avoided. Examples of suitable surfactants are described in WO 97/24177, pages 19-21; and in WO 99/01534.

Emulsions can be further classified as either simple emulsions, wherein the dispersed liquid phase is a simple homogeneous liquid, or a more complex emulsion, wherein the dispersed liquid phase is a heterogeneous combination of liquid or solid phases, such as a double emulsion or a multiple-emulsion. For example, a water-in-oil double emulsion or multiple emulsion may be formed wherein the water phase itself further contains an emulsified oil phase; this type of emulsion may be specified as an oil-in-water-in oil (o/w/o) emulsion. Alternatively, a water-in-oil emulsion may be formed wherein the water phase contains a dispersed solid phase often referred to as a suspension-emulsion. Other more complex emulsions can be described. Because of the inherent difficulty in describing such systems, the term emulsion is used to describe both simple and more complex emulsions without necessarily limiting the form of the emulsion or the type and number of phases present Polyamine: The rigidity/flexibility and permeability of the membrane is mainly influenced by the choice of polyamine. The polyamine according to the invention is a polybranched polyamine. Each branch, preferably ending with a primary amino group serves as a tethering point in the membrane network, thereby giving the favourable properties of the invention. A polybranched polyamine according to the present invention is a polyamine having more than two branching points and more than two reactive amino groups (capable of reacting with the crosslinking agent, i.e., primary and secondary amino groups). The polybranched polyamine is used as starting material when the emulsion is prepared—it is not formed in situ from other starting materials. To obtain the attractive properties, the polybranched structure of the polyamine must be present as starting material.

There is a close relation between number of branching points and number of primary amines, since primary amines will always be positioned at the end of a branch: A linear amine can only contain two primary amines. For each branching point hypothetically introduced in such a linear diamine will allow one or more primary amine(s) to be introduced at the end of the introduced branch(es). In this context we the primary amino group is understood as part of the branch, i.e., the endpoint of the branch. For example, both tris(2-aminoethyl)amine and 1,2,3-propanetriamine is considered as molecules having one branching point. The polyamine preferably has at least four primary amines. Branching points can be introduced from an aliphatic hydrocarbon chain from unsaturated carbon bonds, such as in, e.g., 3,3'-diaminobenzidine, or from tertiary amino groups, such as in N,N,N',N'-tetrakis-(2-aminoethyl)ethylenediamine.

In addition to the number of branching points, the compactness of the reactive amino groups is of high importance. A substance such as, e.g., N,N,N',N'-tetrakis-(12-aminododecyl)ethylenediamine would not be suitable. Neither would a peptide or protein, such as an enzyme, be suitable for membrane formation. Thus, the polybranched polyamine is not a peptide or protein.

The reactive amino groups preferably constitute at least 15% of the molecular weight of the polybranched polyamine, such as more than 20%, or more than 25%. Preferably, the molecular weight of the polybranched polyamine is at least 1 kDa; more preferably, the molecular weight of the polybranched polyamine is at least 1.3 kDa.

The polybranched polyamine may be a polyethyleneimine (PEI), and modifications thereof, having more than two branching points and more than two reactive amino groups; wherein the reactive amino groups constitute at least 15% of the molecular weight of the PEI, such as more than 20%, or more than 25%. Preferably, the molecular weight of the PEI is at least 1 kDa.

Combinations of different polybranched polyamines may be used for preparing the microcapsule.

The advantageous properties (e.g., enzyme storage stability, reduced enzyme leakage, reduced in-flux of detergent ingredients) of the microcapsule may be improved by adding one or more small amines with a molecular weight of less than 1 kDa. The small amine is preferably substantially water-soluble (when in free base form) and can be a material such as ethylene diamine, hexamethylene diamine, hexane diamine, diethylene tetramine, ethylene tetramine, diamino benzene, piperazine, tetramethylene pentamine or, preferably, diethylene triamine (DETA). The small amines may be added in an amount of up to 50%, preferably up to 40%, up to 30%, up to 20%, up to 10%, or up to 5%, by weight of the total content of small amine and polybranched polyamine, when preparing the microcapsule.

Crosslinking agent: The crosslinking agent as used in the present invention is a molecule with at least two groups/sites capable of reacting with amines to form covalent bonds.

The crosslinking agent is preferably oil soluble and can be in the form of an acid anhydride or acid halide, preferably an acid chloride. For example, it can be adipoyl chloride, sebacoyl chloride, dodecanedioc acid chloride, phthaloyl chloride, terephthaloyl chloride, isophthaloyl chloride, or trimesoyl chloride; but preferably, the crosslinking agent is terephthaloyl chloride or trimesoyl chloride.

The liquid detergent composition may comprise a microcapsule, and thus, form part of, any detergent composition in any form, such as liquid and powder detergents, and soap and detergent bars.

The microcapsule, as described above, may be added to the liquid detergent composition in an amount corresponding to from 0.0001% to 5% (w/w) active enzyme protein (AEP); preferably from 0.001% to 5%, more preferably from 0.005% to 5%, more preferably from 0.005% to 4%, more preferably from 0.005% to 3%, more preferably from 0.005% to 2%, even more preferably from 0.01% to 2%, and most preferably from 0.01% to 1% (w/w) active enzyme protein.

The liquid detergent composition has a physical form, which is not solid (or gas). It may be a pourable liquid, a paste, a pourable gel or a non-pourable gel. It may be either isotropic or structured, preferably isotropic. It may be a formulation useful for washing in automatic washing machines or for hand washing. It may also be a personal care product, such as a shampoo, toothpaste, or hand soap.

The microcapsule is further described in WO 2014/177709 which is incorporated by reference.

Formulation of Enzyme in Granules

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The DNase may be formulated as a granule for example as a co-granule that combines one or more enzymes. Each enzyme will then be present in more granules securing a more uniform distribution of enzymes in the detergent. This also reduces the physical segregation of different enzymes due to different particle sizes. Methods for producing multi-enzyme co-granulate for the detergent industry is disclosed in the IP.com disclosure IPCOM000200739D.

Another example of formulation of enzymes by the use of co-granulates are disclosed in WO 2013/188331, which relates to a detergent composition comprising (a) a multi-enzyme co-granule; (b) less than 10 wt zeolite (anhydrous basis); and (c) less than 10 wt phosphate salt (anhydrous basis), wherein said enzyme co-granule comprises from 10 to 98 wt % moisture sink component and the composition additionally comprises from 20 to 80 wt % detergent moisture sink component. WO 2013/188331 also relates to a method of treating and/or cleaning a surface, preferably a fabric surface comprising the steps of (i) contacting said surface with the detergent composition as claimed and described herein in aqueous wash liquor, (ii) rinsing and/or drying the surface.

An embodiment of the invention relates to an enzyme granule/particle comprising the DNase of the invention. The granule is composed of a core, and optionally one or more coatings (outer layers) surrounding the core. Typically, the granule/particle size, measured as equivalent spherical diameter (volume based average particle size), of the granule is 20-2000 μm, particularly 50-1500 μm, 100-1500 μm or 250-1200 μm.

The core may include additional materials such as fillers, fibre materials (cellulose or synthetic fibres), stabilizing agents, solubilising agents, suspension agents, viscosity regulating agents, light spheres, plasticizers, salts, lubricants and fragrances.

The core may include binders, such as synthetic polymer, wax, fat, or carbohydrate.

The core may comprise a salt of a multivalent cation, a reducing agent, an antioxidant, a peroxide decomposing catalyst and/or an acidic buffer component, typically as a homogenous blend.

The core may consist of an inert particle with the enzyme absorbed into it, or applied onto the surface, e.g., by fluid bed coating.

The core may have a diameter of 20-2000 μm, particularly 50-1500 μm, 100-1500 μm or 250-1200 μm.

The core can be prepared by granulating a blend of the ingredients, e.g., by a method comprising granulation techniques such as crystallization, precipitation, pan-coating, fluid bed coating, fluid bed agglomeration, rotary atomization, extrusion, prilling, spheronization, size reduction methods, drum granulation, and/or high shear granulation.

Methods for preparing the core can be found in Handbook of Powder Technology; Particle size enlargement by C. E. Capes; Volume 1; 1980; Elsevier.

The core of the enzyme granule/particle may be surrounded by at least one coating, e.g., to improve the storage stability, to reduce dust formation during handling, or for coloring the granule. The optional coating(s) may include a salt coating, or other suitable coating materials, such as polyethylene glycol (PEG), methyl hydroxy-propyl cellulose (MHPC) and polyvinyl alcohol (PVA). Examples of enzyme granules with multiple coatings are shown in WO 93/07263 and WO 97/23606.

The coating may be applied in an amount of at least 0.1% by weight of the core, e.g., at least 0.5%, 1% or 5%. The amount may be at most 100%, 70%, 50%, 40% or 30%.

The coating is preferably at least 0.1 μm thick, particularly at least 0.5 μm, at least 1 μm or at least 5 μm. In a particular embodiment, the thickness of the coating is below 100 μm. In a more particular embodiment, the thickness of the coating is below 60 μm. In an even more particular embodiment the total thickness of the coating is below 40 μm.

The coating should encapsulate the core unit by forming a substantially continuous layer. A substantially continuous layer is to be understood as a coating having few or no holes, so that the core unit it is encapsulating/enclosing has few or no uncoated areas. The layer or coating should in particular be homogeneous in thickness.

The coating can further contain other materials as known in the art, e.g., fillers, antisticking agents, pigments, dyes, plasticizers and/or binders, such as titanium dioxide, kaolin, calcium carbonate or talc.

A salt coating may comprise at least 60% by weight w/w of a salt, e.g., at least 65%, at least 70%, at least 75%, at least 80%, at least 85%, at least 90%, at least 95% or at least 99% by weight w/w.

The salt may be added from a salt solution where the salt is completely dissolved or from a salt suspension wherein the fine particles is less than 50 μm, such as less than 10 μm or less than 5 μm.

The salt coating may comprise a single salt or a mixture of two or more salts. The salt may be water soluble, in particular having a solubility at least 0.1 grams in 100 g of water at 20° C., preferably at least 0.5 g per 100 g water, e.g., at least 1 g per 100 g water, e.g., at least 5 g per 100 g water.

The salt may be an inorganic salt, e.g., salts of sulfate, sulfite, phosphate, phosphonate, nitrate, chloride or carbonate or salts of simple organic acids (less than 10 carbon atoms, e.g., 6 or less carbon atoms) such as citrate, malonate or acetate. Examples of cations in these salts are alkali or earth alkali metal ions, the ammonium ion or metal ions of the first transition series, such as sodium, potassium, magnesium, calcium, zinc or aluminium. Examples of anions include chloride, bromide, iodide, sulfate, sulfite, bisulfite, thiosulfate, phosphate, monobasic phosphate, dibasic phosphate, hypophosphite, dihydrogen pyrophosphate, tetraborate, borate, carbonate, bicarbonate, metasilicate, citrate, malate, maleate, malonate, succinate, lactate, formate, acetate, butyrate, propionate, benzoate, tartrate, ascorbate or gluconate. In particular, alkali- or earth alkali metal salts of sulfate, sulfite, phosphate, phosphonate, nitrate, chloride or carbonate or salts of simple organic acids such as citrate, malonate or acetate may be used.

The salt in the coating may have a constant humidity at 20° C. above 60%, particularly above 70%, above 80% or above 85%, or it may be another hydrate form of such a salt (e.g., anhydrate). The salt coating may be as described in WO 00/01793 or WO 2006/034710.

Specific examples of suitable salts are NaCl ($CH_{20°\ C.}$=76%), $Na_2CO_3$ ($CH_{20°\ C.}$=92%), $NaNO_3$ ($CH_{20°\ C.}$=73%), $Na_2HPO_4$ ($CH_{20°\ C.}$=95%), $Na_3PO_4$ ($CH_{25°\ C.}$=92%), $NH_4Cl$ ($CH_{20°\ C.}$=79.5%), $(NH_4)_2HPO_4$ ($CH_{20°\ C.}$=93.0%), $NH_4H_2PO_4$ ($CH_{20°\ C.}$=93.1%), $(NH_4)_2SO_4$ ($CH_{20°\ C.}$=81.1%), KCl ($CH_{20°\ C.}$=85%), $K_2HPO_4$ ($CH_{20°\ C.}$=92%), $KH_2PO_4$ ($CH_{20°\ C.}$=96.5%), $KNO_3$ ($CH_{20°\ C.}$=93.5%), $Na_2SO_4$ ($CH_{20°\ C.}$=93%), $K_2SO_4$ ($CH_{20°\ C.}$=98%), $KHSO_4$ ($CH_{20°\ C.}$=86%), $MgSO_4$ ($CH_{20°\ C.}$=90%), $ZnSO_4$ ($CH_{20°\ C.}$=90%) and sodium citrate ($CH_{25°\ C.}$=86%). Other examples include $NaH_2PO_4$, $(NH_4)H_2PO_4$, $CuSO_4$, $Mg(NO_3)_2$ and magnesium acetate.

The salt may be in anhydrous form, or it may be a hydrated salt, i.e., a crystalline salt hydrate with bound water(s) of crystallization, such as described in WO 99/32595. Specific examples include anhydrous sodium sulfate ($Na_2SO_4$), anhydrous magnesium sulfate ($MgSO_4$), magnesium sulfate heptahydrate ($MgSO_4 \cdot 7H_2O$), zinc sulfate heptahydrate ($ZnSO_4 \cdot 7H_2O$), sodium phosphate dibasic heptahydrate ($Na_2HPO_4 \cdot 7H_2O$), magnesium nitrate hexahydrate ($Mg(NO_3)_2(6H_2O)$), sodium citrate dihydrate and magnesium acetate tetrahydrate.

Preferably the salt is applied as a solution of the salt, e.g., using a fluid bed.

Thus, in a further aspect, the present invention provides a granule, which comprises:
  (a) a core comprising a DNase according to the invention, and
  (b) optionally a coating consisting of one or more layer(s) surrounding the core.

Some aspect of the invention relates to a granule, which comprises:
  (a) a core comprising a polypeptide having DNase activity wherein the polypeptide is selected from the group consisting of polypeptides shown in SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 53, SEQ ID NO: 56, SEQ ID NO: 59, SEQ ID NO: 62, SEQ ID NO: 65, SEQ ID NO: 68, SEQ ID NO: 71, SEQ ID NO: 74, SEQ ID NO: 77, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 161, SEQ ID NO: 164, SEQ ID NO: 167, SEQ ID NO: 170, SEQ ID NO: 173, SEQ ID NO: 176, SEQ ID NO: 179, SEQ ID NO: 182, SEQ ID NO: 185, SEQ ID NO: 188, SEQ ID NO: 191, SEQ ID NO: 194 and SEQ ID NO: 197 or polypeptides having at least 60%, e.g., at least 70%, at least 80%, at least 90%, at least 95%, at least 98%, or at least 99% sequence identity thereto, and
  (b) optionally a coating consisting of one or more layer(s) surrounding the core.

One embodiment of the invention relates to a granule comprising a polypeptide having DNase activity, wherein the polypeptide has at least 80% sequence identity to the polypeptide comprising one or more of the motifs [E/D/H]H[I/V/L/F/M]X[P/A/S], [T/D/S][G/N]PQL, [G/T]Y[D/S][R/K/L], [F/L/Y/I]A[N/R]D[L/I/P/V], C[D/N]T[A/R] or [D/Q][I/V]DH, wherein the granule comprises a core comprising said polypeptide and a coating.

One embodiment of the invention relates to a granule comprising a polypeptide having DNase activity, wherein the polypeptide has at least 80% sequence identity to the polypeptide comprising one or more of the motifs [E/D/H]H[I/V/L/F/M]X[P/A/S], [T/D/S][G/N]PQL, [G/T]Y[D/S][R/K/L], [F/L/Y/I]A[N/R]D[L/I/P/V], C[D/N]T[A/R] or [D/Q][I/V]DH, with the proviso that the polypeptide is not the *Trichoderma harzianum* DNase shown in SEQ ID NO: 2 of WO 2015/155351 and wherein the granule comprises a core comprising said polypeptide and a coating.

One embodiment of the invention relates to a granule comprising a polypeptide having DNase activity, wherein the polypeptide has at least 80% sequence identity to the polypeptide comprising one or more of the motifs [D/M/L][S/T]GYSR[D/N] (SEQ ID NO: 204) or ASXNRSKG (SEQ ID NO: 205), wherein the granule comprises a core comprising said polypeptide and a coating.

One embodiment of the invention relates to a granule comprising a polypeptide having DNase activity, wherein the polypeptide has at least 80% sequence identity to the polypeptide comprising one or more of the motifs [V/I]PL[S/A]NAWK (SEQ ID NO: 206) or NPQL (SEQ ID NO: 207), wherein the granule comprises a core comprising said polypeptide and a coating.

One embodiment of the invention relates to a granule comprising a polypeptide having DNase activity, wherein the polypeptide has at least 80% sequence identity to the polypeptide comprising one or more of the motifs P[Q/E]L[W/Y] (SEQ ID NO: 208) or [K/H/E]NAW (SEQ ID NO: 209), wherein the granule comprises a core comprising said polypeptide and a coating.

One embodiment of the invention relates to a granule comprising a polypeptide having DNase activity, wherein the polypeptide has at least 80% sequence identity to the polypeptide comprising one or more of the motifs P[Q/E]L[W/Y] (SEQ ID NO: 208) or [K/H/E]NAW (SEQ ID NO: 209), with the proviso that the polypeptide is not the *Trichoderma harzianum* DNase shown in SEQ ID NO: 2 of WO 2015/155351 and wherein the granule comprises a core comprising said polypeptide and a coating.

One embodiment of the invention relates to a granule comprising a polypeptide having DNase activity, wherein the polypeptide is selected from the group consisting of:
a) a polypeptide having at least 70%, at least 80%, at least 85%, at least 90%, at least 95%, at least 98%, at least 99% or 100% sequence identity to the polypeptide of SEQ ID NO: 8,
b) a polypeptide having at least 70%, at least 80%, at least 85%, at least 90%, at least 95%, at least 98%, at least 99% or 100% sequence identity to the polypeptide of SEQ ID NO: 9,
c) a polypeptide having at least 70%, at least 80%, at least 85%, at least 90%, at least 95%, at least 98%, at least 99% or 100% sequence identity to the polypeptide of SEQ ID NO: 11,
d) a polypeptide having at least 70%, at least 80%, at least 85%, at least 90%, at least 95%, at least 98%, at least 99% or 100% sequence identity to the polypeptide of SEQ ID NO: 12,
e) a polypeptide having at least 70%, at least 80%, at least 85%, at least 90%, at least 95%, at least 98%, at least 99% or 100% sequence identity to the polypeptide of SEQ ID NO: 13,
f) a polypeptide having at least 70%, at least 80%, at least 85%, at least 90%, at least 95%, at least 98%, at least 99% or 100% sequence identity to the polypeptide of SEQ ID NO: 14,
g) a polypeptide having at least 70%, at least 80%, at least 85%, at least 90%, at least 95%, at least 98%, at least 99% or 100% sequence identity to the polypeptide of SEQ ID NO: 15,
h) a polypeptide having at least 70%, at least 80%, at least 85%, at least 90%, at least 95%, at least 98%, at least 99% or 100% sequence identity to the polypeptide of SEQ ID NO: 16,
i) a polypeptide having at least 70%, at least 80%, at least 85%, at least 90%, at least 95%, at least 98%, at least 99% or 100% sequence identity to the polypeptide of SEQ ID NO: 17,
j) a polypeptide having at least 70%, at least 80%, at least 85%, at least 90%, at least 95%, at least 98%, at least 99% or 100% sequence identity to the polypeptide of SEQ ID NO: 18,
k) a polypeptide having at least 70%, at least 80%, at least 85%, at least 90%, at least 95%, at least 98%, at least 99% or 100% sequence identity to the polypeptide of SEQ ID NO: 19,
l) a polypeptide having at least 70%, at least 80%, at least 85%, at least 90%, at least 95%, at least 98%, at least 99% or 100% sequence identity to the polypeptide of SEQ ID NO: 20,
m) a polypeptide having at least 70%, at least 80%, at least 85%, at least 90%, at least 95%, at least 98%, at least 99% or 100% sequence identity to the polypeptide of SEQ ID NO: 21,
n) a polypeptide having at least 70%, at least 80%, at least 85%, at least 90%, at least 95%, at least 98%, at least 99% or 100% sequence identity to the polypeptide of SEQ ID NO: 22,
o) a polypeptide having at least 70%, at least 80%, at least 85%, at least 90%, at least 95%, at least 98%, at least 99% or 100% sequence identity to the polypeptide of SEQ ID NO: 23,
p) a polypeptide having at least 70%, at least 80%, at least 85%, at least 90%, at least 95%, at least 98%, at least 99% or 100% sequence identity to the polypeptide of SEQ ID NO: 53,
q) a polypeptide having at least 70%, at least 80%, at least 85%, at least 90%, at least 95%, at least 98%, at least 99% or 100% sequence identity to the polypeptide of SEQ ID NO: 56,
r) a polypeptide having at least 70%, at least 80%, at least 85%, at least 90%, at least 95%, at least 98%, at least 99% or 100% sequence identity to the polypeptide of SEQ ID NO: 59,
s) a polypeptide having at least 70%, at least 80%, at least 85%, at least 90%, at least 95%, at least 98%, at least 99% or 100% sequence identity to the polypeptide of SEQ ID NO: 62,
t) a polypeptide having at least 70%, at least 80%, at least 85%, at least 90%, at least 95%, at least 98%, at least 99% or 100% sequence identity to the polypeptide of SEQ ID NO: 65, u) a polypeptide having at least 70%, at least 80%, at least 85%, at least 90%, at least 95%, at least 98%, at least 99% or 100% sequence identity to the polypeptide of SEQ ID NO: 68, v) a polypeptide having at least 70%, at least 80%, at least 85%, at least 90%, at least 95%, at least 98%, at least 99% or 100% sequence identity to the polypeptide of SEQ ID NO: 71, w) a polypeptide having at least 70%, at least 80%, at least 85%, at least 90%, at least 95%, at least 98%, at least 99% or 100% sequence identity to the polypeptide of SEQ ID NO: 74, x) a polypeptide having at least 70%, at least 80%, at least 85%, at least 90%, at least 95%, at least 98%, at least 99% or 100% sequence identity to the polypeptide of SEQ ID NO: 77, y) a polypeptide having at least 70%, at least 80%, at least 85%, at least 90%, at least 95%, at least 98%, at least 99% or 100% sequence identity to the polypeptide of SEQ ID NO: 80, z) a polypeptide having at least 70%, at least 80%, at least 85%, at least 90%, at least 95%, at least 98%, at least 99% or 100% sequence identity to the polypeptide of SEQ ID NO: 83, aa) a polypeptide having at least 70%, at least 80%, at least 85%, at least 90%, at least 95%, at least 98%, at least 99% or 100% sequence identity to the polypeptide of SEQ ID NO: 86, bb) a polypeptide having at least 70%, at least 80%, at least 85%, at least 90%, at least 95%, at least 98%, at least 99% or 100% sequence identity to the polypeptide of SEQ ID NO: 89, cc) a polypeptide having at least 70%, at least 80%, at least 85%, at least 90%, at least 95%, at least 98%, at least 99% or 100% sequence identity to the polypeptide of SEQ ID NO: 92, dd) a polypeptide having at least 70%, at least 80%, at least 85%, at least 90%, at least 95%, at least 98%, at least 99% or 100% sequence identity to the polypeptide of SEQ ID NO: 95, ee) a polypeptide having at least 70%, at least 80%, at least 85%, at least 90%, at least 95%, at least 98%, at least 99% or 100% sequence identity to the polypeptide of SEQ ID NO: 98, ff) a polypeptide having at least 70%, at least 80%, at least 85%, at least 90%, at least 95%, at least 98%, at least 99% or 100% sequence identity to the polypeptide of SEQ ID NO: 101, gg) a polypeptide having at least 70%, at least 80%, at least 85%, at least 90%, at least 95%, at least 98%, at least 99% or 100% sequence identity to the polypeptide of SEQ ID NO: 104, hh) a polypeptide having at least 70%, at least 80%, at least 85%, at least 90%, at least 95%, at least 98%, at least 99% or 100% sequence identity to the polypeptide of SEQ ID NO: 107, ii) a polypeptide having at least 70%, at least 80%, at least 85%, at least 90%, at least 95%, at least 98%, at least 99% or 100% sequence identity to the polypeptide of SEQ ID NO: 110, jj) a polypeptide having at least 70%, at least 80%, at least 85%, at least 90%, at least 95%, at least 98%, at least 99% or 100% sequence identity to the polypeptide of SEQ ID NO: 113, kk) a polypeptide having at least 70%, at least 80%, at least 85%, at least 90%, at least 95%, at least 98%, at least 99% or 100% sequence identity to the polypeptide of SEQ ID NO: 116, ll) a polypeptide having at least 70%, at least 80%, at least 85%, at least 90%, at least 95%, at least 98%, at least 99% or 100% sequence identity to the polypeptide of SEQ ID NO: 119, mm) a polypeptide having at least 70%, at least 80%, at least 85%, at least 90%, at least 95%, at least 98%, at least 99% or 100% sequence identity to the polypeptide of SEQ ID NO: 122, nn) a polypeptide having at least 70%, at least 80%, at least 85%, at least 90%, at least 95%, at least 98%, at least 99% or 100% sequence identity to the polypeptide of SEQ ID NO: 125, oo) a polypeptide having at least 70%, at least 80%, at least 85%, at least 90%, at least 95%, at least 98%, at least 99% or 100% sequence identity to the polypeptide of SEQ ID NO: 128, pp) a polypeptide having at least 70%, at least 80%, at least 85%, at least 90%, at least 95%, at least 98%, at least 99% or 100% sequence identity to the polypeptide of SEQ ID NO: 131, qq) a polypeptide having at least 70%, at least 80%, at least 85%, at least 90%, at least 95%, at least 98%, at least 99% or 100% sequence identity to the polypeptide of SEQ ID NO: 134, rr) a polypeptide having at least 70%, at least 80%, at least 85%, at least 90%, at least 95%, at least 98%, at least 99% or 100% sequence identity to the polypeptide of SEQ ID NO: 137, ss) a polypeptide having at least 70%, at least 80%, at least 85%, at least 90%, at least 95%, at least 98%, at least 99% or 100% sequence identity to the polypeptide of SEQ ID NO: 140, tt) a polypeptide having at least 70%, at least 80%, at least 85%, at least 90%, at least 95%, at least 98%, at least 99% or 100% sequence identity to the polypeptide of SEQ ID NO: 143, uu) a polypeptide having at least 70%, at least 80%, at least 85%, at least 90%, at least 95%, at least 98%, at least 99% or 100% sequence identity to the polypeptide of SEQ ID NO: 146, vv) a polypeptide having at least 70%, at least 80%, at least 85%, at least 90%, at least 95%, at least 98%, at least 99% or 100% sequence identity to the polypeptide of SEQ ID NO: 149, ww) a polypeptide having at least 70%, at least 80%, at least 85%, at least 90%, at least 95%, at least 98%, at least 99% or 100% sequence identity to the polypeptide of SEQ ID NO: 152, xx) a polypeptide having at least 70%, at least 80%, at least 85%, at least 90%, at least 95%, at least 98%, at least 99% or 100% sequence identity to the polypeptide of SEQ ID NO: 155, yy) a polypeptide having at least 70%, at least 80%, at least 85%, at least 90%, at least 95%, at least 98%, at least 99% or 100% sequence identity to the polypeptide of SEQ ID NO: 158, zz) a polypeptide having at least 70%, at least 80%, at least 85%, at least 90%, at least 95%, at least 98%, at least 99% or 100% sequence identity to the polypeptide of SEQ ID NO: 161, aaa) a polypeptide having at least 70%, at least 80%, at least 85%, at least 90%, at least 95%, at least 98%, at least 99% or 100% sequence identity to the polypeptide of SEQ ID NO: 164, bbb) a polypeptide having at least 70%, at least 80%, at least 85%, at least 90%, at least 95%, at least 98%, at least 99% or 100% sequence identity to the polypeptide of SEQ ID NO: 167, ccc) a polypeptide having at least 70%, at least 80%, at least 85%, at least 90%, at least 95%, at least 98%, at least 99% or 100% sequence identity to the polypeptide of SEQ ID NO: 170, ddd) a polypeptide having at least 70%, at least 80%, at least 85%, at least 90%, at least 95%, at least 98%, at least 99% or 100% sequence identity to the polypeptide of SEQ ID NO: 173, eee) a polypeptide having at least 70%, at least 80%, at least 85%, at least 90%, at least 95%, at least 98%, at least 99% or 100% sequence identity to the polypeptide of SEQ ID NO: 176, fff) a polypeptide having at least 70%, at least 80%, at least 85%, at least 90%, at least 95%, at least 98%, at least 99% or 100% sequence identity to the polypeptide of SEQ ID NO: 179, ggg) a polypeptide having at least 70%, at least 80%, at least 85%, at least 90%, at least 95%, at least 98%, at least 99% or 100% sequence identity to the polypeptide of SEQ ID NO: 182, hhh) a polypeptide having at least 70%, at least 80%, at least 85%, at least 90%, at least 95%, at least 98%, at least 99% or 100% sequence identity to the polypeptide of SEQ ID NO: 185, iii) a polypeptide having at least 70%, at least 80%, at least 85%, at least 90%, at least 95%, at least 98%, at least 99% or 100% sequence identity to the polypeptide of SEQ ID NO: 188, jjj) a polypeptide having at least 70%, at least 80%, at least 85%, at least 90%, at least 95%, at least 98%, at least 99% or 100% sequence identity to the polypeptide of SEQ ID NO: 191, kkk) a polypeptide having at least 70%, at least 80%, at least 85%, at least 90%, at least 95%, at least 98%, at least 99% or 100% sequence identity to the polypeptide of SEQ ID NO: 194, lll) a polypeptide having at least 70%, at least 80%, at least 85%, at least 90%, at least 95%, at least 98%, at least 99% or 100% sequence identity to the polypeptide of SEQ ID NO: 197, wherein the granule comprises a core comprising said polypeptide and a coating and optionally the polypeptide comprises one or more of the motifs [E/D/H]H[I/V/L/F/M]X[P/A/S], [T/D/S][G/N]PQL, [G/T]Y[D/S][R/K/L], [F/L/Y/I]A[N/R]D[L/I/P/V], C[D/N]T[A/R] and [D/Q][I/V]DH.

One embodiment of the invention relates to a granule comprising a polypeptide having DNase activity, wherein the polypeptide has at least 60%, e.g., at least 70%, at least 80%, at least 90%, at least 95%, at least 98%, or at least 99% sequence identity to the polypeptide shown in SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 53, SEQ ID NO: 56, SEQ ID NO: 59, SEQ ID NO: 62, SEQ ID NO: 65, SEQ ID NO: 68, SEQ ID NO: 71, SEQ ID NO: 74, SEQ ID NO: 77, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 161, SEQ ID NO: 164, SEQ ID NO: 167, SEQ ID NO: 170, SEQ ID NO: 173, SEQ ID NO: 176, SEQ ID NO: 179, SEQ ID NO: 182, SEQ ID NO: 185, SEQ ID NO: 188, SEQ ID NO: 191, SEQ ID NO: 194 and SEQ ID NO: 197, wherein the granule comprises a core comprising the polypeptide and a coating.

Formulation of Detergent

Detergent ingredients can be separated physically from each other by compartments in water dissolvable pouches. Thereby negative storage interaction between components can be avoided. Different dissolution profiles of each of the compartments can also give rise to delayed dissolution of selected components in the wash solution.

The detergent composition may take the form of a unit dose product. A unit dose product is the packaging of a single dose in a non-reusable container. It is increasingly used in detergents for laundry. A detergent unit dose product is the packaging (e.g., in a pouch made from a water soluble film) of the amount of detergent used for a single wash.

Pouches can be of any form, shape and material which is suitable for holding the composition, e.g., without allowing the release of the composition from the pouch prior to water contact. The pouch is made from water soluble film which encloses an inner volume. Said inner volume can be divided into compartments of the pouch. Preferred films are polymeric materials preferably polymers which are formed into a film or sheet. Preferred polymers, copolymers or derivates thereof are selected polyacrylates, and water soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, most preferably polyvinyl alcohol copolymers and, hydroxypropyl methyl cellulose (HPMC). Preferably the level of polymer in the film for example PVA is at least about 60%. Preferred average molecular weight will typically be about 20,000 to about 150,000. Films can also be a blend composition comprising hydrolytically degradable and water soluble polymer blends such as polyactide and polyvinyl alcohol (known under the Trade reference M8630 as sold by Chris Craft In. Prod. Of Gary, Ind., US) plus plasticizers like glycerol, ethylene glycerol, Propylene glycol, sorbitol and mixtures thereof. The pouches can comprise a solid laundry cleaning composition or part components and/or a liquid cleaning composition or part components separated by the water soluble film. The compartment for liquid components can be different in composition than compartments containing solids (see, e.g., US 2009/0011970).

Laundry Soap Bars

The DNase of the invention may be added to laundry soap bars and used for hand washing laundry, fabrics and/or textiles. The term laundry soap bar includes laundry bars, soap bars, combo bars, syndet bars and detergent bars. The types of bar usually differ in the type of surfactant they contain, and the term laundry soap bar includes those containing soaps from fatty acids and/or synthetic soaps. The laundry soap bar has a physical form which is solid and not a liquid, gel or a powder at room temperature. The term solid is defined as a physical form which does not significantly change over time, i.e., if a solid object (e.g., laundry soap bar) is placed inside a container, the solid object does not change to fill the container it is placed in. The bar is a solid typically in bar form but can be in other solid shapes such as round or oval.

The laundry soap bar may contain one or more additional enzymes, protease inhibitors such as peptide aldehydes (or hydrosulfite adduct or hemiacetal adduct), boric acid, borate, borax and/or phenylboronic acid derivatives such as 4-formylphenylboronic acid, one or more soaps or synthetic surfactants, polyols such as glycerine, pH controlling compounds such as fatty acids, citric acid, acetic acid and/or formic acid, and/or a salt of a monovalent cation and an organic anion wherein the monovalent cation may be for example $Na^+$, $K^+$ or $NH_4^+$ and the organic anion may be for example formate, acetate, citrate or lactate such that the salt of a monovalent cation and an organic anion may be, for example, sodium formate.

The laundry soap bar may also contain complexing agents like EDTA and HEDP, perfumes and/or different type of fillers, surfactants, e.g., anionic synthetic surfactants, builders, polymeric soil release agents, detergent chelators, stabilizing agents, fillers, dyes, colorants, dye transfer inhibitors, alkoxylated polycarbonates, suds suppressers, structurants, binders, leaching agents, bleaching activators, clay soil removal agents, anti-redeposition agents, polymeric dispersing agents, brighteners, fabric softeners, perfumes and/or other compounds known in the art.

The laundry soap bar may be processed in conventional laundry soap bar making equipment such as but not limited to: mixers, plodders, e.g., a two stage vacuum plodder, extruders, cutters, logo-stampers, cooling tunnels and wrappers. The invention is not limited to preparing the laundry soap bars by any single method. The premix of the invention may be added to the soap at different stages of the process. For example, the premix containing soap, DNase, optionally one or more additional enzymes, a protease inhibitor, and a salt of a monovalent cation and an organic anion may be prepared and the mixture is then plodded. The DNase and optional additional enzymes may be added at the same time as the protease inhibitor for example in liquid form. Besides the mixing step and the plodding step, the process may further comprise the steps of milling, extruding, cutting, stamping, cooling and/or wrapping.

Pharmaceutical Compositions and Uses

The invention further concerns a pharmaceutical composition comprising a polypeptide having DNase activity and a pharmaceutical adjunct ingredient, wherein the polypeptide having DNase activity. The adjunct ingredient may be any excipient suitable for pharmaceutical compositions. The adjunct/excipient are within the choice of the skilled artisan. The pharmaceutical composition further comprise a polypeptide selected from the group consisting of polypeptides comprising SEQ ID NOs: 8, 9, 10 and 11, or DNases having at least 80% sequence identity thereto. The pharmaceutical compositions can be used for releasing or removing a biofilm or preventing biofilm formation on surfaces such as medical devices.

The use may be indwelling medical device characterized in that at least a portion of a patient-contactable surface of said device is coated with the pharmaceutical composition comprising the DNases of the invention.

The device can be a catheter such as a central venous catheter, intravascular catheter, urinary catheter, Hickman catheter, peritoneal dialysis catheter, endrotracheal catheter, or wherein the device is a mechanical heart valve, a cardiac pacemaker, an arteriovenous shunt, a scleral buckle, a prosthetic joint, a tympanostomy tube, a tracheostomy tube, a voice prosthetic, a penile prosthetic, an artificial urinary sphincter, a synthetic pubovaginal sling, a surgical suture, a bone anchor, a bone screw, an intraocular lens, a contact lens, an intrauterine device, an aortofemoral graft, a vascular graft, a needle, a Luer-Lok connector, a needleless connector or a surgical instrument.

The pharmaceutical composition can be formulated as a liquid, lotion, cream, spray, gel or ointment.

The pharmaceutical composition can be for administration to an animal patient. The animal patient can be a mammalian patient. The mammalian patient can be a human The invention is further summarized in the following paragraphs:

1. Use of a polypeptide having DNase activity, wherein the polypeptide is selected from the group consisting of SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 53, SEQ ID NO: 56, SEQ ID NO: 59, SEQ ID NO: 62, SEQ ID NO: 65, SEQ ID NO: 68, SEQ ID NO: 71, SEQ ID NO: 74, SEQ ID NO: 77, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 161, SEQ ID NO: 164, SEQ ID NO: 167, SEQ ID NO: 170, SEQ ID NO: 173, SEQ ID NO: 176, SEQ ID NO: 179, SEQ ID NO: 182, SEQ ID NO: 185, SEQ ID NO: 188, SEQ ID NO: 191, SEQ ID NO: 194 and SEQ ID NO: 197, or a DNase having at least 80% sequence identity thereto for preventing, reducing or removing a biofilm from an item, wherein the item is a textile.
2. Use according to paragraph 1 for preventing, reducing or removing stickiness of the item.
3. Use according to paragraph 1 or 2 for pretreating stains on the item.
4. Use according to any of paragraphs 1-3 for preventing, reducing or removing redeposition of soil during a wash cycle.
5. Use according to any of paragraphs 1-4 for preventing, reducing or removing adherence of soil to the item.
6. Use according to any of paragraphs 1-5 for maintaining or improving the whiteness of the item.
7. Use according to any of paragraphs 1-6, wherein the polypeptide is the polypeptide of any of paragraphs 45-54.
8. Use according to any of paragraphs 1-7, wherein a malodor is reduced or removed from the item.
9. Use according to any of paragraphs 1-8, wherein the malodor is caused by E-2-nonenal.
10. Use according to any of paragraphs 1-9, wherein the amount of E-2-nonenal present on a wet textile is reduced or removed.
11. Use according to any of paragraphs 1-10, wherein the amount of E-2-nonenal present on a dry textile is reduced or removed.
12. A detergent composition comprising a polypeptide having deoxyribonuclease (DNase) activity selected from the group consisting of SEQ ID NO: 8, SEQ ID NO: 9, SEQ ID NO: 10, SEQ ID NO: 11, SEQ ID NO:

12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 53, SEQ ID NO: 56, SEQ ID NO: 59, SEQ ID NO: 62, SEQ ID NO: 65, SEQ ID NO: 68, SEQ ID NO: 71, SEQ ID NO: 74, SEQ ID NO: 77, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 161, SEQ ID NO: 164, SEQ ID NO: 167, SEQ ID NO: 170, SEQ ID NO: 173, SEQ ID NO: 176, SEQ ID NO: 179, SEQ ID NO: 182, SEQ ID NO: 185, SEQ ID NO: 188, SEQ ID NO: 191, SEQ ID NO: 194 and SEQ ID NO: 197 or DNases having at least 80% sequence identity thereto and a detergent adjunct ingredient.

13. The detergent composition according to paragraph 12, wherein the polypeptide is obtained from *Bacillus* sp. or *Paenibacillus*.

14. The detergent composition according to paragraph 12 or 13, wherein the polypeptides with SEQ ID NOS 7, 8, 9 or 10 are obtained from *Bacillus* sp-62451, *Bacillus horikoshii* or *Paenibacillus* sp-18057 respectively and wherein SEQ ID NO: 11 is obtained from *Bacillus* sp-62520, SEQ ID NO: 12 is obtained from *Bacillus* sp-62520, SEQ ID NO: 13 is obtained from *Bacillus horikoshii*, SEQ ID NO: 14 is obtained from *Bacillus horikoshii*, SEQ ID NO: 15 is obtained from *Bacillus* sp-16840, SEQ ID NO: 16 is obtained from *Bacillus* sp-16840, SEQ ID NO: 17 is obtained from *Bacillus* sp-62668, SEQ ID NO: 18 is obtained from *Bacillus* sp-13395, SEQ ID NO: 19 is obtained from *Bacillus horneckiae*, SEQ ID NO: 20 is obtained from *Bacillus* sp-11238, SEQ ID NO: 21 is obtained from *Bacillus cibi*, SEQ ID NO: 22 is obtained from *Bacillus* sp-18318 and SEQ ID NO: 23 is obtained from *Bacillus idriensis* or is one of the following In one aspect of the invention the polypeptide having DNase activity is obtained from *Vibrissea flavovirens* and comprises or consists of the polypeptide shown in SEQ ID NO: 86. In one aspect of the invention the polypeptide having DNase activity is obtained from *Acremonium dichromosporum* and comprises or consists of the polypeptide shown in SEQ ID NO: 140. In one aspect of the invention the polypeptide having DNase activity is obtained from *Clavicipitaceae* sp-70249 and comprises or consists of the polypeptide shown in SEQ ID NO: 176. In one aspect of the invention the polypeptide having DNase activity is obtained from *Penicillium reticulisporum* and comprises or consists of the polypeptide shown in SEQ ID NO: 107. In one aspect of the invention the polypeptide having DNase activity is obtained from *Pycnidiophora cf. dispera* and comprises or consists of the polypeptide shown in SEQ ID NO: 167. In one aspect of the invention the polypeptide having DNase activity is obtained from *Metapochonia suchlasporia* and comprises or consists of the polypeptide shown in SEQ ID NO: 131. In one aspect of the invention the polypeptide having DNase activity is obtained from *Acremonium* sp. XZ2007 and comprises or consists of the polypeptide shown in SEQ ID NO: 137. In one aspect of the invention the polypeptide having DNase activity is obtained from *Setosphaeria rostrata* and comprises or consists of the polypeptide shown in SEQ ID NO: 89. In one aspect of the invention the polypeptide having DNase activity is obtained from *Sarocladium* sp. XZ2014 and comprises or consists of the polypeptide shown in SEQ ID NO: 143. In one aspect of the invention the polypeptide having DNase activity is obtained from *Metarhizium* sp. HNA15-2 and comprises or consists of the polypeptide shown in SEQ ID NO: 146. In one aspect of the invention the polypeptide having DNase activity is obtained from *Endophragmiella valdina* and comprises or consists of the polypeptide shown in SEQ ID NO: 92. In one aspect of the invention the polypeptide having DNase activity is obtained from *Humicolopsis cephalosporioides* and comprises or consists of the polypeptide shown in SEQ ID NO: 182. In one aspect of the invention the polypeptide having DNase activity is obtained from *Corynespora cassiicola* and comprises or consists of the polypeptide shown in SEQ ID NO: 95. In one aspect of the invention the polypeptide having DNase activity is obtained from *Paraphoma* sp. XZ1965 and comprises or consists of the polypeptide shown in SEQ ID NO: 98. In one aspect of the invention the polypeptide having DNase activity is obtained from *Curvularia lunata* and comprises or consists of the polypeptide shown in SEQ ID NO: 104. In one aspect of the invention the polypeptide having DNase activity is obtained from *Acremonium* sp. XZ2414 and comprises or consists of the polypeptide shown in SEQ ID NO: 149. In one aspect of the invention the polypeptide having DNase activity is obtained from *Isaria tenuipes* and comprises or consists of the polypeptide shown in SEQ ID NO: 152. In one aspect of the invention the polypeptide having DNase activity is obtained from *Roussoella intermedia* and comprises or consists of the polypeptide shown in SEQ ID NO: 188. In one aspect of the invention the polypeptide having DNase activity is obtained from *Scytalidium circinatum* and comprises or consists of the polypeptide shown in SEQ ID NO: 155. In one aspect of the invention the polypeptide having DNase activity is obtained from *Setophaeosphaeria* sp. and comprises or consists of the polypeptide shown in SEQ ID NO: 158. In one aspect of the invention the polypeptide having DNase activity is obtained from *Alternaria* sp. XZ2545 and comprises or consists of the polypeptide shown in SEQ ID NO: 116. In one aspect of the invention the polypeptide having DNase activity is obtained from *Alternaria* sp. and comprises or consists of the polypeptide shown in SEQ ID NO: 119. In one aspect of the invention the polypeptide having DNase activity is obtained from *Metarhizium lepidiotae* and comprises or consists of the polypeptide shown in SEQ ID NO: 158. In one aspect of the invention the polypeptide having DNase activity is obtained from *Pleosporales* and comprises or consists of the polypeptide shown in SEQ ID NO: 191. In one aspect of the invention the polypeptide having DNase activity is obtained from *Phaeosphaeria* sp. and comprises or consists of the polypeptide shown in SEQ ID NO: 194. In one aspect of the invention the polypeptide having DNase activity is obtained from *Didymosphaeria futilis* and comprises or consists of the polypeptide shown in SEQ ID NO: 197. In one aspect of the invention the polypeptide having DNase activity is obtained from

*Bacillus vietnamensis* and comprises or consists of the polypeptide shown in SEQ ID NO: 59. In one aspect of the invention the polypeptide having DNase activity is obtained from *Bacillus hwajinpoensis* and comprises or consists of the polypeptide shown in SEQ ID NO: 62. In one aspect of the invention the polypeptide having DNase activity is obtained from Xanthan alkaline community J and comprises or consists of the polypeptide shown in SEQ ID NO: 56. In one aspect of the invention the polypeptide having DNase activity is obtained from *Bacillus indicus* and comprises or consists of the polypeptide shown in SEQ ID NO: 68. In one aspect of the invention the polypeptide having DNase activity is obtained from *Bacillus marisflavi* and comprises or consists of the polypeptide shown in SEQ ID NO: 71. In one aspect of the invention the polypeptide having DNase activity is obtained from *Bacillus luciferensis* and comprises or consists of the polypeptide shown in SEQ ID NO: 74. In one aspect of the invention the polypeptide having DNase activity is obtained from *Bacillus marisflavi* and comprises or consists of the polypeptide shown in SEQ ID NO: 77. In one aspect of the invention the polypeptide having DNase activity is obtained from *Sporormia fimetaria* and comprises or consists of the polypeptide shown in SEQ ID NO: 164. In one aspect of the invention the polypeptide having DNase activity is obtained from *Daldinia fissa* and comprises or consists of the polypeptide shown in SEQ ID NO. 134. In one aspect of the invention the polypeptide having DNase activity is obtained from *Pyrenochaetopsis* sp. and comprises or consists of the polypeptide shown in SEQ ID NO: 83. In one aspect of the invention the polypeptide having DNase activity is obtained from *Westerdykella* sp. AS85-2 and comprises or consists of the polypeptide shown in SEQ ID NO: 179. In one aspect of the invention the polypeptide having DNase activity is obtained from *Monilinia fructicola* and comprises or consists of the polypeptide shown in SEQ ID NO: 101. In one aspect of the invention the polypeptide having DNase activity is obtained from *Neosartorya massa* and comprises or consists of the polypeptide shown in SEQ ID NO: 185. In one aspect of the invention the polypeptide having DNase activity is obtained from *Penicillium quercetorum* and comprises or consists of the polypeptide shown in SEQ ID NO: 110. In one aspect of the invention the polypeptide having DNase activity is obtained from Xanthan alkaline community D and comprises or consists of the polypeptide shown in SEQ ID NO: 170. In one aspect of the invention the polypeptide having DNase activity is obtained from *Bacillus algicola* and comprises or consists of the polypeptide shown in SEQ ID NO: 53. In one aspect of the invention the polypeptide having DNase activity is obtained from Xanthan alkaline community O and comprises or consists of the polypeptide shown in SEQ ID NO: 173. In one aspect of the invention the polypeptide having DNase activity is obtained from *Scytalidium thermophilum* and comprises or consists of the polypeptide shown in SEQ ID NO: 128.

15. The detergent composition according to any of paragraphs 12-14, wherein the polypeptide is the polypeptide of any of paragraphs 45-54.

16. The detergent composition according to any of paragraphs 12-15, wherein the detergent adjunct ingredient is selected from the group consisting of surfactants, builders, flocculating aid, chelating agents, dye transfer inhibitors, enzymes, enzyme stabilizers, enzyme inhibitors, catalytic materials, bleach activators, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, builders and co-builders, fabric huing agents, anti-foaming agents, dispersants, processing aids, and/or pigments.

17. The detergent composition according to any of paragraphs 12-16, wherein the composition further comprises one or more enzymes selected from the group consisting of proteases, lipases, cutinases, amylases, carbohydrases, cellulases, pectinases, mannanases, arabinases, galactanases, xylanases and oxidases.

18. The detergent composition according to any of paragraphs 12-17, wherein the enzyme is a protease, which is of animal, vegetable or microbial origin.

19. The detergent composition according to any of paragraphs 12-18, wherein the protease is chemically modified or protein engineered.

20. The detergent composition according to any of paragraphs 12-19, wherein the protease is a serine protease or a metalloprotease, preferably an alkaline microbial protease or a trypsin-like protease.

21. The detergent composition according to any of paragraphs 12-20, wherein the protease is selected from the group consisting of *Bacillus*, e.g., subtilisin Novo, subtilisin Carlsberg, subtilisin 309, subtilisin 147, subtilisin 168, trypsin of bovine origin, trypsin of porcine origin and *Fusarium* protease.

22. The detergent composition according to any of paragraphs 12-21, wherein the detergent composition is capable of reducing adhesion of bacteria selected from the group consisting of *Acinetobacter* sp., *Aeromicrobium* sp., *Brevundimonas* sp., *Microbacterium* sp., *Micrococcus luteus*, *Pseudomonas* sp., *Staphylococcus epidermidis*, and *Stenotrophomonas* sp. to a surface, or releasing the bacteria from a surface to which they adhere.

23. The detergent composition according to any of paragraphs 12-22, wherein the surface is a textile surface.

24. The detergent composition according to any of paragraphs 12-23, wherein the textile is made of cotton, Cotton/Polyester, Polyester, Polyamide, Polyacryl and/or silk.

25. The detergent composition according to any of paragraphs 12-24, wherein the composition is a bar, a homogenous tablet, a tablet having two or more layers, a pouch having one or more compartments, a regular or compact powder, a granule, a paste, a gel, or a regular, compact or concentrated liquid.

26. The detergent composition according to any of paragraphs 12-25, wherein the composition is a liquid detergent, a powder detergent or a granule detergent.

27. A laundering method for laundering an item comprising the steps of:
   a. Exposing an item to a wash liquor comprising a polypeptide of any of paragraphs 45-54 or a detergent composition according to any of paragraphs 12-26;
   b. Completing at least one wash cycle; and
   c. Optionally rinsing the item,
wherein the item is a textile.

28. The method according to paragraph 27, wherein the pH of the wash liquor is in the range of 1 to 11.

29. The method according to paragraph 27 or 28, wherein the pH of the wash liquor is in the range 5.5 to 11, such as in the range of 7 to 9, in the range of 7 to 8 or in the range of 7 to 8.5.
30. The method according to any of paragraphs 27-29, wherein the temperature of the wash liquor is in the range of 5° C. to 95° C., or in the range of 10° C. to 80° C., in the range of 10° C. to 70° C., in the range of 10° C. to 60° C., in the range of 10° C. to 50° C., in the range of 15° C. to 40° C. or in the range of 20° C. to 30° C.
31. The method according to any of paragraphs 27-30, wherein the temperature of the wash liquor is 30° C.
32. The method according to any of paragraphs 27-31, wherein the method further comprises draining of the wash liquor or part of the wash liquor after completion of a wash cycle.
33. The method according to any of paragraphs 27-32, wherein the item is exposed to the wash liquor during a first and optionally a second or a third wash cycle.
34. The method according to any of paragraphs 27-33, wherein the item is rinsed after being exposed to the wash liquor.
35. The method according to any of paragraphs 27-34, wherein the item is rinsed with water or with water comprising a conditioner.
36. The method according to any of paragraphs 27-35, wherein stickiness of the item is reduced.
37. The method according to any of paragraphs 27-36, wherein stains present on the item is pretreated with a polypeptide of any of paragraphs 45-54 or a detergent composition according to any of paragraphs 12-26.
38. The method according to any of paragraphs 27-37, wherein redeposition of soil is reduced.
39. The method according to any of paragraphs 27-38, wherein adherence of soil to the item is reduced or removed.
40. The method according to any of paragraphs 27-39, wherein whiteness of the item is maintained or improved.
41. The method according to any of paragraphs 27-40, wherein malodor is reduced or removed from the item.
42. The method according to any of paragraphs 27-41, wherein the malodor is caused by E-2-nonenal.
43. The method according to any of paragraphs 27-42, wherein the amount of E-2-nonenal present on a wet or dry textile is reduced or removed.
44. The method according to any of paragraphs 27-43, wherein the concentration of the polypeptide in the wash liquor is at least 1 mg of DNase protein, such as at least 5 mg of protein, preferably at least 10 mg of protein, more preferably at least 15 mg of protein, even more preferably at least 20 mg of protein, most preferably at least 30 mg of protein, and even most preferably at least 40 mg of protein per liter of wash liquor.
45. A polypeptide having DNase activity, selected from the group consisting of:
   a. a polypeptide having at least 60% sequence identity to the mature polypeptide of SEQ ID NO: 2, 4 or 6 or a polypeptide having at least 80% sequence identity to the polypeptide shown in SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 53, SEQ ID NO: 56, SEQ ID NO: 59, SEQ ID NO: 62, SEQ ID NO: 65, SEQ ID NO: 68, SEQ ID NO: 71, SEQ ID NO: 74, SEQ ID NO: 77, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 161, SEQ ID NO: 164, SEQ ID NO: 167, SEQ ID NO: 170, SEQ ID NO: 173, SEQ ID NO: 176, SEQ ID NO: 179, SEQ ID NO: 182, SEQ ID NO: 185, SEQ ID NO: 188, SEQ ID NO: 191, SEQ ID NO: 194 and SEQ ID NO: 197;
   b. a polypeptide encoded by a polynucleotide that hybridizes under low stringency conditions with
      i. the mature polypeptide coding sequence of SEQ ID NO: 1, or
      ii. the full-length complement of (i) or (ii);
   c. a polypeptide encoded by a polynucleotide having at least 80% sequence identity to the mature polypeptide coding sequence of SEQ ID NO: 1, 3 or 5; or SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 54, SEQ ID NO: 57, SEQ ID NO: 60, SEQ ID NO: 63, SEQ ID NO: 66, SEQ ID NO: 69, SEQ ID NO: 72, SEQ ID NO: 75, SEQ ID NO: 78, SEQ ID NO: 81, SEQ ID NO: 84, SEQ ID NO: 87, SEQ ID NO: 90, SEQ ID NO: 93, SEQ ID NO: 96, SEQ ID NO: 99, SEQ ID NO: 102, SEQ ID NO: 105, SEQ ID NO: 108, SEQ ID NO: 111, SEQ ID NO: 114, SEQ ID NO: 117, SEQ ID NO: 120, SEQ ID NO: 123, SEQ ID NO: 126, SEQ ID NO: 129, SEQ ID NO: 132, SEQ ID NO: 135, SEQ ID NO: 138, SEQ ID NO: 141, SEQ ID NO: 144, SEQ ID NO: 147, SEQ ID NO: 150, SEQ ID NO: 153, SEQ ID NO: 156, SEQ ID NO: 159, SEQ ID NO: 162, SEQ ID NO: 165, SEQ ID NO: 168, SEQ ID NO: 171, SEQ ID NO: 174, SEQ ID NO: 177, SEQ ID NO: 180, SEQ ID NO: 183, SEQ ID NO: 186, SEQ ID NO: 189, SEQ ID NO: 192, SEQ ID NO: 195;
   d. a variant of the mature polypeptide of SEQ ID NO: 2, 4 or 6 comprising a substitution, deletion, and/or insertion at one or more positions or a variant of the mature polypeptide of SEQ ID NO: 8, 9 or 10 comprising a substitution, deletion, and/or insertion at one or more positions; and
   e. a fragment of the polypeptide of (a), (b), (c), or (d) that has DNase activity;
46. The polypeptide of paragraph 45 having at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 2, 4 or 6 or to the mature polypeptide of SEQ ID NO: 8, 9 or 10.
47. The polypeptide according to paragraph 45 or 46, which is encoded by a polynucleotide that hybridizes under low stringency conditions, low-medium stringency conditions, medium stringency conditions, medium-high stringency conditions, high stringency conditions, or very high stringency conditions with
  i. the mature polypeptide coding sequence of SEQ ID NO: 1, or
  ii. the full-length complement of (i) or (ii).
48. The polypeptide according to any of paragraphs 45-47, which is encoded by a polynucleotide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide coding sequence of SEQ ID NO: 1, 3 or 5.
49. The polypeptide according to any of paragraphs 45-48, comprising or consisting of SEQ ID NO: 8, 9 or 10 or the mature polypeptide of SEQ ID NO: 2, 4 or 6.
50. The polypeptide according to any of paragraphs 45-49, which is a variant of the mature polypeptide of SEQ ID NO: 8, 9 or 10 comprising a substitution, deletion, and/or insertion at one or more positions.
51. The polypeptide according to paragraph 50, which is a fragment of SEQ ID NO: 2, 4 or 6, wherein the fragment has DNase activity or a fragment of SEQ ID NO: 9, wherein the fragment has DNase activity.
52. A polynucleotide encoding the polypeptide according to any of paragraphs 45-51.
53. A nucleic acid construct or expression vector comprising the polynucleotide of paragraph 52 operably linked to one or more control sequences that direct the production of the polypeptide in an expression host.
54. A recombinant host cell comprising the polynucleotide of paragraph 52 operably linked to one or more control sequences that direct the production of the polypeptide.
55. A method of producing the polypeptide of any of paragraphs 45-51, comprising cultivating a cell, which in its wild-type form produces the polypeptide, under conditions conducive for production of the polypeptide.
56. The method of paragraph 55, further comprising recovering the polypeptide.
57. A method of producing a polypeptide having DNase activity, comprising cultivating the host cell of paragraph 54 under conditions conducive for production of the polypeptide.
58. The method of paragraph 57, further comprising recovering the polypeptide.
59. A method of producing a protein, comprising cultivating the recombinant host cell comprising a gene encoding a protein operably linked to the polynucleotide of paragraph 52, wherein the gene is foreign to the polynucleotide encoding the propeptide, under conditions conducive for production of the protein.
60. The method of paragraph 59, further comprising recovering the protein.
61. A whole broth formulation or cell culture composition comprising a polypeptide of any of paragraphs 45-51.
62. An Item laundered according to the method of any of paragraphs 27-44.
63. A pharmaceutical composition comprising a polypeptide having DNase activity and a pharmaceutical adjunct ingredient, wherein the polypeptide is obtained from a bacterial source.
64. The pharmaceutical composition according to paragraph 63, wherein the polypeptide having DNase activity is obtained from *Bacillus* or *Paenibacillus*.
65. The pharmaceutical composition according to paragraph 63 or 64, wherein the polypeptide having DNase activity is obtained from *Bacillus* sp-62451, *Bacillus horikoshii* or *Paenibacillus* sp-18057.
66. The pharmaceutical composition according to any of paragraphs 63-65, wherein the polypeptide is the polypeptide of paragraphs 45-51.
67. The pharmaceutical composition according to any of paragraphs 63-66, wherein the composition is formulated as a dental paste, a liquid dentifrice, a mouthwash, a troche or a gingival massage ointment.
68. The pharmaceutical composition according to any of paragraphs 63-66, further comprising one or more of an antimicrobial compound, such as an antibacterial compound, an antiparasitic compound, an antifungal compound and an antiviral compound.
69. An indwelling medical device characterized in that at least a portion of a patient-contactable surface of said device is coated with the pharmaceutical composition of any of paragraphs 63-68.
70. The device according to paragraph 69 wherein said device is a catheter such as a central venous catheter, intravascular catheter, urinary catheter, Hickman catheter, peritoneal dialysis catheter, endrotracheal catheter, or wherein the device is a mechanical heart valve, a cardiac pacemaker, an arteriovenous shunt, a schleral buckle, a prosthetic joint, a tympanostomy tube, a tracheostomy tube, a voice prosthetic, a penile prosthetic, an artificial urinary sphincter, a synthetic pubovaginal sling, a surgical suture, a bone anchor, a bone screw, an intraocular lens, a contact lens, an intrauterine device, an aortofemoral graft, a vascular graft, a needle, a Luer-Lok connector, a needleless connector or a surgical instrument.
71. A method of producing the polypeptide of any of paragraphs 45-51, comprising cultivating the host cell of paragraph 54 under conditions conducive for production of the polypeptide.
72. The method of paragraph 71, further comprising recovering the polypeptide.
73. The recombinant host cell of paragraph 54 further comprising a polynucleotide encoding a second polypeptide of interest; preferably an enzyme of interest; more preferably a secreted enzyme of interest; even more preferably a hydrolase, isomerase, ligase, lyase, oxidoreductase, or a transferase; and most preferably the secreted enzyme is an alpha-galactosidase, alpha-glucosidase, aminopeptidase, amylase, asparaginase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, green fluorescent protein, glucano-transferase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or a xylanase.
74. The recombinant host cell of paragraph 73, wherein the second polypeptide of interest is heterologous or homologous to the host cell.
75. The recombinant host cell of paragraph 73 or 74, which is a fungal host cell; preferably a filamentous fungal host cell; more preferably an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces,*

*Thermoascus, Thielavia, Tolypocladium, Trametes,* or *Trichoderma* cell; most preferably an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

76. The recombinant host cell of paragraph 73 or 74, which is a bacterial host cell; preferably a prokaryotic host cell; more preferably a Gram-positive host cell; even more preferably a *Bacillus, Clostridium, Enterococcus, Geobacillus, Lactobacillus, Lactococcus, Oceanobacillus, Staphylococcus, Streptococcus,* or *Streptomyces* host cell; and most preferably a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* and *Bacillus thuringiensis* host cell.

77. A method of producing the second polypeptide of interest as defined in paragraph 71 or 72, comprising cultivating the host cell of any of paragraphs 73-76 under conditions conducive for production of the second polypeptide of interest.

78. The method of paragraph 77, further comprising recovering the second polypeptide of interest.

79. The detergent composition according to any of the preceding composition paragraphs, wherein the detergent adjunct ingredient is a surfactant.

80. The detergent composition according to any of the preceding composition paragraphs, wherein the detergent adjunct ingredient is a builder.

81. The detergent composition according to any of the preceding composition paragraphs, wherein the detergent adjunct ingredient is a clay soil removal/anti-redeposition agents.

82. The detergent composition according to any of paragraphs 12-26, wherein the composition is a liquid detergent composition, comprising a surfactant and a detergent builder in a total concentration of at least 3% by weight, and a detergent enzyme containing microcapsule, wherein the membrane of the microcapsule is produced by cross-linking of a polybranched polyamine having a molecular weight of more than 1 kDa.

83. The detergent composition according to any of paragraphs 79-82, wherein the reactive amino groups of the polybranched polyamine constitute at least 15% of the molecular weight.

84. The detergent composition according to any of paragraphs 79-83, wherein the microcapsule is produced by using an acid chloride as crosslinking agent.

85. The detergent composition according to any of paragraphs 79-84, wherein the diameter of the microcapsule is at least, or above, 50 micrometers.

86. The detergent composition according to any of paragraphs 79-85, wherein the microcapsule contains at least 1% by weight of active enzyme.

87. The detergent composition according to any of paragraphs 79-86, which further includes an alcohol, such as a polyol.

88. The detergent composition according to any of paragraphs 79-87, wherein the surfactant is an anionic surfactant.

89. The detergent composition according to any of paragraphs 79-88, which is a liquid laundry composition.

90. The detergent composition according to any of paragraphs 79-89, which contains less than 90% by weight of water.

91. The detergent composition according to any of paragraphs 79-90, wherein the detergent enzyme is a polypeptide having DNase activity, protease, amylase, lipase, cellulase, mannanase, pectinase, or oxidoreductase.

92. The detergent composition according to any of paragraphs 79-91, wherein the protease is a metalloprotease or an alkaline serine protease, such as a subtilisin.

93. The detergent composition according to any of paragraphs 79-92, wherein the polypeptide having DNase activity is the polypeptide according to any of paragraphs 45-51.

94. The detergent composition according to any of paragraphs 79-93, wherein the microcapsule is produced by interfacial polymerization using an acid chloride as crosslinking agent.

95. The detergent composition according to any of paragraphs 79-94, wherein the polybranched polyamine is a polyethyleneimine.

96. The detergent composition according to any of paragraphs 79-95, wherein the microcapsule comprises a source of Mg2+, Ca2+, or Zn2+ ions, such as a poorly soluble salt of Mg2+, Ca2+, or Zn2+.

Assays and Detergent Compositions
Detergent Compositions

The below mentioned detergent composition can be used in combination with the enzyme of the invention.
Biotex Black (Liquid)
5-15% Anionic surfactants, <5% Nonionic surfactants, perfume, enzymes, DMDM and hydantoin.
Composition of Ariel Sensitive White & Color, Liquid Detergent Composition
Aqua, Alcohol Ethoxy Sulfate, Alcohol Ethoxylate, Amino Oxide, Citric Acid, C12-18 topped palm kernel fatty acid, Protease, Glycosidase, Amylase, Ethanol, 1,2 Propanediol, Sodium Formate, Calcium Chloride, Sodium hydroxide, Silicone Emulsion, Trans-sulphated EHDQ (the ingredients are listed in descending order).

Composition of WFK IEC-A Model Detergent (Powder)
Linear sodium alkyl benzene sulfonate 8.8%, Ethoxylated fatty alcohol C12-18 (7 EO) 4.7%, Sodium soap 3.2%, Anti foam DC2-4248S 3.9%, Sodium aluminium silicate zeolite 4A 28.3%, Sodium carbonate 11.6%, Sodium salt of a copolymer from acrylic and maleic acid (Sokalan CP5) 2.4%, Sodium silicate 3.0%, Carboxymethylcellulose 1.2%, Dequest 2066 2.8%, Optical whitener 0.2%, Sodium sulfate 6.5%, Protease 0.4%.

Composition of Model Detergent a (Liquid)
12% LAS, 11% AEO Biosoft N25-7 (NI), 7% AEOS (SLES), 6% MPG (monopropylene glycol), 3% ethanol, 3% TEA, 2.75% cocoa soap, 2.75% soya soap, 2% glycerol, 2% sodium hydroxide, 2% sodium citrate, 1% sodium formiate, 0.2% DTMPA and 0.2% PCA (all percentages are w/w)

Composition of Ariel Actilift (Liquid)
5-15% Anionic surfactants; <5% Non-ionic surfactants, Phosphonates, Soap; Enzymes, Optical brighteners, Benzisothiazolinone, Methylisothiazolinone, Perfumes, Alpha-isomethyl ionone, Citronellol, Geraniol, Linalool.

Composition of Ariel Actilift Colour&Style (Liquid)
5-15% Anionic surfactants; <5% Non-ionic surfactants, Phosphonates, Soap; Enzymes, Perfumes, Benzisothiazolinone, Methylisothiazolinone, Alpha-isomethyl ionone, Butylphenyl methylpropional, Citronellol, Geraniol, Linalool.

Composition of Persil Small & Mighty (Liquid)
15-30% Anionic surfactants, Non-ionic surfactants, 5-15% Soap, <5% Polycarboxylates, Perfume, Phosphates, Optical Brighteners Persil 2 in 1 with Comfort Passion Flower Powder
Sodium sulfate, Sodium carbonate, Sodium Dodecylbenzenesulfonate, Bentonite, Sodium Carbonate Peroxide, Sodium Silicate, Zeolite, Aqua, Citric acid, TAED, C12-15 Pareth-7, Stearic Acid, Perfume, Sodium Acrylic Acid/MA Copolymer, Cellulose Gum, Corn Starch Modified, Sodium chloride, Tetrasodium Etidronate, Calcium Sodium EDTMP, Disodium Anilinomorpholinotriazinylaminostilbenesulfonate, Sodium bicarbonate, Phenylpropyl Ethyl Methicone, Butylphenyl Methylpropional, Glyceryl Stearates, Calcium carbonate, Sodium Polyacrylate, Alpha-Isomethyl Ionone, Disodium Distyrylbiphenyl Disulfonate, Cellulose, Protease, Limonene, PEG-75, Titanium dioxide, Dextrin, Sucrose, Sodium Polyaryl Sulphonate, CI 12490, CI 45100, CI 42090, Sodium Thiosulfate, CI 61585.

Persil Biological Powder
Sucrose, Sorbitol, Aluminum Silicate, Polyoxymethylene Melamine, Sodium Polyaryl Sulphonate, CI 61585, CI 45100, Lipase, Amylase, Xanthan gum, Hydroxypropyl methyl cellulose, CI 12490, Disodium Distyrylbiphenyl Disulfonate, Sodium Thiosulfate, CI 42090, Mannanase, CI 11680, Etidronic Acid, Tetrasodium EDTA.

Persil Biological Tablets
Sodium carbonate, Sodium Carbonate Peroxide, Sodium bicarbonate, Zeolite, Aqua, Sodium Silicate, Sodium Lauryl Sulfate, Cellulose, TAED, Sodium Dodecylbenzenesulfonate, Hemicellulose, Lignin, Lauryl Glucoside, Sodium Acrylic Acid/MA Copolymer, Bentonite, Sodium chloride, Perfume, Tetrasodium Etidronate, Sodium sulfate, Sodium Polyacrylate, Dimethicone, Disodium Anilinomorpholinotriazinylaminostilbenesulfonate, Dodecylbenzene Sulfonic Acid, Trimethylsiloxysilicate, Calcium carbonate, Cellulose, PEG-75, Titanium dioxide, Dextrin, Protease, Corn Starch Modified, Sucrose, CI 12490, Sodium Polyaryl Sulphonate, Sodium Thiosulfate, Amylase, Kaolin.

Persil Colour Care Biological Powder
Subtilisin, Imidazolidinone, Hexyl Cinnamal, Sucrose, Sorbitol, Aluminum Silicate, Polyoxymethylene Melamine, CI 61585, CI 45100, Lipase, Amylase, Xanthan gum, Hydroxypropyl methyl cellulose, CI 12490, Disodium Distyrylbiphenyl Disulfonate, Sodium Thiosulfate, CI 42090, Mannanase, CI 11680, Etidronic Acid, Tetrasodium EDTA.

Persil Colour Care Biological Tablets
Sodium bicarbonate, Sodium carbonate, Zeolite, Aqua, Sodium Silicate, Sodium Lauryl Sulfate, Cellulose Gum, Sodium Dodecylbenzenesulfonate, Lauryl Glucoside, Sodium chloride, Sodium Acrylic Acid/MA Copolymer, Perfume, Sodium Thioglycolate, PVP, Sodium sulfate, Tetrasodium Etidronate, Sodium Polyacrylate, Dimethicone, Bentonite, Dodecylbenzene Sulfonic Acid, Trimethylsiloxysilicate, Calcium carbonate, Cellulose, PEG-75, Titanium dioxide, Dextrin, Protease, Corn Starch Modified, Sucrose, Sodium Thiosulfate, Amylase, CI 74160, Kaolin.

Persil Dual Action Capsules Bio
MEA-Dodecylbenzenesulfonate, MEA-Hydrogenated Cocoate, C12-15 Pareth-7, Dipropylene Glycol, Aqua, Tetrasodium Etidronate, Polyvinyl Alcohol, Glycerin, Aziridine, homopolymer ethoxylated, Propylene glycol, Perfume, Sodium Diethylenetriamine Pentamethylene Phosphonate, Sorbitol, MEA-Sulfate, Ethanolamine, Subtilisin, Glycol, Butylphenyl Methylpropional, Boronic acid, (4-formylphenyl), Hexyl Cinnamal, Limonene, Linalool, Disodium Distyrylbiphenyl Disulfonate, Alpha-Isomethyl Ionone, Geraniol, Amylase, Polymeric Blue Colourant, Polymeric Yellow Colourant, Talc, Sodium chloride, Benzisothiazolinone, Mannanase, Denatonium Benzoate.

Persil 2 in 1 with Comfort Sunshiny Days Powder
Sodium sulfate, Sodium carbonate, Sodium Dodecylbenzenesulfonate, Bentonite, Sodium Carbonate Peroxide, Sodium Silicate, Zeolite, Aqua, Citric acid, TAED, C12-15 Pareth-7, Parfum, Stearic Acid, Sodium Acrylic Acid/MA Copolymer, Cellulose Gum, Corn Starch Modified, Sodium chloride, Tetrasodium Etidronate, Calcium Sodium EDTMP, Disodium Anilinomorpholinotriazinylaminostilbenesulfonate, Sodium bicarbonate, Phenylpropyl Ethyl Methicone, Butylphenyl Methylpropional, Glyceryl Stearates, Calcium carbonate, Sodium Polyacrylate, Geraniol, Disodium Distyrylbiphenyl Disulfonate, Cellulose, Protease, PEG-75, Titanium dioxide, Dextrin, Sucrose, Sodium Polyaryl Sulphonate, CI 12490, CI 45100, CI 42090, Sodium Thiosulfate, CI 61585.

Persil Small & Mighty 2 in 1 with Comfort Sunshiny Days
Aqua, C12-15 Pareth-7, Sodium Dodecylbenzenesulfonate, Propylene glycol, Sodium Hydrogenated Cocoate, Triethanolamine, Glycerin, TEA-Hydrogenated Cocoate, Parfum, Sodium chloride, Polyquaternium-10, PVP, Polymeric Pink Colourant, Sodium sulfate, Disodium Distyrylbiphenyl Disulfonate, Butylphenyl Methylpropional, Styrene/Acrylates Copolymer, Hexyl Cinnamal, Citronellol, Eugenol, Polyvinyl Alcohol, Sodium acetate, Isopropyl alcohol, Polymeric Yellow Colourant, Sodium Lauryl Sulfate.

Persil Small & Mighty Bio
Aqua, MEA-Dodecylbenzenesulfonate, Propylene glycol, Sodium Laureth Sulfate, C12-15 Pareth-7, TEA-Hydrogenated Cocoate, MEA-Citrate, Aziridine homopolymer ethoxylated, MEA-Etidronate, Triethanolamine, Parfum, Acrylates Copolymer, Sorbitol, MEA-Sulfate, Sodium Sulfite, Disodium Distyrylbiphenyl Disulfonate, Butylphenyl Methylpropional, Styrene/Acrylates Copolymer, Citronellol, Sodium sulfate, Peptides, salts, sugars from fermentation (process), Subtilisin, Glycerin, Boronic acid, (4-formylphenyl), Geraniol, Pectate Lyase, Amylase, Sodium Lauryl Sulfate, Mannanase, CI 42051.

Persil Small & Mighty Capsules Biological
MEA-Dodecylbenzenesulfonate, MEA-Hydrogenated Cocoate, C12-15 Pareth-7, Dipropylene Glycol, Aqua, Glycerin, Polyvinyl Alcohol, Parfum, Aziridine homopolymer ethoxylated, Sodium Diethylenetriamine Pentamethylene Phosphonate, Propylene glycol, Sorbitol, MEA-Sulfate, Ethanolamine, Subtilisin, Glycol, Butylphenyl Methylpropional, Hexyl Cinnamal, Starch, Boronic acid, (4-formylphenyl), Limonene, Linalool, Disodium Distyrylbiphenyl Disulfonate, Alpha-Isomethyl Ionone, Geraniol, Amylase, Talc, Polymeric Blue Colourant, Sodium chloride, Benzisothiazolinone, Denatonium Benzoate, Polymeric Yellow Colourant, Mannanase.

Persil Small & Mighty Capsules Colour Care
MEA-Dodecylbenzenesulfonate, MEA-Hydrogenated Cocoate, C12-15 Pareth-7, Dipropylene Glycol, Aqua, Glycerin, Polyvinyl Alcohol, Parfum, Aziridine homopolymer ethoxylated, Sodium Diethylenetriamine Pentamethylene Phosphonate, Propylene glycol, MEA-Sulfate, Ethanolamine, PVP, Sorbitol, Butylphenyl Methylpropional, Subtilisin, Hexyl Cinnamal, Starch, Limonene, Linalool, Boronic acid, (4-formylphenyl), Alpha-Isomethyl Ionone, Geraniol, Talc, Polymeric Blue Colourant, Denatonium Benzoate, Polymeric Yellow Colourant.

Persil Small & Mighty Colour Care
Aqua, MEA-Dodecylbenzenesulfonate, Propylene glycol, Sodium Laureth Sulfate, C12-15 Pareth-7, TEA-Hydrogenated Cocoate, MEA-Citrate, Aziridine homopolymer ethoxylated, MEA-Etidronate, Triethanolamine, Parfum, Acrylates Copolymer, Sorbitol, MEA-Sulfate, Sodium Sulfite, Glycerin, Butylphenyl Methylpropional, Citronellol, Sodium sulfate, Peptides, salts, sugars from fermentation (process), Styrene/Acrylates Copolymer, Subtilisin, Boronic acid, (4-formylphenyl), Geraniol, Pectate Lyase, Amylase, Sodium Lauryl Sulfate, Mannanase, CI 61585, CI 45100.

Composition of Fairy Non Bio (Liquid)
15-30% Anionic Surfactants, 5-15% Non-Ionic Surfactants, Soap, Benzisothiazolinone, Methylisothiazolinone, Perfumes Composition of Model Detergent T (Powder)
11% LAS, 2% AS/AEOS, 2% soap, 3% AEO, 15.15% sodium carbonate, 3% sodium silicate, 18.75% zeolite, 0.15% chelant, 2% sodium citrate, 1.65% AA/MA copolymer, 2.5% CMC and 0.5% SRP (all percentages are w/w).

Composition of Model Detergent X (Powder)
16.5% LAS, 15% zeolite, 12% sodium disilicate, 20% sodium carbonate, 1% sokalan, 35.5% sodium sulfate (all percentages are w/w).

Composition of Ariel Actilift Colour&Style (Powder)
15-30% Anionic surfactants, <5% Non-ionic surfactants, Phosphonates, Polycarboxylates, Zeolites; Enzymes, Perfumes, Hexyl cinnamal.

Composition of Ariel Actilift (Powder)
5-15% Anionic surfactants, Oxygen-based bleaching agents, <5% Non-ionic surfactants, Phosphonates, Polycarboxylates, Zeolites, Optical brighteners, Enzymes, Perfumes, Butylphenyl Methylpropional, Coumarin, Hexyl Cinnamal Composition of Persil Megaperls (Powder)
15-30% of the following: anionic surfactants, oxygen-based bleaching agent and zeolites, less than 5% of the following: non-ionic surfactants, phosphonates, polycarboxylates, soap, Further ingredients: Perfumes, Hexyl cinnamal, Benzyl salicylate, Linalool, optical brighteners, Enzymes and Citronellol.

Gain Liquid, Original
Water, Alcohol Ethoxysulfate, Diethylene Glycol, Alcohol Ethoxylate, Ethanolamine, Linear Alkyl Benzene Sulfonate, Sodium Fatty Acids, Polyethyleneimine Ethoxylate, Citric Acid, Borax, Sodium Cumene Sulfonate, Propylene Glycol, DTPA, Disodium Diaminostilbene Disulfonate, Dipropylethyl Tetramine, Sodium Hydroxide, Sodium Formate, Calcium Formate, Dimethicone, Amylase, Protease, Liquitint™, Hydrogenated Castor Oil, Fragrance Tide Liquid, Original
Linear alkylbenzene sulfonate, propylene glycol, citric acid, sodium hydroxide, borax, ethanolamine, ethanol, alcohol sulfate, polyethyleneimine ethoxylate, sodium fatty acids, diquaternium ethoxysulfate, protease, diethylene glycol, laureth-9, alkyldimethylamine oxide, fragrance, amylase, disodium diaminostilbene disulfonate, DTPA, sodium formate, calcium formate, polyethylene glycol 4000, mannanase, Liquitint™ Blue, dimethicone.

Liquid Tide, Free and Gentle
Water, sodium alcoholethoxy sulfate, propylene glycol, borax, ethanol, linear alkylbenzene sulfonate sodium, salt, polyethyleneimine ethoxylate, diethylene glycol, trans sulfated & ethoxylated hexamethylene diamine, alcohol ethoxylate, linear alkylbenzene sulfonate, MEA salt, sodium formate, sodium alkyl sulfate, DTPA, amine oxide, calcium formate, disodium diaminostilbene, disulfonate, amylase, protease, dimethicone, benzisothiazolinone Tide Coldwater Liquid, Fresh Scent
Water, alcoholethoxy sulfate, linear alkylbenzene sulfonate, diethylene glycol, propylene glycol, ethanolamine, citric acid, Borax, alcohol sulfate, sodium hydroxide, polyethyleneimine, ethoxylate, sodium fatty acids, ethanol, protease, Laureth-9, diquaternium ethoxysulfate, lauramine oxide, sodium cumene, sulfonate, fragrance, DTPA, amylase, disodium, diaminostilbene, disulfonate, sodium formate, disodium distyrylbiphenyl disulfonate, calcium formate, polyethylene glycol 4000, mannanase, pectinase, Liquitint™ Blue, dimethicone Tide TOTALCARE™ Liquid, Cool Cotton
Water, alcoholethoxy sulfate, propylene glycol, sodium fatty acids, laurtrimonium chloride, ethanol, sodium hydroxide, sodium cumene sulfonate, citric acid, ethanolamine, diethylene glycol, silicone polyether, borax, fragrance, polyethyleneimine ethoxylate, protease, Laureth-9, DTPA, polyacrylamide quaternium chloride, disodium diaminostilbene disulfonate, sodium formate, Liquitint™ Orange, dipropylethyl tetraamine, dimethicone, cellulase.

Liquid Tide Plus Bleach Alternative™, Vivid White and Bright, Original and Clean Breeze
Water, sodium alcoholethoxy sulfate, sodium alkyl sulfate, MEA citrate, linear alkylbenzene sulfonate, MEA salt, propylene glycol, diethylene glycol, polyethyleneimine ethoxylate, ethanol, sodium fatty acids, ethanolamine, lauramine oxide, borax, Laureth-9, DTPA, sodium cumene sulfonate, sodium formate, calcium formate, linear alkylbenzene sulfonate, sodium salt, alcohol sulfate, sodium hydroxide, diquaternium ethoxysulfate, fragrance, amylase, protease, mannanase, pectinase, disodium diaminostilbene disulfonate, benzisothiazolinone, Liquitint™ Blue, dimethicone, dipropylethyl tetraamine.

Liquid Tide HE, Original Scent
Water, Sodium alcoholethoxy sulfate, MEA citrate, Sodium Alkyl Sulfate, alcohol ethoxylate, linear alkylbenzene sulfonate, MEA salt, sodium fatty acids, polyethyleneimine ethoxylate, diethylene glycol, propylene glycol, diquaternium ethoxysulfate, borax, polyethyleneimine, ethoxylate propoxylate, ethanol, sodium cumene sulfonate, fragrance, DTPA, disodium diaminostilbene disulfonate, Mannanase, cellulase, amylase, sodium formate, calcium formate, Lauramine oxide, Liquitint™ Blue, Dimethicone/polydimethyl silicone.

Tide TOTALCARE HE Liquid, Renewing Rain
Water, alcoholethoxy sulfate, linear alkylbenzene sulfonate, alcohol ethoxylate, citric acid, Ethanolamine, sodium fatty acids, diethylene glycol, propylene glycol, sodium hydroxide, borax, polyethyleneimine ethoxylate, silicone polyether, ethanol, protease, sodium cumene sulfonate, diquaternium ethoxysulfate, Laureth-9, fragrance, amylase, DTPA, disodium diaminostilbene disulfonate, disodium distyrylbiphenyl disulfonate, sodium formate, calcium formate, mannanase, Liquitint™ Orange, dimethicone, polyacrylamide quaternium chloride, cellulase, dipropylethyl tetraamine.

Tide Liquid HE Free
Water, alcoholethoxy sulfate, diethylene glycol, monoethanolamine citrate, sodium formate, propylene glycol, linear alkylbenzene sulfonates, ethanolamine, ethanol, polyethyleneimine ethoxylate, amylase, benzisothiazolin, borax, calcium formate, citric acid, diethylenetriamine pentaacetate sodium, dimethicone, diquaternium ethoxysulfate, disodium diaminostilbene disulfonate, Laureth-9, mannanase, protease, sodium cumene sulfonate, sodium fatty acids.

Tide Coldwater HE Liquid, Fresh Scent
Water, alcoholethoxy sulfate, MEA Citrate, alcohol sulfate, Alcohol ethoxylate, Linear alkylbenzene sulfonate MEA, sodium fatty acids, polyethyleneimine ethoxylate, diethylene glycol, propylene glycol, diquaternium ethoxysulfate, borax, polyethyleneimine ethoxylate propoxylate, ethanol, sodium cumene sulfonate, fragrance, DTPA, disodium diaminostilbene disulfonate, protease, mannanase, cellulase, amylase, sodium formate, calcium formate, lauramine oxide, Liquitint™ Blue, dimethicone.

Tide for Coldwater HE Free Liquid
Water, sodium alcoholethoxy sulfate, MEA Citrate, Linear alkylbenzene sulfonate: sodium salt, Alcohol ethoxylate, Linear alkylbenzene sulfonate: MEA salt, sodium fatty acids, polyethyleneimine ethoxylate, diethylene glycol, propylene glycol, diquaternium ethoxysulfate, Borax, protease, polyethyleneimine ethoxylate propoxylate, ethanol, sodium cumene sulfonate, Amylase, citric acid, DTPA, disodium diaminostilbene disulfonate, sodium formate, calcium formate, dimethicone.

Tide Simply Clean & Fresh
Water, alcohol ethoxylate sulfate, linear alkylbenzene sulfonate Sodium/Mea salts, propylene glycol, diethylene glycol, sodium formate, ethanol, borax, sodium fatty acids, fragrance, lauramine oxide, DTPA, Polyethylene amine ethoxylate, calcium formate, disodium diaminostilbene disulfonate, dimethicone, tetramine, Liquitint™ Blue.

Tide Pods, Ocean Mist, Mystic Forest, Spring Meadow
Linear alkylbenzene sulfonates, C12-16 Pareth-9, propylene glycol, alcoholethoxy sulfate, water, polyethyleneimine ethoxylate, glycerine, fatty acid salts, PEG-136 polyvinyl acetate, ethylene Diamine disuccinic salt, monoethanolamine citrate, sodium bisulfite, diethylenetriamine pentaacetate sodium, disodium distyrylbiphenyl disulfonate, calcium formate, mannanase, exyloglucanase, sodium formate, hydrogenated castor oil, natalase, dyes, termamyl, subtilisin, benzisothiazolin, perfume.

Tide to Go
Deionized water, Dipropylene Glycol Butyl Ether, Sodium Alkyl Sulfate, Hydrogen Peroxide, Ethanol, Magnesium Sulfate, Alkyl Dimethyl Amine Oxide, Citric Acid, Sodium Hydroxide, Trimethoxy Benzoic Acid, Fragrance.

Tide Stain Release Liquid
Water, Alkyl Ethoxylate, Linear Alkylbenzenesulfonate, Hydrogen Peroxide, Diquaternium Ethoxysulfate, Ethanolamine, Disodium Distyrylbiphenyl Disulfonate, tetrabutyl Ethylidinebisphenol, F&DC Yellow 3, Fragrance.

Tide Stain Release Powder
Sodium percarbonate, sodium sulfate, sodium carbonate, sodium aluminosilicate, nonanoyloxy benzene sulfonate, sodium polyacrylate, water, sodium alkylbenzenesulfonate, DTPA, polyethylene glycol, sodium palmitate, amylase, protease, modified starch, FD&C Blue 1, fragrance.

Tide Stain Release, Pre Treater Spray
Water, Alkyl Ethoxylate, MEA Borate, Linear Alkylbenzenesulfonate, Propylene Glycol, Diquaternium Ethoxysulfate, Calcium Chlorideenzyme, Protease, Ethanolamine, Benzoisothiazolinone, Amylase, Sodium Citrate, Sodium Hydroxide, Fragrance.

Tide to Go Stain Eraser
Water, Alkyl Amine Oxide, Dipropylene Glycol Phenyl Ether, Hydrogen Peroxide, Citric Acid, Ethylene Diamine Disuccinic Acid Sodium salt, Sodium Alkyl Sulfate, Fragrance.

Tide Boost with Oxi
Sodium bicarbonate, sodium carbonate, sodium percarbonate, alcohol ethoxylate, sodium chloride, maleic/acrylic copolymer, nonanoyloxy benzene sulfonate, sodium sulfate, colorant, diethylenetriamine pentaacetate sodium salt, hydrated aluminosilicate (zeolite), polyethylene glycol, sodium alkylbenzene sulfonate, sodium palmitate, starch, water, fragrance.

Tide Stain Release Boost Duo Pac:
Polyvinyl Alcoholpouch film, wherein there is packed a liquid part and a powder part:
  Liquid Ingredients: Dipropylene Glycol, diquaternium Ethoxysulfate, Water, Glycerin, Liquitint™ Orange
  Powder Ingredients: sodium percarbonate, nonanoyloxy benzene sulfonate, sodium carbonate, sodium sulfate, sodium aluminosilicate, sodium polyacrylate, sodium alkylbenzenesulfonate, maleic/acrylic copolymer, water, amylase, polyethylene glycol, sodium palmitate, modified starch, protease, glycerine, DTPA, fragrance.

Tide Ultra Stain Release
Water, sodium alcoholethoxy sulfate, linear alkyl benzene sulfonate, sodium/MEA salts, MEA citrate, propylene glycol, polyethyleneimine ethoxylate, ethanol, diethylene glycol, polyethyleneimine propoxyethoxylate, sodium fatty acids, protease, borax, sodium cumene sulfonate, DTPA, fragrance, amylase, disodium diaminostilbene disulfonate, calcium formate, sodium formate, gluconase, dimethicone, Liquitint™ Blue, mannanase.

Ultra Tide with a Touch of Downy® Powdered Detergent, April Fresh/Clean Breeze/April Essence
Sodium Carbonate, Sodium Aluminosilicate, Sodium Sulfate, Linear Alkylbenzene Sulfonate, Bentonite, Water, Sodium Percarbonate, Sodium Polyacrylate, Silicate, Alkyl Sulfate, Nonanoyloxybenzenesulfonate, DTPA, Polyethylene Glycol 4000, Silicone, Ethoxylate, fragrance, Polyethylene Oxide, Palmitic Acid, Disodium Diaminostilbene Disulfonate, Protease, Liquitint™ Red, FD&C Blue 1, Cellulase.

Ultra Tide with a Touch of Downy Clean Breeze
Water, sodium alcoholethoxy sulfate, MEA citrate, linear alkyl benzene sulfonate: sodium/MEA salts, propylene glycol, polyethyleneimine ethoxylate, ethanol, diethylene glycol, polyethyleneimine, propoxyethoxylate, diquaternium ethoxysulfate, alcohol sulfate, dimethicone, fragrance, borax, sodium fatty acids, DTPA, protease, sodium bisulfite, disodium diaminostilbene disulfonate, amylase, gluconase, castor oil, calcium formate, MEA, styrene acrylate copolymer, sodium formate, Liquitint™ Blue.

Ultra Tide with Downy Sun Blossom

Water, sodium alcoholethoxy sulfate, MEA citrate, linear alkyl benzene sulfonate: sodium/MEA salts, propylene glycol, ethanol, diethylene glycol, polyethyleneimine propoxyethoxylate, polyethyleneimine ethoxylate, alcohol sulfate, dimethicone, fragrance, borax, sodium fatty acids, DTPA, protease, sodium bisulfite, disodium diaminostilbene disulfonate, amylase, castor oil, calcium formate, MEA, styrene acrylate copolymer, propanaminium propanamide, gluconase, sodium formate, Liquitint™ Blue.

Ultra Tide with Downy April Fresh/Sweet Dreams

Water, sodium alcoholethoxy sulfate, MEA citrate, linear alkyl benzene sulfonate: sodium/MEA salts, propylene glycol, polyethyleneimine ethoxylate, ethanol, diethylene glycol, polyethyleneimin propoxyethoxylate, diquaternium ethoxysulfate, alcohol sulfate, dimethicone, fragrance, borax, sodium fatty acids, DTPA, protease, sodium bisulfite, disodium diaminostilbene disulfonate, amylase, gluconase, castor oil, calcium formate, MEA, styrene acrylate copolymer, propanaminium propanamide, sodium formate, Liquitint™ Blue.

Ultra Tide Free Powdered Detergent

Sodium Carbonate, Sodium Aluminosilicate, Alkyl Sulfate, Sodium Sulfate, Linear Alkylbenzene Sulfonate, Water, Sodium polyacrylate, Silicate, Ethoxylate, Sodium percarbonate, Polyethylene Glycol 4000, Protease, Disodium Diaminostilbene Disulfonate, Silicone, Cellulase.

Ultra Tide Powdered Detergent, Clean Breeze/Spring Lavender/Mountain Spring

Sodium Carbonate, Sodium Aluminosilicate, Sodium Sulfate, Linear Alkylbenzene Sulfonate, Alkyl Sulfate, Sodium Percarbonate, Water, Sodium Polyacrylate, Silicate, Nonanoyloxybenzenesulfonate, Ethoxylate, Polyethylene Glycol 4000, Fragrance, DTPA, Disodium Diaminostilbene Disulfonate, Palmitic Acid, Protease, Silicone, Cellulase.

Ultra Tide HE (High Efficiency) Powdered Detergent, Clean Breeze

Sodium Carbonate, Sodium Aluminosilicate, Sodium Sulfate, Linear Alkylbenzene Sulfonate, Water, Nonanoyloxybenzenesulfonate, Alkyl Sulfate, Sodium Polyacrylate, Silicate, Sodium Percarbonate, Ethoxylate, Polyethylene Glycol 4000, Fragrance, DTPA, Palmitic Acid, Disodium Diaminostilbene Disulfonate, Protease, Silicone, Cellulase.

Ultra Tide Coldwater Powdered Detergent, Fresh Scent

Sodium Carbonate, Sodium Aluminosilicate, Sodium Sulfate, Sodium Percarbonate, Alkyl Sulfate, Linear Alkylbenzene Sulfonate, Water, Nonanoyloxybenzenesulfonate, Sodium Polyacrylate, Silicate, Ethoxylate, Polyethylene Glycol 4000, DTPA, Fragrance, Natalase, Palmitic Acid, Protease, Disodium, Diaminostilbene Disulfonate, FD&C Blue 1, Silicone, Cellulase, Alkyl Ether Sulfate.

Ultra Tide with bleach Powdered Detergent, Clean Breeze

Sodium Carbonate, Sodium Aluminosilicate, Sodium Sulfate, Linear Alkylbenzene Sulfonate, Sodium Percarbonate, Nonanoyloxybenzenesulfonate, Alkyl Sulfate, Water, Silicate, Sodium Polyacrylate, Ethoxylate, Polyethylene Glycol 4000, Fragrance, DTPA, Palmitic Acid, Protease, Disodium Diaminostilbene Disulfonate, Silicone, FD&C Blue 1, Cellulase, Alkyl Ether Sulfate.

Ultra Tide with Febreeze Freshness™ Powdered Detergent, Spring Renewal

Sodium Carbonate, Sodium Aluminosilicate, Sodium Sulfate, Linear Alkylbenzene Sulfonate, Sodium Percarbonate, Alkyl Sulfate, Water, Sodium Polyacrylate, Silicate, Nonanoyloxybenzenesulfonate, Ethoxylate, Polyethylene Glycol 4000, DTPA, Fragrance, Cellulase, Protease, Disodium Diaminostilbene Disulfonate, Silicone, FD&C Blue 1.

Liquid Tide Plus with Febreeze Freshness—Sport HE Active Fresh

Water, Sodium alcoholethoxy sulfate, MEA citrate, linear alkylbenzene sulfonate, sodium salt, linear alkylbenzene sulfonate: MEA salt, alcohol ethoxylate, sodium fatty acids, propylene glycol, diethylene glycol, polyethyleneimine ethoxylate propoxylate, diquaternium ethoxysulfate, Ethanol, sodium cumene sulfonate, borax, fragrance, DTPA, Sodium bisulfate, disodium diaminostilbene disulfonate, Mannanase, cellulase, amylase, sodium formate, calcium formate, Lauramine oxide, Liquitint™ Blue, Dimethicone/polydimethyl silicone.

Tide Plus Febreeze Freshness Spring & Renewal

Water, sodium alcoholethoxy sulfate, linear alkyl benzene sulfonate: sodium/MEA salts, MEA citrate, propylene glycol, polyethyleneimine ethoxylate, fragrance, ethanol, diethylene glycol, polyethyleneimine propoxyethoxylate, protease, alcohol sulfate, borax, sodium fatty acids, DTPA, disodium diaminostilbene disulfonate, MEA, mannanase, gluconase, sodium formate, dimethicone, Liquitint™ Blue, tetramine.

Liquid Tide Plus with Febreeze Freshness, Sport HE Victory Fresh

Water, Sodium alcoholethoxy sulfate, MEA citrate, linear alkylbenzene sulfonate, sodium salt, linear alkylbenzene sulfonate: MEA salt, alcohol ethoxylate, sodium fatty acids, propylene glycol, diethylene glycol, polyethyleneimine ethoxylate propoxylate, diquaternium ethoxysulfate, ethanol, sodium cumene sulfonate, borax, fragrance, DTPA, Sodium bisulfate, disodium diaminostilbene disulfonate, Mannanase, cellulase, amylase, sodium formate, calcium formate, Lauramine oxide, Liquitint™ Blue, Dimethicone/polydimethyl silicone.

Tide Vivid White+Bright Powder, Original

Sodium Carbonate, Sodium Aluminosilicate, Sodium Sulfate, Linear Alkylbenzene Sulfonate, Sodium Percarbonate, Nonanoyloxybenzenesulfonate, Alkyl Sulfate, Water, Silicate, Sodium Polyacrylate Ethoxylate, Polyethylene Glycol 4000, Fragrance, DTPA, Palmitic Acid, Protease, Disodium Diaminostilbene Disulfonate, Silicone, FD&C Blue 1, Cellulase, Alkyl Ether Sulfate.

HEY SPORT TEX WASH Detergent

Aqua, dodecylbenzenesulfonsäure, laureth-11, peg-75 lanolin, propylene glycol, alcohol denat., potassium soyate, potassium hydroxide, disodium cocoamphodiacetate, ethylendiamine triacetate cocosalkyl acetamide, perfume, zinc ricinoleate, sodium chloride, benzisothiazolinone, methylisothiazolinone, ci 16255, benzyl alcohol.

The products named Tide, Ariel, Gain and Fairy are commercially available products supplied by Procter & Gamble. The products named Persil are commercially available products supplied by Unilever and Henkel. The products named Hey Sport are commercially available products supplied by Hey Sport.

| Ingredient | Amount (in wt %) |
|---|---|
| Anionic detersive surfactant (such as alkyl benzene sulphonate, alkyl ethoxylated sulphate and mixtures | from 8 to 15 wt % |
| Non-ionic detersive surfactant (such as alkyl ethoxylated alcohol) | from 0.5 to 4 wt % |
| Cationic detersive surfactant (such as quaternary ammonium compounds) | from 0 to 4 wt % |
| Other detersive surfactant (such as zwiterionic detersive surfactants, amphoteric surfactants and mixtures thereof) | from 0 to 4 wt % |
| Carboxylate polymer (such as co-polymers of maleic acid and acrylic acid) | from 1 to 4 wt % |
| Polyethylene glycol polymer (such as a polyethylene glycol polymer comprising poly vinyl acetate side chains) | from 0.5 to 4 wt % |
| Polyester soil release polymer (such as Repel-o-tex from and/or Texcare polymers) | 0.1 to 2 wt % |
| Cellulosic polymer (such as carboxymethyl cellulose, methyl cellulose and combinations thereof) | from 0.5 to 2 wt % |
| Other polymer (such as amine polymers, dye transfer inhibitor polymers, hexamethylenediamine derivative polymers, and mixtures thereof) | from 0 to 4 wt % |
| Zeolite builder and phosphate builder (such as zeolite 4A and/or sodium tripolyphosphate) | from 0 to 4 wt % |
| Other builder (such as sodium citrate and/or citric acid) | from 0 to 3 wt % |
| Carbonate salt (such as sodium carbonate and/or sodium bicarbonate) | from 15 to 30 wt % |
| Silicate salt (such as sodium silicate) | from 0 to 10 wt % |
| Filler (such as sodium sulphate and/or bio-fillers) | from 10 to 40 wt % |
| Source of available oxygen (such as sodium percarbonate) | from 10 to 20 wt % |
| Bleach activator (such as tetraacetylethylene diamine (TAED) and/or nonanoyloxybenzenesulphonate (NOBS) | from 2 to 8 wt % |
| Bleach catalyst (such as oxaziridinium-based bleach catalyst and/or transition metal bleach catalyst) | from 0 to 0.1 wt % |
| Other bleach (such as reducing bleach and/or pre-formed peracid) | from 0 to 10 wt % |
| Chelant (such as ethylenediamine-N'N'-disuccinic acid (EDDS) and/or hydroxyethane diphosphonic acid(HEDP) | from 0.2 to 1 wt % |
| Photobleach (such as zinc and/or aluminium sulphonated phthalocyanine) | from 0 to 0.1 wt % |
| Hueing agent (such as direct violet 99, acid red 52, acid blue 80, direct violet 9, solvent violet 13 and any combination thereof) | from 0 to 1 wt % |
| Brightener (such as brightener 15 and/or brightener 49) | from 0.1 to 0.4 wt % |
| Protease (such as Savinase, Savinase Ultra, Purafect, FN3, FN4 and any combination thereof) | from 0.1 to 0.4 wt % |
| Amylase (such as Termamyl, Termamyl ultra Natalase, Optisize, Stainzyme, Stainzyme Plus, and any combination thereof) | from 0.05 to 0.2 wt % |
| Cellulase (such as Carezyme and/or Celluclean) | from 0.05 to 0.2 wt % |
| Lipase (such as Lipex, Lipolex, Lipoclean and any combination thereof) | from 0.2 to 1 wt % |
| Other enzyme (such as xyloglucanase, cutinase, pectate lyase, mannanase, bleaching enzyme) | from 0 to 2 wt % |
| Fabric softener (such as montmorillonite clay and/or polydimethylsiloxane (PDMS) | from 0 to 4 wt % |
| Flocculant (such as polyethylene oxide) | from 0 to 1 wt % |
| Suds suppressor (such as silicone and/or fatty acid) | from 0 to 0.1 wt % |
| Perfume (such as perfume microcapsule, spray-on perfume, starch encapsulated perfume accords, perfume loaded zeolite, and any combination thereof) | from 0.1 to 1 wt % |
| Aesthetics (such as coloured soap rings and/or coloured speckles/noodles) | from 0 to 1 wt % |
| Miscellaneous | Balance |

| Ingredient | Amount |
|---|---|
| Carboxyl group-containing polymer (comprising from about 60% to about 70% by mass of an acrylic acid-based monomer (A); and from about 30% to about 40%) by mass of a sulfonic acid group-containing monomer (B); and wherein the average molecular weight is from about 23,000 to about 50,000 preferably in the range of from about 25,000 to about 38,000 as described in WO 2014/032269. | from about 0.5 to about 1.5 wt % |
| Amylase (Stainzyme Plus(R), having an enzyme activity of 14 mg active enzyme/g) | from about 0.1 to about 0.5 wt % |
| Anionic detersive surfactant (such as alkyl benzene sulphonate, alkyl ethoxylated sulphate and mixtures thereof) | from about 8 to about 15 wt % |
| Non-ionic detersive surfactant (such as alkyl ethoxylated alcohol) | from about 0.5 to 4 wt % |
| Cationic detersive surfactant (such as quaternary ammonium compounds) | from about 0 to about 4 wt % |
| Other detersive surfactant (such as zwiterionic detersive surfactants, amphoteric surfactants and mixtures thereof) | from about 0 to 4 wt % |
| Carboxylate polymer (such as co-polymers of maleic acid and acrylic acid) | from about 1 to about 4 wt % |
| Polyethylene glycol polymer (such as a polyethylene glycol polymer comprising poly vinyl acetate side chains) | from about 0 to about 4 wt % |
| Polyester soil release polymer (such as Repel-O- Tex(R) and/or Texcare(R) polymers) | from about 0.1 to about 2 wt % |
| Cellulosic polymer (such as carboxymethyl cellulose, methyl cellulose and combinations thereof) | from about 0.5 to about 2 wt % |
| Other polymer (such as amine polymers, dye transfer inhibitor polymers, hexamethylenediamine derivative polymers, and mixtures thereof) | from about 0 to about 4 wt % |

| Ingredient | Amount |
|---|---|
| Zeolite builder and phosphate builder (such as zeolite 4A and/or sodium tripolyphosphate) | from about 0 to about 4 wt % |
| Other builder (such as sodium citrate and/or citric acid) | from about 0 to about 3 wt % |
| Carbonate salt (such as sodium carbonate and/or sodium bicarbonate) | from about 15 to about 30 wt % |
| Silicate salt (such as sodium silicate) | from about 0 to about 10 wt % |
| Filler (such as sodium sulphate and/or bio-fillers) | from about 10 to about 40 wt % |
| Source of available oxygen (such as sodium percarbonate) | from about 10 to about 20 wt % |
| Bleach activator (such as tetraacetylethylene diamine (TAED) and/or nonanoyloxybenzenesulphonate (NOBS) | from about 2 to about 8 wt % |
| Bleach catalyst (such as oxaziridinium-based bleach catalyst and/or transition metal bleach catalyst) | from about 0 to about 0.1 wt % |
| Other bleach (such as reducing bleach and/or pre formed peracid) | from about 0 to about 10 wt % |
| Chelant (such as ethylenediamine-N'N'-disuccinic acid (EDDS) and/or hydroxyethane diphosphonic acid (HEDP) | from about 0.2 to about 1 wt % |
| Photobleach (such as zinc and/or aluminium sulphonated phthalocyanine) | from about 0 to about 0.1 wt % |
| Hueing agent (such as direct violet 99, acid red 52, acid blue 80, direct violet 9, solvent violet 13 and any combination thereof) | from about 0 to about 0.5 wt % |
| Brightener (such as brightener 15 and/or brightener 49) | from about 0.1 to about 0.4 wt % |
| Protease (such as Savinase, Polarzyme, Purafect, FN3, FN4 and any combination thereof, typically having an enzyme activity of from about 20 mg to about 100 mg active enzyme/g) | from about 0.1 to about 1.5 wt % |
| Amylase (such as Termamyl(R), Termamyl Ultra(R), Natalase(R), Optisize HT Plus(R), Powerase(R), Stainzyme(R) and any combination thereof, typically having an enzyme activity of from about 10 mg to about 50 mg active enzyme/g) | from about 0.05 to about 0.2 wt % |
| Cellulase (such as Carezyme(R), Celluzyme(R) and/or Celluclean(R), typically having an enzyme activity of about from 10 to 50 mg active enzyme/g) | from about 0.05 to 0.5 wt % |
| Lipase (such as Lipex(R), Lipolex(R), Lipoclean(R) and any combination thereof, typically having an enzyme activity of from about 10 mg to about 50 mg active enzyme/g) | from about 0.2 to about 1 wt % |
| Other enzyme (such as xyloglucanase (e.g., Whitezyme(R)), cutinase, pectate lyase, mannanase, bleaching enzyme, typically having an enzyme activity of from about 10 mg to about 50 mg active enzyme/g) | from 0 to 2 wt % |
| Fabric softener (such as montmorillonite clay and/or polydimethylsiloxane (PDMS)) | from 0 to 15 wt % |
| Flocculant (such as polyethylene oxide) | from 0 to 1 wt % |
| Suds suppressor (such as silicone and/or fatty acid) | from 0 to 0.1 wt % |
| Perfume (such as perfume microcapsule, spray-on perfume, starch encapsulated perfume accords, perfume loaded zeolite, and any combination thereof) | from 0.1 to 1 wt % |
| Aesthetics (such as colored soap rings and/or colored speckles/noodles) | from 0 to 1 wt % |
| Miscellaneous | Balance |

All enzyme levels expressed as rug active enzyme protein per 100 g detergent composition. Surfactant ingredients can be obtained from BASF, Ludwigshafen, Germany (Lutensol®); Shell Chemicals, London, UK; Stepan, Northfield, Ill, USA; Huntsman, Huntsman, Salt Lake City, Utah, USA; Clariant, Sulzbach, Germany (Praepagen®).

Sodium tripolyphosphate can be obtained from Rhodia, Paris, France. Zeolite can be obtained from Industrial Zeolite (UK) Ltd, Grays, Essex, UK. Citric acid and sodium citrate can be obtained from Jungbunzlauer, Easel, Switzerland. NOES is sodium nonanoyloxybenzenesulfonate, supplied by Eastman, Eatesville, Ark., USA.

TAED is tetraacetylethylenediamine, supplied under the Peractive® brand name by Clariant GmbH, Sulzbach, Germany.

Sodium carbonate and sodium bicarbonate can be obtained from Solvay, Brussels, Belgium.

Polyacrylate, polyacrylate/maleate copolymers can be obtained from EASF, Ludwigshafen, Germany.

Repel-O-Tex® can be obtained from Rhodia, Paris, France.

Texcare® can be obtained from Clariant, Sulzbach, Germany. Sodium percarbonate and sodium carbonate can be obtained from Solvay, Houston, Tex., USA.

Na salt of Ethylenediamine-N,N'-disuccinic acid, (S,S) isomer (EDDS) was supplied by Octel, Ellesmere Port, UK.

Hydroxy ethane di phosphonate (HEDP) was supplied by Dow Chemical, Midland, Mich., USA.

Enzymes Savinase®, Savinase® Ultra, Stainzyme® Plus, Lipex®, Lipolex®, Lipoclean®, Celluclean®, Carezyme®, Natalase®, Stainzyme®, Stainzyme® Plus, Termamyl®, Termamyl® ultra, and Mannaway® can be obtained from Novozymes, Bagsvaerd, Denmark.

Enzymes Purafect®, FN3, FN4 and Optisize can be obtained from Genencor International Inc., Palo Alto, California, US.

Direct violet 9 and 99 can be obtained from BASF DE, Ludwigshafen, Germany. Solvent violet 13 can be obtained from Ningbo Lixing Chemical Co., Ltd. Ningbo, Zhejiang, China. Brighteners can be obtained from Ciba Specialty Chemicals, Basel, Switzerland.

All percentages and ratios are calculated by weight unless otherwise indicated. All percentages and ratios are calculated based on the total composition unless otherwise indicated. It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Wash Assays

Launder-O-Meter (LOM) Model Wash System

The Launder-O-Meter (LOM) is a medium scale model wash system that can be applied to test up to 20 different wash conditions simultaneously. A LOM is basically a large temperature controlled water bath with 20 closed metal beakers rotating inside it. Each beaker constitutes one small washing machine and during an experiment, each will contain a solution of a specific detergent/enzyme system to be tested along with the soiled and unsoiled fabrics it is tested on. Mechanical stress is achieved by the beakers being rotated in the water bath and by including metal balls in the beaker.

The LOM model wash system is mainly used in medium scale testing of detergents and enzymes at European wash conditions. In a LOM experiment, factors such as the ballast to soil ratio and the fabric to wash liquor ratio can be varied. Therefore, the LOM provides the link between small scale experiments, such as AMSA and mini-wash, and the more time consuming full scale experiments in front loader washing machines.

Mini Launder-O-Meter (MiniLOM) Model Wash System

MiniLOM is a modified mini wash system of the Launder-O-Meter (LOM), which is a medium scale model wash system that can be applied to test up to 20 different wash conditions simultaneously. A LOM is basically a large temperature controlled water bath with 20 closed metal beakers rotating inside it. Each beaker constitutes one small washing machine and during an experiment, each will contain a solution of a specific detergent/enzyme system to be tested along with the soiled and unsoiled fabrics it is tested on. Mechanical stress is achieved by the beakers being rotated in the water bath and by including metal balls in the beaker.

The LOM model wash system is mainly used in medium scale testing of detergents and enzymes at European wash conditions. In a LOM experiment, factors such as the ballast to soil ratio and the fabric to wash liquor ratio can be varied. Therefore, the LOM provides the link between small scale experiments, such as AMSA and mini-wash, and the more time consuming full scale experiments in front loader washing machines.

In miniLOM, washes are performed in 50 ml test tubes placed in Stuart rotator.

Terg-O-Timeter (TOM) Wash Assay

The Tergo-To-Meter (TOM) is a medium scale model wash system that can be applied to test 12 different wash conditions simultaneously. A TOM is basically a large temperature controlled water bath with up to 12 open metal beakers submerged into it. Each beaker constitutes one small top loader style washing machine and during an experiment, each of them will contain a solution of a specific detergent/ enzyme system and the soiled and unsoiled fabrics its performance is tested on. Mechanical stress is achieved by a rotating stirring arm, which stirs the liquid within each beaker. Because the TOM beakers have no lid, it is possible to withdraw samples during a TOM experiment and assay for information on-line during wash.

The TOM model wash system is mainly used in medium scale testing of detergents and enzymes at US or LA/AP wash conditions. In a TOM experiment, factors such as the ballast to soil ratio and the fabric to wash liquor ratio can be varied. Therefore, the TOM provides the link between small scale experiments, such as AMSA and mini-wash, and the more time consuming full scale experiments in top loader washing machines.

Equipment: The water bath with 12 steel beakers and 1 rotating arm per beaker with capacity of 500 or 1200 mL of detergent solution. Temperature ranges from 5 to 80° C. The water bath has to be filled up with deionised water. Rotational speed can be set up to 70 to 120 rpm/min.

Set temperature in the Terg-O-Tometer and start the rotation in the water bath. Wait for the temperature to adjust (tolerance is +/−0.5° C.). All beakers shall be clean and without traces of prior test material.

The wash solution with desired amount of detergent, temperature and water hardness is prepared in a bucket. The detergent is allowed to dissolve during magnet stirring for 10 min. Wash solution shall be used within 30 to 60 min after preparation.

800 ml wash solution is added into a TOM beaker. The wash solution is agitated at 120 rpm and optionally one or more enzymes are added to the beaker. The swatches are sprinkled into the beaker and then the ballast load. Time measurement starts when the swatches and ballast are added to the beaker. The swatches are washed for 20 minutes after which agitation is terminated. The wash load is subsequently transferred from the TOM beaker to a sieve and rinse with cold tap water. The soiled swatches are separated from the ballast load. The soil swatches are transferred to a 5 L beaker with cold tap water under running water for 5 minutes. The ballast load is kept separately for the coming inactivation. The water is gently pressed out of the swatches by hand and placed on a tray covered with a paper. Another paper is placed on top of the swatches. The swatches are allowed to dry overnight before subjecting the swatches to analysis, such as measuring the color intensity using a Color Eye as described herein.

Enzyme Assays

Assay I: Testing of DNase Activity DNase activity was determined on DNase Test Agar with Methyl Green (BD, Franklin Lakes, NJ, USA), which was prepared according to the manual from supplier. Briefly, 21 g of agar was dissolved in 500 ml water and then autoclaved for 15 min at 121° C. Autoclaved agar was temperated to 48° C. in water bath, and 20 ml of agar was poured into petri dishes with and allowed to solidify by incubation o/n at room temperature. On solidified agar plates, 5 µl of enzyme solutions are added and DNase activity is observed as colorless zones around the spotted enzyme solutions.

Assay II

Analysis of E-2-nonenal on textile using an electronic nose.

One way of testing for the presence of malodor on textiles is by using E-2-Nonenal as a marker for the malodor, as this compound contributes to the malodor on laundry.

Add a solution of E-2-nonenal to a 5 cm×5 cm textile swatch and place the swatch in a 20 mL glass vial for GC analysis and cap the vial. Analyse 5 mL headspace from the capped vials in a Heracles II Electronic nose from Alpha M.O.S., France (double column gas chromatograph with 2 FIDs, column 1: MXT5 and column 2: MXT1701) after 20 minutes incubation at 40° C.

EXAMPLES

Methods

General methods of PCR, cloning, ligation nucleotides etc. are well-known to a person skilled in the art and may for example be found in in "Molecular cloning: A laboratory manual", Sambrook et al. (1989), Cold Spring Harbor lab, Cold Spring Harbor, NY; Ausubel, F. M. et al. (eds.); "Current protocols in Molecular Biology", John Wiley and Sons, (1995); Harwood, C. R., and Cutting, S. M. (eds.); "DNA Cloning: A Practical Approach, Volumes I and II", 1N. Glover ed. (1985); "Oligonucleotide Synthesis", M. J. Gait ed. (1984); "Nucleic Acid Hybridization", B. D. Haes & S. J. Higgins eds (1985); "A Practical Guide To Molecular Cloning", B. Perbal, (1984).

Example 1 Cloning and Expression of Bacterial DNases

The DNases were derived from bacterial strains isolated from environmental samples by standard microbiological isolation techniques. Strains were identified and taxonomy was assigned based on DNA sequencing of the 16S ribosomal genes (Table 1).

TABLE 1

| Strain | Source Country | Mature protein SEQ ID: |
|---|---|---|
| Bacillus sp-62520 | United states | 11 |
| Bacillus sp-62520 | United states | 12 |
| Bacillus horikoshii | United states | 13 |
| Bacillus horikoshii | Denmark | 14 |
| Bacillus sp-16840 | China | 15 |
| Bacillus sp-16840 | United states | 16 |
| Bacillus sp-62668 | United states | 17 |
| Bacillus sp-13395 | Denmark | 18 |
| Bacillus horneckiae | Turkey | 19 |
| Bacillus cibi | Japan | 21 |
| Bacillus sp-18318 | Japan | 22 |
| Bacillus sp-11238 | Nepal | 20 |
| Bacillus idriensis | Antarctica | 23 |
| Bacillus sp-62451 | United States | 8 |
| Bacillus horikoshii | Japan | 9 |
| Paenibacillus sp-18057 | New Zeeland | 10 |

Chromosomal DNA was isolated from pure cultures of the individual strains with the DNeasy Blood & Tissue Kit from Qiagen (Hilden, Germany) and subjected to full genome sequencing using Illumina technology. Genome sequencing, the subsequent assembly of reads and the gene discovery (i.e., annotation of gene functions) is known to the person skilled in the art and the service can be purchased commercially.

The genome sequences were analyzed for putative DNases from the PFAM database families PF14040 and PF07510 (Finn et al., 2014, Nucleic Acids Research 42: D222-D230). This analysis identified sixteen genes encoding putative DNases which were subsequently cloned and recombinantly expressed in Bacillus subtilis. PF07510 corresponds to the DUF1524 domain.

The genes encoding the DNases were amplified by PCR and fused with regulatory elements, affinity purification tag and homology regions for recombination into the B. subtilis genome. The linear integration construct was a SOE-PCR fusion product (Horton et al., 1989, "Engineering hybrid genes without the use of restriction enzymes, gene splicing by overlap extension", Gene 77: 61-68) made by fusion of the gene between two Bacillus subtilis chromosomal regions along with strong promoters and a chloramphenicol resistance marker. The SOE PCR method is also described in patent application WO 2003/095658.

The genes were expressed under the control of a triple promoter system (as described in WO 99/43835), consisting of the promoters from Bacillus licheniformis alpha-amylase gene (amyL), Bacillus amyloliquefaciens alpha-amylase gene (amyQ), and the Bacillus thuringiensis cryIIIA promoter including stabilizing sequence.

The genes were fused with DNA encoding a Bacillus clausii secretion signal (encoding the following amino acid sequence: MKKPLGKIVASTALLISVAFSSSIASA (SEQ ID NO: 24)) replacing the native secretion signal. Furthermore, the expression construct results in the addition of a carboxy-terminal poly histidine tail consisting of 6 consecutive histidine residues.

The SOE-PCR products were transformed into Bacillus subtilis and integrated in the chromosome by homologous recombination into the pectate lyase locus. Subsequently a recombinant Bacillus subtilis clone containing the integrated expression construct was grown in liquid culture. The culture broth was centrifuged (20000×g, 20 min) and the supernatant was carefully decanted from the precipitate and used for purification of the enzyme or alternatively sterile filtered supernatant was used directly for assays.

Example 2 MiniLOM Liquid Detergent

Isolating Laundry Specific Bacterial Strains

One strain of Brevundimonas sp. isolated from laundry was used in the present example. The Brevundimonas sp. was isolated during a study, where the bacterial diversity in laundry after washing at 15, 40 and 60° C., respectively, was investigated. The study was conducted on laundry collected from Danish households. For each wash, 20 g of laundry items (tea towel, towel, dish cloth, bib, T-shirt armpit, T-shirt collar, socks) in the range 4:3:2:2:1:1:1 was used. Washing was performed in a Laundr-O-Meter (LOM) at 15, 40 or 60° C. For washing at 15 and 40° C., Ariel Sensitive White & Color was used, whereas WFK IEC-A* model detergent was used for washing at 60° C. Ariel Sensitive White & Color was prepared by weighing out 5.1 g and adding tap water up to 1000 ml followed by stirring for 5 minutes. WFK IEC-A* model detergent (which is available from WFK Testgewebe GmbH) was prepared by weighing out 5 g and adding tap water up to 1300 ml followed by stirring for 15 min. Washing was performed for 1 hour at 15, 40 and 60° C., respectively, followed by 2 times rinsing with tap water for 20 min at 15° C.

Laundry was sampled immediately after washing at 15, 40 and 60° C., respectively. Twenty grams of laundry was added 0.9% (w/v) NaCl (1.06404; Merck, Damstadt, Germany) with 0.5% (w/w) tween 80 to yield a 1:10 dilution in stomacher bag. The mixture was homogenized using a Stomacher for 2 minutes at medium speed. After homogenization, ten-fold dilutions were prepared in 0.9% (w/v) NaCl. Bacteria were enumerated on Tryptone Soya Agar (TSA) (CM0129, Oxoid, Basingstoke, Hampshire, UK) incubated aerobically at 30° C. for 5-7 days. To suppress growth of yeast and moulds, 0.2% sorbic acid (359769, Sigma) and 0.1% cycloheximide (18079; Sigma) were added. Bacterial colonies were selected from countable plates and purified by restreaking twice on TSA. For long time storage, purified isolates were stored at −80° C. in TSB containing 20% (w/v) glycerol (49779; Sigma).

Preparation of Swatches with Biofilm

Brevundimonas sp. was pre-grown on Tryptone Soya Agar (TSA) (pH 7.3) (CM0131; Oxoid Ltd, Basingstoke, UK) for 2-5 days at 30° C. From a single colony, a loop-full was transferred to 10 mL of TSB and incubated for 1 day at 30° C. with shaking (240 rpm). After propagation, Brevundimonas sp. was pelleted by centrifugation (Sigma Laboratory Centrifuge 6K15) (3000 g at 21° C. in 7 min) and resuspended in 10 mL of TSB diluted twice with water. Optical density (OD) at 600 nm was measured using a spectophometer (POLARstar Omega (BMG Labtech, Ortenberg, Germany). Fresh TSB diluted twice with water was inoculated to an $OD_{600\ nm}$ of 0.03, and 1.6 mL was added into each well of a 12-well polystyrene flat-bottom microplate (3512; Corning Incorporated, Corning, NY, USA), in which a round swatch (diameter 2 cm) of sterile Polyester WFK30A was placed. After incubation (24 h at 15° C. with shaking (100 rpm), swatches were rinsed twice with 0.9% (w/v) NaCl.

Wash Experiment

Wash liquor of liquid model detergent A were prepared by weighing out and dissolving detergent in water with water with hardness 15° dH. Dosing of model detergent A was 3.33 g/L. Pigment soil (Pigmentschmutz, 09V, wfk, Krefeld, Germany) (0.7 g/L) was added to the wash liquor. DNase (0.5 ppm) was added to the wash liquor. As control, wash liquor without DNase was made. Wash liquor (10 ml) was added to a 50 ml test tube, in which five rinsed swatches with Brevundimonas sp. biofilm and five sterile polyester (WFK30A) swatches were placed. Test tubes were placed in a Stuart rotator (Mini LOM) for 1 hour at 30° C. Swatches were rinsed twice with tap water and dried on filter paper over night. Color difference (L values) was measured using a Color Eye (Macbeth Color Eye 7000 reflectance spectrophotometer). The measurements were made without UV in the incident light and the L value from the 62E Lab color space was extracted. The color difference (L value, L*) represents the darkest black at L*=0, and the brightest white at L*=100. Data is represented as Delta L values meaning the L value of the swatch washed with DNase minus the L value of swatch washed without DNase.

TABLE 2

Deep cleaning effect of the DNase from Bacillus horikoshii with SEQ ID NO: 9 and closely related homologues

| Host name | L-value Model detergent A | ΔL Model detergent A |
|---|---|---|
| No enzyme | 83.59 | n/a |
| Bacillus horikoshii | 88.50 | 4.91 |
| Bacillus sp-62520 | 92.77 | 3.50 |
| Bacillus sp-62520 | 93.17 | 3.90 |
| Bacillus horikoshii | 93.41 | 4.14 |
| Bacillus horikoshii | 93.28 | 4.01 |
| Bacillus sp-16840 | 93.74 | 4.47 |
| Bacillus sp-16840 | 92.47 | 3.20 |
| Bacillus sp-62668 | 92.95 | 3.68 |
| Bacillus sp-13395 | 92.31 | 3.04 |
| Bacillus horneckiae | 90.01 | 0.74 |

TABLE 3

Deep cleaning effect of the DNase from Bacillus sp-62451 with SEQ ID NO: 8 and closely related homologues.

| Host name | L-value Model detergent A | ΔL Model detergent A |
|---|---|---|
| No enzyme | 83.59 | n/a |
| Bacillus sp-62451 | 88.71 | 5.13 |
| Bacillus cibi | 91.80 | 2.53 |
| Bacillus sp-18318 | 92.91 | 3.64 |
| Bacillus idriensis | 92.41 | 3.14 |

TABLE 4

Deep cleaning effect of the DNase from Paenibacillus sp-18057 with SEQ ID NO: 10

| Host name | L-value Model detergent A | ΔL Model detergent A |
|---|---|---|
| No enzyme | 83.59 | n/a |
| Paenibacillus sp-18057 | 88.82 | 5.24 |

Tables 2, 3 and 4 show that all the tested DNases have "deep cleaning" effect meaning that they disrupt, reduce or remove the biofilm or components of the biofilm swatches in a liquid detergent.

Below is shown the cleaning effect of Benzonase (SEQ ID NO: 7) another polypeptide having DNase activity.

TABLE 5

Deep-cleaning of Benzonase (SEQ ID NO: 7).

| Detergent | DNase conc. (ppm) | L-value | L-value$_{with\ DNase}$ L-value$_{without\ DNase}$ |
|---|---|---|---|
| No enzyme | 0 | 83.5 | n/a |
| Benzonase | 0.5 | 88.1 | 4.6 |

Table 5 shows that Benzonase DNase also has deep cleaning effect in liquid detergent.

Example 3 MiniLOM Wash in Powder Detergent

Isolating Laundry Specific Bacterial Strains

One strain of Brevundimonas sp. isolated from laundry was used in the present example. The Brevundimonas sp. was isolated during a study, where the bacterial diversity in laundry after washing at 15, 40 and 60° C., respectively, was investigated. The study was conducted on laundry collected from Danish households. For each wash, 20 g of laundry items (tea towel, towel, dish cloth, bib, T-shirt armpit, T-shirt collar, socks) in the range 4:3:2:2:1:1:1 was used. Washing was performed in a Laundr-O-Meter (LOM) at 15, 40 or 60° C. For washing at 15 and 40° C., Ariel Sensitive White & Color was used, whereas WFK IEC-A* model detergent was used for washing at 60° C. Ariel Sensitive White & Color was prepared by weighing out 5.1 g and adding tap water up to 1000 ml followed by stirring for 5 minutes. WFK IEC-A* model detergent (which is available from WFK Testgewebe GmbH) was prepared by weighing out 5 g and adding tap water up to 1300 ml followed by stirring for 15 min. Washing was performed for 1 hour at 15, 40 and 60° C., respectively, followed by 2 times rinsing with tap water for 20 min at 15° C.

Laundry was sampled immediately after washing at 15, 40 and 60° C., respectively. Twenty grams of laundry was added 0.9% (w/v) NaCl (1.06404; Merck, Damstadt, Germany) with 0.5% (w/w) tween 80 to yield a 1:10 dilution in stomacher bag. The mixture was homogenized using a Stomacher for 2 minutes at medium speed. After homogenization, ten-fold dilutions were prepared in 0.9% (w/v) NaCl. Bacteria were enumerated on Tryptone Soya Agar (TSA) (CM0129, Oxoid, Basingstoke, Hampshire, UK) incubated aerobically at 30° C. for 5-7 days. To suppress growth of yeast and moulds, 0.2% sorbic acid (359769, Sigma) and 0.1% cycloheximide (18079; Sigma) were added. Bacterial colonies were selected from countable plates and purified by restreaking twice on TSA. For long time storage, purified isolates were stored at −80° C. in TSB containing 20% (w/v) glycerol (49779; Sigma).

Preparation of Swatches with Biofilm

Brevundimonas sp. was pre-grown on Tryptone Soya Agar (TSA) (pH 7.3) (CM0131; Oxoid Ltd, Basingstoke, UK) for 2-5 days at 30° C. From a single colony, a loop-full was transferred to 10 mL of TSB and incubated for 1 day at 30° C. with shaking (240 rpm). After propagation, Brevundimonas sp. was pelleted by centrifugation (Sigma Laboratory Centrifuge 6K15) (3000 g at 21° C. in 7 min) and resuspended in 10 mL of TSB diluted twice with water. Optical density (OD) at 600 nm was measured using a spectophometer (POLARstar Omega (BMG Labtech, Ortenberg, Germany). Fresh TSB diluted twice with water was inoculated to an $OD_{600\ nm}$ of 0.03, and 1.6 mL was added into each well of a 12-well polystyrene flat-bottom microplate (3512; Corning Incorporated, Corning, NY, USA), in which a round swatch (diameter 2 cm) of sterile Polyester WFK30A was placed. After incubation (24 h at 15° C. with shaking (100 rpm), swatches were rinsed twice with 0.9% (w/v) NaCl.

Wash Experiment

Wash liquors of powder model detergent T without bleach and powder model detergent T with bleach were prepared by weighing out and dissolving detergents in water with water with hardness 15° dH. Dosing of detergent T without bleach and model detergent T with bleach model detergent was 5.30 g/L. The AEO Biosoft N25-7 (NI) (0.16 g/l) component of model detergent T without bleach and model detergent T with bleach was added separately. Pigment soil (Pigmentschmutz, 09V, wfk, Krefeld, Germany) (0.7 g/L) was added to the wash liquor. DNase (0.5 ppm) was added to the wash liquor. As control, wash liquor without DNase was made. Wash liquor (10 ml) was added to a 50 ml test tube, in which five rinsed swatches with Brevundimonas sp. biofilm and five sterile polyester (WFK30A) swatches were placed. Test tubes were placed in a Stuart rotator (Mini LOM) for 1 hour at 30° C. Swatches were rinsed twice with tap water and dried on filter paper over night. Color difference (L values) was measured using a Color Eye (Macbeth Color Eye 7000 reflectance spectrophotometer). The measurements were made without UV in the incident light and the L value from the CIE Lab color space was extracted. The color difference (L value, L*) represents the darkest black at L*=0, and the brightest white at L*=100. Data is represented as Delta L values meaning the L value of the swatch washed with DNase minus the L value of swatch washed without DNase.

TABLE 6

| Host name | ΔL Model detergent T w/o bleach | L-value Model detergent T w bleach | ΔL Model detergent T w bleach |
|---|---|---|---|
| No enzyme | n/a | 83.49 | n/a |
| Bacillus sp-62451 | 4.47 | 87.01 | 3.51 |
| Bacillus horikoshii | 3.61 | 85.58 | 2.08 |
| Paenibacillus sp-18057 | 4.82 | 87.40 | 3.91 |

Example 4 Cloning and Expression of Bacterial DNases

The DNases were derived from bacterial strains isolated from environmental samples by standard microbiological isolation techniques or from mixed bacterial communities. Isolated pure strains were identified and taxonomy was assigned based on DNA sequencing of the 16S ribosomal genes (Table 7).

TABLE 7

| Strain or community | Source Country | Mature protein SEQ ID: |
|---|---|---|
| Bacillus algicola | Denmark | 53 |
| Xanthan alkaline community J | United States | 56 |
| Xanthan alkaline community D | Spain | 170 |
| Paenibacilus mucilaginosus 3016 | Public China SWISSPROT:H6NAU2 | 65 |
| Bacillus vietnamensis | Himalaya | 59 |
| Bacillus hwajinpoensis | Denmark | 62 |
| Xanthan alkaline community O | Denmark | 173 |
| Bacillus indicus | United States | 68 |
| Bacillus marisflavi | United States | 71 |
| Bacillus luciferensis | United States | 74 |
| Bacillus marisflavi | United States | 77 |
| Bacillus sp. SA2-6 | Public India UNIPROT: A0A0M2T1U6 | 80 |
| Thermobispora bispora DSM 43833 | Public Germany SWISSPROT: D6Y838 | 161 |

Chromosomal DNA was isolated from either pure cultures of the individual strains or from mixed cultured communities in the case of Xanthan alkaline community J, D and O with the DNeasy Blood & Tissue Kit from Qiagen (Hilden, Germany) and subjected to full genome sequencing using Illumina technology. Genome sequencing, the subsequent assembly of reads and the gene discovery (i.e., annotation of gene functions) is known to the person skilled in the art and the service can be purchased commercially.

The genome sequences of the strains Paenibacilus mucilaginosus 3016, Bacillus sp. SA2-6 and Thermobispora bispora DSM 43833 are publically available in the Genbank database under accession numbers NC_016935.1, NZ_LAYY00000000.1 and NC_014165.1 respectively.

The genome sequences were analyzed for putative DNases from the PFAM database families PF14040 and PF07510 (Finn et al., 2014, Nucleic Acids Research 42: D222-D230). This analysis identified twenty-nine genes encoding putative DNases which were subsequently cloned and recombinantly expressed in Bacillus subtilis. The PF07510 corresponds to the DUF1524 family.

The genes encoding the DNases were amplified by PCR or in the case of Paenibacilus mucilaginosus 3016, Bacillus sp. SA2-6 and Thermobispora bispora ordered as synthetic genes and fused with regulatory elements, affinity purification tag and homology regions for recombination into the pel locus of the B. subtilis genome. The linear integration construct was a SOE-PCR fusion product (Horton et al., 1989, "Engineering hybrid genes without the use of restriction enzymes, gene splicing by overlap extension", Gene 77: 61-68) made by fusion of the gene between two *Bacillus subtilis* chromosomal regions along with strong promoters and a chloramphenicol resistance marker. The SOE PCR method is also described in patent application WO 2003/095658.

The genes were expressed under the control of a triple promoter system (as described in WO 99/43835), consisting of the promoters from *Bacillus licheniformis* alpha-amylase gene (amyL), *Bacillus amyloliquefaciens* alpha-amylase gene (amyQ), and the *Bacillus thuringiensis* cryIIIA promoter including stabilizing sequence.

The genes were fused with DNA encoding a *Bacillus clausii* secretion signal (encoding the following amino acid sequence: MKKPLGKIVASTALLISVAFSSSIASA (SEQ ID NO: 24)) replacing the native secretion signal. Furthermore, the expression construct results in the addition of a carboxy-terminal poly histidine tail consisting of 6 consecutive histidine residues.

The SOE-PCR products were transformed into *Bacillus subtilis* and integrated in the chromosome by homologous recombination into the pectate lyase locus. Subsequently a recombinant *Bacillus subtilis* clone containing the integrated expression construct was grown in liquid culture. The culture broth was centrifuged (20000×g, 20 min) and the supernatant was carefully decanted from the precipitate and used for purification of the enzyme or alternatively sterile filtered supernatant was used directly for assays.

Example 5 Cloning and Expression of Fungal DNases

Strains
*Escherichia coli* Top-10 strain purchased from TIANGEN (TIANGEN Biotech Co. Ltd., Beijing, China) was used to propagate the expression vector. *Aspergillus oryzae* MT3568 strain was used for heterologous expression of the gene encoding a polypeptide having homology with polypeptides with phospholipase activity. *A. oryzae* MT3568 is an amdS (acetamidase) disrupted gene derivative of *A. oryzae* JaL355 (WO 02/40694) in which pyrG auxotrophy was restored by disrupting the *A. oryzae* acetamidase (amdS) gene with the pyrG gene.

Media
YPM medium composition: 10 g yeast extract, 20 g Bacto-peptone, 20 g maltose, and deionised water to 1000 ml.
LB plates composed of: 10 g of Bacto-tryptone, 5 g of yeast extract, 10 g of sodium chloride, 15 g of Bacto-agar, and deionised water to 1000 ml.
LB medium composed of: 1 g of Bacto-tryptone, 5 g of yeast extract, and 10 g of sodium chloride, and deionised water to 1000 ml.
COVE sucrose plates were composed of: 342 g of sucrose, 20 g of agar powder, 20 ml of COVE salt solution, and deionized water to 1 liter.
The medium was sterilized by autoclaving at 15 psi for 15 minutes. The medium was then cooled to 60° C. and 10 mM acetamide, 15 mM CsCl, Triton X-100 (50 µl/500 ml) were added.
COVE-2 plate/tube for isolation: 30 g/L sucrose, 20 ml/L COVE salt solution, 10 mM acetamide, 30 g/L noble agar (Difco, Cat #214220).

COVE salt solution composed of: 26 g of $MgSO_4 \cdot 7H_2O$, 26 g of KCL, 26 g of $KH_2PO_4$, 50 ml of COVE trace metal solution, and deionised water to 1000 ml.
COVE trace metal solution composed of: 0.04 g of $Na_2B_4O_7 \cdot 10H_2O$, 0.4 g of $CuSO_4 \cdot 5H_2O$, 1.2 g of $FeSO_4 \cdot 7H_2O$, 0.7 g of $MnSO_4 \cdot H_2O$, 0.8 g of $Na_2MoO_4 \cdot 2H_2O$, 10 g of $ZnSO_4 \cdot 7H_2O$, and deionised water to 1000 ml.
Methyl green DNA test agar plates was made by suspending 42.05 g "DNase Test Agar Base w/methyl green" (HiMedia Laboratories Pvt. Ltd., Inida) in 1000 ml distilled water and sterilized by autoclaving.

Example 6: Cloning, Expression and Fermentation of Fungal DNases

The DNases were derived from fungal strains isolated from environmental samples by standard microbiological isolation techniques. Strains were identified and taxonomy was assigned based on DNA sequencing (Table 6).

TABLE 6

| Donor Organism name | source country | Mature protein SEQ ID: |
|---|---|---|
| *Scytalidium circinatum* | China | 155 |
| *Metarhizium* sp. HNA15-2 | China | 146 |
| *Humicolopsis cephalosporioides* | Argentina | 182 |
| *Alternaria* sp. XZ2545 | China | 116 |
| *Alternaria* sp. | China | 119 |
| *Corynespora cassiicola* | China | 95 |
| *Curvularia lunata* | China | 104 |
| *Endophragmiella valdina* | China | 92 |
| *Setophaeosphaeria* sp. | China | 113 |
| *Setosphaeria rostrate* | China | 89 |
| *Paraphoma* sp. XZ1965 | China | 98 |
| *Metapochonia suchlasporia* | China | 131 |
| *Acremonium* sp. XZ2007 | China | 137 |
| *Acremonium* sp. XZ2414 | China | 149 |
| *Isaria tenuipes* | China | 152 |
| *Metarhizium lepidiotae* | China | 158 |
| *Sarocladium* sp. XZ2014 | China | 143 |
| *Didymosphaeria futilis* | China | 197 |
| *Pycnidiophora* cf. *dispera* | China | 167 |
| *Pleosporales* | China | 191 |
| *Phaeosphaeria* sp. | China | 194 |
| *Roussoella intermedia* | China | 188 |
| *Monilinia fructicola* | Australia | 101 |
| *Westerdykella* sp. AS85-2 | China | 179 |
| *Sporormia fimetaria* | China | 164 |
| *Chaetomium thermophilum* var. *thermophilum* | United Kingdom | 125 |
| *Daldinia fissa* | China | 134 |
| *Scytalidium thermophilum* | China | 128 |

Chromosomal DNA from individual strains (Table. 6) was isolated by QIAamp DNA Blood Mini Kit (Qiagen, Hilden, Germany). 5 µg of chromosomal DNA were sent for full genome sequencing using Illumina technology. Genomic DNA was isolated from the strains and the genomic sequences were determined, assembled and annotated by standard methods or by purchasing the services commercially.

The genome sequences were analyzed for putative DNases from the PFAM database families DUF1524 (Finn et al. 2014, *Nucleic Acids Research* 42:D222-D230). This analysis identified 29 genes encoding putative DNases which were subsequently cloned and recombinantly expressed in *Aspergillus oryzae*.

Those 29 genes were amplified by PCR from above isolated fungal genomic DNA. The purified PCR product was cloned into the expression vector pCaHj505 by ligation with an IN-FUSION™ CF Dry-down Cloning Kit (Clontech Laboratories, Inc., Mountain View, CA, USA) according to the manufacturer's instructions. The ligation mixture was used to transform *E. coli* TOP10 chemically competent cells (described in Strains). Correct colonies containing DNases were selected and verified by DNA sequencing (by SinoGenoMax Company Limited, Beijing, China). The DNase comprising colonies were cultivated overnight in 3 ml of LB medium supplemented with 100 μg of ampicillin per ml. Plasmid DNA was purified using a Qiagen Spin Miniprep kit (Cat. 27106) (QIAGEN GmbH, Hilden, Germany) according to the manufacturer's instructions. Using the SignalP program v.3 (Nielsen et al., 1997, *Protein Engineering* 10: 1-6), the signal peptide and accordingly the mature peptide were predicted.

Protoplasts of *Aspergillus oryzae* MT3568 were prepared according to WO 95/02043. 100 μl of protoplasts were respectively mixed with 2.5-10 μg of each *Aspergillus* expression vector comprising DNases and 250 μl of 60% PEG 4000, 10 mM $CaCl_2$, and 10 mM Tris-HCl pH 7.5 and gently mixed. The mixture was incubated at 37° C. for 30 minutes and the protoplasts were spread onto COVE sucrose plates for selection. After incubation for 4-7 days at 37° C. spores of 4 transformants were inoculated into 3 ml of YPM medium. After 3 days cultivation at 30° C., the culture broths were analyzed by SDS-PAGE using Novex® 4-20% Tris-Glycine Gel (Invitrogen Corporation, Carlsbad, CA, USA) to identify the transformants producing the largest amount of recombinant DNases with respective estimated mature peptide size.

The hydrolytic activity of the DNase produced by the *Aspergillus* transformants was investigated using methyl green DNA test agar plates. 20 μl aliquots of the culture broth from the different transformants, or buffer (negative control) were distributed into punched holes with a diameter of 3 mm and incubated for 1 hour at 37° C. The plates were subsequently examined for the presence or absence of a white zone around the holes corresponding to phospholipase activity. Based on those two selection criteria, spores of the best transformant were spread on COVE-2 plates for re-isolation in order to isolate single colonies. Then a single colony was spread on a COVE-2 tube until sporulation. Spores from the best expressed transformant were cultivated in 2400 ml of YPM medium in shake flasks during 3 days at a temperature of 30° C. under 80 rpm agitation. Culture broth was harvested by filtration using a 0.2 μm filter device. The filtered fermentation broth was used for enzyme characterization.

Example 7 Purification of Recombinant DNase by Metal Ion Affinity Chromatography (IMAC)

The culture broth harvested in example 7 was precipitated with ammonium sulfate (80% saturated). Precipitates were re-dissolved in 50 ml of 20 mM PBS pH 7.0, and then filtered through a 0.45 μm filter. The filtered crude protein solution was applied to a 50 ml self-packed Ni sepharose excel affinity column (GE Healthcare, Buckinghamshire, UK) equilibrated with 20 mM PBS pH 7.0 and 300 mM sodium chloride. Proteins were eluted with a linear 0-0.5 M imidazole gradient. Fractions were analyzed by SDS-PAGE using a Mini-PROTEAN TGX Stain-Free 4-15% Precast Gel (Bio-Rad Laboratories, CA, United States). DNase activities of fractions were assessed on BD Difco™ DNase Test Agar with Methyl Green (Becton, Dickinson and Company, New Jersey, United States) at pH 8.0, 40° C. Fractions were pooled containing recombinant protein bands and showing positive activities. Then the pooled solution was concentrated by ultrafiltration.

Example 8: Purification of Recombinant DNase by Hydrophobic Interaction Chromatography (HIC)

The culture broth harvested in example 7 was precipitated with ammonium sulfate (80% saturated). Precipitates were re-dissolved in 50 ml of 20 mM PBS pH 7.0, and ammonium sulfate was replenished to get final concentration 1.8 M. Crude protein solution was filtered through a 0.45 μm filter, and then applied to a 20 ml pre-packed Hiprep Phenyl HP 16/10 column (GE Healthcare, Buckinghamshire, UK) equilibrated with 20 mM PBS pH 7.0 and 1.8 M ammonium sulfate buffer. Proteins were eluted with a linear 1.8 M-0 M ammonium sulfate gradient. Fractions were analyzed by SDS-PAGE using a Mini-PROTEAN TGX Stain-Free 4-15% Precast Gel (Bio-Rad Laboratories, CA, United States). DNase activities of fractions were assessed on BD Difco™ DNase Test Agar with Methyl Green (Becton, Dickinson and Company, New Jersey, United States) at pH 8.0, 40° C. Fractions were pooled containing recombinant protein bands and showing positive activities. Then the pooled solution was concentrated by ultrafiltration.

Example 9: Cloning, Expression and Fermentation of DNases

The DNases were cloned from fungal strains obtained from a variety of sources. *Pyrenochaetopsis* sp. was isolated in Denmark and received from the University of Copenhagen and is the source of the mature polypeptide SEQ ID NO: 83. *Penicillium quercetorum* was isolated from a soils sample in Japan and is the source for the mature peptide with SEQ ID NO: 110. *Trichoderma reesei* strain RUT-C30 was obtained from Rutgers University and is available from the ATCC, Manassas, Virginia, USA, as ATCC56765, and is the source for the mature peptide with SEQ ID NO: 122. *Neosartorya massa* strain CBS117265 was purchased from the CBS-KNAW Fungal Biodiversity Centre, Utrecht, The Netherlands, and is the source for the mature peptide with SEQ ID NO: 185. Genomic DNA was isolated from the strains and the genomic sequences were determined, assembled and annotated by standard methods or by purchasing the services commercially. The annotated genomes were searched for putative DNases with the NUC1_A domain. The predicted peptides with SEQ ID NO: 82, 109, 121, and 184 were found to have a NUC1_A domain and the corresponding DNA sequences encoding them with SEQ ID NO: 81, 108, 120, and 183 were PCR amplified from genomic DNA isolated from *Pyrenochaetopsis* sp., *Penicillium quercetorum*, *Trichoderma reesei* and *Neosartorya massa* and cloned into the *Aspergillus* expression vector pMStr57 (WO 2004/032648). The sequences of the NUC1_A encoding genes cloned in the expression vector were confirmed, and the expression constructs were transformed into the *Aspergillus oryzae* strain MT3568 (WO 2011/057140). Transformants were selected on acetamide during regeneration from protoplasts and subsequently re-isolated under selection (Christensen et al., 1988, *Biotechnology* 6, 1419-1422 and WO 2004/032648). For production of the recombinant DNases, a single *Aspergillus* transformant was selected for each DNase and the transformants were cultured in 500 ml baffled flasks containing 150 ml of DAP-4C-1 medium (WO 2012/103350). The cultures were shaken on a rotary table at 150 RPM at 30° C. for 4 days. The culture broth was subsequently separated from cellular material by passage through a 0.22 um filter.

Example 10: Chromatographic Purification of Recombinant DNases pH of the filtered sample was adjusted to around pH 7.5 and 1.8 M ammonium sulfate was added. The sample was applied to a 5 ml HiTrap™ Phenyl (HS) column on an Äkta Explorer. Prior to loading, the column had been equilibrated in 5 column volumes (CV) of 50 mM HEPES+1.8 M AMS pH 7. In order to remove unbound material, the column was washed with 5 CV of 50 mM HEPES+1.8M AMS pH 7. The target protein was eluted from the column into a 10 ml loop using 50 mM HEPES+20% isopropanol pH 7. From the loop, the sample was loaded onto a desalting column (HiPrep™ 26/10 Desalting), which had been equilibrated with 3CV of 50 mM HEPES+100 mM NaCl pH 7.0. The target protein was eluted with 50 mM HEPES+100 mM NaCl pH 7.0 and relevant fractions were selected and pooled based on the chromatogram. The flow rate was 5 ml/min.

Protein concentration in the final sample was estimated by measuring absorption at 280 nm.

Example 11: Construction of Phylogenetic Trees

The NUC1 domain includes the polypeptides of the invention having DNase activity and comprises the NUC1_A domain as well as the clusters such as the clades.

A phylogenetic tree was constructed, of polypeptide sequences containing a DUF1524 domain, as defined in PFAM (PF07510, Pfam version 30.0, Finn, 2016, *Nucleic Acids Research*, Database Issue 44: D279-D285). The phylogenetic tree was constructed from a multiple alignment of mature polypeptide sequences containing at least one DUF1524 domain. The sequences were aligned using the MUSCLE algorithm version 3.8.31 (Edgar, 2004, *Nucleic Acids Research* 32(5): 1792-1797), and the trees were constructed using FastTree version 2.1.8 (Price et al., 2010, *PloS one* 5(3)) and visualized using iTOL (Letunic & Bork, 2007, *Bioinformatics* 23(1): 127-128).

The polypeptide comprises of the DUF1524 domain comprises several motifs one example is [E/D/H]H[I/V/L/F/M]X[P/A/S] (SEQ ID NO: 200) situated in positions corresponding to positions 87 to 91 in *B. cibi* (SEQ ID NO: 21). H88 is a catalytic residue involved in the catalytic activity of DUF1524, and part of the HXXP motif. Residue N128 (SEQ ID NO: 21) is predicted to bind catalytic metal ions. Another motif which may be comprised by the polypeptides of the invention is [T/D/S][G/N]PQL (SEQ ID NO: 198), where Q is involved in stabilizing backbone of HXXP motif. Yet another motif is [G/T]Y[D/S][R/K/L] (SEQ ID NO: 199) corresponding to pos 28 to 31 of SEQ ID NO: 21, where R31 is part of catalytic motif of GYS clade, described below.

The polypeptides in DUF1524 can be separated into distinct sub-clusters, where we denoted one sub-cluster comprising the motif [F/L/Y/I]A[N/R]D[L/I/P/V][ (SEQ ID NO: 201) as family NUC1. The motif is located at positions corresponding to positions 110 to 114 of SEQ ID NO: 21. Another motif characteristic of this domain is C[D/N]T[A/R] (SEQ ID NO: 202), located at positions corresponding to positions 43 to 46 of (SEQ ID NO: 21).

Generation of NUC1_a Domain

A phylogenetic tree was constructed, of polypeptide sequences containing a NUC1 domain, as defined above. The phylogenetic tree was constructed from a multiple alignment of mature polypeptide sequences containing at least one NUC1 domain. The sequences were aligned using the MUSCLE algorithm version 3.8.31 (Edgar, 2004, *Nucleic Acids Research* 32(5): 1792-1797), and the tree was constructed using FastTree version 2.1.8 (Price et al., 2010, *PloS one* 5(3)) and visualized using iTOL (Letunic & Bork, 2007, *Bioinformatics* 23(1): 127-128). The polypeptides in NUC1 can be separated into at least distinct sub-clusters, one where denoted NUC1_A. A characteristic motif for this subgroup is the motif [DQ][IV]D[H] (SEQ ID NO: 203) corresponding to amino acid 85 to 88 in the reference polypeptide (SEQ ID NO: 21). The D at the position corresponding to position 85 of SEQ ID NO: 21 is predicted to be involved in binding of catalytic metal ion cofactor.

Generation of Phylogenetic Trees

A phylogenetic tree was constructed, of polypeptide sequences containing a NUC1_A domain, as defined above. The phylogenetic tree was constructed from a multiple alignment of mature polypeptide sequences containing at least one NUC1_A domain. The sequences were aligned using the MUSCLE algorithm version 3.8.31 (Edgar, 2004, *Nucleic Acids Research* 32(5): 1792-1797), and the tree was constructed using FastTree version 2.1.8 (Price et al., 2010, *PloS one* 5(3)) and visualized using iTOL (Letunic & Bork, 2007, *Bioinformatics* 23(1): 127-128). The polypeptides in NUC1_A can be separated into multiple distinct sub-clusters, or clades, where we denoted the clades listed below. The distinct motifs for each clade are described in detail below.

(a) GYS Clade

Figures 1, 1A, 1C:
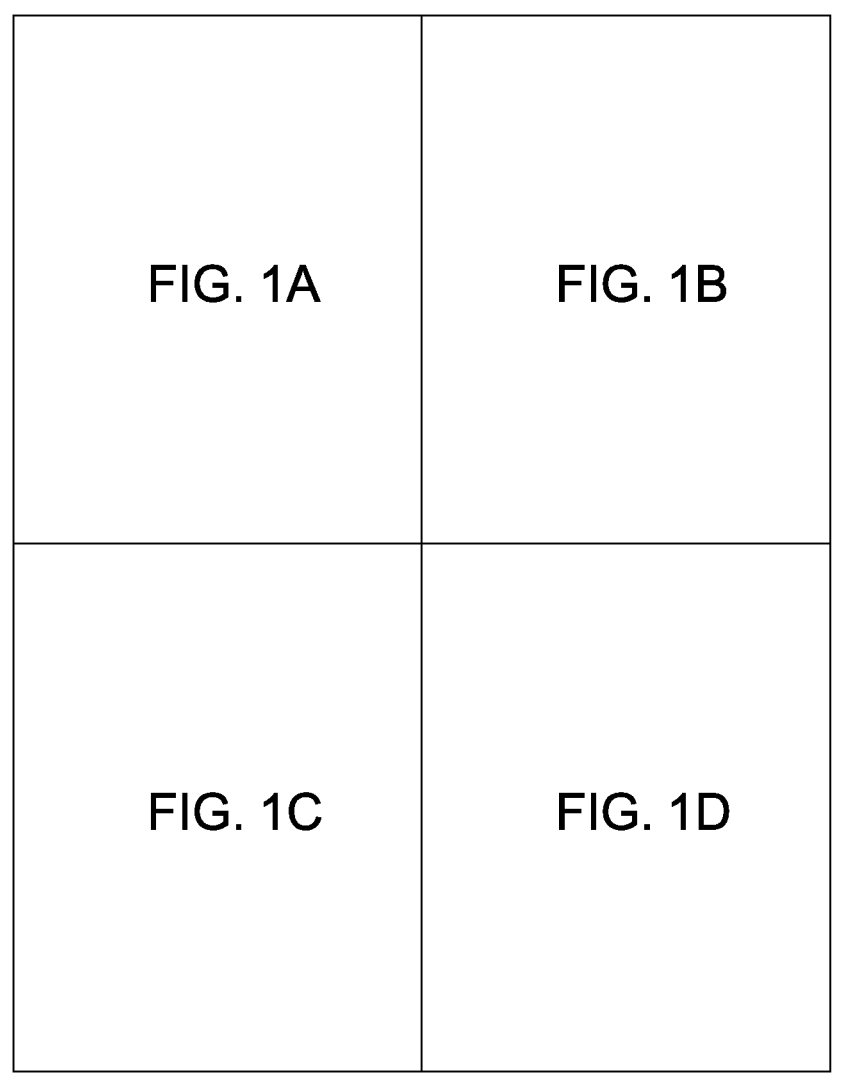

The GYS clade comprises NUC1_A polypeptides having DNase activity, primarily bacterial class of *bacillus*. The polypeptides of the clade comprise several motifs one example is ASXNRSKG (SEQ ID NO: 205), corresponding to pos 125 to 133 of SEQ ID NO: 21, where R (corresponding to position 129 of SEQ ID NO: 21) is fully conserved in GYS clade. The motif is located on the surface of the protein, and is putatively involved in DNA binding. The N (corresponding to position 128 of SEQ ID NO: 21) is predicted to be involved in catalytic metal ion binding. Another example on a motif within the GYS clade [D/M/L][S/T]GYSR[D/N] (SEQ ID NO: 204) corresponding to positions 26 to 32 of SEQ ID NO: 21. The R located at a position corresponding to position 31 of SEQ ID NO: 21 is part of catalytic motif of GYS clade. An alignment of the polypeptides of the invention comprised in the clade is shown in FIG. 1.

(b) NAWK Clade

This clade comprises polypeptides having DNase activity and which comprises primarily of fungal DNases, particularly from the class of dothideomycetes. The polypeptides of this clade comprises one or more motifs, examples of such motifs are [V/I]PL[S/A]NAWK (SEQ ID NO: 206) and NPQL (SEQ ID NO: 207). An alignment of the polypeptides of the invention comprised in the clade is shown in FIG. 2.

(c) KNAW Clade

The polypeptides of this clade comprise primarily polypeptides originating from fungal source, e.g., Sordariomycetes taxonomic group. The polypeptides of the clade comprise one or more motifs. Examples of such motifs are P[Q/E]L[W/Y] (SEQ ID NO: 208), which is predicted to be involved in calcium binding. Another motif is [K/H/E]NAW (SEQ ID NO: 209).

Hidden Markov Model (HMM):

The strategy for creating the Hidden Markov Model is as indicated below. The polypeptide sequences of the experimentally verified functional NUC1_A endo-nucleases were analyzed using the HMMER software package (available at http://hmmer.org; the theory behind profile HMMs is described in R. Durbin, S. Eddy, A. Krogh, and G. Mitchison, Biological sequence analysis: probabilistic models of proteins and nucleic acids, Cambridge University Press, 1998; Krogh et al., 1994, *J. Mol. Biol.* 235:1501-1531), following the user guide which is available from HMMER (Janelia Farm Research Campus, Ashburn, Va., http://hmmer.org). Hidden Markov models are used in a number of databases that aim at classifying proteins, for review see Bateman and Haft, 2002, Brief Bioinform 3; 236-245. The output of the HMMER hmmbuild software program is a profile Hidden Markov Model (profile HMM) that characterizes the input sequences. As stated in the user guide, profile HMMs are statistical descriptions of the consensus of a multiple sequence alignment. They use position-specific scores for amino acids (or nucleotides) and position specific scores for opening and extending an insertion or deletion. Compared to other profile based methods, HMMs have a formal probabilistic basis. Profile HMMs for a large number of protein families are publicly available in the PFAM database (Janelia Farm Research Campus, Ashburn, Va.).

The profile HMM was built as follows:

Step 1. Build a Sequence Alignment

The polypeptides shown in SEQ ID NO: 8, SEQ ID NO: 9, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 53, SEQ ID NO: 56, SEQ ID NO: 59, SEQ ID NO: 62, SEQ ID NO: 65, SEQ ID NO: 68, SEQ ID NO: 71, SEQ ID NO: 74, SEQ ID NO: 77, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 161, SEQ ID NO: 164, SEQ ID NO: 167, SEQ ID NO: 170, SEQ ID NO: 173, SEQ ID NO: 176, SEQ ID NO: 179, SEQ ID NO: 182, SEQ ID NO: 185, SEQ ID NO: 188, SEQ ID NO: 191, SEQ ID NO: 194, SEQ ID NO: 197 were aligned using the MUSCLE algorithm version 3.8.31 with default parameters (Edgar, R. C. (2004). *Nucleic Acids Research*, 32(5), 1792-1797), and from this multiple sequence alignment the HMM was built with the software program hmmbuild version 3.1b2 (available at http://hmmer.org). hmmbuild reads the multiple sequence alignment file created by MUSCLE, builds a new profile HMM, and saves the profile HMM to a HMMER profile file. A profile HMM is completely described in a HMMER profile file, which contains all the probabilities that are used to parameterize the HMM. The profile HMM for the set of NUC1_A polypeptides.

Step 2. Test the Specificity and Sensitivity of the Built Profile HMMs

The Profile HMM was evaluated using hmmsearch version 3.1b2 software program with default settings, which reads a Profile HMM file and searches a sequence file for significantly similar sequence matches. The sequence file searched contained all Uniprot sequences annotated with DUF1524 (Pfam DUF1524, Trusted domain cut-off 21.2 Pfam family PF07510, database version 30.0 UniProt annotated 1412 sequences). During the search, the size of the database (Z parameter) was set to 1 billion. This size setting ensures that significant E-values against the current database will remain significant in the foreseeable future. The hmmsearch domT trusted cutoff was set at 157.0.

A hmmer search, using hmmsearch, with the profile HMM generated from the alignment of the 64 NUC1_A experimentally active endo-nucleases, matched 2966 sequences in UniProt above a Trusted domain cut-off of 157.0; all matching pFam domain DUF1524 and all comprising NUC1_A motif [D/Q][I/V]DH. This result indicates that members of the NUC1_A family share significant sequence similarity. A hmmer search with a Trusted domain cut-off of 157 was used to separate NUC1_A from other proteins.

Example 12: Wash Assay

Preparation of Biofilm Swatches

Biofilm swatches were made by growing *Brevundimonas* sp. on polyester swatches for two days. The biofilm swatches were rinsed twice in water and dried for 1 h under a flow and subsequently punched into small circles and stored at 4° C. for further use.

Washing Experiment

Biofilm swatches punctures were placed in a deep well 96 format plate. The 96 well plate was placed in a Hamilton robot and subjected to a wash simulation program using the following conditions: Shaking speed: 30 sec at 1000 rpm. Duration of wash cycle: 30 minutes with shaking; temperature 30° C.; Volume of wash liquor (total): 0.5 ml per well. (490 wash liquor+10 ul sample). For screening of wash performance of WT DNases, Model detergent A (3.3 g/L) dissolved in water hardness 15° dH was used. Soil was subsequently added to reach a concentration of 0.7 g soil/L (WFK 09V pigment soil). A 96 well plate was filled with each enzyme sample, and the program was started on the robot. DNases were tested in on concentration 0.05 ppm. The blank consisted of biofilm swatches without any enzyme addition. After completion of the wash simulation cycle, the swatch punctures were removed from the wash liquor and dried on a filter paper. The dried swatch punctures were fixed on a sheet of white paper for scanning. The scanned picture was further used with the software colour-analyzer. Each sample will have an intensity measurement, from the colour analyzer software analysis, that will be used to calculate the delta intensity (remission), by subtracting the intensity of the blank, without enzyme. Values over 70 are visual for the human eye.

Data for KNAW:

TABLE 7

|  | REM Without enzyme | REM With enzyme | ΔREM |
|---|---|---|---|
| *Trichoderma reesei* SEQ ID NO: 122 | 285 | 372 | 87 |
| *Chaetomium thermophilum* var. SEQ ID NO: 125 | 285 | 382 | 97 |
| *Scytalidium thermophilum* SEQ ID NO: 128 | 285 | 356 | 71 |
| *Daldinia fissa* SEQ ID NO: 134 | 285 | 391 | 106 |

Data for NAWK:

TABLE 8

| | REM Without enzyme | REM With enzyme | ΔREM |
|---|---|---|---|
| Pyrenochaetopsis sp. SEQ ID NO: 83 | 285 | 393 | 108 |
| Monilinia fructicola SEQ ID NO: 101 | 285 | 385 | 100 |

Data for NUC1_A

TABLE 9

| | REM Without enzyme | REM With enzyme | ΔREM |
|---|---|---|---|
| Sporormia fimetaria SEQ ID NO: 164 | 285 | 378 | 93 |
| Neosartorya massa SEQ ID NO: 185 | 285 | 383 | 98 |

Example 13: MiniLOM Liquid Detergent

Isolating Laundry Specific Bacterial Strains

One strain of Brevundimonas sp. isolated from laundry was used in the present example. The Brevundimonas sp. was isolated during a study, where the bacterial diversity in laundry after washing at 15, 40 and 60° C., respectively, was investigated. The study was conducted on laundry collected from Danish households. For each wash, 20 g of laundry items (tea towel, towel, dish cloth, bib, T-shirt armpit, T-shirt collar, socks) in the range 4:3:2:2:1:1:1 was used. Washing was performed in a Laundr-O-Meter (LOM) at 15, 40 or 60° C. For washing at 15 and 40° C., Ariel Sensitive White & Colour was used, whereas WFK IEC-A* model detergent was used for washing at 60° C. Ariel Sensitive White & Colour was prepared by weighing out 5.1 g and adding tap water up to 1000 ml followed by stirring for 5 minutes. WFK IEC-A* model detergent (which is available from WFK Testgewebe GmbH) was prepared by weighing out 5 g and adding tap water up to 1300 ml followed by stirring for 15 min. Washing was performed for 1 hour at 15, 40 and 60° C., respectively, followed by 2 times rinsing with tap water for 20 min at 15° C.

Laundry was sampled immediately after washing at 15, 40 and 60° C., respectively. Twenty grams of laundry was added 0.9% (w/v) NaCl (1.06404; Merck, Damstadt, Germany) with 0.5% (w/w) tween 80 to yield a 1:10 dilution in stomacher bag. The mixture was homogenized using a Stomacher for 2 minutes at medium speed. After homogenization, ten-fold dilutions were prepared in 0.9% (w/v) NaCl. Bacteria were enumerated on Tryptone Soya Agar (TSA) (CM0129, Oxoid, Basingstoke, Hampshire, UK) incubated aerobically at 30° C. for 5-7 days. To suppress growth of yeast and moulds, 0.2% sorbic acid (359769, Sigma) and 0.1% cycloheximide (18079; Sigma) were added. Bacterial colonies were selected from countable plates and purified by restreaking twice on TSA. For long time storage, purified isolates were stored at −80° C. in TSB containing 20% (w/v) glycerol (49779; Sigma).

Preparation of Swatches with Biofilm

Brevundimonas sp. was pre-grown on Tryptone Soya Agar (TSA) (pH 7.3) (CM0131; Oxoid Ltd, Basingstoke, UK) for 2-5 days at 30° C. From a single colony, a loop-full was transferred to 10 mL of TSB and incubated for 1 day at 30° C. with shaking (240 rpm). After propagation, Brevundimonas sp. was pelleted by centrifugation (Sigma Laboratory Centrifuge 6K15) (3000 g at 21° C. in 7 min) and resuspended in 10 mL of TSB diluted twice with water. Optical density (OD) at 600 nm was measured using a spectophometer (POLARstar Omega (BMG Labtech, Ortenberg, Germany). Fresh TSB diluted twice with water was inoculated to an $OD_{600\,nm}$ of 0.03, and 1.6 mL was added into each well of a 12-well polystyrene flat-bottom microplate (3512; Corning Incorporated, Corning, NY, USA), in which a round swatch (diameter 2 cm) of sterile Polyester WFK30A was placed. After incubation (24 h at 15° C. with shaking (100 rpm), swatches were rinsed twice with 0.9% (w/v) NaCl.

Wash Experiment

Wash liquor of liquid model detergent A were prepared by weighing out and dissolving detergent in water with water with hardness 15° dH. Dosing of model detergent A was 3.33 g/L. Pigment soil (Pigmentschmutz, 09V, wfk, Krefeld, Germany) (0.7 g/L) was added to the wash liquor. DNase (0.5 ppm) was added to the wash liquor. As control, wash liquor without DNase was made. Wash liquor (10 ml) was added to a 50 ml test tube, in which five rinsed swatches with Brevundimonas sp. biofilm and five sterile polyester (WFK30A) swatches were placed. Test tubes were placed in a Stuart rotator (Mini LOM) for 1 hour at 30° C. Swatches were rinsed twice with tap water and dried on filter paper over night. Colour difference (L values) was measured using a Colour Eye (Macbeth Colour Eye 7000 reflectance spectrophotometer). The measurements were made without UV in the incident light and the L value from the CIE Lab colour space was extracted. The colour difference (L value, L*) represents the darkest black at L*=0, and the brightest white at L*=100. Data is represented as Delta L values meaning the L value of the swatch washed with DNase minus the L value of swatch washed without DNase.

TABLE 10

Deep cleaning of biofilm established on polyester by DNases in miniLOM.

| Host name | L-value Model detergent A | ΔL Model detergent A |
|---|---|---|
| No enzyme | 88.09 | 0 |
| Vibressea flavovirens (SEQ ID NO: 86) | 83.48 | 4.61 |
| Penicillium reticulisporum (SEQ ID NO: 107) | 88.00 | 4.41 |

Example 14: MiniLOM Wash in Powder Detergent

Isolating Laundry Specific Bacterial Strains

One strain of Brevundimonas sp. isolated from laundry was used in the present example. The Brevundimonas sp. was isolated during a study, where the bacterial diversity in laundry after washing at 15, 40 and 60° C., respectively, was investigated. The study was conducted on laundry collected from Danish households. For each wash, 20 g of laundry items (tea towel, towel, dish cloth, bib, T-shirt armpit, T-shirt collar, socks) in the range 4:3:2:2:1:1:1 was used. Washing was performed in a Laundr-O-Meter (LOM) at 15, 40 or 60° C. For washing at 15 and 40° C., Ariel Sensitive White & Colour was used, whereas WFK IEC-A* model detergent was used for washing at 60° C. Ariel Sensitive White & Colour was prepared by weighing out 5.1 g and adding tap water up to 1000 ml followed by stirring for 5 minutes. WFK IEC-A* model detergent (which is available from WFK Testgewebe GmbH) was prepared by weighing out 5 g and adding tap water up to 1300 ml followed by stirring for 15 min. Washing was performed for 1 hour at 15, 40 and 60° C., respectively, followed by 2 times rinsing with tap water for 20 min at 15° C.

Laundry was sampled immediately after washing at 15, 40 and 60° C., respectively. Twenty grams of laundry was added 0.9% (w/v) NaCl (1.06404; Merck, Damstadt, Germany) with 0.5% (w/w) tween 80 to yield a 1:10 dilution in stomacher bag. The mixture was homogenized using a Stomacher for 2 minutes at medium speed. After homogenization, ten-fold dilutions were prepared in 0.9% (w/v) NaCl. Bacteria were enumerated on Tryptone Soya Agar (TSA) (CM0129, Oxoid, Basingstoke, Hampshire, UK) incubated aerobically at 30° C. for 5-7 days. To suppress growth of yeast and moulds, 0.2% sorbic acid (359769, Sigma) and 0.1% cycloheximide (18079; Sigma) were added. Bacterial colonies were selected from countable plates and purified by restreaking twice on TSA. For long time storage, purified isolates were stored at −80° C. in TSB containing 20% (w/v) glycerol (49779; Sigma).

Preparation of Swatches with Biofilm

*Brevundimonas* sp. was pre-grown on Tryptone Soya Agar (TSA) (pH 7.3) (CM0131; Oxoid Ltd, Basingstoke, UK) for 2-5 days at 30° C. From a single colony, a loop-full was transferred to 10 mL of TSB and incubated for 1 day at 30° C. with shaking (240 rpm). After propagation, *Brevundimonas* sp. was pelleted by centrifugation (Sigma Laboratory Centrifuge 6K15) (3000 g at 21° C. in 7 min) and resuspended in 10 mL of TSB diluted twice with water. Optical density (OD) at 600 nm was measured using a spectophometer (POLARstar Omega (BMG Labtech, Ortenberg, Germany). Fresh TSB diluted twice with water was inoculated to an ODeoonm of 0.03, and 1.6 mL was added into each well of a 12-well polystyrene flat-bottom microplate (3512; Corning Incorporated, Corning, NY, USA), in which a round swatch (diameter 2 cm) of sterile Polyester WFK30A was placed. After incubation (24 h at 15° C. with shaking (100 rpm), swatches were rinsed twice with 0.9% (w/v) NaCl.

Wash Experiment

Wash liquors of powder model detergent T without bleach and powder model detergent T with bleach were prepared by weighing out and dissolving detergents in water with water with hardness 15° dH. Dosing of detergent T without bleach and model detergent T with bleach model detergent was 5.30 g/L. The AEO Biosoft N25-7 (NI) (0.16 g/l) component of model detergent T without bleach and model detergent T with bleach was added separately. Pigment soil (Pigmentschmutz, 09V, wfk, Krefeld, Germany) (0.7 g/L) was added to the wash liquor. DNase (0.5 ppm) was added to the wash liquor. As control, wash liquor without DNase was made. Wash liquor (10 ml) was added to a 50 ml test tube, in which five rinsed swatches with *Brevundimonas* sp. biofilm and five sterile polyester (WFK30A) swatches were placed. Test tubes were placed in a Stuart rotator (Mini LOM) for 1 hour at 30° C. Swatches were rinsed twice with tap water and dried on filter paper over night. Colour difference (L values) was measured using a Colour Eye (Macbeth Colour Eye 7000 reflectance spectrophotometer). The measurements were made without UV in the incident light and the L value from the CIE Lab colour space was extracted. The colour difference (L value, L*) represents the darkest black at L*=0, and the brightest white at L*=100. Data is represented as Delta L values meaning the L value of the swatch washed with DNase minus the L value of swatch washed without DNase.

TABLE 11

Deep cleaning of biofilm by *Vibressea flavovirens* DNase in miniLOM.

| Detergent | Type of textile | Soil (g/L) | DNase conc. (ppm) | L-value | L-value$_{with\ DNase}$ L-value$_{without\ DNase}$ |
|---|---|---|---|---|---|
| Model detergent T w/o bleach | Polyester | 0.7 | 0 | 85.58 | |
| Model detergent T w/o bleach | Polyester | 0.7 | 0.5 | 82.39 | 3.19 |
| Model detergent T w bleach | Polyester | 0.7 | 0 | 85.62 | |
| Model detergent T w bleach | Polyester | 0.7 | 0.5 | 84.95 | 0.67 |

The invention claimed is:

1. A polynucleotide encoding a polypeptide having DNase activity, wherein the polypeptide comprises the motif HXXP (SEQ ID NO: 210), where H is histidine, P is proline and X is any amino acid and comprises one or both of the motifs [D/M/L][S/T]GYSR[D/N] (SEQ ID NO: 204) or ASXNR-SKG (SEQ ID NO: 205), and wherein the polypeptide has at least 80% sequence identity to the amino acid sequence of SEQ ID NO: 21.

2. A nucleic acid construct or expression vector comprising the polynucleotide of claim 1 operably linked to one or more control sequences that direct the production of the polypeptide in an expression host.

3. A recombinant host cell comprising the polynucleotide of claim 1 operably linked to one or more control sequences that direct the production of the polypeptide.

4. A method of producing a polypeptide having DNase activity, comprising:

(a) cultivating the recombinant host cell of claim 3 under conditions conducive for production of the polypeptide; and (b) recovering the polypeptide.

5. The method of claim 4, wherein the polypeptide having DNase activity has at least 85% sequence identity to the amino acid sequence of SEQ ID NO: 21.

6. The method of claim 4, wherein the polypeptide having DNase activity has at least 90% sequence identity to the amino acid sequence of SEQ ID NO: 21.

7. The method of claim 4, wherein the polypeptide having DNase activity has at least 95% sequence identity to the amino acid sequence of SEQ ID NO: 21.

8. The method of claim 4, wherein the polypeptide having DNase activity has at least 97% sequence identity to the amino acid sequence of SEQ ID NO: 21.

9. The method of claim 4, wherein the polypeptide comprises the amino acid sequence of SEQ ID NO: 21.

10. The method of claim 4, wherein the recombinant host cell comprises more than one copy of a polynucleotide.

11. The method of claim 4, wherein the recombinant host cell is a Gram-positive bacterium selected from the group consisting of *Bacillus, Clostridium, Enterococcus, Geobacillus, Lactobacillus, Lactococcus, Oceanobacillus, Staphylococcus, Streptococcus*, and *Streptomyces*.

12. The method of claim 4, wherein the recombinant host cell is a *Bacillus* host cell.

13. The method of claim 4, wherein the recombinant host cell is a filamentous fungal host cell selected from the group consisting of *Acremonium, Aspergillus, Aureobasidium, Bjerkandera, Ceriporiopsis, Chrysosporium, Coprinus, Coriolus, Cryptococcus, Filibasidium, Fusarium, Flumicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, and *Trichoderma*.

14. The method of claim 4, wherein at least one of the one or more control sequences is foreign to the polynucleotide.

15. The method of claim 4, wherein the polynucleotide is heterologous to the recombinant host cell.

16. The method of claim 4, wherein the polypeptide is heterologous to the recombinant host cell.

\* \* \* \* \*